US012667562B2

(12) United States Patent
Ravina et al.

(10) Patent No.: US 12,667,562 B2
(45) **Date of Patent: *Jun. 30, 2026**

(54) THERAPEUTIC METHODS AND COMPOSITIONS FOR TREATING MOVEMENT DISORDERS

(71) Applicant: Vima Therapeutics, Inc., Cambridge, MA (US)

(72) Inventors: Bernard Mayer Ravina, Cambridge, MA (US); Maria G. Beconi-Barker, Cambridge, MA (US); Judith Dunn, Cambridge, MA (US); Mark Rogge, Cambridge, MA (US)

(73) Assignee: Vima Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/198,458

(22) Filed: May 5, 2025

(65) Prior Publication Data

US 2025/0268883 A1 Aug. 28, 2025

Related U.S. Application Data

(63) Continuation of application No. 18/655,062, filed on May 3, 2024, now Pat. No. 12,290,513.

(60) Provisional application No. 63/615,960, filed on Dec. 29, 2023, provisional application No. 63/464,409, filed on May 5, 2023.

(51) Int. Cl.

*A61K 31/445* (2006.01)
*A61K 31/27* (2006.01)
*A61K 31/444* (2006.01)

(52) U.S. Cl.

CPC ........... *A61K 31/445* (2013.01); *A61K 31/27* (2013.01); *A61K 31/444* (2013.01)

(58) Field of Classification Search

CPC ..... A61K 31/445; A61K 31/27; A61K 31/444
See application file for complete search history.

(56) References Cited

U.S. PATENT DOCUMENTS

| | | | |
|---|---|---|---|
| 6,063,792 A | 5/2000 | Fabiano et al. | |
| 6,207,681 B1 * | 3/2001 | Fabiano | A61K 31/4453 546/241 |
| 8,268,352 B2 | 9/2012 | Vaya et al. | |
| 11,464,742 B2 | 10/2022 | Shelke et al. | |
| 11,684,580 B2 | 6/2023 | Vaka et al. | |
| 12,290,513 B2 | 5/2025 | Ravina et al. | |
| 2013/0116215 A1 | 5/2013 | Coma et al. | |
| 2013/0289019 A1 | 10/2013 | Chau | |
| 2021/0330657 A1 | 10/2021 | Shelke et al. | |
| 2025/0339418 A1 | 11/2025 | Ravina et al. | |

FOREIGN PATENT DOCUMENTS

| | | | |
|---|---|---|---|
| GB | 750156 A | 6/1956 | |
| WO | WO-2011011060 A1 | 1/2011 | |
| WO | WO-2014176460 A1 * | 10/2014 | A61K 31/5513 |
| WO | WO-2019182321 A1 | 9/2019 | |
| WO | WO-2020061308 A1 | 3/2020 | |
| WO | WO-2024059631 A1 | 3/2024 | |
| WO | WO-2024233396 A1 | 11/2024 | |

OTHER PUBLICATIONS

Boyson, S.J. (1988), Bethanechol for anticholinergic side effects. Ann Neurol., 23: 422-423. https://doi.org/10.1002/ana.410230429 (Year: 1988).*

Mamada, H., Iwamoto, K., Nomura, Y. et al. Predicting blood-to-plasma concentration ratios of drugs from chemical structures and volumes of distribution in humans. Mol Divers 25, 1261-1270 (2021). https://doi.org/10.1007/s11030-021-10186-7 (Year: 2021).*

Abdelhamid, G., et al., "Assessing Cognitive Abilities Using the WAIS-IV: An Item Response Theory Approach," Int J Environ Res Public Health 18(13):6835, MDPI, Switzerland (Jun. 2021).

Arkin, M.R., et al., "FLIPR™ Assays for GPCR and Ion Channel Targets," Assay Guidance Manual, Eli Lilly & Company and the National Center for Advancing Translational Sciences, United States (May 2012).

Artane FOI Register Package for Center Drug Evaluation and Research, Department of Health and Human Services, sent Aug. 16, 1999, 47 pages.

Berge, S.M., et al., "Pharmaceutical Salts," J Pharm Sci 66(1): 1-19, Elsevier, Netherlands (Jan. 1977).

Blake, M.R., et al., "Validity and reliability of the Bristol Stool Form Scale in healthy adults and patients with diarrhoea-predominant irritable bowel syndrome," Aliment Pharmacology Ther., 44(7):693-703, Wiley, United States (Aug. 2016).

Bledsoe, I.O., et al., "Treatment of Dystonia: Medications, Neurotoxins, Neuromodulation, and Rehabilitation," Neurotherapeutics 17:1622-1644, Springer Science+Business Media, United States (Oct. 2020).

Boyson, S., "Bethanechol for Anticholinergic Side Effects," Ann Neurol 23:422-23, Wiley, United States (Apr. 1988).

(Continued)

*Primary Examiner* — Valerie Rodriguez-Garcia
*Assistant Examiner* — Josmalen M. Ramos-Lewis
(74) *Attorney, Agent, or Firm* — Sterne, Kessler, Goldstein & Fox P.L.L.C.

(57) ABSTRACT

The invention provides therapeutic methods, pharmaceutical compositions, and unit dose formulations for treating movement disorders, such as using a muscarinic acetylcholine receptor inhibitor in combination with a muscarinic acetylcholine receptor activator to treat dystonia. In some aspects, the invention provides a method of treating a movement disorder in a patient, where the method comprises administering to a patient in need thereof (i) a muscarinic acetylcholine receptor inhibitor in an amount effective to treat the movement disorder and (ii) a muscarinic acetylcholine receptor activator in an amount effective to reduce the frequency and/or magnitude of at least one side effect of the muscarinic acetylcholine receptor inhibitor, to thereby treat the movement disorder.

18 Claims, 22 Drawing Sheets

(56) References Cited

OTHER PUBLICATIONS

Brans, J.W.M., et al., "Botulinum toxin versus trihexyphenidyl in cervical dystonia: a prospective, randomized, double-blind controlled trial," Neurology 46(4):1066-72, Wolters Kluwer, United States (Apr. 1996).
Burke, R., et al., "Pharmacokinetics of Trihexyphenidyl after Short-Term and Long-Term Administration to Dystonic Patients," Ann Neurol 18(1):35-40, Wiley, United States (Jul. 1985).
Burke, R., et al., "Torsion dystonia: A double-bind, prospective trial of high-dosage trihexyphenidyl," Neurology 36(2):160-64, Wolters Kluwer, United States (Feb. 1986).
Cardozo, L., et al., "Validation of the urgency perception scale," BJU Int'l., 95(4):591-596, Wiley-Blackwell, United States (Mar. 2005).
Center for Drug Evaluation and Research Approval Package for Artane, Application No. 6-773/36, approved Jun. 25, 2003, 30 pages.
Cheung, W.K., et al., "Pharmacokinetic evaluation of a sustained-release formulation of trihexyphenidyl in healthy volunteers," J Pharm Sci 77(9):748-50, Elsevier, Netherlands (Sep. 1988).
Choppin, A., et al., "Pharmacological characterization of muscarinic receptors in rabbit isolated iris sphincter muscle and urinary bladder smooth muscle," Brit. J. of Pharmacology, 124(5):883-888, Wiley-Blackwell, United States (Mar. 1998).
Deik, A., et al., "Etiology, clinical features, and diagnostic evaluation of dystonia," UpToDate article, updated Dec. 13, 2022, Wolters Kluwer, United States, 52 pages.
Deik, A., et al., "Treatment of dystonia in children and adults," UpToDate article, updated Aug. 16, 2021, Wolters Kluwer, United States, 29 pages.
Di Biase, L., et al., "Classification of Dystonia," Life 12:206, MDPI, Switzerland (Jan. 2022).
Dorje, F., et al., "Antagonist Binding Profiles of Five Cloned Human Muscarinic Receptor Subtypes," J Pharmacol Exp Ther 256(2):727-33, American Society for Pharmacology and Experimental Therapeutics, United States (Feb. 1991).
Fahn, S., "Systemic Therapy of Dystonia," Canadian Journal of Neurological Sciences 14:528-532, Cambridge University Press, United Kingdom (Aug. 1987).
Fallon, B.S., et al., "The use of BokaFlo™ instrument to measure salivary flow," BMC Oral Health, 21(1):191, BioMed Central, United Kingdom (Apr. 2021).
Farber, N.B., et al., "Receptor mechanisms and circuitry underlying NMDA antagonist neurotoxicity," Molecular Psychiatry 7:32-43, Springer, Germany (Jan. 2002).
Giachetti, A., et al., "Binding and functional profiles of the selective M1 muscarinic receptor antagonists trihexyphenidyl and dicyclomine," Br. J. Pharmac. 89:83-90, Wiley, United States (Sep. 1986).
Gould, P.L., "Salt selection for basic drugs," International Journal of Pharmaceutics 33:201-217, Elsevier, Netherlands (Nov. 1986).
Greene, P., et al., "Analysis of Open-Label Trials in Torsion Dystonia Using High Dosages of Anticholinergics and Other Drugs," Movement Disorders 3(1):46-60, Wiley, United States (Mar. 1988).
Ishizaki, J., et al., "Characteristic subcellular distribution, in brain, heart and lung, of biperiden, trihexyphenidyl, and (−)-quinuclidinyl benzylate in rats," Biol Pharm Bull 21(1):67-71, Pharmaceutical Society of Japan, Japan (Jan. 1998).
Jabbari, B., et al. ,"Treatment of Movement Disorders with Trihexyphenidyl," Movement Disorders 4(3):202-212, Wiley, United States (Apr. 1989).
Rubinstein, J.S., "Abuse of Anticholinergic Drugs," New. Eng. J. Med., 299(15):834, Massachusetts Medical Society, United States (Oct. 1978).
Kaida, K., et al., "Validation of the Karolinska sleepiness scale against performance and EEG variables," Clin. Neurophysiology, 117(7):1574-1581, Elsevier, Netherlands (May 2006).
Kloosterboer, A., et al., "Diagnostic tests in dry eye," Expert Rev. Ophthalmology, 14(4-5):237-246, Taylor & Francis, United Kingdom (Aug. 2019).
Mahdy, M.M., et al., "Preparation and Evaluation of Novel Extended Release Trihexyphenidyl Hydrochloride Tablets," Journal of Advance Biomedical and Pharmaceutical Sciences 3:89-100, Faculty of Pharmacy, Egypt (Feb. 2020).
Mencacci, N., et al., "Dystonia genes functionally converge in specific neurons and share neurobiology with psychiatric disorders," Brain 43:2771-2787, Oxford University Press, United Kingdom (Sep. 2020).
Mitchelson, F., "Muscarinic Receptor Agonists and Antagonists: Effects on Ocular Function," Handb Exp Pharmacol 208:263-98, Springer, Germany (Jan. 2012).
Mohan, D., et al., "Trihexyphenidyl Abuse," Brit. J. of Addiction, 76:195-197, Wiley, United States (Jun. 1981).
Nelson, D., et al., "Accuracy of automated blood pressure monitors," J. Dent. Hygiene, 82(4):35, American Dental Hygienists Association, United States (Jul. 2008).
Obara, K., et al., "Sustainable Effects of Distigmine Bromide on Urinary Bladder Contractile Function," Pharmacology 105(3-4):135-144, Karger Publishers, Switzerland (Mar. 2020).
Ozenil, M., et al., "Synthesis, Biological, and Computational Evaluation of Antagonistic, Chiral Hydrobenzoin Esters of Arecaidine Targeting mAChR M1," Pharmaceuticals (Basel) 13(12):437, MDPI, Switzerland (Nov. 2020).
Padmini, S., et al., "Development of pulse oximeter for heart rate monitoring," AIP Conf Proceedings, 2117(1):020009, AIP Publishing, United States (Jun. 2019).
Pakala, R., et al., "Cholinergic Medications," Medical Reference, updated Sep. 21, 2022, Statpearls, United States, 6 pages.
Poppi, L.A., et al., "Recurrent Implication of Striatal Cholinergic Interneurons in a Range of Neurodevelopmental, Neurodegenerative, and Neuropsychiatric Disorders," Cells 10:907, MDPI, Switzerland (Apr. 2021).
PubChem, "Pyridostigmine Bromide," created Mar. 26, 2005, accessed at https://pubchem.ncbi.nlm.nih.gov/compound/7550, 42 pages.
PubChem, "Trihexyphenidyl," created Mar. 25, 2005, accessed at https://pubchem.ncbi.nlm.nih.gov/compound/Trihexyphenidyl, 40 pages.
Putilov, A.A., et al., "Construction and validation of the EEG analogues of the Karolinska sleepiness scale based on the Karolinska drowsiness test," Clin. Neurophysiology, 124(7):1346-1352, Elsevier, Netherlands (Jul. 2013).
Pyridostigmine Bromide Label, Defense Supply Center, Philadelphia, PA, 17 pages (Feb. 2003).
Richter, F., et al., "Genetic animal models of dystonia: Common features and diversities," Progress in Neurobiology 121:91-113, Elsevier, Netherlands (Jul. 2014).
Ruchinskas, R., "Wechsler adult intelligence scale—4th edition digit span performance in subjective cognitive complaints, amnestic mild cognitive impairment, and probable dementia of the Alzheimer type," Clin. Neuropsychology, 33(8): 1436-1444, Taylor & Francis, United Kingdom (Nov. 2019).
Salagen Tablets, Medical Information, Food and Drug Administration, United States, Approved Apr. 18, 2003, 10 pages.
Schjelderup, L., et al., "Syntheses of (S)-(+)-trihexyphenidyl hydrochloride and (S)-(+)-procyclidine hydrochloride, two anticholinergics, using (S)-(−)-3-cyclohexyl-3-hydroxy-3-phenylpropanoic acid as chiral synthon," Acta Chem Scand B 41(5):356-61, Wiley, United States (May 1987).
Schwab, R.S., et al., "Slow-Release Trihexyphenidyl in Parkinson's Disease," JAMA 180:159-61, American Medical Association, United States (Apr. 1962).
Sellers, D.J., et al., "Muscarinic Agonists and Antagonists: Effects on the Urinary Bladder," Handb Exp Pharmacol 208:375-400, Springer, Germany (Jan. 2012).
Shinotoh, H., et al., "Effects of trihexyphenidyl and L-dopa on brain muscarinic cholinergic receptor binding measured by positron emission tomography," J Neural Transm Park Dis Dement Sect 7(1):35-46, Springer, Germany (Feb. 1994).
Sipos, M.L., et al., "Dose-response curves and time-course effects of selected anticholinergics on locomotor activity in rats," Psychopharmacology (Berl) 147(3):250-56, Springer, Germany (Dec. 1999).

(56) References Cited

OTHER PUBLICATIONS

Smith, J., et al., “A comparison of manual pupil examination versus an automated pupillometer in a specialised neurosciences intensive care unit,” Aust Critical Care, 33(2):162-166, Elsevier, Netherlands (Mar. 2020).
Sogo, K., et al., “Centrally acting anticholinergic drug trihexyphenidyl is highly effective in reducing nightmares associated with post-traumatic stress disorder,” Brain Behav 11(6):e02147, Wiley, United States (May 2021).
Tanabe, L.M., et al., “Primary dystonia: molecules and mechanisms,” Nat Rev Neurol 5(11):598-609, Springer, Germany (Nov. 2009).
Temsarasab, P., et al., “Medical Treatment of Dystonia,” J Clin Mov Disord. 3:19, BioMed Central, United Kingdom (Dec. 2016).
Torrents, R., et al., “Misuse of Trihexyphenidyl (Artane) on Réunion Island,” J. Clinical Psychophannacology, 38:250-235, Lippincott Williams & Wilkins, United States (Jun. 2018).
Toupet, M., et al., “Visual analog scale to assess vertigo and dizziness after repositioning maneuvers for benign paroxysmal positional vertigo,” J. of Vestibular Res., 21(4):235-241, IOS Press, Amsterdam (Aug. 2011).
Trihexyphenidyl Hydrochloride Tablets I.P. 2 mg Pacitane Tablets, Medicinal Product Information, Pfizer Limited, India, 9 pages (2019).
Ueda, M., et al., “Profile of acotiamide in the treatment of functional dyspepsia,” Clinical and Experimental Gastroenterology 9:83-88, Dove Press, United Kingdom (Apr. 2016).
UpToDate, “Lexicomp Drug Interactions,” Wolters Kluwer, United States, 2 pages (2022).
UpToDate, “Pyridostigmine: Drug Information,” Wolters Kluwer, United States, 17 pages (2022).
UpToDate, “Trihexyphenidyl: Drug Information,” Wolters Kluwer, United States, 13 pages (2022).
Yamanaka, T., et al., “Assessing changes in mood state in university students following short-term study abroad ,” PLos One, 16(12): e0261762, Public Library of Science, United States (Dec. 2021).
Zhou, J., et al., “Trihexyphenidyl increases delta activity in non-rapid eye movement sleep without impairing cognitive function in rodent models,” Neuropharmacology 218:109217, Elsevier, Netherlands (Nov. 2022).
Volz-Zang, C., et al., “Comparison of the effects of atropine in vivo and ex vivo (radioreceptor assay) after oral and intramuscular administration to man,” Eur J Clin Pharamacol 49:45-49, Springer, Germany (Nov. 1995).
Loscher, W., et al., “Effects of pharmacological manipulation of dopaminergic and cholinergic neurotransmission in genetically dystonic hamsters,” European Journal of Pharmacology, 213(1):31-39, Elsevier, Netherlands, (Mar. 1992).
Jankovic, J., “Treatment of hyperkinetic movement disorders,” The Lancet Neurology, 8(9):844-856, Elsevier, Netherlands, (Sep. 2009).
Downs, A.M., et al., “The neurological basis for novel experimental therapeutics in dystonia,” Neurobiology of Disease, 130:104526, Elsevier, Netherlands, (Jul. 2019).
Ben-Sreti, M.M., et al., “Effects of Enantiomers Of 2 Benzomorphan Narcotic Antagonists and Atropine on Analgesia Tremor and Hypothermia Produced by Oxo Tremorine,” Accession No. PREV198375036344, Biosis Information Service, United States (2017), 2 pages.
International Search Report and Written Opinion for International Application No. PCT/US2024/027850, European Patent Office, Netherlands, mailed Sep. 18, 2024, 11 pages.
PubChem, “(R)-trihexyphenidyl,” PubChem CID 207843, accessed at https://pubchem.ncbi.nlm.nih.gov/compound/R_-trihexyphenidyl, accessed on Nov. 27, 2024, 15 pages.
Pirio Richardson, S., et al., “Dystonia treatment Patterns of medication use in an international cohort,” Neurology 88(6):543-550, Wolters Kluwer's, Netherlands (2017).
Kane, M., “CYP2D6 Overview: Allele and Phenotype Frequencies,” in Medical Genetics Summaries [Internet], Pratt, V.M., et al., ed., National Center for Biotechnology Information, Bethesda, United States (2021).
Mamada, H., et al., “Predicting Blood-to-plasma Concentration Ratios of Drugs From Chemical Structures and Volumes of Distribution in Humans,” Molecular Diversity 25(3):1261-1270, ESCOM Science Publishers, Netherlands (Aug. 2021).
Paton, W.D., and Zar, M.A., “The Origin of Acetylcholine Released From Guinea-pig Intestine and Longitudinal Muscle Strips,” The Journal of Physiology 194(1):13-33, Cambridge University Press, United Kingdom (Jan. 1968).
Co-pending U.S. Appl. No. 19/092,490, inventors Ravina, B.M., et al., filed Mar. 27, 2025 (Not yet Published).
Donato, M.T., and Castell, J.V., “Strategies and Molecular Probes to Investigate the Role of Cytochrome P450 in Drug Metabolism: Focus on in Vitro Studies,” Clinical Pharmacokinetics 42(2):153-178, Adis, Switzerland (Feb. 2003).
Gaedigk, A., et al., “The CYP2D6 activity score: translating genotype information into a qualitative measure of phenotype,” Clinical Pharmacology and Therapeutics 83(2):234-242, Wiley, United States (Feb. 2008).
Vardanyan, R., “Chapter 2—1-Substituted Piperidines,” in *Piperidine-Based Drug Discovery*, pp. 83-101, Elsevier, Netherlands (Jun. 2017).
Trihexyphenidyl Hydrochloride Tablet, Drug Label and Insert, A-S Medication Solutions, updated Nov. 2021, 5 pages.

* cited by examiner

THP 2 mg/kg
1:1 Combo
1:1 Stagger
3:1 Combo
5:1 Combo
BTC 2 mg/kg
L+R Ave_% of BSL
150
100
50
0
Pre
1
4

THERAPEUTIC METHODS AND COMPOSITIONS FOR TREATING MOVEMENT DISORDERS

CROSS-REFERENCE TO RELATED APPLICATIONS

This application is a continuation of Ser. No. 18/655,062, filed May 3, 2024, which claims priority to and benefit of U.S. Provisional Application No. 63/464,409, filed on May 5, 2023, and 63/615,960, filed on Dec. 29, 2023, each of which is hereby incorporated by reference in its entirety.

FIELD OF THE INVENTION

The invention provides therapeutic methods, pharmaceutical compositions, and unit dose formulations for treating movement disorders, such as using a muscarinic acetylcholine receptor inhibitor in combination with a muscarinic acetylcholine receptor activator to treat dystonia.

BACKGROUND

Movement disorders impact a substantial number of patients. One such movement disorder, dystonia, is a neurological movement disorder characterized by involuntary (unintended) muscle contractions that cause slow repetitive movements or abnormal postures that can sometimes be painful. The condition can affect one part of the body (focal dystonia), two or more adjacent parts (segmental dystonia), or multiple parts of the body (general dystonia) including the trunk. The muscle spasms can range from mild to severe. Dystonia can be described as primary or secondary. Primary dystonia is when the dystonia is the sole neurological condition experienced by a subject. Secondary dystonia is when the dystonia is caused by outside factors and can be attributed to a specific cause such as exposure to certain medications, toxins, infections, stroke, spinal cord injury, head injury, or peripheral injury. Dystonia is reported to be associated with overactivity of cholinergic interneurons (ChIs) that provide acetylcholine (Ach) to medium spiny neurons (MSNs). Overactivity of cholinergic interneurons produces more acetylcholine for signaling to medium spiny neurons and other neuronal populations leading to dystonia. Treatment options currently available for patients with dystonia do not provide adequate therapeutic benefit for all patients and/or have significant adverse side effects.

Trihexyphenidyl-HCl (THP), a phenyl propylamine, is an anticholinergic agent that was first approved by the FDA in 1949. THP is a synthetic antispasmodic drug that is widely used in the treatment of patients with parkinsonism, including primary or idiopathic Parkinson's disease, secondary symptomatic parkinsonism (postencephalitic, arteriosclerotic, infection-induced, tumor-induced, trauma-induced, and drug-induced), and involuntary movements due to side effects of certain psychiatric drugs. See, for example, Cheung et al. in "Pharmacokinetic evaluation of a sustained release formulation of trihexyphenidyl in healthy volunteers" *J. Pharm. Sci.* (1988) 77 (9): 748-50. THP is approved by the FDA as an adjunct in the treatment of parkinsonism and for the control of extrapyramidal disorders caused by central nervous system drugs such as dibenzoxazepines, phenothiazines, thioxanthenes, and butyrophenones. THP is widely used off-label for treating certain types of dystonia. However, there are major problems associated with using THP to treat dystonia and Parkinsonism, including that it causes significant adverse side effects at the dosage typically used to treat dystonia and current reports describe frequent administration of THP; each of the foregoing contribute to poor patient compliance with THP therapy and concomitant poor therapeutic outcomes.

Accordingly, the need exists for new therapeutic methods and pharmaceutical composition for treating movement disorders, including dystonia. The present invention addresses the foregoing needs and provides other related advantages.

SUMMARY

The invention provides therapeutic methods, pharmaceutical compositions, and unit dose formulations for treating movement disorders, such as using a muscarinic acetylcholine receptor inhibitor in combination with a muscarinic acetylcholine receptor activator to treat dystonia. In particular, one aspect of the invention provides a method of treating a movement disorder in a patient, where the method comprises administering to a patient in need thereof (i) a muscarinic acetylcholine receptor inhibitor in an amount effective to treat the movement disorder and (ii) a muscarinic acetylcholine receptor activator in an amount effective to reduce the frequency and/or magnitude of at least one side effect of the muscarinic acetylcholine receptor inhibitor, to thereby treat the movement disorder. The muscarinic acetylcholine receptor inhibitor may be, for example, trihexyphenidyl or a pharmaceutically acceptable salt thereof. The muscarinic acetylcholine receptor activator may be, for example, bethanechol or a pharmaceutically acceptable salt thereof. Use of the muscarinic acetylcholine receptor inhibitor in combination with the muscarinic acetylcholine receptor activator reduces the frequency and/or magnitude of at least one side effect of the muscarinic acetylcholine receptor inhibitor, and also provides the further benefit of permitting a higher dose of muscarinic acetylcholine receptor inhibitor to be administered to the patient while maintaining a side effect profile that is tolerable for patients. Use of the muscarinic acetylcholine receptor inhibitor in combination with the muscarinic acetylcholine receptor activator also allows for a subject taking the combination to initiate treatment at a dose of the muscarinic receptor inhibitor that is higher than taking the muscarinic receptor inhibitor alone. Such combination also allows for fewer doses of the muscarinic receptor inhibitor at a subtherapeutic dose before reaching a therapeutic dose compared to administering the muscarinic receptor inhibitor alone.

Certain aspects of the present disclosure provide a method of treating a movement disorder in a patient, wherein the method comprises administering to a patient in need thereof (i) a muscarinic acetylcholine receptor inhibitor in an amount effective to treat the movement disorder and (ii) a muscarinic acetylcholine receptor activator, wherein the muscarinic acetylcholine receptor activator does not prevent the therapeutic benefit of the muscarinic acetylcholine receptor inhibitor, to thereby treat the movement disorder.

In some aspects, the method comprises administering to a patient in need thereof (i) a therapeutically effective amount of a muscarinic acetylcholine receptor inhibitor selected from (R)-trihexyphenidyl having a stereochemical purity of at least 95% enantiomeric excess or a pharmaceutically acceptable salt thereof and (ii) a muscarinic acetylcholine receptor activator, to thereby treat the movement disorder. Use of the muscarinic acetylcholine receptor inhibitor in combination with the muscarinic acetylcholine receptor activator reduces the frequency and/or magnitude of at least one side effect of the muscarinic acetylcholine receptor inhibitor, and also provides the further benefit of permitting a higher dose of muscarinic acetylcholine receptor inhibitor to be administered to the patient while maintaining a side effect profile that is tolerable for patients.

In some aspects, the method comprises administering to a patient in need thereof (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor, to thereby treat the movement disorder, wherein the second therapeutic agent is administered to the patient in an amount effective to reduce the frequency and/or magnitude of at least one side effect of the muscarinic acetylcholine receptor inhibitor.

In some aspects, provided is an oral pharmaceutical composition comprising (i) a muscarinic acetylcholine receptor inhibitor, (ii) a muscarinic acetylcholine receptor activator in an amount effective to reduce the frequency and/or magnitude of at least one side effect of the muscarinic acetylcholine receptor inhibitor, and (iii) a pharmaceutically acceptable carrier. The muscarinic acetylcholine receptor inhibitor may be, for example, trihexyphenidyl or a pharmaceutically acceptable salt thereof. The muscarinic acetylcholine receptor inhibitor may be, for example, trihexyphenidyl hydrochloride. The muscarinic acetylcholine receptor activator may be, for example, bethanechol or a pharmaceutically acceptable salt thereof. The muscarinic acetylcholine receptor activator may be, for example, bethanechol chloride.

In some aspects, provided is an oral pharmaceutical composition, comprising (i) a muscarinic acetylcholine receptor inhibitor, (ii) a second therapeutic agent selected from a muscarinic acetylcholine receptor activator, a procholinergic agent, and an acetylcholinesterase inhibitor, and (iii) a pharmaceutically acceptable carrier, wherein the second therapeutic agent is present in an amount effective to reduce the frequency and/or magnitude of at least one side effect of the muscarinic acetylcholine receptor inhibitor.

In some aspects, provided is a pharmaceutical composition, comprising (i) a muscarinic acetylcholine receptor inhibitor selected from (R)-trihexyphenidyl having a stereochemical purity of at least 95% enantiomeric excess or a pharmaceutically acceptable salt thereof, (ii) a muscarinic acetylcholine receptor activator, and (iii) a pharmaceutically acceptable carrier.

In some aspects, provided is a pharmaceutical composition, comprising (i) a muscarinic acetylcholine receptor inhibitor selected from (R)-trihexyphenidyl having a stereochemical purity of at least 95% enantiomeric excess or a pharmaceutically acceptable salt thereof, (ii) a muscarinic acetylcholine receptor activator selected from racemic bethanechol or a pharmaceutically acceptable salt thereof, and (iii) a pharmaceutically acceptable carrier.

In some aspects, provided is a pharmaceutical composition, comprising (i) a muscarinic acetylcholine receptor inhibitor selected from (R)-trihexyphenidyl having a stereochemical purity of at least 95% enantiomeric excess or a pharmaceutically acceptable salt thereof, (ii) a muscarinic acetylcholine receptor activator selected from (S)-bethanechol having a stereochemical purity of at least 95% enantiomeric excess or a pharmaceutically acceptable salt thereof, and (iii) a pharmaceutically acceptable carrier. The pharmaceutical composition may be, for example, formulated for oral administration.

In some aspects, provided is a pharmaceutical composition described herein for use in medicine. In some aspects, provided is a pharmaceutical composition described herein for use in the treatment of a disorder described herein, such as movement disorders described herein. The muscarinic acetylcholine receptor inhibitor may be, for example, trihexyphenidyl or a pharmaceutically acceptable salt thereof. The muscarinic acetylcholine receptor inhibitor may be, for example, trihexyphenidyl hydrochloride. The muscarinic acetylcholine receptor activator may be, for example, bethanechol or a pharmaceutically acceptable salt thereof. The muscarinic acetylcholine receptor activator may be, for example, bethanechol chloride. In some aspects, the trihexyphenidyl or a pharmaceutically acceptable salt thereof is racemic trihexyphenidyl. In some aspects, the trihexyphenidyl or a pharmaceutically acceptable salt thereof is (R)-trihexyphenidyl. In some aspects, the (R)-trihexyphenidyl or a pharmaceutically acceptable salt thereof has a stereochemical purity of at least 95% enantiomeric excess. In some aspect, the bethanechol or a pharmaceutically acceptable salt thereof is racemic bethanechol. In some aspects, the bethanechol or a pharmaceutically acceptable salt thereof is (S)-bethanechol. In some aspects, the (S)-bethanechol or a pharmaceutically acceptable salt thereof has a stereochemical purity of at least 95% enantiomeric excess.

In some aspects, provided is a combination comprising a muscarinic acetylcholine receptor inhibitor and a muscarinic acetylcholine receptor activator. In some aspects, the combination is for use medicine. In some aspects, the combination is for use in the treatment of a disorder described herein, such as movement disorders described herein. The muscarinic acetylcholine receptor inhibitor may be, for example, trihexyphenidyl or a pharmaceutically acceptable salt thereof. The muscarinic acetylcholine receptor inhibitor may be, for example, trihexyphenidyl hydrochloride. The muscarinic acetylcholine receptor activator may be, for example, bethanechol or a pharmaceutically acceptable salt thereof. The muscarinic acetylcholine receptor activator may be, for example, bethanechol chloride. In some aspects, the trihexyphenidyl or a pharmaceutically acceptable salt thereof is racemic trihexyphenidyl. In some aspects, the trihexyphenidyl or a pharmaceutically acceptable salt thereof is (R)-trihexyphenidyl. In some aspects, the (R)-trihexyphenidyl or a pharmaceutically acceptable salt thereof has a stereochemical purity of at least 95% enantiomeric excess. In some aspect, the bethanechol or a pharmaceutically acceptable salt thereof is racemic bethanechol. In some aspects, the bethanechol or a pharmaceutically acceptable salt thereof is (S)-bethanechol. In some aspects, the (S)-bethanechol or a pharmaceutically acceptable salt thereof has a stereochemical purity of at least 95% enantiomeric excess.

BRIEF DESCRIPTION OF FIGURES

FIG. 9A shows the THP alone treatment group. FIG. 9B shows the 1:1 THP:BTC combination treatment group. FIG. 9C shows the 1:1:THP:BTC staggered dosage treatment group. FIG. 9D shows the 1:3 THP:BTC combination treatment group. FIG. 9E shows the 1:5 THP:BTC combination treatment group. FIG. 9F shows the BTC alone treatment group.

DETAILED DESCRIPTION

Figure 1:
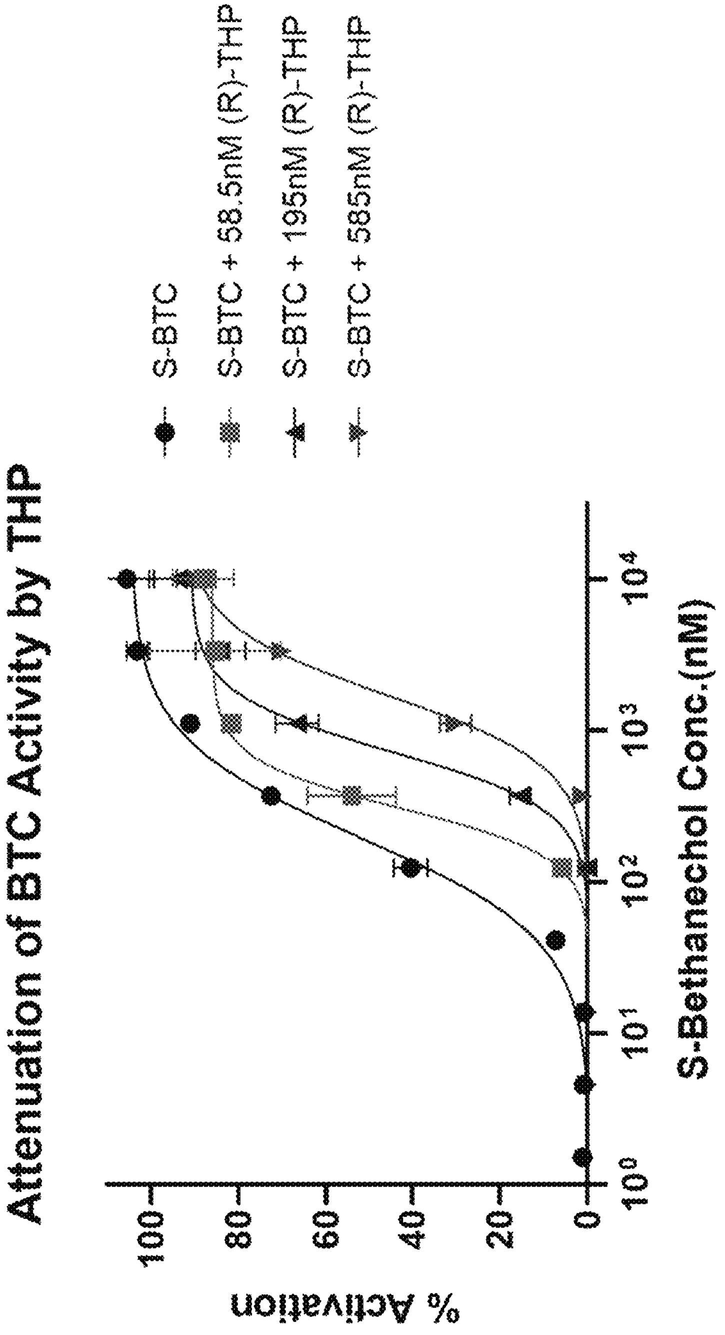
FIG. 1 is a graph depicting results of an assay measuring agonist activity of compound (S)-bethanechol chloride ((S)-BTC) toward the human M1 muscarinic receptor in the presence of (R)-trihexyphenidyl-HCl ((R)-THP), as described in more detail in Example 5.

The invention provides therapeutic methods, pharmaceutical compositions, and unit dose formulations for treating movement disorders, such as using a muscarinic acetylcholine receptor inhibitor in combination with a muscarinic acetylcholine receptor activator to treat dystonia. Use of the muscarinic acetylcholine receptor inhibitor in combination with the muscarinic acetylcholine receptor activator reduces the frequency and/or magnitude of at least one side effect of the muscarinic acetylcholine receptor inhibitor, and also provides the further benefit of permitting a higher dose of muscarinic acetylcholine receptor inhibitor to be administered to the patient while maintaining a side effect profile that is tolerable for patients. The practice of the present invention employs, unless otherwise indicated, conventional techniques of organic chemistry, pharmacology, molecular biology (including recombinant techniques), cell biology, biochemistry, and immunology. Such techniques are explained in the literature, such as in "Comprehensive Organic Synthesis" (B. M. Trost & I. Fleming, eds., 1991-1992); "Handbook of experimental immunology" (D. M. Weir & C. C. Blackwell, eds.); "Current protocols in molecular biology" (F. M. Ausubel et al., eds., 1987, and periodic updates); and "Current protocols in immunology" (J. E. Coligan et al., eds., 1991).

Various aspects of the invention are set forth below in sections; however, aspects of the invention described in one particular section are not to be limited to any particular section. Further, when a variable is not accompanied by a definition, the previous definition of the variable controls.

Definitions

Compounds of the present invention include those described generally herein, and are further illustrated by the classes, subclasses, and species disclosed herein. As used herein, the following definitions shall apply unless otherwise indicated. These definitions apply regardless of whether a term is used by itself or in combination with other terms, unless otherwise indicated. Hence, the definition of "alkyl" applies to "alkyl" as well as the "alkyl" portions of "—O-alkyl" etc. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "cycloaliphatic"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e., carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e., carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

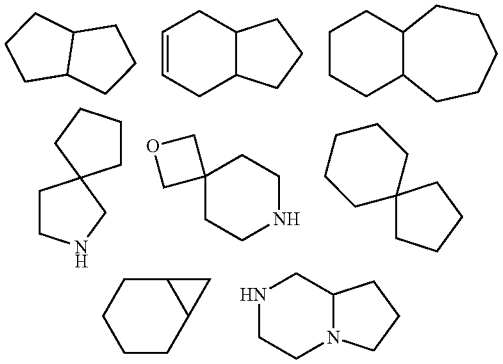

Exemplary bridged bicyclics include:

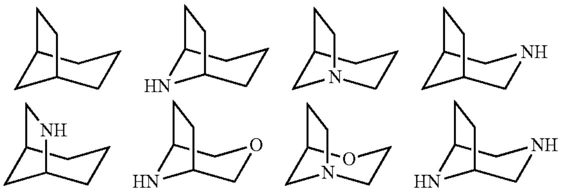

-continued

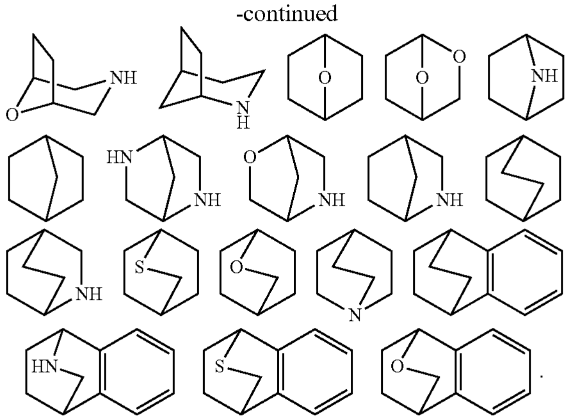

.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "$-(C_0$ alkylene)-" refers to a bond. Accordingly, the term "$-(C_{0-3}$ alkylene)-" encompasses a bond (i.e., $C_0$) and a $-(C_{1-3}$ alkylene)- group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In some aspects, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in some aspects, their recovery, purification, and use for one or more of the purposes disclosed herein.

Each optional substituent on a substitutable carbon is a monovalent substituent independently selected from halogen; $—(CH_2)_{0-4}R^{\circ}$; $—(CH_2)_{0-4}OR^{\circ}$; $—O(CH_2)_{0-4}R^{\circ}$, $—O—(CH_2)_{0-4}C(O)OR^{\circ}$; $—(CH_2)_{0-4}CH(OR^{\circ})_2$; $—(CH_2)_{0-4}SR^{\circ}$; $—(CH_2)_{0-4}Ph$, which may be substituted with $R^{\circ}$; $—(CH_2)_{0-4}$ $O(CH_2)_{0-1}Ph$ which may be substituted with $R^{\circ}$; $—CH{=}CHPh$, which may be substituted with $R^{\circ}$; $—(CH_2)_{0-4}$ $O(CH_2)_{0-1}$-pyridyl which may be substituted with $R^{\circ}$; $—NO_2$; —CN; $—N_3$; $(CH_2)_{0-4}N(R^{\circ})_2$; $—(CH_2)_{0-4}N(R^{\circ})C(O)R^{\circ}$; $—N(R^{\circ})C(S)R^{\circ}$; $—(CH_2)_{0-4}N(R^{\circ})C(O)NR^{\circ}_2$; $N(R^{\circ})C(S)NR^{\circ}_2$; $—(CH_2)_{0-4}N(R^{\circ})C(O)OR^{\circ}$; $—N(R^{\circ})N(R^{\circ})C(O)R^{\circ}$; $N(R^{\circ})N(R^{\circ})C(O)NR^{\circ}_2$; $N(R^{\circ})N(R^{\circ})C(O)OR^{\circ}$; $—(CH_2)_{0-4}C(O)R^{\circ}$; $—C(S)R^{\circ}$; $—(CH_2)_{0-4}C(O)OR^{\circ}$; $—(CH_2)_{0-4}C(O)SR^{\circ}$; $(CH_2)_{0-4}C(O)OSiR^{\circ}_3$; $—(CH_2)_{0-4}OC(O)R^{\circ}$; $—OC(O)(CH_2)_{0-4}SR—$, $SC(S)SR^{\circ}$; $—(CH_2)_{0-4}SC(O)R^{\circ}$; $—(CH_2)_{0-4}C(O)NR^{\circ}_2$; $—C(S)NR^{\circ}_2$; $—C(S)SR^{\circ}$; $—SC(S)SR^{\circ}$, $—(CH_2)_{0-4}OC(O)NR^{\circ}_2$; $C(O)N(OR^{\circ})R^{\circ}$; $—C(O)C(O)R^{\circ}$; $—C(O)CH_2C(O)R^{\circ}$; $—C(NOR^{\circ})R^{\circ}$; $(CH_2)_{0-4}SSR^{\circ}$; $—(CH_2)_{0-4}S(O)_2R^{\circ}$; $—(CH_2)_{0-4}S(O)_2OR^{\circ}$; $—(CH_2)_{0-4}OS(O)_2R^{\circ}$; $—S(O)_2NR^{\circ}_2$; $—S(O)(NR^{\circ})R^{\circ}$; $—S(O)_2N{=}C(NR^{\circ}_2)_2$; $(CH_2)_{0-4}S(O)R^{\circ}$; $N(R^{\circ})S(O)_2NR^{\circ}_2$; $—N(R^{\circ})S(O)_2R^{\circ}$; $—N(OR^{\circ})R^{\circ}$; $—C(NH)NR^{\circ}_2$; $—P(O)_2R^{\circ}$; $P(O)R^{\circ}_2$; $OP(O)R^{\circ}_2$; $—OP(O)(OR^{\circ})_2$; $SiR^{\circ}_3$; $—(C_{1-4}$ straight or branched alkylene)O—$N(R^{\circ})_2$; or $—(C_{1-4}$ straight or branched alkylene)C(O)O—$N(R^{\circ})_2$.

Each $R^{\circ}$ is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^{\circ}$ selected from $=O$ and $=S$; or each $R^{\circ}$ is optionally substituted with a monovalent substituent independently selected from halogen, $—(CH_2)_{0-2}R^{\bullet}$, $-(haloR^{\bullet})$, $—(CH_2)_{0-2}OH$, $—(CH_2)_{0-2}OR^{\bullet}$, $—(CH_2)_{0-2}CH(OR^{\bullet})_2$; $O(haloR^{\bullet})$, —CN, $—N_3$, $—(CH_2)_{0-2}C(O)R^{\circ}$, $—(CH_2)_{0-2}C(O)OH$, $—(CH_2)_{0-2}C(O)OR^{\bullet}$, $—(CH_2)_{0-2}SR^{\bullet}$, $—(CH_2)_{0-2}SH$, $—(CH_2)_{0-2}NH_2$, $—(CH_2)_{0-2}NHR^{\bullet}$, $—(CH_2)_{0-2}NR^{\bullet}_2$, —$NO_2$, —$SiR^{\bullet}_3$, —$OSiR^{\bullet}_3$, $C(O)SR^{\bullet}$, —($C_{1-4}$ straight or branched alkylene)$C(O)OR^{\bullet}$, or —$SSR^{\bullet}$.

Each $R^{\bullet}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens; or wherein an optional substituent on a saturated carbon is a divalent substituent independently selected from =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, or a divalent substituent bound to vicinal substitutable carbons of an "optionally substituted" group is —$O(CR^*_2)_{2-3}O$—, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, —$R^{\bullet}$, (halo$R^{\bullet}$), OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens.

An optional substituent on a substitutable nitrogen is independently —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, $S(O)_2R^{\dagger}$, $S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^{\dagger}$ is $C_{1-6}$ aliphatic, $R^{\dagger}$ is optionally substituted with halogen, —$R^{\bullet}$, (halo$R^{\bullet}$), OH, —$OR^{\bullet}$, —O(halo$R^{\bullet}$), —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{\bullet}$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Further, acids which are generally considered suitable for the formation of pharmaceutically useful salts from basic pharmaceutical compounds are discussed, for example, by P. Stahl et al., Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1): 1-19; P. Gould, *International J. of Pharmaceutics* (1986) 33:201-217; Anderson et al., *The Practice of Medicinal Chemistry* (1996), Academic Press, New York; and in *The Orange Book* (Food & Drug Administration, Washington, D.C. on their website).

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. The invention includes compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

Diastereomeric mixtures can be separated into their individual diastereomers on the basis of their physical chemical differences by methods known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Alternatively, a particular enantiomer of a compound of the present invention may be prepared by asymmetric synthesis. Still further, where the molecule contains a basic functional group (such as amino) or an acidic functional group (such as carboxylic acid) diastereomeric salts are formed with an appropriate optically-active acid or base, followed by resolution of the diastereomers thus formed by fractional crystallization or chromatographic means known in the art, and subsequent recovery of the pure enantiomers.

Individual stereoisomers of the compounds of the invention may, for example, be substantially free of other isomers, or may be admixed, for example, as racemates or with all other, or other selected, stereoisomers. Chiral center(s) in a compound of the present invention can have the S or R configuration as defined by the *IUPAC* 1974 Recommendations. Further, to the extent a compound described herein may exist as an atropisomer (e.g., substituted biaryls), all forms of such atropisomer are considered part of this invention.

Chemical names, common names, and chemical structures may be used interchangeably to describe the same structure. If a chemical compound is referred to using both a chemical structure and a chemical name, and an ambiguity exists between the structure and the name, the structure predominates. It should also be noted that any carbon as well as heteroatom with unsatisfied valences in the text, schemes, examples and tables herein is assumed to have the sufficient number of hydrogen atom(s) to satisfy the valences.

The terms "a" and "an" as used herein mean "one or more" and include the plural unless the context is inappropriate.

The term "alkyl" refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_3$-$C_6$ cycloalkyl," derived from a cycloalkane. Exemplary cycloalkyl groups include cyclohexyl, cyclopentyl, cyclobutyl, and cyclopropyl. The term "cycloalkylene" refers to a bivalent cycloalkyl group.

The symbol "〰" indicates a point of attachment.

When any substituent or variable occurs more than one time in any constituent or the compound of the invention, its definition on each occurrence is independent of its definition at every other occurrence, unless otherwise indicated.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

As used herein, the terms "subject" and "patient" are used interchangeable and refer to organisms to be treated by the methods of the present invention. Such organisms preferably include, but are not limited to, mammals (e.g., murines, simians, equines, bovines, porcines, canines, felines, and the like), and most preferably includes humans.

The term "$IC_{50}$" is art-recognized and refers to the concentration of a compound that is required to achieve 50% inhibition of the target.

The term "$EC_{50}$" is art-recognized and refers to the concentration of a compound that is required to achieve 50% activation of the target.

As used herein, the term "effective amount" or "amount effective" are used interchangeably and refer to the amount of a compound sufficient to effect beneficial or desired results (e.g., a therapeutic, ameliorative, inhibitory or preventative result). An effective amount can be administered in one or more administrations, applications or dosages and is not intended to be limited to a particular formulation or administration route. As used herein, the terms "treat," "treating," and "treatment" include any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

In addition, when a compound of the invention contains both a basic moiety (such as, but not limited to, a pyridine or imidazole) and an acidic moiety (such as, but not limited to, a carboxylic acid) zwitterions ("inner salts") may be formed. Such acidic and basic salts used within the scope of the invention are pharmaceutically acceptable (i.e., non-toxic, physiologically acceptable) salts. Such salts of the compounds of the invention may be formed, for example, by reacting a compound of the invention with an amount of acid or base, such as an equivalent amount, in a medium such as one in which the salt precipitates or in an aqueous medium followed by lyophilization.

As used herein, the term "THP" refers to trihexyphenidyl or a pharmaceutically acceptable salt thereof. As used herein, "Rac-THP" or "Racemic-THP" refer to racemic trihexyphenidyl or a pharmaceutically acceptable salt thereof. As used herein, "(R)-THP" or "R-THP" refers to (R)-trihexyphenidyl or a pharmaceutically acceptable salt thereof. As used herein, "(S)-THP" or "S-THP" refers to (S)-trihexyphenidyl or a pharmaceutically acceptable salt thereof. As used herein, the term "BTC" refers to bethanechol or a pharmaceutically acceptable salt thereof. As used herein, "Rac-BTC" or "Racemic-BTC" refer to racemic bethanechol or a pharmaceutically acceptable salt thereof. As used herein, "(R)-BTC" or "R-BTC" refers to (R)-bethanechol or a pharmaceutically acceptable salt thereof. As used herein, "(S)-BTC" or "S-BTC" refers to (S)-bethanechol or a pharmaceutically acceptable salt thereof.

As used herein, the terms "magnitude" and "severity" are used interchangeably.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified.

I. Therapeutic Methods

The invention provides therapeutic methods using a muscarinic acetylcholine receptor inhibitor in combination with a muscarinic acetylcholine receptor activator. The therapeutic methods are useful for treating a movement disorder. Various aspects and embodiments of the therapeutic methods are described in the sections below. The sections are arranged for convenience and information in one section is not to be limited to that section, but may be applied to methods in other sections.

A. First Therapeutic Method

One aspect of the invention provides a method of treating a movement disorder in a patient, wherein the method comprises administering to a patient in need thereof (i) a muscarinic acetylcholine receptor inhibitor in an amount effective to treat the movement disorder and (ii) a muscarinic acetylcholine receptor activator in an amount effective to reduce the frequency and/or magnitude of at least one side effect of the muscarinic acetylcholine receptor inhibitor, to thereby treat the movement disorder.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency and magnitude of at least one side effect of the muscarinic acetylcholine receptor inhibitor.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency or magnitude of at least one side effect of the muscarinic acetylcholine receptor inhibitor.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the magnitude of at least one side effect of the muscarinic acetylcholine receptor inhibitor.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency of at least one side effect of the muscarinic acetylcholine receptor inhibitor.

One aspect of the invention provides a method of treating a movement disorder in a patient, wherein the method comprises administering to a patient in need thereof (i) a muscarinic acetylcholine receptor inhibitor in an amount effective to treat the movement disorder and (ii) a muscarinic acetylcholine receptor activator in an amount effective to reduce the frequency and/or magnitude of at least one side effect of the muscarinic acetylcholine receptor inhibitor, to thereby treat the movement disorder, wherein the muscarinic acetylcholine receptor inhibitor is trihexyphenidyl or pharmaceutically acceptable salt thereof, and wherein the muscarinic acetylcholine receptor activator is bethanechol or pharmaceutically acceptable salt thereof.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency and magnitude of at least one side effect of the muscarinic acetylcholine receptor inhibitor, wherein the muscarinic acetylcholine receptor inhibitor is trihexyphenidyl or pharmaceutically acceptable salt thereof, and wherein the muscarinic acetylcholine receptor activator is bethanechol or pharmaceutically acceptable salt thereof.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency or magnitude of at least one side effect of the muscarinic acetylcholine receptor inhibitor, wherein the muscarinic acetylcholine receptor inhibitor is trihexyphenidyl or pharmaceutically acceptable salt thereof, and wherein the muscarinic acetylcholine receptor activator is bethanechol or pharmaceutically acceptable salt thereof.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the magnitude of at least one side effect of the muscarinic acetylcholine receptor inhibitor, wherein the muscarinic acetylcholine receptor inhibitor is trihexyphenidyl or pharmaceutically acceptable salt thereof, and wherein the muscarinic acetylcholine receptor activator is bethanechol or pharmaceutically acceptable salt thereof.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency of at least one side effect of the muscarinic acetylcholine receptor inhibitor, wherein the muscarinic acetylcholine receptor inhibitor is trihexyphenidyl or pharmaceutically acceptable salt thereof, and wherein the muscarinic acetylcholine receptor activator is bethanechol or pharmaceutically acceptable salt thereof.

One aspect of the invention provides a method of treating a movement disorder in a patient, wherein the method comprises administering to a patient in need thereof (i) a muscarinic acetylcholine receptor inhibitor in an amount effective to treat the movement disorder and (ii) a muscarinic acetylcholine receptor activator in an amount effective to reduce the frequency and/or magnitude of at least one side effect of the muscarinic acetylcholine receptor inhibitor, to thereby treat the movement disorder, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency and magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency or magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

One aspect of the invention provides a method of treating a movement disorder in a patient, wherein the method comprises administering to a patient in need thereof (i) a muscarinic acetylcholine receptor inhibitor in an amount effective to treat the movement disorder and (ii) a muscarinic acetylcholine receptor activator in an amount effective to reduce the frequency and/or magnitude of at least one side effect of the muscarinic acetylcholine receptor inhibitor, to thereby treat the movement disorder, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency and magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency or magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

One aspect of the invention provides a method of treating a movement disorder in a patient, wherein the method comprises administering to a patient in need thereof (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency and/or magnitude of at least one side effect of the muscarinic acetylcholine receptor inhibitor, to thereby treat the movement disorder, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency and magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency or magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

One aspect of the invention provides a method of treating a movement disorder in a patient, wherein the method comprises administering to a patient in need thereof (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency and/or magnitude of at least one side effect of the muscarinic acetylcholine receptor inhibitor, to thereby treat the movement disorder, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency and magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency or magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

One aspect of the invention provides a method of treating a movement disorder in a patient, wherein the method comprises administering to a patient in need thereof (i) a muscarinic acetylcholine receptor inhibitor in an amount effective to treat the movement disorder and (ii) a muscarinic acetylcholine receptor activator in an amount effective to reduce the frequency and/or magnitude of at least one side effect of the muscarinic acetylcholine receptor inhibitor, to thereby treat the movement disorder, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency and magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency or magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

One aspect of the invention provides a method of treating a movement disorder in a patient, wherein the method comprises administering to a patient in need thereof (i) a muscarinic acetylcholine receptor inhibitor in an amount effective to treat the movement disorder and (ii) a muscarinic acetylcholine receptor activator in an amount effective to reduce the frequency and/or magnitude of at least one side effect of the muscarinic acetylcholine receptor inhibitor, to thereby treat the movement disorder, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency and magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency or magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

One aspect of the invention provides a method of treating a movement disorder in a patient, wherein the method comprises administering to a patient in need thereof (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency and/or magnitude of at least one side effect of the muscarinic acetylcholine receptor inhibitor, to thereby treat the movement disorder, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency and magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency or magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the magnitude of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

One aspect of the invention provides a method of treating a movement disorder in a patient, wherein the method comprises administering to a patient in need thereof (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency and/or magnitude of at least one side effect of the muscarinic acetylcholine receptor inhibitor, to thereby treat the movement disorder, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency and magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency or magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the magnitude of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor in an amount effective to reduce the frequency of at least one side effect of the muscarinic acetylcholine receptor inhibitor, wherein the muscarinic acetylcholine receptor inhibitor is racemic-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:10.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio of about 1:1.1 to about 1:20.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein the muscarinic acetylcholine receptor inhibitor and the muscarinic acetylcholine receptor activator are administered at a weight ratio greater than 1:1 and wherein the muscarinic acetylcholine receptor activator is administered in excess of the muscarinic acetylcholine receptor inhibitor.

In some aspects, the present disclosure provides a method of treating a movement disorder in a subject in need thereof comprising administering to the subject (i) a muscarinic acetylcholine receptor inhibitor in an amount effective to treat the movement disorder and (ii) a muscarinic acetylcholine receptor activator in an amount effective to reduce the frequency of at least one side effect of the muscarinic acetylcholine receptor inhibitor, wherein the muscarinic acetylcholine receptor inhibitor is (R)-trihexyphenidyl or pharmaceutically acceptable salt thereof, wherein the muscarinic acetylcholine receptor activator is racemic bethanechol or pharmaceutically acceptable salt thereof, and wherein a greater amount of the muscarinic acetylcholine receptor activator is administered compared to the amount of the muscarinic acetylcholine receptor inhibitor administered.

In some aspects, the present disclosure provides a method of treating a movement disorder in a subject in need thereof comprising administering to the subject (i) a muscarinic acetylcholine receptor inhibitor and (ii) a muscarinic receptor activator, wherein the amount of muscarinic acetylcholine receptor inhibitor is at a dose level insufficient to reach an efficacious dose if it were to be dosed in the absence of the muscarinic receptor activator.

In some aspects, the present disclosure provides a method of treating a movement disorder in a subject in need thereof comprising administering to the subject (i) (R)-trihexyphenidyl or pharmaceutically acceptable salt thereof and (ii) a muscarinic receptor activator, wherein the amount of the (R)-trihexyphenidyl or pharmaceutically acceptable salt thereof is at a dose level insufficient to reach an efficacious dose if it were to be dosed in the absence of the muscarinic receptor activator.

In some aspects, the present disclosure provides a method of treating a movement disorder in a subject in need thereof comprising administering to the subject (i) (R)-trihexyphenidyl or pharmaceutically acceptable salt thereof and (ii) a muscarinic receptor activator, wherein the dose of (R)-trihexyphenidyl or pharmaceutically acceptable salt thereof is about 50% less than the dose of racemic-trihexyphenidyl or pharmaceutically acceptable salt thereof, and wherein the (R)-trihexyphenidyl or pharmaceutically acceptable salt thereof is at a dose level insufficient to reach an efficacious dose if it were to be dosed in the absence of the muscarinic receptor activator.

In some aspects, the present disclosure provides a method of treating a movement disorder in a subject in need thereof comprising administering to the subject (i) racemic-trihexyphenidyl or pharmaceutically acceptable salt thereof and (ii) a muscarinic receptor activator, wherein the amount of the racemic-trihexyphenidyl or pharmaceutically acceptable salt thereof is at a dose level insufficient to reach an efficacious dose if it were to be dosed in the absence of the muscarinic receptor activator.

In some aspects, the present disclosure provides a method of treating a movement disorder in a subject in need thereof comprising administering to the subject (i) racemic-trihexyphenidyl or pharmaceutically acceptable salt thereof (ii) a second therapeutic agent selected from a muscarinic acetylcholine receptor activator, a procholinergic agent, and an acetylcholinesterase inhibitor, to thereby treat the movement disorder, wherein the amount of the racemic-trihexyphenidyl or pharmaceutically acceptable salt thereof is at a dose level insufficient to reach an efficacious dose if it were to be dosed in the absence of the muscarinic receptor activator.

In some aspects, the present disclosure provides a method of treating a movement disorder in a subject in need thereof comprising administering to the subject (i) a muscarinic acetylcholine receptor inhibitor and (ii) a muscarinic receptor activator, wherein if the subject is administered a standard, monotherapy dose of a muscarinic acetylcholine receptor inhibitor, which would be known to those in the art, in combination with a muscarinic receptor activator, the subject would experience increased frequency, increased magnitude, and/or more severe adverse effects compared to a subject who was administered a standard, monotherapy dose of a muscarinic acetylcholine receptor inhibitor.

In some aspects, the present disclosure provides a method of treating a movement disorder in a subject in need thereof comprising administering to the subject (i) (R)-trihexyphenidyl or pharmaceutically acceptable salt thereof and (ii) a muscarinic receptor activator, wherein if the subject is administered a standard, monotherapy dose of (R)-trihexyphenidyl or a pharmaceutically acceptable salt thereof, which would be known to those in the art, in combination with a muscarinic receptor activator, the subject would experience increased frequency, increased magnitude, or more severe adverse effects compared to a subject who was administered a standard, monotherapy dose of (R)-trihexyphenidyl alone.

In some aspects, the present disclosure provides a method of treating a movement disorder in a subject in need thereof comprising administering to the subject (i) racemic-trihexyphenidyl or pharmaceutically acceptable salt thereof and (ii) a muscarinic receptor activator, wherein if the subject is administered a standard, monotherapy dose of racemic-trihexyphenidyl, which would be known to those in the art, or a pharmaceutically acceptable salt thereof in combination with a muscarinic receptor activator, the subject would experience increased frequency, increased magnitude, or more severe adverse effects compared to a subject who was administered a standard, monotherapy dose of racemic-trihexyphenidyl alone.

In some aspects, the present disclosure provides a method of treating a movement disorder in a subject in need thereof comprising administering to the subject (i) a muscarinic acetylcholine receptor inhibitor and (ii) a second therapeutic agent selected from a muscarinic acetylcholine receptor activator, a procholinergic agent, and an acetylcholinesterase inhibitor, to thereby treat the movement disorder, wherein if the subject is administered a standard, monotherapy dose of a muscarinic acetylcholine receptor inhibitor, which would be known to those in the art, in combination with a second therapeutic agent selected from a muscarinic acetylcholine receptor activator, a procholinergic agent, and an acetylcholinesterase inhibitor, the subject would experience increased frequency, increased magnitude, or more severe adverse effects compared to a subject who was administered a standard dose of a muscarinic acetylcholine receptor inhibitor.

The method may be characterized by additional features, such as the identity of the muscarinic acetylcholine receptor inhibitor, identity of the muscarinic acetylcholine receptor activator, order of administration, and other features as described herein in more detail.

Muscarinic Acetylcholine Receptor Inhibitor

The method may be characterized by the identity of the muscarinic acetylcholine receptor inhibitor. For example, in some aspects, the muscarinic acetylcholine receptor inhibitor distributes to the central nervous system and the peripheral nervous system in the patient.

In some aspects, the muscarinic acetylcholine receptor inhibitor is trihexyphenidyl or a pharmaceutically acceptable salt thereof. In some aspects, the muscarinic acetylcholine receptor inhibitor is trihexyphenidyl. In some aspects, the muscarinic acetylcholine receptor inhibitor is trihexyphenidyl hydrochloride.

In some aspects, the muscarinic acetylcholine receptor inhibitor is racemic trihexyphenidyl or a pharmaceutically acceptable salt thereof. In some aspects, the muscarinic acetylcholine receptor inhibitor is racemic trihexyphenidyl. In some aspects, the muscarinic acetylcholine receptor inhibitor is racemic trihexyphenidyl hydrochloride.

In some aspects, the muscarinic acetylcholine receptor inhibitor is (R)-trihexyphenidyl or a pharmaceutically acceptable salt thereof. In some aspects, the muscarinic acetylcholine receptor inhibitor is (R)-trihexyphenidyl. In some aspects, the muscarinic acetylcholine receptor inhibitor is (R)-trihexyphenidyl hydrochloride.

In some aspects, the muscarinic acetylcholine receptor inhibitor is (R)-trihexyphenidyl having a stereochemical purity of at least 90% enantiomeric excess, or a pharmaceutically acceptable salt thereof. In some aspects, the muscarinic acetylcholine receptor inhibitor is (R)-trihexyphenidyl having a stereochemical purity of at least 95% enantiomeric excess, or a pharmaceutically acceptable salt thereof. In some aspects, the muscarinic acetylcholine receptor inhibitor is (R)-trihexyphenidyl having a stereochemical purity of at least 98% enantiomeric excess, or a pharmaceutically acceptable salt thereof. In some aspects, the muscarinic acetylcholine receptor inhibitor is (R)-trihexyphenidyl having a stereochemical purity of at least 99% enantiomeric excess, or a pharmaceutically acceptable salt thereof.

In some aspects, (a) the muscarinic acetylcholine receptor activator is racemic bethanechol or a pharmaceutically acceptable salt thereof and (b) the muscarinic acetylcholine receptor inhibitor is (R)-trihexyphenidyl or a pharmaceutically acceptable salt thereof.

In some aspects, the muscarinic acetylcholine receptor inhibitor is Aclidinium bromide, Aclidinium bromide/formoterol, Acotiamide, AH 9700, Alvameline, AQRA 721, AQRA 741, AZD 9164, BIBN 99, CEB 1957, Clozapine, Darenzepine, Darifenacin, Darotropium bromide, Dextromequitamium iodide, Ebeinone, Esoxybutynin, Espatropate, Ethopropazine, Fesoterodine, Glycopyrrolate/indacaterol, Glycopyrronium bromide, GSK 1160724, GSK 202405, GSK 573719, GSK 656398, GSK 961081, GYKI 46903, Homatropine methylbromide, Imidafenacin, glycopyrrolate, Ipratropium bromide, Ipratropium bromide/xylometazoline, J 104129, J 106366, L 696986, LAS 35201, Levosalbutamol/ipratropium inhalation solution, Liriodenine, LK 12, Mequitamium iodide, Methantheline, Methantheline bromide, Methscopolamine bromide, N-butylscopolamine, N-methyl-4-piperidyl benzylate, N-methylatropine, NPC 14695, NX 303, Otenzepad, Oxybutynin-Labopharm, Oxybutynin, Oxybutynin chloride, Oxybutynin intravesical, Oxybutynin transdermal, Oxybutynin transdermal, Oxybutynin transdermal gel, Oxvbutynin transmucosal, Oxybutynin vaginal, PG 1000, Pirenzepine ophthalmic, Pirmenol, PNU 200577, Promethazine/hydrocodone/paracetamol, Propantheline, Propantheline bromide, Propiverine, PSD 506, PTAC, QAT 370, FF2-Nuada, Revatropate, Rispenzepine, RL 315535, RO 465934, SCH 211803, SCH 57790, Scopolamine intranasal, Scopolamine transmucosal, Secoverine, S-ET 126, Sintropium bromide, Solifenacin, Solifenacin/tamsulosin, SVT 40776, TD 6301, Telenzepine, Temiverine, Tiotropium bromide, Tolterodine, Tolterodine/tamsulosin, Tropenzilium, Trospium chloride, V 0162, YM 35636, YM 46303, YM 53705, YM 58790, or Zamifenacin, or a pharmaceutically acceptable salt thereof.

B. Second Therapeutic Method

Another aspect of the invention provides a method of treating a movement disorder in a patient, wherein the method comprises administering to a patient in need thereof (i) a therapeutically effective amount of a muscarinic acetylcholine receptor inhibitor selected from (R)-trihexyphenidyl having a stereochemical purity of at least 95% enantiomeric excess or a pharmaceutically acceptable salt thereof and (ii) a muscarinic acetylcholine receptor activator, to thereby treat the movement disorder.

The method may be characterized by additional features, such as the amount of muscarinic acetylcholine receptor activator administered to the patient, the identity of the muscarinic acetylcholine receptor activator, order of administration, and other features as described herein in more detail.

In some aspects, the muscarinic acetylcholine receptor activator is administered to the patient in an amount effective to reduce side effects of the muscarinic acetylcholine receptor inhibitor.

C. Third Therapeutic Method

Another aspect of the invention provides a method of treating a movement disorder in a patient, wherein the method comprises administering to a patient in need thereof (i) a muscarinic acetylcholine receptor inhibitor and (ii) a muscarinic acetylcholine receptor activator, to thereby treat the movement disorder.

In some aspects, the muscarinic acetylcholine receptor activator does not prevent the therapeutic benefit of the muscarinic acetylcholine receptor inhibitor, to thereby treat the movement disorder.

The method may be characterized by additional features, such as the identity of the muscarinic acetylcholine receptor inhibitor, identity of the muscarinic acetylcholine receptor activator, order of administration, and other features as described herein in more detail.

D. Fourth Therapeutic Method

Another aspect of the invention provides a method of treating a movement disorder in a patient, wherein the method comprises administering to a patient in need thereof a single enantiomer of a muscarinic acetylcholine receptor inhibitor, wherein the enantiomer has a stereochemical purity of at least 90% enantiomeric excess.

E. Fifth Therapeutic Method

In some aspects, provided is a method of treating a movement disorder in a patient, comprising administering to a patient in need thereof (i) a muscarinic acetylcholine receptor inhibitor in an amount effective to treat the movement disorder and (ii) a second therapeutic agent selected from a muscarinic acetylcholine receptor activator, a procholinergic agent, and an acetylcholinesterase inhibitor, to thereby treat the movement disorder, wherein the second therapeutic agent is administered to the patient in an amount effective to reduce the frequency and/or magnitude of at least one side effect of the muscarinic acetylcholine receptor inhibitor.

In some aspects, the present disclosure provides a method of treating a movement disorder in a subject in need thereof comprising administering to the subject (i) a muscarinic acetylcholine receptor inhibitor and (ii) a second therapeutic agent selected from a muscarinic acetylcholine receptor activator, a procholinergic agent, and an acetylcholinesterase inhibitor, to thereby treat the movement disorder, wherein the amount of muscarinic acetylcholine receptor inhibitor is at a dose level insufficient to reach an efficacious dose if it were to be dosed in the absence of the second therapeutic agent.

In some aspects, the present disclosure provides a method of treating a movement disorder in a subject in need thereof comprising administering to the subject (i) (R)-trihexyphenidyl or pharmaceutically acceptable salt thereof and (ii) a second therapeutic agent selected from a muscarinic acetylcholine receptor activator, a procholinergic agent, and an acetylcholinesterase inhibitor, to thereby treat the movement disorder, wherein the amount of the (R)-trihexyphenidyl or pharmaceutically acceptable salt thereof is at a dose level insufficient to reach an efficacious dose if it were to be dosed in the absence of the second therapeutic agent.

In some aspects, the present disclosure provides a method of treating a movement disorder in a subject in need thereof comprising administering to the subject (i) racemic-trihexyphenidyl or pharmaceutically acceptable salt thereof and (ii) a second therapeutic agent selected from a muscarinic acetylcholine receptor activator, a procholinergic agent, and an acetylcholinesterase inhibitor, to thereby treat the movement disorder, wherein the amount of the racemic-trihexyphenidyl or pharmaceutically acceptable salt thereof is at a dose level insufficient to reach an efficacious dose if it were to be dosed in the absence of the second therapeutic agent.

In some aspects, the present disclosure provides a method of treating a movement disorder in a subject in need thereof comprising administering to the subject (i) a muscarinic acetylcholine receptor inhibitor and (ii) a second therapeutic agent selected from a muscarinic acetylcholine receptor activator, a procholinergic agent, and an acetylcholinesterase inhibitor, to thereby treat the movement disorder, wherein the amount of muscarinic acetylcholine receptor inhibitor is at a dose level insufficient to reach an efficacious dose if it were to be dosed in the absence of the second therapeutic agent, and wherein the dose of the muscarinic acetylcholine receptor inhibitor reduces the frequency, magnitude and/or severity of at least one central nervous system adverse effect when administered in combination with the second therapeutic agent selected from a muscarinic acetylcholine receptor activator, a procholinergic agent, and an acetylcholinesterase inhibitor to reduce the frequency, magnitude and/or severity of at least one peripheral nervous system adverse effect.

In some aspects, the present disclosure provides a method of treating a movement disorder in a subject in need thereof comprising administering to the subject (i) (R)-trihexyphenidyl or pharmaceutically acceptable salt thereof and (ii) a second therapeutic agent selected from a muscarinic acetylcholine receptor activator, a procholinergic agent, and an acetylcholinesterase inhibitor, to thereby treat the movement disorder, wherein the amount of the (R)-trihexyphenidyl or pharmaceutically acceptable salt thereof is at a dose level insufficient to reach an efficacious dose if it were to be dosed in the absence of the second therapeutic agent, and wherein the dose of the (R)-trihexyphenidyl or pharmaceutically acceptable salt thereof reduces the frequency, magnitude and/or severity of at least one central nervous system adverse effects when administered in combination with the second therapeutic agent selected from a muscarinic acetylcholine receptor activator, a procholinergic agent, and an acetylcholinesterase inhibitor to reduce the frequency, magnitude and/or severity of at least one peripheral nervous system adverse effects.

In some aspects, the present disclosure provides a method of treating a movement disorder in a subject in need thereof comprising administering to the subject (i) racemic-trihexyphenidyl or pharmaceutically acceptable salt thereof and (ii) a second therapeutic agent selected from a muscarinic acetylcholine receptor activator, a procholinergic agent, and an acetylcholinesterase inhibitor, to thereby treat the movement disorder, wherein the amount of the racemic-trihexyphenidyl or pharmaceutically acceptable salt thereof is at a dose level insufficient to reach an efficacious dose if it were to be dosed in the absence of the second therapeutic agent, and wherein the dose of the racemic-trihexyphenidyl or pharmaceutically acceptable salt thereof reduces the frequency, magnitude and/or severity of at least one central nervous system adverse effects when administered in combination with the second therapeutic agent selected from a muscarinic acetylcholine receptor activator, a procholinergic agent, and an acetylcholinesterase inhibitor to reduce the frequency, magnitude and/or severity of at least one peripheral nervous system adverse effects.

In some aspects, the second therapeutic agent is a procholinergic agent. In some aspects, the second therapeutic agent is an acetylcholinesterase inhibitor. In some aspects, the second therapeutic agent is pyridostigmine, neostigmine, physostigmine, edrophonium, or a pharmaceutically acceptable salt thereof. In some aspects, the second therapeutic agent is distigmine bromide.

Muscarinic Acetylcholine Receptor Inhibitor

The method may be characterized by the identity of the muscarinic acetylcholine receptor inhibitor. For example, in some aspects, the muscarinic acetylcholine receptor inhibitor distributes to the central nervous system and the peripheral nervous system in the patient.

In some aspects, the muscarinic acetylcholine receptor inhibitor is trihexyphenidyl or a pharmaceutically acceptable salt thereof. In some aspects, the muscarinic acetylcholine receptor inhibitor is trihexyphenidyl. In some aspects, the muscarinic acetylcholine receptor inhibitor is trihexyphenidyl hydrochloride.

In some aspects, the muscarinic acetylcholine receptor inhibitor is racemic trihexyphenidyl or a pharmaceutically acceptable salt thereof. In some aspects, the muscarinic acetylcholine receptor inhibitor is racemic trihexyphenidyl. In some aspects, the muscarinic acetylcholine receptor inhibitor is racemic trihexyphenidyl hydrochloride.

In some aspects, the muscarinic acetylcholine receptor inhibitor is (R)-trihexyphenidyl or a pharmaceutically acceptable salt thereof. In some aspects, the muscarinic acetylcholine receptor inhibitor is (R)-trihexyphenidyl. In some aspects, the muscarinic acetylcholine receptor inhibitor is (R)-trihexyphenidyl hydrochloride.

In some aspects, the muscarinic acetylcholine receptor inhibitor is (R)-trihexyphenidyl having a stereochemical purity of at least 90% enantiomeric excess, or a pharmaceutically acceptable salt thereof. In some aspects, the muscarinic acetylcholine receptor inhibitor is (R)-trihexyphenidyl having a stereochemical purity of at least 95% enantiomeric excess, or a pharmaceutically acceptable salt thereof. In some aspects, the muscarinic acetylcholine receptor inhibitor is (R)-trihexyphenidyl having a stereochemical purity of at least 98% enantiomeric excess, or a pharmaceutically acceptable salt thereof. In some aspects, the muscarinic acetylcholine receptor inhibitor is (R)-trihexyphenidyl having a stereochemical purity of at least 99% enantiomeric excess, or a pharmaceutically acceptable salt thereof.

In some aspects, the patient does not experience any adverse side effect due to the second therapeutic agent. In some aspects, the patient does not experience any adverse side effect due to the muscarinic acetylcholine receptor activator.

F. Additional Embodiments for First, Second, Third, Fourth and Fifth Therapeutic Method Additional embodiments for the First, Second, Third, and Fourth Therapeutic Method are described herein below. These include, for example, the identity of the muscarinic acetylcholine receptor activator, administration features, identity of the movement disorder, and identity of the patient.

Muscarinic Acetylcholine Receptor Activator

The method may be characterized by the identity of the muscarinic acetylcholine receptor activator. For example, in some aspects, the muscarinic acetylcholine receptor activator distributes predominately to the peripheral nervous system in the patient.

In some aspects, the mole ratio of (i) muscarinic acetylcholine receptor activator present in the peripheral nervous system of the patient to (ii) muscarinic acetylcholine receptor activator present in the central nervous system of the patient is 1 to 1. In some aspects, the mole ratio of (i) muscarinic acetylcholine receptor activator present in the peripheral nervous system of the patient to (ii) muscarinic acetylcholine receptor activator present in the central nervous system of the patient is at least 2 to 1. In some aspects, the mole ratio of (i) muscarinic acetylcholine receptor activator present in the peripheral nervous system of the patient to (ii) muscarinic acetylcholine receptor activator present in the central nervous system of the patient is at least 3 to 1. In some aspects, the mole ratio of (i) muscarinic acetylcholine receptor activator present in the peripheral nervous system of the patient to (ii) muscarinic acetylcholine receptor activator present in the central nervous system of the patient is at least 4 to 1. In some aspects, the mole ratio of (i) muscarinic acetylcholine receptor activator present in the peripheral nervous system of the patient to (ii) muscarinic acetylcholine receptor activator present in the central nervous system of the patient is at least 5 to 1. In some aspects, the mole ratio of (i) muscarinic acetylcholine receptor activator present in the peripheral nervous system of the patient to (ii) muscarinic acetylcholine receptor activator present in the central nervous system of the patient is at least 8 to 1. In some aspects, the mole ratio of (i) muscarinic acetylcholine receptor activator present in the peripheral nervous system of the patient to (ii) muscarinic acetylcholine receptor activator present in the central nervous system of the patient is at least 10 to 1. In some aspects, the mole ratio of (i) muscarinic acetylcholine receptor activator present in the peripheral nervous system of the patient to (ii) muscarinic acetylcholine receptor activator present in the central nervous system of the patient is at least 15 to 1. In some aspects, the mole ratio of (i) muscarinic acetylcholine receptor activator present in the peripheral nervous system of the patient to (ii) muscarinic acetylcholine receptor activator present in the central nervous system of the patient is at least 20 to 1. In some aspects, the mole ratio of (i) muscarinic acetylcholine receptor activator present in the peripheral nervous system of the patient to (ii) muscarinic acetylcholine receptor activator present in the central nervous system of the patient is at least 50 to 1. In some aspects, the mole ratio of (i) muscarinic acetylcholine receptor activator present in the peripheral nervous system of the patient to (ii) muscarinic acetylcholine receptor activator present in the central nervous system of the patient is at least 75 to 1. In some aspects, the mole ratio of (i) muscarinic acetylcholine receptor activator present in the peripheral nervous system of the patient to (ii) muscarinic acetylcholine receptor activator present in the central nervous system of the patient is at least 100 to 1. In some aspects, the mole ratio of (i) muscarinic acetylcholine receptor activator present in the peripheral nervous system of the patient to (ii) muscarinic acetylcholine receptor activator present in the central nervous system of the patient is at least 1,000 to 1.

In some aspects, the weight ratio of (i) Racemic-THP to (ii) Racemic-BTC administered is about 1:1.1 to about 1:20. In some aspects, the weight ratio of (i) Racemic-THP to (ii) Racemic-BTC administered is about 1:1.2 to about 1:19.9. In some aspects, the weight ratio of (i) Racemic-THP to (ii) Racemic-BTC administered is about 1:1.3 to about 1:19.8. In some aspects, the weight ratio of (i) Racemic-THP to (ii) Racemic-BTC administered is about 1:1.4 to about 1:19.7. In some aspects, the weight ratio of (i) Racemic-THP to (ii) Racemic-BTC administered is about 1:1.5 to about 1:19.6. In some aspects, the weight ratio of (i) Racemic-THP to (ii) Racemic-BTC administered is about 1:1.6 to about 1:19.5. In some aspects, the weight ratio of (i) Racemic-THP to (ii) Racemic-BTC administered is about 1:1.7 to about 1:19.4. In some aspects, the weight ratio of (i) Racemic-THP to (ii) Racemic-BTC administered is about 1:1.8 to about 1:19.3. In some aspects, the weight ratio of (i) Racemic-THP to (ii) Racemic-BTC administered is about 1:1.9 to about 1:19.2. In some aspects, the weight ratio of (i) Racemic-THP to (ii) Racemic-BTC administered is about 1:2 to about 1:19.1.

In some aspects, the weight ratio of (i) Racemic-THP to (ii) Racemic-BTC administered is about 1:2.1 to about 1:19. In some aspects, the weight ratio of (i) Racemic-THP to (ii) Racemic-BTC administered is about 1:2.2 to about 1:18.9. In some aspects, the weight ratio of (i) Racemic-THP to (ii) Racemic-BTC administered is about 1:2.3 to about 1:18.8. In some aspects, the weight ratio of (i) Racemic-THP to (ii) Racemic-BTC administered is about 1:2.4 to about 1:18.7. In some aspects, the weight ratio of (i) Racemic-THP to (ii) Racemic-BTC administered is about 1:2.5 to about 1:18.6. In some aspects, the weight ratio of (i) Racemic-THP to (ii) Racemic-BTC administered is about 1:2.6 to about 1:18.5. In some aspects, the weight ratio of (i) Racemic-THP to (ii) Racemic-BTC administered is about 1:2.7 to about 1:18.4. In some aspects, the weight ratio of (i) Racemic-THP to (ii)

Racemic-BTC administered is about 1:2.8 to about 1:18.3. In some aspects, the weight ratio of (i) Racemic-THP to (ii) Racemic-BTC administered is about 1:2.9 to about 1:18.2.

In some aspects, the weight ratio of (i) Racemic-THP to (ii) Racemic-BTC administered is about 1:3 to about 1:18.1. In some aspects, the weight ratio of (i) Racemic-THP to (ii) Racemic-BTC administered is about 1:3.1 to about 1:18. In some aspects, the weight ratio of (i) Racemic-THP to (ii) Racemic-BTC administered is about 1:3.2 to about 1:17.9. In some aspects, the weight ratio of (i) Racemic-THP to (ii) Racemic-BTC administered is about 1:3.3 to about 1:17.8. In some aspects, the weight ratio of (i) Racemic-THP to (ii) Racemic-BTC administered is about 1:3.4 to about 1:17.7. In some aspects, the weight ratio of (i) Racemic-THP to (ii) Racemic-BTC administered is about 1:3.5 to about 1:17.6. In some aspects, the weight ratio of (i) Racemic-THP to (ii) Racemic-BTC administered is about 1:3.6 to about 1:17.5. In some aspects, the weight ratio of (i) Racemic-THP to (ii) Racemic-BTC administered is about 1:3.7 to about 1:17.4. In some aspects, the weight ratio of (i) Racemic-THP to (ii) Racemic-BTC administered is about 1:3.8 to about 1:17.3. In some aspects, the weight ratio of (i) Racemic-THP to (ii) Racemic-BTC administered is about 1:3.9 to about 1:17.2.

In some aspects, the weight ratio of (i) Racemic-THP to (ii) Racemic-BTC administered is about 1:4 to about 1:17.1. In some aspects, the weight ratio of (i) Racemic-THP to (ii) Racemic-BTC administered is about 1:4.1 to about 1:17. In some aspects, the weight ratio of (i) Racemic-THP to (ii) Racemic-BTC administered is about 1:4.2 to about 1:16.9. In some aspects, the weight ratio of (i) Racemic-THP to (ii) Racemic-BTC administered is about 1:4.3 to about 1:16.8. In some aspects, the weight ratio of (i) Racemic-THP to (ii) Racemic-BTC administered is about 1:4.4 to about 1:16.7. In some aspects, the weight ratio of (i) Racemic-THP to (ii) Racemic-BTC administered is about 1:4.5 to about 1:16.6. In some aspects, the weight ratio of (i) Racemic-THP to (ii) Racemic-BTC administered is about 1:4.6 to about 1:16.5. In some aspects, the weight ratio of (i) Racemic-THP to (ii) Racemic-BTC administered is about 1:4.7 to about 1:16.4. In some aspects, the weight ratio of (i) Racemic-THP to (ii) Racemic-BTC administered is about 1:4.8 to about 1:16.3. In some aspects, the weight ratio of (i) Racemic-THP to (ii) Racemic-BTC administered is about 1:4.9 to about 1:16.2.

In some aspects, the weight ratio of (i) Racemic-THP to (ii) Racemic-BTC administered is about 1:5 to about 1:16.1. In some aspects, the weight ratio of (i) Racemic-THP to (ii) Racemic-BTC administered is about 1:5.1 to about 1:16. In some aspects, the weight ratio of (i) Racemic-THP to (ii) Racemic-BTC administered is about 1:5.2 to about 1:15.9. In some aspects, the weight ratio of (i) Racemic-THP to (ii) Racemic-BTC administered is about 1:5.3 to about 1:15.8. In some aspects, the weight ratio of (i) Racemic-THP to (ii) Racemic-BTC administered is about 1:5.4 to about 1:15.7. In some aspects, the weight ratio of (i) Racemic-THP to (ii) Racemic-BTC administered is about 1:5.5 to about 1:15.6. In some aspects, the weight ratio of (i) Racemic-THP to (ii) Racemic-BTC administered is about 1:5.6 to about 1:15.5. In some aspects, the weight ratio of (i) Racemic-THP to (ii) Racemic-BTC administered is about 1:5.7 to about 1:15.4. In some aspects, the weight ratio of (i) Racemic-THP to (ii) Racemic-BTC administered is about 1:5.8 to about 1:15.3. In some aspects, the weight ratio of (i) Racemic-THP to (ii) Racemic-BTC administered is about 1:5.9 to about 1:15.2.

In some aspects, the weight ratio of (i) Racemic-THP to (ii) Racemic-BTC administered is about 1:6 to about 1:15.1. In some aspects, the weight ratio of (i) Racemic-THP to (ii) Racemic-BTC administered is about 1:6.1 to about 1:15. In some aspects, the weight ratio of (i) Racemic-THP to (ii) Racemic-BTC administered is about 1:6.2 to about 1:14.9. In some aspects, the weight ratio of (i) Racemic-THP to (ii) Racemic-BTC administered is about 1:6.3 to about 1:14.8. In some aspects, the weight ratio of (i) Racemic-THP to (ii) Racemic-BTC administered is about 1:6.4 to about 1:14.7. In some aspects, the weight ratio of (i) Racemic-THP to (ii) Racemic-BTC administered is about 1:6.5 to about 1:14.6. In some aspects, the weight ratio of (i) Racemic-THP to (ii) Racemic-BTC administered is about 1:6.6 to about 1:14.5. In some aspects, the weight ratio of (i) Racemic-THP to (ii) Racemic-BTC administered is about 1:6.7 to about 1:14.4. In some aspects, the weight ratio of (i) Racemic-THP to (ii) Racemic-BTC administered is about 1:6.8 to about 1:14.3. In some aspects, the weight ratio of (i) Racemic-THP to (ii) Racemic-BTC administered is about 1:6.9 to about 1:14.2.

In some aspects, the weight ratio of (i) Racemic-THP to (ii) Racemic-BTC administered is about 1:7 to about 1:14.1. In some aspects, the weight ratio of (i) Racemic-THP to (ii) Racemic-BTC administered is about 1:7.1 to about 1:14. In some aspects, the weight ratio of (i) Racemic-THP to (ii) Racemic-BTC administered is about 1:7.2 to about 1:13.9. In some aspects, the weight ratio of (i) Racemic-THP to (ii) Racemic-BTC administered is about 1:7.3 to about 1:13.8. In some aspects, the weight ratio of (i) Racemic-THP to (ii) Racemic-BTC administered is about 1:7.4 to about 1:13.7. In some aspects, the weight ratio of (i) Racemic-THP to (ii) Racemic-BTC administered is about 1:7.5 to about 1:13.6. In some aspects, the weight ratio of (i) Racemic-THP to (ii) Racemic-BTC administered is about 1:7.6 to about 1:13.5. In some aspects, the weight ratio of (i) Racemic-THP to (ii) Racemic-BTC administered is about 1:7.7 to about 1:13.4. In some aspects, the weight ratio of (i) Racemic-THP to (ii) Racemic-BTC administered is about 1:7.8 to about 1:13.3. In some aspects, the weight ratio of (i) Racemic-THP to (ii) Racemic-BTC administered is about 1:7.9 to about 1:13.2.

In some aspects, the weight ratio of (i) Racemic-THP to (ii) Racemic-BTC administered is about 1:8 to about 1:13.1. In some aspects, the weight ratio of (i) Racemic-THP to (ii) Racemic-BTC administered is about 1:8.1 to about 1:13. In some aspects, the weight ratio of (i) Racemic-THP to (ii) Racemic-BTC administered is about 1:8.2 to about 1:12.9. In some aspects, the weight ratio of (i) Racemic-THP to (ii) Racemic-BTC administered is about 1:8.3 to about 1:12.8. In some aspects, the weight ratio of (i) Racemic-THP to (ii) Racemic-BTC administered is about 1:8.4 to about 1:12.7. In some aspects, the weight ratio of (i) Racemic-THP to (ii) Racemic-BTC administered is about 1:8.5 to about 1:12.6. In some aspects, the weight ratio of (i) Racemic-THP to (ii) Racemic-BTC administered is about 1:8.6 to about 1:12.5. In some aspects, the weight ratio of (i) Racemic-THP to (ii) Racemic-BTC administered is about 1:8.7 to about 1:12.4. In some aspects, the weight ratio of (i) Racemic-THP to (ii) Racemic-BTC administered is about 1:8.8 to about 1:12.3. In some aspects, the weight ratio of (i) Racemic-THP to (ii) Racemic-BTC administered is about 1:8.9 to about 1:12.2.

In some aspects, the weight ratio of (i) Racemic-THP to (ii) Racemic-BTC administered is about 1:9 to about 1:12.1. In some aspects, the weight ratio of (i) Racemic-THP to (ii) Racemic-BTC administered is about 1:9.1 to about 1:13. In some aspects, the weight ratio of (i) Racemic-THP to (ii) Racemic-BTC administered is about 1:9.2 to about 1:11.9. In some aspects, the weight ratio of (i) Racemic-THP to (ii) Racemic-BTC administered is about 1:9.3 to about 1:11.8. In some aspects, the weight ratio of (i) Racemic-THP to (ii) Racemic-BTC administered is about 1:9.4 to about 1:11.7. In some aspects, the weight ratio of (i) Racemic-THP to (ii)

Racemic-BTC administered is about 1:9.5 to about 1:11.6. In some aspects, the weight ratio of (i) Racemic-THP to (ii) Racemic-BTC administered is about 1:9.6 to about 1:11.5. In some aspects, the weight ratio of (i) Racemic-THP to (ii) Racemic-BTC administered is about 1:9.7 to about 1:11.4. In some aspects, the weight ratio of (i) Racemic-THP to (ii) Racemic-BTC administered is about 1:9.8 to about 1:11.3. In some aspects, the weight ratio of (i) Racemic-THP to (ii) Racemic-BTC administered is about 1:9.9 to about 1:11.2.

In some aspects, the weight ratio of (i) Racemic-THP to (ii) Racemic-BTC administered is about 1:10 to about 1:11.1. In some aspects, the weight ratio of (i) Racemic-THP to (ii) Racemic-BTC administered is about 1:10.1 to about 1:11. In some aspects, the weight ratio of (i) Racemic-THP to (ii) Racemic-BTC administered is about 1:10.2 to about 1:10.9. In some aspects, the weight ratio of (i) Racemic-THP to (ii) Racemic-BTC administered is about 1:10.3 to about 1:10.8. In some aspects, the weight ratio of (i) Racemic-THP to (ii) Racemic-BTC administered is about 1:10.4 to about 1:10.7. In some aspects, the weight ratio of (i) Racemic-THP to (ii) Racemic-BTC administered is about 1:10.5 to about 1:10.6.

In some aspects, the weight ratio of (i) Racemic-THP to (ii) Racemic-BTC administered is about 1:3 to about 1:7.1 In some aspects, the weight ratio of (i) Racemic-THP to (ii) Racemic-BTC administered is about 1:3.1 to about 1:6.9. In some aspects, the weight ratio of (i) Racemic-THP to (ii) Racemic-BTC administered is about 1:3.2 to about 1:6.9. In some aspects, the weight ratio of (i) Racemic-THP to (ii) Racemic-BTC administered is about 1:3.3 to about 1:6.8. In some aspects, the weight ratio of (i) Racemic-THP to (ii) Racemic-BTC administered is about 1:3.4 to about 1:6.7. In some aspects, the weight ratio of (i) Racemic-THP to (ii) Racemic-BTC administered is about 1:3.5 to about 1:6.6. In some aspects, the weight ratio of (i) Racemic-THP to (ii) Racemic-BTC administered is about 1:3.6 to about 1:6.5. In some aspects, the weight ratio of (i) Racemic-THP to (ii) Racemic-BTC administered is about 1:3.7 to about 1:6.4. In some aspects, the weight ratio of (i) Racemic-THP to (ii) Racemic-BTC administered is about 1:3.8 to about 1:6.3. In some aspects, the weight ratio of (i) Racemic-THP to (ii) Racemic-BTC administered is about 1:3.9 to about 1:6.2.

In some aspects, the weight ratio of (i) Racemic-THP to (ii) Racemic-BTC administered is about 1:4 to about 1:6.1. In some aspects, the weight ratio of (i) Racemic-THP to (ii) Racemic-BTC administered is about 1:4.1 to about 1:5.9. In some aspects, the weight ratio of (i) Racemic-THP to (ii) Racemic-BTC administered is about 1:4.2 to about 1:5.9. In some aspects, the weight ratio of (i) Racemic-THP to (ii) Racemic-BTC administered is about 1:4.3 to about 1:5.8. In some aspects, the weight ratio of (i) Racemic-THP to (ii) Racemic-BTC administered is about 1:4.4 to about 1:5.7. In some aspects, the weight ratio of (i) Racemic-THP to (ii) Racemic-BTC administered is about 1:4.5 to about 1:5.6. In some aspects, the weight ratio of (i) Racemic-THP to (ii) Racemic-BTC administered is about 1:4.6 to about 1:5.5. In some aspects, the weight ratio of (i) Racemic-THP to (ii) Racemic-BTC administered is about 1:4.7 to about 1:5.4. In some aspects, the weight ratio of (i) Racemic-THP to (ii) Racemic-BTC administered is about 1:4.8 to about 1:5.3. In some aspects, the weight ratio of (i) Racemic-THP to (ii) Racemic-BTC administered is about 1:4.9 to about 1:5.2. In some aspects, the weight ratio of (i) Racemic-THP to (ii) Racemic-BTC administered is about 1:5 to about 1:5.1.

In some aspects, the weight ratio of (i) Racemic-THP to (ii) Racemic-BTC administered is about 1:1.1 to about 1:10. In some aspects, the weight ratio of (i) Racemic-THP to (ii) Racemic-BTC administered is about 1:1.2 to about 1:9.9. In some aspects, the weight ratio of (i) Racemic-THP to (ii) Racemic-BTC administered is about 1:1.3 to about 1:9.8. In some aspects, the weight ratio of (i) Racemic-THP to (ii) Racemic-BTC administered is about 1:1.4 to about 1:9.7. In some aspects, the weight ratio of (i) Racemic-THP to (ii) Racemic-BTC administered is about 1:1.5 to about 1:9.6. In some aspects, the weight ratio of (i) Racemic-THP to (ii) Racemic-BTC administered is about 1:1.6 to about 1:9.5. In some aspects, the weight ratio of (i) Racemic-THP to (ii) Racemic-BTC administered is about 1:1.7 to about 1:9.4. In some aspects, the weight ratio of (i) Racemic-THP to (ii) Racemic-BTC administered is about 1:1.8 to about 1:9.3. In some aspects, the weight ratio of (i) Racemic-THP to (ii) Racemic-BTC administered is about 1:1.9 to about 1:9.2. In some aspects, the weight ratio of (i) Racemic-THP to (ii) Racemic-BTC administered is about 1:2 to about 1:9.1.

In some aspects, the weight ratio of (i) Racemic-THP to (ii) Racemic-BTC administered is about 1:2.1 to about 1:9. In some aspects, the weight ratio of (i) Racemic-THP to (ii) Racemic-BTC administered is about 1:2.2 to about 1:8.9. In some aspects, the weight ratio of (i) Racemic-THP to (ii) Racemic-BTC administered is about 1:2.3 to about 1:8.8. In some aspects, the weight ratio of (i) Racemic-THP to (ii) Racemic-BTC administered is about 1:2.4 to about 1:8.7. In some aspects, the weight ratio of (i) Racemic-THP to (ii) Racemic-BTC administered is about 1:2.5 to about 1:8.6. In some aspects, the weight ratio of (i) Racemic-THP to (ii) Racemic-BTC administered is about 1:2.6 to about 1:8.5. In some aspects, the weight ratio of (i) Racemic-THP to (ii) Racemic-BTC administered is about 1:2.7 to about 1:8.4. In some aspects, the weight ratio of (i) Racemic-THP to (ii) Racemic-BTC administered is about 1:2.8 to about 1:8.3. In some aspects, the weight ratio of (i) Racemic-THP to (ii) Racemic-BTC administered is about 1:2.9 to about 1:8.2.

In some aspects, the weight ratio of (i) Racemic-THP to (ii) Racemic-BTC administered is about 1:3 to about 1:8.1. In some aspects, the weight ratio of (i) Racemic-THP to (ii) Racemic-BTC administered is about 1:3.1 to about 1:8. In some aspects, the weight ratio of (i) Racemic-THP to (ii) Racemic-BTC administered is about 1:3.2 to about 1:7.9. In some aspects, the weight ratio of (i) Racemic-THP to (ii) Racemic-BTC administered is about 1:3.3 to about 1:7.8. In some aspects, the weight ratio of (i) Racemic-THP to (ii) Racemic-BTC administered is about 1:3.4 to about 1:7.7. In some aspects, the weight ratio of (i) Racemic-THP to (ii) Racemic-BTC administered is about 1:3.5 to about 1:7.6. In some aspects, the weight ratio of (i) Racemic-THP to (ii) Racemic-BTC administered is about 1:3.6 to about 1:7.5. In some aspects, the weight ratio of (i) Racemic-THP to (ii) Racemic-BTC administered is about 1:3.7 to about 1:7.4. In some aspects, the weight ratio of (i) Racemic-THP to (ii) Racemic-BTC administered is about 1:3.8 to about 1:7.3. In some aspects, the weight ratio of (i) Racemic-THP to (ii) Racemic-BTC administered is about 1:3.9 to about 1:7.2.

In some aspects, the weight ratio of (i) Racemic-THP to (ii) Racemic-BTC administered is about 1:4 to about 1:7.1. In some aspects, the weight ratio of (i) Racemic-THP to (ii) Racemic-BTC administered is about 1:4.1 to about 1:7. In some aspects, the weight ratio of (i) Racemic-THP to (ii) Racemic-BTC administered is about 1:4.2 to about 1:6.9. In some aspects, the weight ratio of (i) Racemic-THP to (ii) Racemic-BTC administered is about 1:4.3 to about 1:6.8. In some aspects, the weight ratio of (i) Racemic-THP to (ii) Racemic-BTC administered is about 1:4.4 to about 1:6.7. In some aspects, the weight ratio of (i) Racemic-THP to (ii) Racemic-BTC administered is about 1:4.5 to about 1:6.6. In some aspects, the weight ratio of (i) Racemic-THP to (ii) Racemic-BTC administered is about 1:4.6 to about 1:6.5. In some aspects, the weight ratio of (i) Racemic-THP to (ii) Racemic-BTC administered is about 1:4.7 to about 1:6.4. In some aspects, the weight ratio of (i) Racemic-THP to (ii) Racemic-BTC administered is about 1:4.8 to about 1:6.3. In some aspects, the weight ratio of (i) Racemic-THP to (ii) Racemic-BTC administered is about 1:4.9 to about 1:6.2.

In some aspects, the weight ratio of (i) Racemic-THP to (ii) Racemic-BTC administered is about 1:5 to about 1:6.1. In some aspects, the weight ratio of (i) Racemic-THP to (ii) Racemic-BTC administered is about 1:5.1 to about 1:6. In some aspects, the weight ratio of (i) Racemic-THP to (ii) Racemic-BTC administered is about 1:5.2 to about 1:5.9. In some aspects, the weight ratio of (i) Racemic-THP to (ii) Racemic-BTC administered is about 1:5.3 to about 1:5.8. In some aspects, the weight ratio of (i) Racemic-THP to (ii) Racemic-BTC administered is about 1:5.4 to about 1:5.7. In some aspects, the weight ratio of (i) Racemic-THP to (ii) Racemic-BTC administered is about 1:5.5 to about 1:5.6.

In some aspects, the weight ratio of (i) Racemic-THP to (ii) Racemic-BTC administered is about 1:>1. In some aspects, the weight ratio of (i) Racemic-THP to (ii) Racemic-BTC administered is about 1:>2. In some aspects, the weight ratio of (i) Racemic-THP to (ii) Racemic-BTC administered is about 1:>3. In some aspects, the weight ratio of (i) Racemic-THP to (ii) Racemic-BTC administered is about 1:>4. In some aspects, the weight ratio of (i) Racemic-THP to (ii) Racemic-BTC administered is about 1:>5. In some aspects, the weight ratio of (i) Racemic-THP to (ii) Racemic-BTC administered is about 1:>6. In some aspects, the weight ratio of (i) Racemic-THP to (ii) Racemic-BTC administered is about 1:>7. In some aspects, the weight ratio of (i) Racemic-THP to (ii) Racemic-BTC administered is about 1:>8. In some aspects, the weight ratio of (i) Racemic-THP to (ii) Racemic-BTC administered is about 1:>9. In some aspects, the weight ratio of (i) Racemic-THP to (ii) Racemic-BTC administered is about 1:>10. In some aspects, the weight ratio of (i) Racemic-THP to (ii) Racemic-BTC administered is about 1:>11. In some aspects, the weight ratio of (i) Racemic-THP to (ii) Racemic-BTC administered is about 1:>12. In some aspects, the weight ratio of (i) Racemic-THP to (ii) Racemic-BTC administered is about 1:>13. In some aspects, the weight ratio of (i) Racemic-THP to (ii) Racemic-BTC administered is about 1:>14. In some aspects, the weight ratio of (i) Racemic-THP to (ii) Racemic-BTC administered is about 1:>15. In some aspects, the weight ratio of (i) Racemic-THP to (ii) Racemic-BTC administered is about 1:>16. In some aspects, the weight ratio of (i) Racemic-THP to (ii) Racemic-BTC administered is about 1:>17. In some aspects, the weight ratio of (i) Racemic-THP to (ii) Racemic-BTC administered is about 1:>18. In some aspects, the weight ratio of (i) Racemic-THP to (ii) Racemic-BTC administered is about 1:>19. In some aspects, the weight ratio of (i) Racemic-THP to (ii) Racemic-BTC administered is about 1:>20.

In some aspects, the weight ratio of (i) Racemic-THP to (ii) Racemic-BTC administered is about 1:1.1. In some aspects, the weight ratio of (i) Racemic-THP to (ii) Racemic-BTC administered is about 1:2. In some aspects, the weight ratio of (i) Racemic-THP to (ii) Racemic-BTC administered is about 1:3. In some aspects, the weight ratio of (i) Racemic-THP to (ii) Racemic-BTC administered is about 1:4. In some aspects, the weight ratio of (i) Racemic-THP to (ii) Racemic-BTC administered is about 1:5. In some aspects, the weight ratio of (i) Racemic-THP to (ii) Racemic-BTC administered is about 1:6. In some aspects, the weight ratio of (i) Racemic-THP to (ii) Racemic-BTC administered is about 1:7. In some aspects, the weight ratio of (i) Racemic-THP to (ii) Racemic-BTC administered is about 1:8. In some aspects, the weight ratio of (i) Racemic-THP to (ii) Racemic-BTC administered is about 1:9. In some aspects, the weight ratio of (i) Racemic-THP to (ii) Racemic-BTC administered is about 1:10. In some aspects, the weight ratio of (i) Racemic-THP to (ii) Racemic-BTC administered is about 1:11. In some aspects, the weight ratio of (i) Racemic-THP to (ii) Racemic-BTC is about 1:12. In some aspects, the weight ratio of (i) Racemic-THP to (ii) Racemic-BTC administered is about 1:13. In some aspects, the weight ratio of (i) Racemic-THP to (ii) Racemic-BTC administered is about 1:14. In some aspects, the weight ratio of (i) Racemic-THP to (ii) Racemic-BTC administered is about 1:15. In some aspects, the weight ratio of (i) Racemic-THP to (ii) Racemic-BTC administered is about 1:16. In some aspects, the weight ratio of (i) Racemic-THP to (ii) Racemic-BTC administered is about 1:17. In some aspects, the weight ratio of (i) Racemic-THP to (ii) Racemic-BTC administered is about 1:18. In some aspects, the weight ratio of (i) Racemic-THP to (ii) Racemic-BTC administered is about 1:19. In some aspects, the weight ratio of (i) Racemic-THP to (ii) Racemic-BTC administered is about 1:20.

In some aspects, the weight ratio of (i) (R)-THP to (ii) Racemic-BTC administered is about 1:4 to about 1:40. In some aspects, the weight ratio of (i) (R)-THP to (ii) Racemic-BTC administered is about 1:5 to about 1:39. In some aspects, the weight ratio of (i) (R)-THP to (ii) Racemic-BTC administered is about 1:6 to about 1:38. In some aspects, the weight ratio of (i) (R)-THP to (ii) Racemic-BTC administered is about 1:7 to about 1:37. In some aspects, the weight ratio of (i) (R)-THP to (ii) Racemic-BTC administered is about 1:8 to about 1:36. In some aspects, the weight ratio of (i) (R)-THP to (ii) Racemic-BTC administered is about 1:9 to about 1:35. In some aspects, the weight ratio of (i) (R)-THP to (ii) Racemic-BTC administered is about 1:10 to about 1:34. In some aspects, the weight ratio of (i) (R)-THP to (ii) Racemic-BTC administered is about 1:11 to about 1:33. In some aspects, the weight ratio of (i) (R)-THP to (ii) Racemic-BTC administered is about 1:12 to about 1:32. In some aspects, the weight ratio of (i) (R)-THP to (ii) Racemic-BTC administered is about 1:13 to about 1:31. In some aspects, the weight ratio of (i) (R)-THP to (ii) Racemic-BTC administered is about 1:14 to about 1:30. In some aspects, the weight ratio of (i) (R)-THP to (ii) Racemic-BTC administered is about 1:15 to about 1:29. In some aspects, the weight ratio of (i) (R)-THP to (ii) Racemic-BTC administered is about 1:16 to about 1:28. In some aspects, the weight ratio of (i) (R)-THP to (ii) Racemic-BTC administered is about 1:17 to about 1:27. In some aspects, the weight ratio of (i) (R)-THP to (ii) Racemic-BTC administered is about 1:18 to about 1:26. In some aspects, the weight ratio of (i) (R)-THP to (ii) Racemic-BTC administered is about 1:19 to about 1:25. In some aspects, the weight ratio of (i) (R)-THP to (ii) Racemic-BTC administered is about 1:20 to about 1:24. In some aspects, the weight ratio of (i) (R)-THP to (ii) Racemic-BTC administered is about 1:21 to about 1:23.

In some aspects, the weight ratio of (i) (R)-THP to (ii) Racemic-BTC administered is about 1:4. In some aspects, the weight ratio of (i) (R)-THP to (ii) Racemic-BTC administered is about 1:5. In some aspects, the weight ratio of (i) (R)-THP to (ii) Racemic-BTC administered is about 1:6. In some aspects, the weight ratio of (i) (R)-THP to (ii) Racemic-BTC administered is about 1:7. In some aspects, the weight ratio of (i) (R)-THP to (ii) Racemic-BTC administered is about 1:8. In some aspects, the weight ratio of (i)

(R)-THP to (ii) Racemic-BTC administered is about 1:9. In some aspects, the weight ratio of (i) (R)-THP to (ii) Racemic-BTC administered is about 1:10. In some aspects, the weight ratio of (i) (R)-THP to (ii) Racemic-BTC administered is about 1:11. In some aspects, the weight ratio of (i) (R)-THP to (ii) Racemic-BTC administered is about 1:12. In some aspects, the weight ratio of (i) (R)-THP to (ii) Racemic-BTC administered is about 1:13. In some aspects, the weight ratio of (i) (R)-THP to (ii) Racemic-BTC administered is about 1:14. In some aspects, the weight ratio of (i) (R)-THP to (ii) Racemic-BTC administered is about 1:15. In some aspects, the weight ratio of (i) (R)-THP to (ii) Racemic-BTC administered is about 1:16. In some aspects, the weight ratio of (i) (R)-THP to (ii) Racemic-BTC administered is about 1:17. In some aspects, the weight ratio of (i) (R)-THP to (ii) Racemic-BTC administered is about 1:18. In some aspects, the weight ratio of (i) (R)-THP to (ii) Racemic-BTC administered is about 1:19. In some aspects, the weight ratio of (i) (R)-THP to (ii) Racemic-BTC administered is about 1:20. In some aspects, the weight ratio of (i) (R)-THP to (ii) Racemic-BTC administered is about 1:21. In some aspects, the weight ratio of (i) (R)-THP to (ii) Racemic-BTC administered is about 1:22. In some aspects, the weight ratio of (i) (R)-THP to (ii) Racemic-BTC administered is about 1:23. In some aspects, the weight ratio of (i) (R)-THP to (ii) Racemic-BTC administered is about 1:24. In some aspects, the weight ratio of (i) (R)-THP to (ii) Racemic-BTC administered is about 1:25. In some aspects, the weight ratio of (i) (R)-THP to (ii) Racemic-BTC administered is about 1:26. In some aspects, the weight ratio of (i) (R)-THP to (ii) Racemic-BTC administered is about 1:27. In some aspects, the weight ratio of (i) (R)-THP to (ii) Racemic-BTC administered is about 1:28. In some aspects, the weight ratio of (i) (R)-THP to (ii) Racemic-BTC administered is about 1:29. In some aspects, the weight ratio of (i) (R)-THP to (ii) Racemic-BTC administered is about 1:30. In some aspects, the weight ratio of (i) (R)-THP to (ii) Racemic-BTC administered is about 1:31. In some aspects, the weight ratio of (i) (R)-THP to (ii) Racemic-BTC administered is about 1:32. In some aspects, the weight ratio of (i) (R)-THP to (ii) Racemic-BTC administered is about 1:33. In some aspects, the weight ratio of (i) (R)-THP to (ii) Racemic-BTC administered is about 1:34. In some aspects, the weight ratio of (i) (R)-THP to (ii) Racemic-BTC administered is about 1:35. In some aspects, the weight ratio of (i) (R)-THP to (ii) Racemic-BTC administered is about 1:36. In some aspects, the weight ratio of (i) (R)-THP to (ii) Racemic-BTC administered is about 1:37. In some aspects, the weight ratio of (i) (R)-THP to (ii) Racemic-BTC administered is about 1:38. In some aspects, the weight ratio of (i) (R)-THP to (ii) Racemic-BTC administered is about 1:39. In some aspects, the weight ratio of (i) (R)-THP to (ii) Racemic-BTC administered is about 1:40.

In some aspects, the weight ratio of (i) (R)-THP to (ii) (S)-BTC administered is about 1:2 to about 1:20. In some aspects, the weight ratio of (i) (R)-THP to (ii) (S)-BTC administered is about 1:3 to about 1:19. In some aspects, the weight ratio of (i) (R)-THP to (ii) (S)-BTC administered is about 1:4 to about 1:18. In some aspects, the weight ratio of (i) (R)-THP to (ii) (S)-BTC administered is about 1:5 to about 1:17. In some aspects, the weight ratio of (i) (R)-THP to (ii) (S)-BTC administered is about 1:6 to about 1:16. In some aspects, the weight ratio of (i) (R)-THP to (ii) (S)-BTC administered is about 1:7 to about 1:15. In some aspects, the weight ratio of (i) (R)-THP to (ii) (S)-BTC administered is about 1:8 to about 1:14. In some aspects, the weight ratio of (i) (R)-THP to (ii) (S)-BTC administered is about 1:9 to about 1:13. In some aspects, the weight ratio of (i) (R)-THP to (ii) (S)-BTC administered is about 1:10 to about 1:12.

In some aspects, the weight ratio of (i) (R)-THP to (ii) (S)-BTC administered is about 1:2. In some aspects, the weight ratio of (i) (R)-THP to (ii) (S)-BTC administered is about 1:3. In some aspects, the weight ratio of (i) (R)-THP to (ii) (S)-BTC administered is about 1:4. In some aspects, the weight ratio of (i) (R)-THP to (ii) (S)-BTC administered is about 1:5. In some aspects, the weight ratio of (i) (R)-THP to (ii) (S)-BTC administered is about 1:6. In some aspects, the weight ratio of (i) (R)-THP to (ii) (S)-BTC administered is about 1:7. In some aspects, the weight ratio of (i) (R)-THP to (ii) (S)-BTC administered is about 1:8. In some aspects, the weight ratio of (i) (R)-THP to (ii) (S)-BTC administered is about 1:9. In some aspects, the weight ratio of (i) (R)-THP to (ii) (S)-BTC administered is about 1:10. In some aspects, the weight ratio of (i) (R)-THP to (ii) (S)-BTC administered is about 1:11. In some aspects, the weight ratio of (i) (R)-THP to (ii) (S)-BTC administered is about 1:12. In some aspects, the weight ratio of (i) (R)-THP to (ii) (S)-BTC administered is about 1:13. In some aspects, the weight ratio of (i) (R)-THP to (ii) (S)-BTC administered is about 1:14. In some aspects, the weight ratio of (i) (R)-THP to (ii) (S)-BTC administered is about 1:15. In some aspects, the weight ratio of (i) (R)-THP to (ii) (S)-BTC administered is about 1:16. In some aspects, the weight ratio of (i) (R)-THP to (ii) (S)-BTC administered is about 1:17. In some aspects, the weight ratio of (i) (R)-THP to (ii) (S)-BTC administered is about 1:18. In some aspects, the weight ratio of (i) (R)-THP to (ii) (S)-BTC administered is about 1:19. In some aspects, the weight ratio of (i) (R)-THP to (ii) (S)-BTC administered is about 1:20.

In some aspects, the weight ratio of (i) a muscarinic acetylcholine receptor inhibitor to (ii) a muscarinic acetylcholine receptor activator administered is about 1:1 to about 1:40. In some aspects, the weight ratio of (i) a muscarinic acetylcholine receptor inhibitor to (ii) a muscarinic acetylcholine receptor activator administered is about 1:2 to about 1:39. In some aspects, the weight ratio of (i) a muscarinic acetylcholine receptor inhibitor to (ii) a muscarinic acetylcholine receptor activator administered is about 1:3 to about 1:38. In some aspects, the weight ratio of (i) a muscarinic acetylcholine receptor inhibitor to (ii) a muscarinic acetylcholine receptor activator administered is about 1:4 to about 1:37. In some aspects, the weight ratio of (i) a muscarinic acetylcholine receptor inhibitor to (ii) a muscarinic acetylcholine receptor activator administered is about 1:5 to about 1:36. In some aspects, the weight ratio of (i) a muscarinic acetylcholine receptor inhibitor to (ii) a muscarinic acetylcholine receptor activator administered is about 1:6 to about 1:35. In some aspects, the weight ratio of (i) a muscarinic acetylcholine receptor inhibitor to (ii) a muscarinic acetylcholine receptor activator administered is about 1:7 to about 1:34. In some aspects, the weight ratio of (i) a muscarinic acetylcholine receptor inhibitor to (ii) a muscarinic acetylcholine receptor activator administered is about 1:8 to about 1:33. In some aspects, the weight ratio of (i) a muscarinic acetylcholine receptor inhibitor to (ii) a muscarinic acetylcholine receptor activator administered is about 1:9 to about 1:32. In some aspects, the weight ratio of (i) a muscarinic acetylcholine receptor inhibitor to (ii) a muscarinic acetylcholine receptor activator administered is about 1:10 to about 1:31. In some aspects, the weight ratio of (i) a muscarinic acetylcholine receptor inhibitor to (ii) a muscarinic acetylcholine receptor activator administered is about 1:11 to about 1:30. In some aspects, the weight ratio of (i) a muscarinic acetylcholine receptor inhibitor to (ii) a muscarinic acetylcholine receptor activator administered is about 1:12 to about 1:29. In some aspects, the weight ratio of (i) a muscarinic acetylcholine receptor inhibitor to (ii) a muscarinic acetylcholine receptor activator administered is about 1:13 to about 1:28. In some aspects, the weight ratio of (i) a muscarinic acetylcholine receptor inhibitor to (ii) a muscarinic acetylcholine receptor activator administered is about 1:14 to about 1:27. In some aspects, the weight ratio of (i) a muscarinic acetylcholine receptor inhibitor to (ii) a muscarinic acetylcholine receptor activator administered is about 1:15 to about 1:26. In some aspects, the weight ratio of (i) a muscarinic acetylcholine receptor inhibitor to (ii) a muscarinic acetylcholine receptor activator administered is about 1:16 to about 1:25. In some aspects, the weight ratio of (i) a muscarinic acetylcholine receptor inhibitor to (ii) a muscarinic acetylcholine receptor activator administered is about 1:17 to about 1:24. In some aspects, the weight ratio of (i) a muscarinic acetylcholine receptor inhibitor to (ii) a muscarinic acetylcholine receptor activator administered is about 1:18 to about 1:23. In some aspects, the weight ratio of (i) a muscarinic acetylcholine receptor inhibitor to (ii) a muscarinic acetylcholine receptor activator administered is about 1:19 to about 1:22. In some aspects, the weight ratio of (i) a muscarinic acetylcholine receptor inhibitor to (ii) a muscarinic acetylcholine receptor activator administered is about 1:20 to about 1:21. In some aspects, the muscarinic acetylcholine receptor inhibitor is selected from scopolamine, benztropine, and ethopropazine or a pharmaceutically acceptable salt thereof.

In some aspects, the weight ratio of (i) a muscarinic acetylcholine receptor inhibitor to (ii) a muscarinic acetylcholine receptor activator administered is about 1:2 to about 1:8. In some aspects, the weight ratio of (i) a muscarinic acetylcholine receptor inhibitor to (ii) a muscarinic acetylcholine receptor activator administered is about 1:3 to about 1:7. In some aspects, the weight ratio of (i) a muscarinic acetylcholine receptor inhibitor to (ii) a muscarinic acetylcholine receptor activator administered is about 1:4 to about 1:6. In some aspects, the muscarinic acetylcholine receptor inhibitor is selected from scopolamine, benztropine, and ethopropazine or a pharmaceutically acceptable salt thereof.

In some aspects, the weight ratio of (i) a muscarinic acetylcholine receptor inhibitor to (ii) a muscarinic acetylcholine receptor activator administered is about 1:1.1. In some aspects, the weight ratio of (i) a muscarinic acetylcholine receptor inhibitor to (ii) a muscarinic acetylcholine receptor activator administered is about 1:2. In some aspects, the weight ratio of (i) a muscarinic acetylcholine receptor inhibitor to (ii) a muscarinic acetylcholine receptor activator administered is about 1:3. In some aspects, the weight ratio of (i) a muscarinic acetylcholine receptor inhibitor to (ii) a muscarinic acetylcholine receptor activator administered is about 1:4. In some aspects, the weight ratio of (i) a muscarinic acetylcholine receptor inhibitor to (ii) a muscarinic acetylcholine receptor activator administered is about 1:5. In some aspects, the weight ratio of (i) a muscarinic acetylcholine receptor inhibitor to (ii) a muscarinic acetylcholine receptor activator administered is about 1:6. In some aspects, the weight ratio of (i) a muscarinic acetylcholine receptor inhibitor to (ii) a muscarinic acetylcholine receptor activator administered is about 1:7. In some aspects, the weight ratio of (i) a muscarinic acetylcholine receptor inhibitor to (ii) a muscarinic acetylcholine receptor activator administered is about 1:8. In some aspects, the weight ratio of (i) a muscarinic acetylcholine receptor inhibitor to (ii) a muscarinic acetylcholine receptor activator administered is about 1:9. In some aspects, the weight ratio of (i) a muscarinic acetylcholine receptor inhibitor to (ii) a muscarinic acetylcholine receptor activator administered is about 1:10. In some aspects, the weight ratio of (i) a muscarinic acetylcholine receptor inhibitor to (ii) a muscarinic acetylcholine receptor activator administered is about 1:11. In some aspects, the weight ratio of (i) a muscarinic acetylcholine receptor inhibitor to (ii) a muscarinic acetylcholine receptor activator administered is about 1:12. In some aspects, the weight ratio of (i) a muscarinic acetylcholine receptor inhibitor to (ii) a muscarinic acetylcholine receptor activator administered is about 1:13. In some aspects, the weight ratio of (i) a muscarinic acetylcholine receptor inhibitor to (ii) a muscarinic acetylcholine receptor activator administered is about 1:14. In some aspects, the weight ratio of (i) a muscarinic acetylcholine receptor inhibitor to (ii) a muscarinic acetylcholine receptor activator administered is about 1:15. In some aspects, the weight ratio of (i) a muscarinic acetylcholine receptor inhibitor to (ii) a muscarinic acetylcholine receptor activator administered is about 1:16. In some aspects, the weight ratio of (i) a muscarinic acetylcholine receptor inhibitor to (ii) a muscarinic acetylcholine receptor activator administered is about 1:17. In some aspects, the weight ratio of (i) a muscarinic acetylcholine receptor inhibitor to (ii) a muscarinic acetylcholine receptor activator administered is about 1:18. In some aspects, the weight ratio of (i) a muscarinic acetylcholine receptor inhibitor to (ii) a muscarinic acetylcholine receptor activator administered is about 1:19. In some aspects, the weight ratio of (i) a muscarinic acetylcholine receptor inhibitor to (ii) a muscarinic acetylcholine receptor activator administered is about 1:20. In some aspects, the weight ratio of (i) a muscarinic acetylcholine receptor inhibitor to (ii) a muscarinic acetylcholine receptor activator administered is about 1:21. In some aspects, the weight ratio of (i) a muscarinic acetylcholine receptor inhibitor to (ii) a muscarinic acetylcholine receptor activator administered is about 1:22. In some aspects, the weight ratio of (i) a muscarinic acetylcholine receptor inhibitor to (ii) a muscarinic acetylcholine receptor activator administered is about 1:23. In some aspects, the weight ratio of (i) a muscarinic acetylcholine receptor inhibitor to (ii) a muscarinic acetylcholine receptor activator administered is about 1:24. In some aspects, the weight ratio of (i) a muscarinic acetylcholine receptor inhibitor to (ii) a muscarinic acetylcholine receptor activator administered is about 1:25. In some aspects, the weight ratio of (i) a muscarinic acetylcholine receptor inhibitor to (ii) a muscarinic acetylcholine receptor activator administered is about 1:26. In some aspects, the weight ratio of (i) a muscarinic acetylcholine receptor inhibitor to (ii) a muscarinic acetylcholine receptor activator administered is about 1:27. In some aspects, the weight ratio of (i) a muscarinic acetylcholine receptor inhibitor to (ii) a muscarinic acetylcholine receptor activator administered is about 1:28. In some aspects, the weight ratio of (i) a muscarinic acetylcholine receptor inhibitor to (ii) a muscarinic acetylcholine receptor activator administered is about 1:29. In some aspects, the weight ratio of (i) a muscarinic acetylcholine receptor inhibitor to (ii) a muscarinic acetylcholine receptor activator administered is about 1:30. In some aspects, the weight ratio of (i) a muscarinic acetylcholine receptor inhibitor to (ii) a muscarinic acetylcholine receptor activator administered is about 1:31. In some aspects, the weight ratio of (i) a muscarinic acetylcholine receptor inhibitor to (ii) a muscarinic acetylcholine receptor activator administered is about 1:32. In some aspects, the weight ratio of (i) a muscarinic acetylcholine receptor inhibitor to (ii) a muscarinic acetylcholine receptor activator administered is about 1:33. In some aspects, the weight ratio of (i) a muscarinic acetylcholine receptor inhibitor to (ii) a muscarinic acetylcholine receptor activator administered is about 1:34. In some aspects, the weight ratio of (i) a muscarinic acetylcholine receptor inhibitor to (ii) a muscarinic acetylcholine receptor activator administered is about 1:35. In some aspects, the weight ratio of (i) a muscarinic acetylcholine receptor inhibitor to (ii) a muscarinic acetylcholine receptor activator administered is about 1:36. In some aspects, the weight ratio of (i) a muscarinic acetylcholine receptor inhibitor to (ii) a muscarinic acetylcholine receptor activator administered is about 1:37. In some aspects, the weight ratio of (i) a muscarinic acetylcholine receptor inhibitor to (ii) a muscarinic acetylcholine receptor activator administered is about 1:38. In some aspects, the weight ratio of (i) a muscarinic acetylcholine receptor inhibitor to (ii) a muscarinic acetylcholine receptor activator administered is about 1:39. In some aspects, the weight ratio of (i) a muscarinic acetylcholine receptor inhibitor to (ii) a muscarinic acetylcholine receptor activator administered is about 1:40. In some aspects, the muscarinic acetylcholine receptor inhibitor is selected from scopolamine, benztropine, and ethopropazine or a pharmaceutically acceptable salt thereof.

In some aspects, the serum concentration ratio of (i) Racemic-THP to (ii) Racemic-BTC is about 1:20 ng/mL to about 1:40 ng/mL after administration. In some aspects, the serum concentration ratio of (i) Racemic-THP to (ii) Racemic-BTC is about 1:21 ng/mL to about 1:39 ng/mL after administration. In some aspects, the serum concentration ratio of (i) Racemic-THP to (ii) Racemic-BTC is about 1:22 ng/mL to about 1:38 ng/ml after administration. In some aspects, the serum concentration ratio of (i) Racemic-THP to (ii) Racemic-BTC is about 1:23 ng/mL to about 1:37 ng/mL after administration. In some aspects, the serum concentration ratio of (i) Racemic-THP to (ii) Racemic-BTC is about 1:24 ng/mL to about 1:36 ng/ml after administration. In some aspects, the serum concentration ratio of (i) Racemic-THP to (ii) Racemic-BTC is about 1:25 ng/mL to about 1:35 ng/ml after administration. In some aspects, the serum concentration ratio of (i) Racemic-THP to (ii) Racemic-BTC is about 1:26 ng/ml to about 1:34 ng/mL after administration. In some aspects, the serum concentration ratio of (i) Racemic-THP to (ii) Racemic-BTC is about 1:27 ng/mL to about 1:33 ng/ml after administration. In some aspects, the serum concentration ratio of (i) Racemic-THP to (ii) Racemic-BTC is about 1:28 ng/ml to about 1:32 ng/mL after administration. In some aspects, the serum concentration ratio of (i) Racemic-THP to (ii) Racemic-BTC is about 1:29 ng/ml to about 1:31 ng/mL after administration. In some aspects, the serum concentration ratio determined about 30 minutes to about 24 hours after the administration. In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the serum concentration ratio of (i) (R)-THP to (ii) Racemic-BTC is about 1:20 ng/ml to about 1:40 ng/ml after administration. In some aspects, the serum concentration ratio of (i) (R)-THP to (ii) Racemic-BTC is about 1:21 ng/mL to about 1:39 ng/ml after administration. In some aspects, the serum concentration ratio of (i) (R)-THP to (ii) Racemic-BTC is about 1:22 ng/ml to about 1:38 ng/mL after administration. In some aspects, the serum concentration ratio of (i) (R)-THP to (ii) Racemic-BTC is about 1:23 ng/ml to about 1:37 ng/mL after administration. In some aspects, the serum concentration ratio of (i) (R)-THP to (ii) Racemic-BTC is about 1:24 ng/mL to about 1:36 ng/mL after administration. In some aspects, the serum concentration ratio of (i) (R)-THP to (ii) Racemic-BTC is about 1:25 ng/ml to about 1:35 ng/mL after administration. In some aspects, the serum concentration ratio of (i) (R)-THP to (ii) Racemic-BTC is about 1:26 ng/mL to about 1:34 ng/ml after administration. In some aspects, the serum concentration ratio of (i) (R)-THP to (ii) Racemic-BTC is about 1:27 ng/mL to about 1:33 ng/mL after administration. In some aspects, the serum concentration ratio of (i) (R)-THP to (ii) Racemic-BTC is about 1:28 ng/mL to about 1:32 ng/mL after administration. In some aspects, the serum concentration ratio of (i) (R)-THP to (ii) Racemic-BTC is about 1:29 ng/ml to about 1:31 ng/mL after administration. In some aspects, the serum concentration ratio determined about 30 minutes to about 24 hours after the administration.

In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the serum concentration ratio of (i) (R)-THP to (ii) (S)-BTC is about 1:20 ng/ml to about 1:40 ng/mL after administration. In some aspects, the serum concentration ratio of (i) (R)-THP to (ii) (S)-BTC is about 1:21 ng/mL to about 1:39 ng/ml after administration. In some aspects, the serum concentration ratio of (i) (R)-THP to (ii) (S)-BTC is about 1:22 ng/mL to about 1:38 ng/ml after administration. In some aspects, the serum concentration ratio of (i) (R)-THP to (ii) (S)-BTC is about 1:23 ng/mL to about 1:37 ng/ml after administration. In some aspects, the serum concentration ratio of (i) (R)-THP to (ii) (S)-BTC is about 1:24 ng/ml to about 1:36 ng/mL after administration. In some aspects, the serum concentration ratio of (i) (R)-THP to (ii) (S)-BTC about 1:25 ng/mL to about 1:35 ng/ml after administration. In some aspects, the serum concentration ratio of (i) (R)-THP to (ii) (S)-BTC is about 1:26 ng/ml to about 1:34 ng/mL after administration. In some aspects, the serum concentration ratio of (i) (R)-THP to (ii) (S)-BTC is about 1:27 ng/mL to about 1:33 ng/mL after administration. In some aspects, the serum concentration ratio of (i) (R)-THP to (ii) (S)-BTC is about 1:28 ng/ml to about 1:32 ng/mL after administration. In some aspects, the serum concentration ratio of (i) (R)-THP to (ii) (S)-BTC is about 1:29 ng/mL to about 1:31 ng/ml after administration. In some aspects, the serum concentration ratio determined about 30 minutes to about 24 hours after the administration. In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the serum concentration ratio of (i) Racemic-THP to (ii) Racemic-BTC is about 1:20 ng/mL after administration. In some aspects, the serum concentration ratio of (i) Racemic-THP to (ii) Racemic-BTC is about 1:21 ng/mL after administration. In some aspects, the serum concentration ratio of (i) Racemic-THP to (ii) Racemic-BTC is about 1:22 ng/ml after administration. In some aspects, the serum concentration ratio of (i) Racemic-THP to (ii) Racemic-BTC is about 1:23 ng/ml after administration. In some aspects, the serum concentration ratio of (i) Racemic-THP to (ii) Racemic-BTC is about 1:24 ng/mL after administration. In some aspects, the serum concentration ratio of (i) Racemic-THP to (ii) Racemic-BTC is about 1:25 ng/mL after administration. In some aspects, the serum concentration ratio of (i) Racemic-THP to (ii) Racemic-BTC is about 1:26 ng/ml after administration. In some aspects, the serum concentration ratio of (i) Racemic-THP to (ii) Racemic-BTC is about 1:27 ng/mL after administration. In some aspects, the serum concentration ratio of (i) Racemic-THP to (ii) Racemic-BTC is about 1:28 ng/ml after administration. In some aspects, the serum concentration ratio of (i) Racemic-THP to (ii) Racemic-BTC is about 1:29 ng/mL after administration. In some aspects, the serum concentration ratio of (i) Racemic-THP to (ii) Racemic-BTC is about 1:30 ng/ml after administration. In some aspects, the serum concentration ratio of (i) Racemic-THP to (ii) Racemic-BTC is about 1:31 ng/mL after administration. In some aspects, the serum concentration ratio of (i) Racemic-THP to (ii) Racemic-BTC is about 1:32 ng/mL after administration. In some aspects, the serum concentration ratio of (i) Racemic-THP to (ii) Racemic-BTC is about 1:33 ng/mL after administration. In some aspects, the serum concentration ratio of (i) Racemic-THP to (ii) Racemic-BTC is about 1:34 ng/ml after administration. In some aspects, the serum concentration ratio of (i) Racemic-THP to (ii) Racemic-BTC is about 1:35 ng/ml after administration. In some aspects, the serum concentration ratio of (i) Racemic-THP to (ii) Racemic-BTC is about 1:36 ng/ml after administration. In some aspects, the serum concentration ratio of (i) Racemic-THP to (ii) Racemic-BTC is about 1:37 ng/mL after administration. In some aspects, the serum concentration ratio of (i) Racemic-THP to (ii) Racemic-BTC is about 1:38 ng/ml after administration. In some aspects, the serum concentration ratio of (i) Racemic-THP to (ii) Racemic-BTC is about 1:39 ng/mL after administration. In some aspects, the serum concentration ratio of (i) Racemic-THP to (ii) Racemic-BTC is about 1:40 ng/ml after administration. In some aspects, the serum concentration ratio determined about 30 minutes to about 24 hours after the administration. In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the serum concentration ratio of (i) (R)-THP to (ii) Racemic-BTC is about 1:20 ng/mL after administration. In some aspects, the serum concentration ratio of (i) (R)-THP to (ii) Racemic-BTC is about 1:21 ng/mL after administration. In some aspects, the serum concentration ratio of (i) (R)-THP to (ii) Racemic-BTC is about 1:22 ng/mL after administration. In some aspects, the serum concentration ratio of (i) (R)-THP to (ii) Racemic-BTC is about 1:23 ng/mL after administration. In some aspects, the serum concentration ratio of (i) (R)-THP to (ii) Racemic-BTC is about 1:24 ng/mL after administration. In some aspects, the serum concentration ratio of (i) (R)-THP to (ii) Racemic-BTC is about 1:25 ng/mL after administration. In some aspects, the serum concentration ratio of (i) (R)-THP to (ii) Racemic-BTC is about 1:26 ng/mL after administration. In some aspects, the serum concentration ratio of (i) (R)-THP to (ii) Racemic-BTC is about 1:27 ng/ml after administration. In some aspects, the serum concentration ratio of (i) (R)-THP to (ii) Racemic-BTC is about 1:28 ng/mL after administration. In some aspects, the serum concentration ratio of (i) (R)-THP to (ii) Racemic-BTC is about 1:29 ng/ml after administration. In some aspects, the serum concentration ratio of (i) (R)-THP to (ii) Racemic-BTC is about 1:30 ng/mL after administration. In some aspects, the serum concentration ratio of (i) (R)-THP to (ii) Racemic-BTC is about 1:31 ng/mL after administration. In some aspects, the serum concentration ratio of (i) (R)-THP to (ii) Racemic-BTC is about 1:32 ng/mL after administration. In some aspects, the serum concentration ratio of (i) (R)-THP to (ii) Racemic-BTC is about 1:33 ng/mL after administration. In some aspects, the serum concentration ratio of (i) (R)-THP to (ii) Racemic-BTC is about 1:34 ng/mL after administration. In some aspects, the serum concentration ratio of (i) (R)-THP to (ii) Racemic-BTC is about 1:35 ng/mL after administration. In some aspects, the serum concentration ratio of (i) (R)-THP to (ii) Racemic-BTC is about 1:36 ng/mL after administration. In some aspects, the serum concentration ratio of (i) (R)-THP to (ii) Racemic-BTC is about 1:37 ng/mL after administration. In some aspects, the serum concentration ratio of (i) (R)-THP to (ii) Racemic-BTC is about 1:38 ng/mL after administration. In some aspects, the serum concentration ratio of (i) (R)-THP to (ii) Racemic-BTC is about 1:39 ng/mL after administration. In some aspects, the serum concentration ratio of (i) (R)-THP to (ii) Racemic-BTC is about 1:40 ng/mL after administration. In some aspects, the serum concentration ratio determined about 30 minutes to about 24 hours after the administration. In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the serum concentration ratio of (i) (R)-THP to (ii) (S)-BTC is about 1:20 ng/mL after administration. In some aspects, the serum concentration ratio of (i) (R)-THP to (ii) (S)-BTC is about 1:21 ng/mL after administration. In some aspects, the serum concentration ratio of (i) (R)-THP to (ii) (S)-BTC is about 1:22 ng/mL after administration. In some aspects, the serum concentration ratio of (i) (R)-THP to (ii) (S)-BTC is about 1:23 ng/ml after administration. In some aspects, the serum concentration ratio of (i) (R)-THP to (ii) (S)-BTC is about 1:24 ng/mL after administration. In some aspects, the serum concentration ratio of (i) (R)-THP to (ii) (S)-BTC is about 1:25 ng/mL after administration. In some aspects, the serum concentration ratio of (i) (R)-THP to (ii) (S)-BTC is about 1:26 ng/mL after administration. In some aspects, the serum concentration ratio of (i) (R)-THP to (ii) (S)-BTC is about 1:27 ng/ml after administration. In some aspects, the serum concentration ratio of (i) (R)-THP to (ii) (S)-BTC is about 1:28 ng/mL after administration. In some aspects, the serum concentration ratio of (i) (R)-THP to (ii) (S)-BTC is about 1:29 ng/mL after administration. In some aspects, the serum concentration ratio of (i) (R)-THP to (ii) (S)-BTC is about 1:30 ng/mL after administration. In some aspects, the serum concentration ratio of (i) (R)-THP to (ii) (S)-BTC is about 1:31 ng/ml after administration. In some aspects, the serum concentration ratio of (i) (R)-THP to (ii) (S)-BTC is about 1:32 ng/mL after administration. In some aspects, the serum concentration ratio of (i) (R)-THP to (ii) (S)-BTC is about 1:33 ng/mL after administration. In some aspects, the serum concentration ratio of (i) (R)-THP to (ii) (S)-BTC is about 1:34 ng/mL after administration. In some aspects, the serum concentration ratio of (i) (R)-THP to (ii) (S)-BTC is about 1:35 ng/ml after administration. In some aspects, the serum concentration ratio of (i) (R)-THP to (ii) (S)-BTC is about 1:36 ng/mL after administration. In some aspects, the serum concentration ratio of (i) (R)-THP to (ii) (S)-BTC is about 1:37 ng/mL after administration. In some aspects, the serum concentration ratio of (i) (R)-THP to (ii) (S)-BTC is about 1:38 ng/mL after administration. In some aspects, the serum concentration ratio of (i) (R)-THP to (ii) (S)-BTC is about 1:39 ng/ml after administration. In some aspects, the serum concentration ratio of (i) (R)-THP to (ii) (S)-BTC is about 1:40 ng/mL after administration. In some aspects, the serum concentration ratio determined about 30 minutes to about 24 hours after the administration. In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:20 ng/mL to about 1:40 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:21 ng/ml to about 1:39 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:22 ng/ml to about 1:38 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:23 ng/mL to about 1:37 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:24 ng/mL to about 1:36 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:25 ng/mL to about 1:35 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:26 ng/ml to about 1:34 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:27 ng/mL to about 1:33 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:28 ng/ml to about 1:32 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:29 ng/ml to about 1:31 ng/mL after administration. In some aspects, the muscarinic acetylcholine receptor inhibitor is selected from scopolamine, benztropine, and ethopropazine or a pharmaceutically acceptable salt thereof. In some aspects, the serum concentration ratio determined about 30 minutes to about 24 hours after the administration. In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:20 ng/mL to about 1:40 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:21 ng/mL to about 1:39 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:22 ng/mL to about 1:38 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:23 ng/mL to about 1:37 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:24 ng/mL to about 1:36 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:25 ng/ml to about 1:35 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:26 ng/mL to about 1:34 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:27 ng/mL to about 1:33 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:28 ng/mL to about 1:32 ng/ml after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:29 ng/mL to about 1:31 ng/mL after administration. In some aspects, the muscarinic acetylcholine receptor inhibitor is selected from scopolamine, benztropine, and ethopropazine or a pharmaceutically acceptable salt thereof. In some aspects, the serum concentration ratio determined about 30 minutes to about 24 hours after the administration. In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the serum concentration ratio of (i) muscarinic acetylcholine receptor inhibitor to (ii) a second therapeutic agent selected from a muscarinic acetylcholine receptor activator, a procholinergic agent, and an acetylcholine esterase inhibitor is about 1:20 ng/mL to about 1:40 ng/ml after administration. In some aspects, the serum concentration ratio of (i) Muscarinic acetylcholine receptor inhibitor to (ii) a second therapeutic agent selected from a muscarinic acetylcholine receptor activator, a procholinergic agent, and an acetylcholine esterase inhibitor is about 1:21 ng/ml to about 1:39 ng/ml after administration. In some aspects, the serum concentration ratio of (i) muscarinic acetylcholine receptor inhibitor to (ii) a second therapeutic agent selected from a muscarinic acetylcholine receptor activator, a procholinergic agent, and an acetylcholine esterase inhibitor is about 1:22 ng/ml to about 1:38 ng/ml after administration. In some aspects, the serum concentration ratio of (i) muscarinic acetylcholine receptor inhibitor to (ii) a second therapeutic agent selected from a muscarinic acetylcholine receptor activator, a procholinergic agent, and an acetylcholine esterase inhibitor is about 1:23 ng/mL to about 1:37 ng/mL after administration. In some aspects, the serum concentration ratio of (i) muscarinic acetylcholine receptor inhibitor to (ii) a second therapeutic agent selected from a muscarinic acetylcholine receptor activator, a procholinergic agent, and an acetylcholine esterase inhibitor is about 1:24 ng/mL to about 1:36 ng/ml after administration. In some aspects, the serum concentration ratio of (i) muscarinic acetylcholine receptor inhibitor to (ii) a second therapeutic agent selected from a muscarinic acetylcholine receptor activator, a procholinergic agent, and an acetylcholine esterase inhibitor is about 1:25 ng/mL to about 1:35 ng/ml after administration. In some aspects, the serum concentration ratio of (i) muscarinic acetylcholine receptor inhibitor to (ii) a second therapeutic agent selected from a muscarinic acetylcholine receptor activator, a procholinergic agent, and an acetylcholine esterase inhibitor is about 1:26 ng/ml to about 1:34 ng/mL after administration. In some aspects, the serum concentration ratio of (i) muscarinic acetylcholine receptor inhibitor to (ii) a second therapeutic agent selected from a muscarinic acetylcholine receptor activator, a procholinergic agent, and an acetylcholine esterase inhibitor is about 1:27 ng/mL to about 1:33 ng/mL after administration. In some aspects, the serum concentration ratio of (i) muscarinic acetylcholine receptor inhibitor to (ii) a second therapeutic agent selected from a muscarinic acetylcholine receptor activator, a procholinergic agent, and an acetylcholine esterase inhibitor is about 1:28 ng/mL to about 1:32 ng/mL after administration. In some aspects, the serum concentration ratio of (i) muscarinic acetylcholine receptor inhibitor to (ii) a second therapeutic agent selected from a muscarinic acetylcholine receptor activator, a procholinergic agent, and an acetylcholine esterase inhibitor is about 1:29 ng/ml to about 1:31 ng/mL after administration. In some aspects, the muscarinic acetylcholine receptor inhibitor is selected from scopolamine, benztropine, and ethopropazine or a pharmaceutically acceptable salt thereof. In some aspects, the serum concentration ratio determined about 30 minutes to about 24 hours after the administration. In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:20 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:21 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:22 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:23 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:24 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:25 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:26 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:27 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:28 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:29 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:30 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:31 ng/mL after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:32 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:33 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:34 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:35 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:36 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:37 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:38 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:39 ng/ml after administration. In some aspects, the serum concentration ratio of (i) Racemic-THP to (ii) a second therapeutic agent selected from a muscarinic acetylcholine receptor activator, a procholinergic agent, and an acetylcholine esterase inhibitor is about 1:40 ng/ml after administration. In some aspects, the muscarinic acetylcholine receptor inhibitor is selected from scopolamine, benztropine, and ethopropazine or a pharmaceutically acceptable salt thereof. In some aspects, the serum concentration ratio determined about 30 minutes to about 24 hours after the administration. In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:20 ng/ml after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:21 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:22 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:23 ng/ml after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:24 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:25 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:26 ng/ml after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:27 ng/ml after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:28 ng/ml after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:29 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:30 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:31 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:32 ng/ml after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:33 ng/ml after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:34 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:35 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:36 ng/ml after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:37 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:38 ng/ml after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:39 ng/mL after administration. In some aspects, the serum concentration ratio of (i) (R)-THP to (ii) a second therapeutic agent selected from a muscarinic acetylcholine receptor activator, a procholinergic agent, and an acetylcholine esterase inhibitor is about 1:40 ng/mL after administration. In some aspects, the muscarinic acetylcholine receptor inhibitor is selected from scopolamine, benztropine, and ethopropazine or a pharmaceutically acceptable salt thereof. In some aspects, the serum concentration ratio determined about 30 minutes to about 24 hours after the administration. In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:20 ng/ml after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:21 ng/ml after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:22 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:23 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:24 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:25 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:26 ng/ml after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:27 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:28 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:29 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:30 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:31 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:32 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:33 ng/ml after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:34 ng/mL after administration. In some aspects, the serum concentration ratio of (i) a muscarinic acetylcholine receptor inhibitor to (ii) a second therapeutic agent selected from a muscarinic acetylcholine receptor activator, a cholinergic agent, and an acetylcholine esterase inhibitor is about 1:35 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:36 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:37 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:38 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:39 ng/mL after administration. In some aspects, the serum concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:40 ng/ml after administration. In some aspects, the muscarinic acetylcholine receptor inhibitor is selected from scopolamine, benztropine, and ethopropazine or a pharmaceutically acceptable salt thereof. In some aspects, the serum concentration ratio determined about 30 minutes to about 24 hours after the administration. In some aspects, the serum concentration ratio determined about 1 hour to about 22 hours after the administration. In some aspects, the serum concentration ratio determined about 2 hours to about 20 hours after the administration. In some aspects, the serum concentration ratio determined about 3 hours to about 17 hours after the administration. In some aspects, the serum concentration ratio determined about 4 hours to about 15 hours after the administration. In some aspects, the serum concentration ratio determined about 5 hours to about 12 hours after the administration. In some aspects, the serum concentration ratio determined about 6 hours to about 10 hours after the administration. In some aspects, the serum concentration ratio determined about 7 hours to about 9 hours after the administration. In some aspects, the serum concentration ratio determined about 30 minutes after the administration. In some aspects, the serum concentration ratio determined about 1 hour after the administration. In some aspects, the serum concentration ratio determined about 2 hours after the administration. In some aspects, the serum concentration ratio determined about 3 hours after the administration. In some aspects, the serum concentration ratio determined about 4 hours after the administration. In some aspects, the serum concentration ratio determined about 5 hours after the administration. In some aspects, the serum concentration ratio determined about 6 hours after the administration. In some aspects, the serum concentration ratio determined about 7 hours after the administration. In some aspects, the serum concentration ratio determined about 8 hours after the administration. In some aspects, the serum concentration ratio determined about 9 hours after the administration. In some aspects, the serum concentration ratio determined about 10 hours after the administration. In some aspects, the serum concentration ratio determined about 11 hours after the administration. In some aspects, the serum concentration ratio determined about 12 hours after the administration. In some aspects, the serum concentration ratio determined about 13 hours after the administration. In some aspects, the serum concentration ratio determined about 14 hours after the administration. In some aspects, the serum concentration ratio determined about 15 hours after the administration. In some aspects, the serum concentration ratio determined about 16 hours after the administration. In some aspects, the serum concentration ratio determined about 17 hours after the administration. In some aspects, the serum concentration ratio determined about 18 hours after the administration. In some aspects, the serum concentration ratio determined about 19 hours after the administration. In some aspects, the serum concentration ratio determined about 20 hours after the administration. In some aspects, the serum concentration ratio determined about 21 hours after the administration. In some aspects, the serum concentration ratio determined about 22 hours after the administration. In some aspects, the serum concentration ratio determined about 23 hours after the administration. In some aspects, the serum concentration ratio determined about 24 hours after the administration.

In some aspects, the rate of rise of serum concentration of the muscarinic acetylcholine receptor inhibitor is less than 20 ng/ml/hr. In some aspects, the rate of rise of serum concentration of the muscarinic acetylcholine receptor inhibitor is less than 19 ng/mL/hr. In some aspects, the rate of rise of serum concentration of the muscarinic acetylcholine receptor inhibitor is less than 18 ng/ml/hr. In some aspects, the rate of rise of serum concentration of the muscarinic acetylcholine receptor inhibitor is less than 17 ng/ml/hr. In some aspects, the rate of rise of serum concentration of the muscarinic acetylcholine receptor inhibitor is less than 16 ng/ml/hr. In some aspects, the rate of rise of serum concentration of the muscarinic acetylcholine receptor inhibitor is less than 15 ng/ml/hr. In some aspects, the rate of rise of serum concentration of the muscarinic acetylcholine receptor inhibitor is less than 14 ng/ml/hr. In some aspects, the rate of rise of serum concentration of the muscarinic acetylcholine receptor inhibitor is less than 13 ng/ml/hr. In some aspects, the rate of rise of serum concentration of the muscarinic acetylcholine receptor inhibitor is less than 12 ng/mL/hr. In some aspects, the rate of rise of serum concentration of the muscarinic acetylcholine receptor inhibitor is less than 10 ng/ml/hr. In some aspects, the rate of rise of serum concentration of the muscarinic acetylcholine receptor inhibitor is less than 9 ng/ml/hr. In some aspects, the rate of rise of serum concentration of the muscarinic acetylcholine receptor inhibitor is less than 8 ng/ml/hr. In some aspects, the rate of rise of serum concentration of the muscarinic acetylcholine receptor inhibitor is less than 7 ng/ml/hr. In some aspects, the rate of rise of serum concentration of the muscarinic acetylcholine receptor inhibitor is less than 6 ng/ml/hr. In some aspects, the rate of rise of serum concentration of the muscarinic acetylcholine receptor inhibitor is less than 5 ng/ml/hr. In some aspects, the rate of rise of serum concentration of the muscarinic acetylcholine receptor inhibitor is less than 4 ng/ml/hr. In some aspects, the rate of rise of serum concentration of the muscarinic acetylcholine receptor inhibitor is less than 3 ng/ml/hr. In some aspects, the rate of rise of serum concentration of the muscarinic acetylcholine receptor inhibitor is less than 2 ng/ml/hr. In some aspects, the rate of rise of serum concentration of the muscarinic acetylcholine receptor inhibitor is less than 1 ng/ml/hr.

In some aspects, the rate of rise of serum concentration of the muscarinic acetylcholine receptor inhibitor is less than about 1 ng/ml/hr to about 20 ng/ml/hr. In some aspects, the rate of rise of serum concentration of the muscarinic acetylcholine receptor inhibitor is less than about 2 ng/mL/hr to about 19 ng/mL/hr. In some aspects, the rate of rise of serum concentration of the muscarinic acetylcholine receptor inhibitor is less than about 3 ng/mL/hr to 18 ng/ml/hr. In some aspects, the rate of rise of serum concentration of the muscarinic acetylcholine receptor inhibitor is less than about about 4 ng/ml/hr to about 17 ng/ml/hr. In some aspects, the rate of rise of serum concentration of the muscarinic acetylcholine receptor inhibitor is less than about 5 ng/ml/hr to about 16 ng/ml/hr. In some aspects, the rate of rise of serum concentration of the muscarinic acetylcholine receptor inhibitor is about 6 ng/ml/hr to about 15 ng/mL/hr. In some aspects, the rate of rise of serum concentration of the muscarinic acetylcholine receptor inhibitor is about 7 ng/ml/hr to about 14 ng/ml/hr. In some aspects, the rate of rise of serum concentration of the muscarinic acetylcholine receptor inhibitor is about 8 ng/ml/hr to about 13 ng/ml/hr. In some aspects, the rate of rise of serum concentration of the muscarinic acetylcholine receptor inhibitor is about 9 ng/ml/hr to about 12 ng/ml/hr. In some aspects, the rate of rise of serum concentration of the muscarinic acetylcholine receptor inhibitor is about 10 ng/ml/hr to about 11 ng/ml/hr. In some aspects, the rate of rise of serum concentration of the muscarinic acetylcholine receptor inhibitor is about 1 ng/mL/hr to about 15 ng/ml/hr. In some aspects, the rate of rise of serum concentration of the muscarinic acetylcholine receptor inhibitor is about 2 ng/ml/hr to about 14 ng/ml/hr. In some aspects, the rate of rise of serum concentration of the muscarinic acetylcholine receptor inhibitor is about 3 ng/ml/hr to about 13 ng/ml/hr. In some aspects, the rate of rise of serum concentration of the muscarinic acetylcholine receptor inhibitor is about 4 ng/ml/hr to about 12 ng/ml/hr. In some aspects, the rate of rise of serum concentration of the muscarinic acetylcholine receptor inhibitor is about 5 ng/ml/hr to about 11 ng/mL/hr. In some aspects, the rate of rise of serum concentration of the muscarinic acetylcholine receptor inhibitor is about 6 ng/ml/hr to about 10 ng/ml/hr. In some aspects, the rate of rise of serum concentration of the muscarinic acetylcholine receptor inhibitor is about 7 ng/ml/hr to about 9 ng/ml/hr.

In some aspects, the C(average) serum concentration ratio of the muscarinic acetylcholine receptor inhibitor to the muscarinic receptor activator is about 1:5 to about 1:50 over the 24-hour period after administration. In some aspects, the C(average) serum concentration ratio of the muscarinic acetylcholine receptor inhibitor to the muscarinic receptor activator is about 1:6 to about 1:49 over the 24-hour period after administration. In some aspects, the C(average) serum concentration ratio of the muscarinic acetylcholine receptor inhibitor to the muscarinic receptor activator is about 1:7 to about 1:48 over the 24-hour period after administration. In some aspects, the C(average) serum concentration ratio of the muscarinic acetylcholine receptor inhibitor to the muscarinic receptor activator is about 1:8 to about 1:47 over the 24-hour period after administration. In some aspects, the C(average) serum concentration ratio of the muscarinic acetylcholine receptor inhibitor to the muscarinic receptor activator is about 1:9 to about 1:46 over the 24-hour period after administration. In some aspects, the C(average) serum concentration ratio of the muscarinic acetylcholine receptor inhibitor to the muscarinic receptor activator is about 1:10 to about 1:45 over the 24-hour period after administration. In some aspects, the C(average) serum concentration ratio of the muscarinic acetylcholine receptor inhibitor to the muscarinic receptor activator is about 1:11 to about 1:44 over the 24-hour period after administration. In some aspects, the C(average) serum concentration ratio of the muscarinic acetylcholine receptor inhibitor to the muscarinic receptor activator is about 1:12 to about 1:43 over the 24-hour period after administration. In some aspects, the C(average) serum concentration ratio of the muscarinic acetylcholine receptor inhibitor to the muscarinic receptor activator is about 1:13 to about 1:42 over the 24-hour period after administration. In some aspects, the C(average) serum concentration ratio of the muscarinic acetylcholine receptor inhibitor to the muscarinic receptor activator is about 1:14 to about 1:41 over the 24-hour period after administration. In some aspects, the C(average) serum concentration ratio of the muscarinic acetylcholine receptor inhibitor to the muscarinic receptor activator is about 1:15 to about 1:40 over the 24-hour period after administration. In some aspects, the C(average) serum concentration ratio of the muscarinic acetylcholine receptor inhibitor to the muscarinic receptor activator is about 1:16 to about 1:39 over the 24-hour period after administration. In some aspects, the C(average) serum concentration ratio of the muscarinic acetylcholine receptor inhibitor to the muscarinic receptor activator is about 1:17 to about 1:38 over the 24-hour period after administration. In some aspects, the C(average) serum concentration ratio of the muscarinic acetylcholine receptor inhibitor to the muscarinic receptor activator is about 1:18 to about 1:37 over the 24-hour period after administration. In some aspects, the C(average) serum concentration ratio of the muscarinic acetylcholine receptor inhibitor to the muscarinic receptor activator is about 1:19 to about 1:36 over the 24-hour period after administration. In some aspects, the C(average) serum concentration ratio of the muscarinic acetylcholine receptor inhibitor to the muscarinic receptor activator is about 1:20 to about 1:35 over the 24-hour period after administration. In some aspects, the C(average) serum concentration ratio of the muscarinic acetylcholine receptor inhibitor to the muscarinic receptor activator is about 1:21 to about 1:34 over the 24-hour period after administration. In some aspects, the C(average) serum concentration ratio of the muscarinic acetylcholine receptor inhibitor to the muscarinic receptor activator is about 1:22 to about 1:33 over the 24-hour period after administration. In some aspects, the C(average) serum concentration ratio of the muscarinic acetylcholine receptor inhibitor to the muscarinic receptor activator is about 1:23 to about 1:32 over the 24-hour period after administration. In some aspects, the C(average) serum concentration ratio of the muscarinic acetylcholine receptor inhibitor to the muscarinic receptor activator is about 1:24 to about 1:31 over the 24-hour period after administration. In some aspects, the C(average) serum concentration ratio of the muscarinic acetylcholine receptor inhibitor to the muscarinic receptor activator is about 1:25 to about 1:30 over the 24-hour period after administration. In some aspects, the C(average) serum concentration ratio of the muscarinic acetylcholine receptor inhibitor to the muscarinic receptor activator is about 1:26 to about 1:29 over the 24-hour period after administration. In some aspects, the C(average) serum concentration ratio of the muscarinic acetylcholine receptor inhibitor to the muscarinic receptor activator is about 1:27 to about 1:28 over the 24-hour period after administration.

In some aspects, (i) the area under the curve (AUC) serum ratio of the muscarinic acetylcholine receptor inhibitor to the muscarinic receptor activator is about 1:1 to about 1:42 and (ii) the C(max) serum concentration ratio of the muscarinic acetylcholine receptor inhibitor to the muscarinic receptor activator is about 1:5 to about 1:50 over the 24-hour period after administration. In some aspects, (i) the AUC serum ratio of the muscarinic acetylcholine receptor inhibitor to the muscarinic receptor activator is about 1:2 to about 1:41 and (ii) the C(max) serum concentration ratio of the muscarinic acetylcholine receptor inhibitor to the muscarinic receptor activator is about 1:6 to about 1:4 over the 24-hour period after administration. In some aspects, (i) the AUC serum ratio of the muscarinic acetylcholine receptor inhibitor to the muscarinic receptor activator is about 1:3 to about 1:40 and (ii) the C(max) serum concentration ratio of the muscarinic acetylcholine receptor inhibitor to the muscarinic receptor activator is about 1:7 to about 1:48 over the 24-hour period after administration. In some aspects, (i) the AUC serum ratio of the muscarinic acetylcholine receptor inhibitor to the muscarinic receptor activator is about 1:4 to about 1:39 and (ii) the C(max) serum concentration ratio of the muscarinic acetylcholine receptor inhibitor to the muscarinic receptor activator is about 1:8 to about 1:47 over the 24-hour period after administration. In some aspects, (i) the AUC serum ratio of the muscarinic acetylcholine receptor inhibitor to the muscarinic receptor activator is about 1:5 to about 1:38 and (ii) the C(max) serum concentration ratio of the muscarinic acetylcholine receptor inhibitor to the muscarinic receptor activator is about 1:9 to about 1:46 over the 24-hour period after administration. In some aspects, (i) the AUC serum ratio of the muscarinic acetylcholine receptor inhibitor to the muscarinic receptor activator is about 1:6 to about 1:37 and (ii) the C(max) serum concentration ratio of the muscarinic acetylcholine receptor inhibitor to the muscarinic receptor activator is about 1:10 to about 1:45 over the 24-hour period after administration. In some aspects, (i) the AUC serum ratio of the muscarinic acetylcholine receptor inhibitor to the muscarinic receptor activator is about 1:7 to about 1:36 and (ii) the C(max) serum concentration ratio of the muscarinic acetylcholine receptor inhibitor to the muscarinic receptor activator is about 1:11 to about 1:44 over the 24-hour period after administration. In some aspects, (i) the AUC serum ratio of the muscarinic acetylcholine receptor inhibitor to the muscarinic receptor activator is about 1:8 to about 1:35 and (ii) the C(max) serum concentration ratio of the muscarinic acetylcholine receptor inhibitor to the muscarinic receptor activator is about 1:12 to about 1:43 over the 24-hour period after administration. In some aspects, (i) the AUC serum ratio of the muscarinic acetylcholine receptor inhibitor to the muscarinic receptor activator is about 1:9 to about 1:33 and (ii) the C(max) serum concentration ratio of the muscarinic acetylcholine receptor inhibitor to the muscarinic receptor activator is about 1:13 to about 1:42 over the 24-hour period after administration. In some aspects, (i) the AUC serum ratio of the muscarinic acetylcholine receptor inhibitor to the muscarinic receptor activator is about 1:10 to about 1:32 and (ii) the C(max) serum concentration ratio of the muscarinic acetylcholine receptor inhibitor to the muscarinic receptor activator is about 1:14 to about 1:41 over the 24-hour period after administration. In some aspects, (i) the AUC serum ratio of the muscarinic acetylcholine receptor inhibitor to the muscarinic receptor activator is about 1:11 to about 1:31 and (ii) the C(max) serum concentration ratio of the muscarinic acetylcholine receptor inhibitor to the muscarinic receptor activator is about 1:15 to about 1:40 over the 24-hour period after administration. In some aspects, (i) the AUC serum ratio of the muscarinic acetylcholine receptor inhibitor to the muscarinic receptor activator is about 1:12 to about 1:29 and (ii) the C(max) serum concentration ratio of the muscarinic acetylcholine receptor inhibitor to the muscarinic receptor activator is about 1:16 to about 1:39 over the 24-hour period after administration. In some aspects, (i) the AUC serum ratio of the muscarinic acetylcholine receptor inhibitor to the muscarinic receptor activator is about 1:13 to about 1:28 and (ii) the C(max) serum concentration ratio of the muscarinic acetylcholine receptor inhibitor to the muscarinic receptor activator is about 1:17 to about 1:38 over the 24-hour period after administration. In some aspects, (i) the AUC serum ratio of the muscarinic acetylcholine receptor inhibitor to the muscarinic receptor activator is about 1:14 to about 1:27 and (ii) the C(max) serum concentration ratio of the muscarinic acetylcholine receptor inhibitor to the muscarinic receptor activator is about 1:18 to about 1:37 over the 24-hour period after administration. In some aspects, (i) the AUC serum ratio of the muscarinic acetylcholine receptor inhibitor to the muscarinic receptor activator is about 1:15 to about 1:26 and (ii) the C(max) serum concentration ratio of the muscarinic acetylcholine receptor inhibitor to the muscarinic receptor activator is about 1:19 to about 1:36 over the 24-hour period after administration. In some aspects, (i) the AUC serum ratio of the muscarinic acetylcholine receptor inhibitor to the muscarinic receptor activator is about 1:16 to about 1:25 and (ii) the C(max) serum concentration ratio of the muscarinic acetylcholine receptor inhibitor to the muscarinic receptor activator is about 1:20 to about 1:35 over the 24-hour period after administration. In some aspects, (i) the AUC serum ratio of the muscarinic acetylcholine receptor inhibitor to the muscarinic receptor activator is about 1:17 to about 1:24 and (ii) the C(max) serum concentration ratio of the muscarinic acetylcholine receptor inhibitor to the muscarinic receptor activator is about 1:21 to about 1:34 over the 24-hour period after administration. In some aspects, (i) the AUC serum ratio of the muscarinic acetylcholine receptor inhibitor to the muscarinic receptor activator is about 1:18 to about 1:23 and (ii) the C(max) serum concentration ratio of the muscarinic acetylcholine receptor inhibitor to the muscarinic receptor activator is about 1:22 to about 1:33 over the 24-hour period after administration. In some aspects, (i) the AUC serum ratio of the muscarinic acetylcholine receptor inhibitor to the muscarinic receptor activator is about 1:19 to about 1:22 and (ii) the C(max) serum concentration ratio of the muscarinic acetylcholine receptor inhibitor to the muscarinic receptor activator is about 1:23 to about 1:32 over the 24-hour period after administration. In some aspects, (i) the AUC serum ratio of the muscarinic acetylcholine receptor inhibitor to the muscarinic receptor activator is about 1:20 to about 1:21 and (ii) the C(max) serum concentration ratio of the muscarinic acetylcholine receptor inhibitor to the muscarinic receptor activator is about 1:24 to about 1:31 over the 24-hour period after administration. In some aspects, (i) the AUC serum ratio of the muscarinic acetylcholine receptor inhibitor to the muscarinic receptor activator is about 1:15 to about 1:21 and (ii) the C(max) serum concentration ratio of the muscarinic acetylcholine receptor inhibitor to the muscarinic receptor activator is about 1:25 to about 1:30 over the 24-hour period after administration. In some aspects, (i) the AUC serum ratio of the muscarinic acetylcholine receptor inhibitor to the muscarinic receptor activator is about 1:16 to about 1:20 and (ii) the C(max) serum concentration ratio of the muscarinic acetylcholine receptor inhibitor to the muscarinic receptor activator is about 1:26 to about 1:29 over the 24-hour period after administration. In some aspects, (i) the AUC serum ratio of the muscarinic acetylcholine receptor inhibitor to the muscarinic receptor activator is about 1:17 to about 1:18 and (ii) the C(max) serum concentration ratio of the muscarinic acetylcholine receptor inhibitor to the muscarinic receptor activator is about 1:27 to about 1:28 over the 24-hour period after administration. In some aspects, (i) the AUC serum ratio of the muscarinic acetylcholine receptor inhibitor to the muscarinic receptor activator is about 1:16 to about 1:20 and (ii) the C(max) serum concentration ratio of the muscarinic acetylcholine receptor inhibitor to the muscarinic receptor activator is about 1:8 to about 1:11 over the 24-hour period after administration. In some aspects, (i) the AUC serum ratio of the muscarinic acetylcholine receptor inhibitor to the muscarinic receptor activator is about 1:17 to about 1:18 and (ii) the C(max) serum concentration ratio of the muscarinic acetylcholine receptor inhibitor to the muscarinic receptor activator is about 1:9 to about 1:10 over the 24-hour period after administration.

In some aspects, the C(max) serum ratio of the muscarinic acetylcholine receptor inhibitor to the muscarinic receptor activator is about 1:1 to about 1:20 over the 24-hour period after administration. In some aspects, the C(max) serum ratio of the muscarinic acetylcholine receptor inhibitor to the muscarinic receptor activator is about 1:2 to about 1:19 over the 24-hour period after administration. In some aspects, the C(max) serum ratio of the muscarinic acetylcholine receptor inhibitor to the muscarinic receptor activator is about 1:3 to about 1:18 over the 24-hour period after administration. In some aspects, the C(max) serum ratio of the muscarinic acetylcholine receptor inhibitor to the muscarinic receptor activator is about 1:4 to about 1:17 over the 24-hour period after administration. In some aspects, the C(max) serum ratio of the muscarinic acetylcholine receptor inhibitor to the muscarinic receptor activator is about 1:5 to about 1:16 over the 24-hour period after administration. In some aspects, the C(max) serum ratio of the muscarinic acetylcholine receptor inhibitor to the muscarinic receptor activator is about 1:6 to about 1:15 over the 24-hour period after administration. In some aspects, the C(max) serum ratio of the muscarinic acetylcholine receptor inhibitor to the muscarinic receptor activator is about 1:7 to about 1:14 over the 24-hour period after administration. In some aspects, the C(max) serum ratio of the muscarinic acetylcholine receptor inhibitor to the muscarinic receptor activator is about 1:8 to about 1:13 over the 24-hour period after administration. In some aspects, the C(max) serum ratio of the muscarinic acetylcholine receptor inhibitor to the muscarinic receptor activator is about 1:9 to about 1:12 over the 24-hour period after administration. In some aspects, the C(max) serum ratio of the muscarinic acetylcholine receptor inhibitor to the muscarinic receptor activator is about 1:10 to about 1:11 over the 24-hour period after administration. In some aspects, the C(max) serum ratio of the muscarinic acetylcholine receptor inhibitor to the muscarinic receptor activator is about 1:9 to about 1:11 over the 24-hour period after administration.

In some aspects, the area under the curve (AUC) serum ratio of the muscarinic acetylcholine receptor inhibitor to the muscarinic receptor activator is about 1:1 to about 1:38 over the 24-hour period after administration. In some aspects, the area under the curve (AUC) serum ratio of the muscarinic acetylcholine receptor inhibitor to the muscarinic receptor activator is about 1:2 to about 1:37 over the 24-hour period after administration. In some aspects, the area under the curve (AUC) serum ratio of the muscarinic acetylcholine receptor inhibitor to the muscarinic receptor activator is about 1:3 to about 1:36 over the 24-hour period after administration. In some aspects, the area under the curve (AUC) serum ratio of the muscarinic acetylcholine receptor inhibitor to the muscarinic receptor activator is about 1:4 to about 1:35 over the 24-hour period after administration. In some aspects, the area under the curve (AUC) serum ratio of the muscarinic acetylcholine receptor inhibitor to the muscarinic receptor activator is about 1:5 to about 1:34 over the 24-hour period after administration. In some aspects, the area under the curve (AUC) serum ratio of the muscarinic acetylcholine receptor inhibitor to the muscarinic receptor activator is about 1:6 to about 1:33 over the 24-hour period after administration. In some aspects, the area under the curve (AUC) serum ratio of the muscarinic acetylcholine receptor inhibitor to the muscarinic receptor activator is about 1:7 to about 1:32 over the 24-hour period after administration. In some aspects, the area under the curve (AUC) serum ratio of the muscarinic acetylcholine receptor inhibitor to the muscarinic receptor activator is about 1:8 to about 1:31 over the 24-hour period after administration. In some aspects, the area under the curve (AUC) serum ratio of the muscarinic acetylcholine receptor inhibitor to the muscarinic receptor activator is about 1:9 to about 1:30 over the 24-hour period after administration. In some aspects, the area under the curve (AUC) serum ratio of the muscarinic acetylcholine receptor inhibitor to the muscarinic receptor activator is about 1:10 to about 1:29 over the 24-hour period after administration. In some aspects, the area under the curve (AUC) serum ratio of the muscarinic acetylcholine receptor inhibitor to the muscarinic receptor activator is about 1:11 to about 1:28 over the 24-hour period after administration. In some aspects, the area under the curve (AUC) serum ratio of the muscarinic acetylcholine receptor inhibitor to the muscarinic receptor activator is about 1:12 to about 1:27 over the 24-hour period after administration. In some aspects, the area under the curve (AUC) serum ratio of the muscarinic acetylcholine receptor inhibitor to the muscarinic receptor activator is about 1:13 to about 1:26 over the 24-hour period after administration. In some aspects, the area under the curve (AUC) serum ratio of the muscarinic acetylcholine receptor inhibitor to the muscarinic receptor activator is about 1:14 to about 1:25 over the 24-hour period after administration. In some aspects, the area under the curve (AUC) serum ratio of the muscarinic acetylcholine receptor inhibitor to the muscarinic receptor activator is about 1:15 to about 1:24 over the 24-hour period after administration. In some aspects, the area under the curve (AUC) serum ratio of the muscarinic acetylcholine receptor inhibitor to the muscarinic receptor activator is about 1:16 to about 1:23 over the 24-hour period after administration. In some aspects, the area under the curve (AUC) serum ratio of the muscarinic acetylcholine receptor inhibitor to the muscarinic receptor activator is about 1:17 to about 1:22 over the 24-hour period after administration. In some aspects, the area under the curve (AUC) serum ratio of the muscarinic acetylcholine receptor inhibitor to the muscarinic receptor activator is about 1:18 to about 1:21 over the 24-hour period after administration. In some aspects, the area under the curve (AUC) serum ratio of the muscarinic acetylcholine receptor inhibitor to the muscarinic receptor activator is about 1:14 to about 1:22 over the 24-hour period after administration. In some aspects, the area under the curve (AUC) serum ratio of the muscarinic acetylcholine receptor inhibitor to the muscarinic receptor activator is about 1:15 to about 1:21 over the 24-hour period after administration. In some aspects, the area under the curve (AUC) serum ratio of the muscarinic acetylcholine receptor inhibitor to the muscarinic receptor activator is about 1:16 to about 1:20 over the 24-hour period after administration. In some aspects, the area under the curve (AUC) serum ratio of the muscarinic acetylcholine receptor inhibitor to the muscarinic receptor activator is about 1:17 to about 1:19 over the 24-hour period after administration. In some aspects, the area under the curve (AUC) serum ratio of the muscarinic acetylcholine receptor inhibitor to the muscarinic receptor activator is about 1:17 to about 1:20 over the 24-hour period after administration.

In some aspects, the AUC serum ratio of the muscarinic acetylcholine receptor inhibitor to the muscarinic receptor activator is about 1:1 over the 24-hour period after administration. In some aspects, the AUC serum ratio of the muscarinic acetylcholine receptor inhibitor to the muscarinic receptor activator is about 1:2 over the 24-hour period after administration. In some aspects, the AUC serum ratio of the muscarinic acetylcholine receptor inhibitor to the muscarinic receptor activator is about 1:3 over the 24-hour period after administration. In some aspects, the AUC serum ratio of the muscarinic acetylcholine receptor inhibitor to the muscarinic receptor activator is about 1:4 over the 24-hour period after administration. In some aspects, the AUC serum ratio of the muscarinic acetylcholine receptor inhibitor to the muscarinic receptor activator is about 1:5 over the 24-hour period after administration. In some aspects, the AUC serum ratio of the muscarinic acetylcholine receptor inhibitor to the muscarinic receptor activator is about 1:6 over the 24-hour period after administration. In some aspects, the AUC serum ratio of the muscarinic acetylcholine receptor inhibitor to the muscarinic receptor activator is about 1:7 over the 24-hour period after administration. In some aspects, the AUC serum ratio of the muscarinic acetylcholine receptor inhibitor to the muscarinic receptor activator is about 1:8 over the 24-hour period after administration. In some aspects, the AUC serum ratio of the muscarinic acetylcholine receptor inhibitor to the muscarinic receptor activator is about 1:9 over the 24-hour period after administration. In some aspects, the AUC serum ratio of the muscarinic acetylcholine receptor inhibitor to the muscarinic receptor activator is about 1:10 over the 24-hour period after administration. In some aspects, the AUC serum ratio of the muscarinic acetylcholine receptor inhibitor to the muscarinic receptor activator is about 1:11 over the 24-hour period after administration. In some aspects, the AUC serum ratio of the muscarinic acetylcholine receptor inhibitor to the muscarinic receptor activator is about 1:12 over the 24-hour period after administration. In some aspects, the AUC serum ratio of the muscarinic acetylcholine receptor inhibitor to the muscarinic receptor activator is about 1:13 over the 24-hour period after administration. In some aspects, the AUC serum ratio of the muscarinic acetylcholine receptor inhibitor to the muscarinic receptor activator is about 1:14 over the 24-hour period after administration. In some aspects, the AUC serum ratio of the muscarinic acetylcholine receptor inhibitor to the muscarinic receptor activator is about 1:15 over the 24-hour period after administration. In some aspects, the AUC serum ratio of the muscarinic acetylcholine receptor inhibitor to the muscarinic receptor activator is about 1:16 over the 24-hour period after administration. In some aspects, the AUC serum ratio of the muscarinic acetylcholine receptor inhibitor to the muscarinic receptor activator is about 1:17 over the 24-hour period after administration. In some aspects, the AUC serum ratio of the muscarinic acetylcholine receptor inhibitor to the muscarinic receptor activator is about 1:18 over the 24-hour period after administration. In some aspects, the AUC serum ratio of the muscarinic acetylcholine receptor inhibitor to the muscarinic receptor activator is about 1:19 over the 24-hour period after administration. In some aspects, the AUC serum ratio of the muscarinic acetylcholine receptor inhibitor to the muscarinic receptor activator is about 1:20 over the 24-hour period after administration. In some aspects, the AUC serum ratio of the muscarinic acetylcholine receptor inhibitor to the muscarinic receptor activator is about 1:21 over the 24-hour period after administration. In some aspects, the AUC serum ratio of the muscarinic acetylcholine receptor inhibitor to the muscarinic receptor activator is about 1:22 over the 24-hour period after administration. In some aspects, the AUC serum ratio of the muscarinic acetylcholine receptor inhibitor to the muscarinic receptor activator is about 1:23 over the 24-hour period after administration. In some aspects, the AUC serum ratio of the muscarinic acetylcholine receptor inhibitor to the muscarinic receptor activator is about 1:24 over the 24-hour period after administration. In some aspects, the AUC serum ratio of the muscarinic acetylcholine receptor inhibitor to the muscarinic receptor activator is about 1:25 over the 24-hour period after administration. In some aspects, the AUC serum ratio of the muscarinic acetylcholine receptor inhibitor to the muscarinic receptor activator is about 1:26 over the 24-hour period after administration. In some aspects, the AUC serum ratio of the muscarinic acetylcholine receptor inhibitor to the muscarinic receptor activator is about 1:27 over the 24-hour period after administration. In some aspects, the AUC serum ratio of the muscarinic acetylcholine receptor inhibitor to the muscarinic receptor activator is about 1:28 over the 24-hour period after administration. In some aspects, the AUC serum ratio of the muscarinic acetylcholine receptor inhibitor to the muscarinic receptor activator is about 1:29 over the 24-hour period after administration. In some aspects, the AUC serum ratio of the muscarinic acetylcholine receptor inhibitor to the muscarinic receptor activator is about 1:30 over the 24-hour period after administration. In some aspects, the AUC serum ratio of the muscarinic acetylcholine receptor inhibitor to the muscarinic receptor activator is about 1:31 over the 24-hour period after administration. In some aspects, the AUC serum ratio of the muscarinic acetylcholine receptor inhibitor to the muscarinic receptor activator is about 1:31 over the 24-hour period after administration. In some aspects, the AUC serum ratio of the muscarinic acetylcholine receptor inhibitor to the muscarinic receptor activator is about 1:32 over the 24-hour period after administration. In some aspects, the AUC serum ratio of the muscarinic acetylcholine receptor inhibitor to the muscarinic receptor activator is about 1:33 over the 24-hour period after administration. In some aspects, the AUC serum ratio of the muscarinic acetylcholine receptor inhibitor to the muscarinic receptor activator is about 1:34 over the 24-hour period after administration. In some aspects, the AUC serum ratio of the muscarinic acetylcholine receptor inhibitor to the muscarinic receptor activator is about 1:35 over the 24-hour period after administration. In some aspects, the AUC serum ratio of the muscarinic acetylcholine receptor inhibitor to the muscarinic receptor activator is about 1:36 over the 24-hour period after administration. In some aspects, the AUC serum ratio of the muscarinic acetylcholine receptor inhibitor to the muscarinic receptor activator is about 1:37 over the 24-hour period after administration. In some aspects, the AUC serum ratio of the muscarinic acetylcholine receptor inhibitor to the muscarinic receptor activator is about 1:38 over the 24-hour period after administration. In some aspects, the AUC serum ratio of the muscarinic acetylcholine receptor inhibitor to the muscarinic receptor activator is about 1:39 over the 24-hour period after administration. In some aspects, the AUC serum ratio of the muscarinic acetylcholine receptor inhibitor to the muscarinic receptor activator is about 1:40 over the 24-hour period after administration.

In some aspects, the C(max) serum ratio of the muscarinic acetylcholine receptor inhibitor to the muscarinic receptor activator is about 1:1 over the 24-hour period after administration. In some aspects, the C(max) serum ratio of the muscarinic acetylcholine receptor inhibitor to the muscarinic receptor activator is about 1:2 over the 24-hour period after administration. In some aspects, the C(max) serum ratio of the muscarinic acetylcholine receptor inhibitor to the muscarinic receptor activator is about 1:3 over the 24-hour period after administration. In some aspects, the C(max) serum ratio of the muscarinic acetylcholine receptor inhibitor to the muscarinic receptor activator is about 1:4 over the 24-hour period after administration. In some aspects, the C(max) serum ratio of the muscarinic acetylcholine receptor inhibitor to the muscarinic receptor activator is about 1:5 over the 24-hour period after administration. In some aspects, the C(max) serum ratio of the muscarinic acetylcholine receptor inhibitor to the muscarinic receptor activator is about 1:6 over the 24-hour period after administration. In some aspects, the C(max) serum ratio of the muscarinic acetylcholine receptor inhibitor to the muscarinic receptor activator is about 1:7 over the 24-hour period after administration. In some aspects, the C(max) serum ratio of the muscarinic acetylcholine receptor inhibitor to the muscarinic receptor activator is about 1:8 over the 24-hour period after administration. In some aspects, the C(max) serum ratio of the muscarinic acetylcholine receptor inhibitor to the muscarinic receptor activator is about 1:9 over the 24-hour period after administration. In some aspects, the C(max) serum ratio of the muscarinic acetylcholine receptor inhibitor to the muscarinic receptor activator is about 1:10 over the 24-hour period after administration. In some aspects, the C(max) serum ratio of the muscarinic acetylcholine receptor inhibitor to the muscarinic receptor activator is about 1:11 over the 24-hour period after administration. In some aspects, the C(max) serum ratio of the muscarinic acetylcholine receptor inhibitor to the muscarinic receptor activator is about 1:12 over the 24-hour period after administration. In some aspects, the C(max) serum ratio of the muscarinic acetylcholine receptor inhibitor to the muscarinic receptor activator is about 1:13 over the 24-hour period after administration. In some aspects, the C(max) serum ratio of the muscarinic acetylcholine receptor inhibitor to the muscarinic receptor activator is about 1:14 over the 24-hour period after administration. In some aspects, the C(max) serum ratio of the muscarinic acetylcholine receptor inhibitor to the muscarinic receptor activator is about 1:15 over the 24-hour period after administration. In some aspects, the C(max) serum ratio of the muscarinic acetylcholine receptor inhibitor to the muscarinic receptor activator is about 1:16 over the 24-hour period after administration. In some aspects, the C(max) serum ratio of the muscarinic acetylcholine receptor inhibitor to the muscarinic receptor activator is about 1:17 over the 24-hour period after administration. In some aspects, the C(max) serum ratio of the muscarinic acetylcholine receptor inhibitor to the muscarinic receptor activator is about 1:18 over the 24-hour period after administration. In some aspects, the C(max) serum ratio of the muscarinic acetylcholine receptor inhibitor to the muscarinic receptor activator is about 1:19 over the 24-hour period after administration. In some aspects, the C(max) serum ratio of the muscarinic acetylcholine receptor inhibitor to the muscarinic receptor activator is about 1:20 over the 24-hour period after administration.

In some aspects, the plasma concentration ratio of (i) Racemic-THP to (ii) Racemic-BTC is about 1:20 ng/ml to about 1:40 ng/mL after administration. In some aspects, the plasma concentration ratio of (i) Racemic-THP to (ii) Racemic-BTC is about 1:21 ng/mL to about 1:39 ng/mL after administration. In some aspects, the plasma concentration ratio of (i) Racemic-THP to (ii) Racemic-BTC is about 1:22 ng/ml to about 1:38 ng/mL after administration. In some aspects, the plasma concentration ratio of (i) Racemic-THP to (ii) Racemic-BTC is about 1:23 ng/ml to about 1:37 ng/mL after administration. In some aspects, the plasma concentration ratio of (i) Racemic-THP to (ii) Racemic-BTC is about 1:24 ng/ml to about 1:36 ng/ml after administration. In some aspects, the plasma concentration ratio of (i) Racemic-THP to (ii) Racemic-BTC is about 1:25 ng/mL to about 1:35 ng/ml after administration. In some aspects, the plasma concentration ratio of (i) Racemic-THP to (ii) Racemic-BTC is about 1:26 ng/ml to about 1:34 ng/ml after administration. In some aspects, the plasma concentration ratio of (i) Racemic-THP to (ii) Racemic-BTC is about 1:27 ng/mL to about 1:33 ng/ml after administration. In some aspects, the plasma concentration ratio of (i) Racemic-THP to (ii) Racemic-BTC is about 1:28 ng/ml to about 1:32 ng/ml after administration. In some aspects, the plasma concentration ratio of (i) Racemic-THP to (ii) Racemic-BTC is about 1:29 ng/ml to about 1:31 ng/mL after administration. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the plasma concentration ratio of (i) (R)-THP to (ii) Racemic-BTC is about 1:20 ng/mL to about 1:40 ng/ml after administration. In some aspects, the plasma concentration ratio of (i) (R)-THP to (ii) Racemic-BTC is about 1:21 ng/mL to about 1:39 ng/ml after administration. In some aspects, the plasma concentration ratio of (i) (R)-THP to (ii) Racemic-BTC is about 1:22 ng/ml to about 1:38 ng/mL after administration. In some aspects, the plasma concentration ratio of (i) (R)-THP to (ii) Racemic-BTC is about 1:23 ng/mL to about 1:37 ng/mL after administration. In some aspects, the plasma concentration ratio of (i) (R)-THP to (ii) Racemic-BTC is about 1:24 ng/mL to about 1:36 ng/mL after administration. In some aspects, the plasma concentration ratio of (i) (R)-THP to (ii) Racemic-BTC is about 1:25 ng/ml to about 1:35 ng/mL after administration. In some aspects, the plasma concentration ratio of (i) (R)-THP to (ii) Racemic-BTC is about 1:26 ng/mL to about 1:34 ng/mL after administration. In some aspects, the plasma concentration ratio of (i) (R)-THP to (ii) Racemic-BTC is about 1:27 ng/ml to about 1:33 ng/mL after administration. In some aspects, the plasma concentration ratio of (i) (R)-THP to (ii) Racemic-BTC is about 1:28 ng/ml to about 1:32 ng/mL after administration. In some aspects, the plasma concentration ratio of (i) (R)-THP to (ii) Racemic-BTC is about 1:29 ng/mL to about 1:31 ng/mL after administration. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the plasma concentration ratio of (i) (R)-THP to (ii) (S)-BTC is about 1:20 ng/ml to about 1:40 ng/ml after administration. In some aspects, the plasma concentration ratio of (i) (R)-THP to (ii) (S)-BTC is about 1:21 ng/mL to about 1:39 ng/mL after administration. In some aspects, the plasma concentration ratio of (i) (R)-THP to (ii) (S)-BTC is about 1:22 ng/mL to about 1:38 ng/mL after administration. In some aspects, the plasma concentration ratio of (i) (R)-THP to (ii) (S)-BTC is about 1:23 ng/mL to about 1:37 ng/ml after administration. In some aspects, the plasma concentration ratio of (i) (R)-THP to (ii) (S)-BTC is about 1:24 ng/mL to about 1:36 ng/ml after administration. In some aspects, the plasma concentration ratio of (i) (R)-THP to (ii) (S)-BTC about 1:25 ng/mL to about 1:35 ng/ml after administration. In some aspects, the plasma concentration ratio of (i) (R)-THP to (ii) (S)-BTC is about 1:26 ng/ml to about 1:34 ng/mL after administration. In some aspects, the plasma concentration ratio of (i) (R)-THP to (ii) (S)-BTC is about 1:27 ng/mL to about 1:33 ng/ml after administration. In some aspects, the plasma concentration ratio of (i) (R)-THP to (ii) (S)-BTC is about 1:28 ng/mL to about 1:32 ng/mL after administration. In some aspects, the plasma concentration ratio of (i) (R)-THP to (ii) (S)-BTC is about 1:29 ng/mL to about 1:31 ng/ml after administration. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the plasma concentration ratio of (i) Racemic-THP to (ii) Racemic-BTC is about 1:20 ng/mL after administration. In some aspects, the plasma concentration ratio of (i) Racemic-THP to (ii) Racemic-BTC is about 1:21 ng/mL after administration. In some aspects, the plasma concentration ratio of (i) Racemic-THP to (ii) Racemic-BTC is about 1:22 ng/ml after administration. In some aspects, the plasma concentration ratio of (i) Racemic-THP to (ii) Racemic-BTC is about 1:23 ng/mL after administration. In some aspects, the plasma concentration ratio of (i) Racemic-THP to (ii) Racemic-BTC is about 1:24 ng/ml after administration. In some aspects, the plasma concentration ratio of (i) Racemic-THP to (ii) Racemic-BTC is about 1:25 ng/mL after administration. In some aspects, the plasma concentration ratio of (i) Racemic-THP to (ii) Racemic-BTC is about 1:26 ng/ml after administration. In some aspects, the plasma concentration ratio of (i) Racemic-THP to (ii) Racemic-BTC is about 1:27 ng/mL after administration. In some aspects, the plasma concentration ratio of (i) Racemic-THP to (ii) Racemic-BTC is about 1:28 ng/mL after administration. In some aspects, the plasma concentration ratio of (i) Racemic-THP to (ii) Racemic-BTC is about 1:29 ng/mL after administration. In some aspects, the plasma concentration ratio of (i) Racemic-THP to (ii) Racemic-BTC is about 1:30 ng/mL after administration. In some aspects, the plasma concentration ratio of (i) Racemic-THP to (ii) Racemic-BTC is about 1:31 ng/mL after administration. In some aspects, the plasma concentration ratio of (i) Racemic-THP to (ii) Racemic-BTC is about 1:32 ng/mL after administration. In some aspects, the plasma concentration ratio of (i) Racemic-THP to (ii) Racemic-BTC is about 1:33 ng/mL after administration. In some aspects, the plasma concentration ratio of (i) Racemic-THP to (ii) Racemic-BTC is about 1:34 ng/ml after administration. In some aspects, the plasma concentration ratio of (i) Racemic-THP to (ii) Racemic-BTC is about 1:35 ng/mL after administration. In some aspects, the plasma concentration ratio of (i) Racemic-THP to (ii) Racemic-BTC is about 1:36 ng/mL after administration. In some aspects, the plasma concentration ratio of (i) Racemic-THP to (ii) Racemic-BTC is about 1:37 ng/mL after administration. In some aspects, the plasma concentration ratio of (i) Racemic-THP to (ii) Racemic-BTC is about 1:38 ng/ml after administration. In some aspects, the plasma concentration ratio of (i) Racemic-THP to (ii) Racemic-BTC is about 1:39 ng/mL after administration. In some aspects, the plasma concentration ratio of (i) Racemic-THP to (ii) Racemic-BTC is about 1:40 ng/mL after administration. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the plasma concentration ratio of (i) (R)-THP to (ii) Racemic-BTC is about 1:20 ng/mL after administration. In some aspects, the plasma concentration ratio of (i) (R)-THP to (ii) Racemic-BTC is about 1:21 ng/mL after administration. In some aspects, the plasma concentration ratio of (i) (R)-THP to (ii) Racemic-BTC is about 1:22 ng/mL after administration. In some aspects, the plasma concentration ratio of (i) (R)-THP to (ii) Racemic-BTC is about 1:23 ng/mL after administration. In some aspects, the plasma concentration ratio of (i) (R)-THP to (ii) Racemic-BTC is about 1:24 ng/mL after administration. In some aspects, the plasma concentration ratio of (i) (R)-THP to (ii) Racemic-BTC is about 1:25 ng/mL after administration. In some aspects, the plasma concentration ratio of (i) (R)-THP to (ii) Racemic-BTC is about 1:26 ng/mL after administration. In some aspects, the plasma concentration ratio of (i) (R)-THP to (ii) Racemic-BTC is about 1:27 ng/mL after administration. In some aspects, the plasma concentration ratio of (i) (R)-THP to (ii) Racemic-BTC is about 1:28 ng/mL after administration. In some aspects, the plasma concentration ratio of (i) (R)-THP to (ii) Racemic-BTC is about 1:29 ng/mL after administration. In some aspects, the plasma concentration ratio of (i) (R)-THP to (ii) Racemic-BTC is about 1:30 ng/mL after administration. In some aspects, the plasma concentration ratio of (i) (R)-THP to (ii) Racemic-BTC is about 1:31 ng/mL after administration. In some aspects, the plasma concentration ratio of (i) (R)-THP to (ii) Racemic-BTC is about 1:32 ng/mL after administration. In some aspects, the plasma concentration ratio of (i) (R)-THP to (ii) Racemic-BTC is about 1:33 ng/mL after administration. In some aspects, the plasma concentration ratio of (i) (R)-THP to (ii) Racemic-BTC is about 1:34 ng/mL after administration. In some aspects, the plasma concentration ratio of (i) (R)-THP to (ii) Racemic-BTC is about 1:35 ng/mL after administration. In some aspects, the plasma concentration ratio of (i) (R)-THP to (ii) Racemic-BTC is about 1:36 ng/mL after administration. In some aspects, the plasma concentration ratio of (i) (R)-THP to (ii) Racemic-BTC is about 1:37 ng/mL after administration. In some aspects, the plasma concentration ratio of (i) (R)-THP to (ii) Racemic-BTC is about 1:38 ng/mL after administration. In some aspects, the plasma concentration ratio of (i) (R)-THP to (ii) Racemic-BTC is about 1:39 ng/ml after administration. In some aspects, the plasma concentration ratio of (i) (R)-THP to (ii) Racemic-BTC is about 1:40 ng/mL after administration. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the plasma concentration ratio of (i) (R)-THP to (ii) (S)-BTC is about 1:20 ng/mL after administration. In some aspects, the plasma concentration ratio of (i) (R)-THP to (ii) (S)-BTC is about 1:21 ng/mL after administration. In some aspects, the plasma concentration ratio of (i) (R)-THP to (ii) (S)-BTC is about 1:22 ng/mL after administration. In some aspects, the plasma concentration ratio of (i) (R)-THP to (ii) (S)-BTC is about 1:23 ng/ml after administration. In some aspects, the plasma concentration ratio of (i) (R)-THP to (ii) (S)-BTC is about 1:24 ng/mL after administration. In some aspects, the plasma concentration ratio of (i) (R)-THP to (ii) (S)-BTC is about 1:25 ng/mL after administration. In some aspects, the plasma concentration ratio of (i) (R)-THP to (ii) (S)-BTC is about 1:26 ng/mL after administration. In some aspects, the plasma concentration ratio of (i) (R)-THP to (ii) (S)-BTC is about 1:27 ng/ml after administration. In some aspects, the plasma concentration ratio of (i) (R)-THP to (ii) (S)-BTC is about 1:28 ng/mL after administration. In some aspects, the plasma concentration ratio of (i) (R)-THP to (ii) (S)-BTC is about 1:29 ng/mL after administration. In some aspects, the plasma concentration ratio of (i) (R)-THP to (ii) (S)-BTC is about 1:30 ng/mL after administration. In some aspects, the plasma concentration ratio of (i) (R)-THP to (ii) (S)-BTC is about 1:31 ng/ml after administration. In some aspects, the plasma concentration ratio of (i) (R)-THP to (ii) (S)-BTC is about 1:32 ng/mL after administration. In some aspects, the plasma concentration ratio of (i) (R)-THP to (ii) (S)-BTC is about 1:33 ng/mL after administration. In some aspects, the plasma concentration ratio of (i) (R)-THP to (ii) (S)-BTC is about 1:34 ng/mL after administration. In some aspects, the plasma concentration ratio of (i) (R)-THP to (ii) (S)-BTC is about 1:35 ng/ml after administration. In some aspects, the plasma concentration ratio of (i) (R)-THP to (ii) (S)-BTC is about 1:36 ng/mL after administration. In some aspects, the plasma concentration ratio of (i) (R)-THP to (ii) (S)-BTC is about 1:37 ng/mL after administration. In some aspects, the plasma concentration ratio of (i) (R)-THP to (ii) (S)-BTC is about 1:38 ng/mL after administration. In some aspects, the plasma concentration ratio of (i) (R)-THP to (ii) (S)-BTC is about 1:39 ng/ml after administration. In some aspects, the plasma concentration ratio of (i) (R)-THP to (ii) (S)-BTC is about 1:40 ng/mL after administration. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:20 ng/mL to about 1:40 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:21 ng/mL to about 1:39 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:22 ng/mL to about 1:38 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:23 ng/mL to about 1:37 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:24 ng/ml to about 1:36 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:25 ng/ml to about 1:35 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:26 ng/ml to about 1:34 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:27 ng/ml to about 1:33 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:28 ng/mL to about 1:32 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:29 ng/mL to about 1:31 ng/mL after administration. In some aspects, the muscarinic acetylcholine receptor inhibitor is selected from scopolamine, benztropine, and ethopropazine or a pharmaceutically acceptable salt thereof. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:20 ng/mL to about 1:40 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:21 ng/mL to about 1:39 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:22 ng/mL to about 1:38 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:23 ng/ml to about 1:37 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:24 ng/mL to about 1:36 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:25 ng/ml to about 1:35 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:26 ng/mL to about 1:34 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:27 ng/mL to about 1:33 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:28 ng/mL to about 1:32 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:29 ng/mL to about 1:31 ng/mL after administration. In some aspects, the muscarinic acetylcholine receptor inhibitor is selected from scopolamine, benztropine, and ethopropazine or a pharmaceutically acceptable salt thereof. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:20 ng/ml to about 1:40 ng/mL after administration. In some aspects, the plasma concentration ratio of (i) Muscarinic acetylcholine receptor inhibitor to (ii) a second therapeutic agent selected from a muscarinic acetylcholine receptor activator, a procholinergic agent, and an acetylcholine esterase inhibitor is about 1:21 ng/ml to about 1:39 ng/ml after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:22 ng/mL to about 1:38 ng/ml after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:23 ng/ml to about 1:37 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:24 ng/mL to about 1:36 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:25 ng/ml to about 1:35 ng/ml after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:26 ng/ml to about 1:34 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:27 ng/mL to about 1:33 ng/ml after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:28 ng/mL to about 1:32 ng/ml after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:29 ng/mL to about 1:31 ng/mL after administration. In some aspects, the muscarinic acetylcholine receptor inhibitor is selected from scopolamine, benztropine, and ethopropazine or a pharmaceutically acceptable salt thereof. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:20 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:21 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:22 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:23 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:24 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:25 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:26 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:27 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:28 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:29 ng/mL after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:30 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:31 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:32 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:33 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:34 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:35 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:36 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:37 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:38 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:39 ng/ml after administration. In some aspects, the plasma concentration ratio of (i) Racemic-THP to (ii) a second therapeutic agent selected from a muscarinic acetylcholine receptor activator, a procholinergic agent, and an acetylcholine esterase inhibitor is about 1:40 ng/mL after administration. In some aspects, the muscarinic acetylcholine receptor inhibitor is selected from scopolamine, benztropine, and ethopropazine or a pharmaceutically acceptable salt thereof. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:20 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:21 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:22 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:23 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:24 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:25 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:26 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:27 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:28 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:29 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:30 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:31 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:32 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:33 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:34 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:35 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:36 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:37 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:38 ng/ml after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:39 ng/mL after administration. In some aspects, the plasma concentration ratio of (i) (R)-THP to (ii) a second therapeutic agent selected from a muscarinic acetylcholine receptor activator, a procholinergic agent, and an acetylcholine esterase inhibitor is about 1:40 ng/mL after administration. In some aspects, the muscarinic acetylcholine receptor inhibitor is selected from scopolamine, benztropine, and ethopropazine or a pharmaceutically acceptable salt thereof. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:20 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:21 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:22 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:23 ng/ml after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:24 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:25 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:26 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:27 ng/ml after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:28 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:29 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:30 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:31 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:32 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:33 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:34 ng/mL after administration. In some aspects, the plasma concentration ratio of (i) a muscarinic acetylcholine receptor inhibitor to (ii) a second therapeutic agent selected from a muscarinic acetylcholine receptor activator, a cholinergic agent, and an acetylcholine esterase inhibitor is about 1:35 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:36 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:37 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:38 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:39 ng/mL after administration. In some aspects, the plasma concentration ratio of (i) a muscarinic acetylcholine receptor inhibitor to (ii) a second therapeutic agent selected from a muscarinic acetylcholine receptor activator, a procholinergic agent, and an acetylcholine esterase inhibitor is about 1:40 ng/mL after administration. In some aspects, the muscarinic acetylcholine receptor inhibitor is selected from scopolamine, benztropine, and ethopropazine or a pharmaceutically acceptable salt thereof. In some aspects, the plasma concentration ratio determined about 30 minutes to about 24 hours after the administration. In some aspects, the plasma concentration ratio determined about 1 hour to about 22 hours after the administration. In some aspects, the plasma concentration ratio determined about 2 hours to about 20 hours after the administration. In some aspects, the plasma concentration ratio determined about 3 hours to about 17 hours after the administration. In some aspects, the plasma concentration ratio determined about 4 hours to about 15 hours after the administration. In some aspects, the plasma concentration ratio determined about 5 hours to about 12 hours after the administration. In some aspects, the plasma concentration ratio determined about 6 hours to about 10 hours after the administration. In some aspects, the plasma concentration ratio determined about 7 hours to about 9 hours after the administration. In some aspects, the plasma concentration ratio determined about 30 minutes after the administration. In some aspects, the plasma concentration ratio determined about 1 hour after the administration. In some aspects, the plasma concentration ratio determined about 2 hours after the administration. In some aspects, the plasma concentration ratio determined about 3 hours after the administration. In some aspects, the plasma concentration ratio determined about 4 hours after the administration. In some aspects, the plasma concentration ratio determined about 5 hours after the administration. In some aspects, the plasma concentration ratio determined about 6 hours after the administration. In some aspects, the plasma concentration ratio determined about 7 hours after the administration. In some aspects, the plasma concentration ratio determined about 8 hours after the administration. In some aspects, the plasma concentration ratio determined about 9 hours after the administration. In some aspects, the plasma concentration ratio determined about 10 hours after the administration. In some aspects, the plasma concentration ratio determined about 11 hours after the administration. In some aspects, the plasma concentration ratio determined about 12 hours after the administration. In some aspects, the plasma concentration ratio determined about 13 hours after the administration. In some aspects, the plasma concentration ratio determined about 14 hours after the administration. In some aspects, the plasma concentration ratio determined about 15 hours after the administration. In some aspects, the plasma concentration ratio determined about 16 hours after the administration. In some aspects, the plasma concentration ratio determined about 17 hours after the administration. In some aspects, the plasma concentration ratio determined about 18 hours after the administration. In some aspects, the plasma concentration ratio determined about 19 hours after the administration. In some aspects, the plasma concentration ratio determined about 20 hours after the administration. In some aspects, the plasma concentration ratio determined about 21 hours after the administration. In some aspects, the plasma concentration ratio determined about 22 hours after the administration. In some aspects, the plasma concentration ratio determined about 23 hours after the administration. In some aspects, the plasma concentration ratio determined about 24 hours after the administration.

In some aspects, the rate of rise of serum concentration of the muscarinic acetylcholine receptor inhibitor is less than 20 ng/ml/hr. In some aspects, the rate of rise of serum concentration of the muscarinic acetylcholine receptor inhibitor is less than 19 ng/ml/hr. In some aspects, the rate of rise of serum concentration of the muscarinic acetylcholine receptor inhibitor is less than 18 ng/ml/hr. In some aspects, the rate of rise of serum concentration of the muscarinic acetylcholine receptor inhibitor is less than 17 ng/ml/hr. In some aspects, the rate of rise of serum concentration of the muscarinic acetylcholine receptor inhibitor is less than 16 ng/ml/hr. In some aspects, the rate of rise of plasma concentration of the muscarinic acetylcholine receptor inhibitor is less than 15 ng/ml/hr. In some aspects, the rate of rise of plasma concentration of the muscarinic acetylcholine receptor inhibitor is less than 14 ng/mL/hr. In some aspects, the rate of rise of plasma concentration of the muscarinic acetylcholine receptor inhibitor is less than 13 ng/mL/hr. In some aspects, the rate of rise of plasma concentration of the muscarinic acetylcholine receptor inhibitor is less than 12 ng/ml/hr. In some aspects, the rate of rise of plasma concentration of the muscarinic acetylcholine receptor inhibitor is less than 10 ng/mL/hr. In some aspects, the rate of rise of plasma concentration of the muscarinic acetylcholine receptor inhibitor is less than 9 ng/ml/hr. In some aspects, the rate of rise of plasma concentration of the muscarinic acetylcholine receptor inhibitor is less than 8 ng/ml/hr. In some aspects, the rate of rise of plasma concentration of the muscarinic acetylcholine receptor inhibitor is less than 7 ng/ml/hr. In some aspects, the rate of rise of plasma concentration of the muscarinic acetylcholine receptor inhibitor is less than 6 ng/ml/hr. In some aspects, the rate of rise of plasma concentration of the muscarinic acetylcholine receptor inhibitor is less than 5 ng/ml/hr. In some aspects, the rate of rise of plasma concentration of the muscarinic acetylcholine receptor inhibitor is less than 4 ng/ml/hr. In some aspects, the rate of rise of plasma concentration of the muscarinic acetylcholine receptor inhibitor is less than 3 ng/mL/hr. In some aspects, the rate of rise of plasma concentration of the muscarinic acetylcholine receptor inhibitor is less than 2 ng/ml/hr. In some aspects, the rate of rise of plasma concentration of the muscarinic acetylcholine receptor inhibitor is less than 1 ng/ml/hr.

In some aspects, the rate of rise of plasma concentration of the muscarinic acetylcholine receptor inhibitor is less than about 1 ng/mL/hr to about 20 ng/ml/hr. In some aspects, the rate of rise of plasma concentration of the muscarinic acetylcholine receptor inhibitor is less than about 2 ng/ml/hr to about 19 ng/ml/hr. In some aspects, the rate of rise of plasma concentration of the muscarinic acetylcholine receptor inhibitor is less than about 3 ng/ml/hr to 18 ng/ml/hr. In some aspects, the rate of rise of plasma concentration of the muscarinic acetylcholine receptor inhibitor is less than about about 4 ng/ml/hr to about 17 ng/ml/hr. In some aspects, the rate of rise of plasma concentration of the muscarinic acetylcholine receptor inhibitor is less than about 5 ng/ml/hr to about 16 ng/mL/hr. In some aspects, the rate of rise of plasma concentration of the muscarinic acetylcholine receptor inhibitor is about 6 ng/ml/hr to about 15 ng/ml/hr. In some aspects, the rate of rise of plasma concentration of the muscarinic acetylcholine receptor inhibitor is about 7 ng/ml/hr to about 14 ng/ml/hr. In some aspects, the rate of rise of plasma concentration of the muscarinic acetylcholine receptor inhibitor is about 8 ng/ml/hr to about 13 ng/ml/hr. In some aspects, the rate of rise of plasma concentration of the muscarinic acetylcholine receptor inhibitor is about 9 ng/mL/hr to about 12 ng/mL/hr. In some aspects, the rate of rise of plasma concentration of the muscarinic acetylcholine receptor inhibitor is about 10 ng/mL/hr to about 11 ng/mL/hr. In some aspects, the rate of rise of plasma concentration of the muscarinic acetylcholine receptor inhibitor is about 1 ng/ml/hr to about 15 ng/ml/hr. In some aspects, the rate of rise of plasma concentration of the muscarinic acetylcholine receptor inhibitor is about 2 ng/ml/hr to about 14 ng/mL/hr. In some aspects, the rate of rise of plasma concentration of the muscarinic acetylcholine receptor inhibitor is about 3 ng/ml/hr to about 13 ng/ml/hr. In some aspects, the rate of rise of plasma concentration of the muscarinic acetylcholine receptor inhibitor is about 4 ng/ml/hr to about 12 ng/ml/hr. In some aspects, the rate of rise of plasma concentration of the muscarinic acetylcholine receptor inhibitor is about 5 ng/ml/hr to about 11 ng/ml/hr. In some aspects, the rate of rise of plasma concentration of the muscarinic acetylcholine receptor inhibitor is about 6 ng/ml/hr to about 10 ng/ml/hr. In some aspects, the rate of rise of plasma concentration of the muscarinic acetylcholine receptor inhibitor is about 7 ng/ml/hr to about 9 ng/ml/hr.

In some aspects, the C(average) plasma concentration ratio of the muscarinic acetylcholine receptor inhibitor to the muscarinic receptor activator is about 1:5 to about 1:50 over the 24-hour period after administration. In some aspects, the C(average) plasma concentration ratio of the muscarinic acetylcholine receptor inhibitor to the muscarinic receptor activator is about 1:6 to about 1:49 over the 24-hour period after administration. In some aspects, the C(average) plasma concentration ratio of the muscarinic acetylcholine receptor inhibitor to the muscarinic receptor activator is about 1:7 to about 1:48 over the 24-hour period after administration. In some aspects, the C(average) plasma concentration ratio of the muscarinic acetylcholine receptor inhibitor to the muscarinic receptor activator is about 1:8 to about 1:47 over the 24-hour period after administration. In some aspects, the C(average) plasma concentration ratio of the muscarinic acetylcholine receptor inhibitor to the muscarinic receptor activator is about 1:9 to about 1:46 over the 24-hour period after administration. In some aspects, the C(average) plasma concentration ratio of the muscarinic acetylcholine receptor inhibitor to the muscarinic receptor activator is about 1:10 to about 1:45 over the 24-hour period after administration. In some aspects, the C(average) plasma concentration ratio of the muscarinic acetylcholine receptor inhibitor to the muscarinic receptor activator is about 1:11 to about 1:44 over the 24-hour period after administration. In some aspects, the C(average) plasma concentration ratio of the muscarinic acetylcholine receptor inhibitor to the muscarinic receptor activator is about 1:12 to about 1:43 over the 24-hour period after administration. In some aspects, the C(average) plasma concentration ratio of the muscarinic acetylcholine receptor inhibitor to the muscarinic receptor activator is about 1:13 to about 1:42 over the 24-hour period after administration. In some aspects, the C(average) plasma concentration ratio of the muscarinic acetylcholine receptor inhibitor to the muscarinic receptor activator is about 1:14 to about 1:41 over the 24-hour period after administration. In some aspects, the C(average) plasma concentration ratio of the muscarinic acetylcholine receptor inhibitor to the muscarinic receptor activator is about 1:15 to about 1:40 over the 24-hour period after administration. In some aspects, the C(average) plasma concentration ratio of the muscarinic acetylcholine receptor inhibitor to the muscarinic receptor activator is about 1:16 to about 1:39 over the 24-hour period after administration. In some aspects, the C(average) plasma concentration ratio of the muscarinic acetylcholine receptor inhibitor to the muscarinic receptor activator is about 1:17 to about 1:38 over the 24-hour period after administration. In some aspects, the C(average) plasma concentration ratio of the muscarinic acetylcholine receptor inhibitor to the muscarinic receptor activator is about 1:18 to about 1:37 over the 24-hour period after administration. In some aspects, the C(average) plasma concentration ratio of the muscarinic acetylcholine receptor inhibitor to the muscarinic receptor activator is about 1:19 to about 1:36 over the 24-hour period after administration. In some aspects, the C(average) plasma concentration ratio of the muscarinic acetylcholine receptor inhibitor to the muscarinic receptor activator is about 1:20 to about 1:35 over the 24-hour period after administration. In some aspects, the C(average) plasma concentration ratio of the muscarinic acetylcholine receptor inhibitor to the muscarinic receptor activator is about 1:21 to about 1:34 over the 24-hour period after administration. In some aspects, the C(average) plasma concentration ratio of the muscarinic acetylcholine receptor inhibitor to the muscarinic receptor activator is about 1:22 to about 1:33 over the 24-hour period after administration. In some aspects, the C(average) plasma concentration ratio of the muscarinic acetylcholine receptor inhibitor to the muscarinic receptor activator is about 1:23 to about 1:32 over the 24-hour period after administration. In some aspects, the C(average) plasma concentration ratio of the muscarinic acetylcholine receptor inhibitor to the muscarinic receptor activator is about 1:24 to about 1:31 over the 24-hour period after administration. In some aspects, the C(average) plasma concentration ratio of the muscarinic acetylcholine receptor inhibitor to the muscarinic receptor activator is about 1:25 to about 1:30 over the 24-hour period after administration. In some aspects, the C(average) plasma concentration ratio of the muscarinic acetylcholine receptor inhibitor to the muscarinic receptor activator is about 1:26 to about 1:29 over the 24-hour period after administration. In some aspects, the C(average) plasma concentration ratio of the muscarinic acetylcholine receptor inhibitor to the muscarinic receptor activator is about 1:27 to about 1:28 over the 24-hour period after administration.

In some aspects, (i) the area under the curve (AUC) plasma ratio of the muscarinic acetylcholine receptor inhibitor to the muscarinic receptor activator is about 1:1 to about 1:42 and (ii) the C(max) plasma concentration ratio of the muscarinic acetylcholine receptor inhibitor to the muscarinic receptor activator is about 1:5 to about 1:50 over the 24-hour period after administration. In some aspects, (i) the AUC plasma ratio of the muscarinic acetylcholine receptor inhibitor to the muscarinic receptor activator is about 1:2 to about 1:41 and (ii) the C(max) plasma concentration ratio of the muscarinic acetylcholine receptor inhibitor to the muscarinic receptor activator is about 1:6 to about 1:4 over the 24-hour period after administration. In some aspects, (i) the AUC plasma ratio of the muscarinic acetylcholine receptor inhibitor to the muscarinic receptor activator is about 1:3 to about 1:40 and (ii) the C(max) plasma concentration ratio of the muscarinic acetylcholine receptor inhibitor to the muscarinic receptor activator is about 1:7 to about 1:48 over the 24-hour period after administration. In some aspects, (i) the AUC plasma ratio of the muscarinic acetylcholine receptor inhibitor to the muscarinic receptor activator is about 1:4 to about 1:39 and (ii) the C(max) plasma concentration ratio of the muscarinic acetylcholine receptor inhibitor to the muscarinic receptor activator is about 1:8 to about 1:47 over the 24-hour period after administration. In some aspects, (i) the AUC plasma ratio of the muscarinic acetylcholine receptor inhibitor to the muscarinic receptor activator is about 1:5 to about 1:38 and (ii) the C(max) plasma concentration ratio of the muscarinic acetylcholine receptor inhibitor to the muscarinic receptor activator is about 1:9 to about 1:46 over the 24-hour period after administration. In some aspects, (i) the AUC plasma ratio of the muscarinic acetylcholine receptor inhibitor to the muscarinic receptor activator is about 1:6 to about 1:37 and (ii) the C(max) plasma concentration ratio of the muscarinic acetylcholine receptor inhibitor to the muscarinic receptor activator is about 1:10 to about 1:45 over the 24-hour period after administration. In some aspects, (i) the AUC plasma ratio of the muscarinic acetylcholine receptor inhibitor to the muscarinic receptor activator is about 1:7 to about 1:36 and (ii) the C(max) plasma concentration ratio of the muscarinic acetylcholine receptor inhibitor to the muscarinic receptor activator is about 1:11 to about 1:44 over the 24-hour period after administration. In some aspects, (i) the AUC plasma ratio of the muscarinic acetylcholine receptor inhibitor to the muscarinic receptor activator is about 1:8 to about 1:35 and (ii) the C(max) plasma concentration ratio of the muscarinic acetylcholine receptor inhibitor to the muscarinic receptor activator is about 1:12 to about 1:43 over the 24-hour period after administration. In some aspects, (i) the AUC plasma ratio of the muscarinic acetylcholine receptor inhibitor to the muscarinic receptor activator is about 1:9 to about 1:33 and (ii) the C(max) plasma concentration ratio of the muscarinic acetylcholine receptor inhibitor to the muscarinic receptor activator is about 1:13 to about 1:42 over the 24-hour period after administration. In some aspects, (i) the AUC plasma ratio of the muscarinic acetylcholine receptor inhibitor to the muscarinic receptor activator is about 1:10 to about 1:32 and (ii) the C(max) plasma concentration ratio of the muscarinic acetylcholine receptor inhibitor to the muscarinic receptor activator is about 1:14 to about 1:41 over the 24-hour period after administration. In some aspects, (i) the AUC plasma ratio of the muscarinic acetylcholine receptor inhibitor to the muscarinic receptor activator is about 1:11 to about 1:31 and (ii) the C(max) plasma concentration ratio of the muscarinic acetylcholine receptor inhibitor to the muscarinic receptor activator is about 1:15 to about 1:40 over the 24-hour period after administration. In some aspects, (i) the AUC plasma ratio of the muscarinic acetylcholine receptor inhibitor to the muscarinic receptor activator is about 1:12 to about 1:29 and (ii) the C(max) plasma concentration ratio of the muscarinic acetylcholine receptor inhibitor to the muscarinic receptor activator is about 1:16 to about 1:39 over the 24-hour period after administration. In some aspects, (i) the AUC plasma ratio of the muscarinic acetylcholine receptor inhibitor to the muscarinic receptor activator is about 1:13 to about 1:28 and (ii) the C(max) plasma concentration ratio of the muscarinic acetylcholine receptor inhibitor to the muscarinic receptor activator is about 1:17 to about 1:38 over the 24-hour period after administration. In some aspects, (i) the AUC plasma ratio of the muscarinic acetylcholine receptor inhibitor to the muscarinic receptor activator is about 1:14 to about 1:27 and (ii) the C(max) plasma concentration ratio of the muscarinic acetylcholine receptor inhibitor to the muscarinic receptor activator is about 1:18 to about 1:37 over the 24-hour period after administration. In some aspects, (i) the AUC plasma ratio of the muscarinic acetylcholine receptor inhibitor to the muscarinic receptor activator is about 1:15 to about 1:26 and (ii) the C(max) plasma concentration ratio of the muscarinic acetylcholine receptor inhibitor to the muscarinic receptor activator is about 1:19 to about 1:36 over the 24-hour period after administration. In some aspects, (i) the AUC plasma ratio of the muscarinic acetylcholine receptor inhibitor to the muscarinic receptor activator is about 1:16 to about 1:25 and (ii) the C(max) plasma concentration ratio of the muscarinic acetylcholine receptor inhibitor to the muscarinic receptor activator is about 1:20 to about 1:35 over the 24-hour period after administration. In some aspects, (i) the AUC plasma ratio of the muscarinic acetylcholine receptor inhibitor to the muscarinic receptor activator is about 1:17 to about 1:24 and (ii) the C(max) plasma concentration ratio of the muscarinic acetylcholine receptor inhibitor to the muscarinic receptor activator is about 1:21 to about 1:34 over the 24-hour period after administration. In some aspects, (i) the AUC plasma ratio of the muscarinic acetylcholine receptor inhibitor to the muscarinic receptor activator is about 1:18 to about 1:23 and (ii) the C(max) plasma concentration ratio of the muscarinic acetylcholine receptor inhibitor to the muscarinic receptor activator is about 1:22 to about 1:33 over the 24-hour period after administration. In some aspects, (i) the AUC plasma ratio of the muscarinic acetylcholine receptor inhibitor to the muscarinic receptor activator is about 1:19 to about 1:22 and (ii) the C(max) plasma concentration ratio of the muscarinic acetylcholine receptor inhibitor to the muscarinic receptor activator is about 1:23 to about 1:32 over the 24-hour period after administration. In some aspects, (i) the AUC plasma ratio of the muscarinic acetylcholine receptor inhibitor to the muscarinic receptor activator is about 1:20 to about 1:21 and (ii) the C(max) plasma concentration ratio of the muscarinic acetylcholine receptor inhibitor to the muscarinic receptor activator is about 1:24 to about 1:31 over the 24-hour period after administration. In some aspects, (i) the AUC plasma ratio of the muscarinic acetylcholine receptor inhibitor to the muscarinic receptor activator is about 1:15 to about 1:21 and (ii) the C(max) plasma concentration ratio of the muscarinic acetylcholine receptor inhibitor to the muscarinic receptor activator is about 1:25 to about 1:30 over the 24-hour period after administration. In some aspects, (i) the AUC plasma ratio of the muscarinic acetylcholine receptor inhibitor to the muscarinic receptor activator is about 1:16 to about 1:20 and (ii) the C(max) plasma concentration ratio of the muscarinic acetylcholine receptor inhibitor to the muscarinic receptor activator is about 1:26 to about 1:29 over the 24-hour period after administration. In some aspects, (i) the AUC plasma ratio of the muscarinic acetylcholine receptor inhibitor to the muscarinic receptor activator is about 1:17 to about 1:18 and (ii) the C(max) plasma concentration ratio of the muscarinic acetylcholine receptor inhibitor to the muscarinic receptor activator is about 1:27 to about 1:28 over the 24-hour period after administration. In some aspects, (i) the AUC plasma ratio of the muscarinic acetylcholine receptor inhibitor to the muscarinic receptor activator is about 1:16 to about 1:20 and (ii) the C(max) plasma concentration ratio of the muscarinic acetylcholine receptor inhibitor to the muscarinic receptor activator is about 1:8 to about 1:11 over the 24-hour period after administration. In some aspects, (i) the AUC plasma ratio of the muscarinic acetylcholine receptor inhibitor to the muscarinic receptor activator is about 1:17 to about 1:18 and (ii) the C(max) plasma concentration ratio of the muscarinic acetylcholine receptor inhibitor to the muscarinic receptor activator is about 1:9 to about 1:10 over the 24-hour period after administration.

In some aspects, the C(max) plasma ratio of the muscarinic acetylcholine receptor inhibitor to the muscarinic receptor activator is about 1:1 to about 1:20 over the 24-hour period after administration. In some aspects, the C(max) plasma ratio of the muscarinic acetylcholine receptor inhibitor to the muscarinic receptor activator is about 1:2 to about 1:19 over the 24-hour period after administration. In some aspects, the C(max) plasma ratio of the muscarinic acetylcholine receptor inhibitor to the muscarinic receptor activator is about 1:3 to about 1:18 over the 24-hour period after administration. In some aspects, the C(max) plasma ratio of the muscarinic acetylcholine receptor inhibitor to the muscarinic receptor activator is about 1:4 to about 1:17 over the 24-hour period after administration. In some aspects, the C(max) plasma ratio of the muscarinic acetylcholine receptor inhibitor to the muscarinic receptor activator is about 1:5 to about 1:16 over the 24-hour period after administration.

In some aspects, the C(max) plasma ratio of the muscarinic acetylcholine receptor inhibitor to the muscarinic receptor activator is about 1:6 to about 1:15 over the 24-hour period after administration. In some aspects, the C(max) plasma ratio of the muscarinic acetylcholine receptor inhibitor to the muscarinic receptor activator is about 1:7 to about 1:14 over the 24-hour period after administration. In some aspects, the C(max) plasma ratio of the muscarinic acetylcholine receptor inhibitor to the muscarinic receptor activator is about 1:8 to about 1:13 over the 24-hour period after administration. In some aspects, the C(max) plasma ratio of the muscarinic acetylcholine receptor inhibitor to the muscarinic receptor activator is about 1:9 to about 1:12 over the 24-hour period after administration. In some aspects, the C(max) plasma ratio of the muscarinic acetylcholine receptor inhibitor to the muscarinic receptor activator is about 1:10 to about 1:11 over the 24-hour period after administration. In some aspects, the C(max) plasma ratio of the muscarinic acetylcholine receptor inhibitor to the muscarinic receptor activator is about 1:9 to about 1:11 over the 24-hour period after administration.

In some aspects, the area under the curve (AUC) plasma ratio of the muscarinic acetylcholine receptor inhibitor to the muscarinic receptor activator is about 1:1 to about 1:38 over the 24-hour period after administration. In some aspects, the area under the curve (AUC) plasma ratio of the muscarinic acetylcholine receptor inhibitor to the muscarinic receptor activator is about 1:2 to about 1:37 over the 24-hour period after administration. In some aspects, the area under the curve (AUC) plasma ratio of the muscarinic acetylcholine receptor inhibitor to the muscarinic receptor activator is about 1:3 to about 1:36 over the 24-hour period after administration. In some aspects, the area under the curve (AUC) plasma ratio of the muscarinic acetylcholine receptor inhibitor to the muscarinic receptor activator is about 1:4 to about 1:35 over the 24-hour period after administration. In some aspects, the area under the curve (AUC) plasma ratio of the muscarinic acetylcholine receptor inhibitor to the muscarinic receptor activator is about 1:5 to about 1:34 over the 24-hour period after administration. In some aspects, the area under the curve (AUC) plasma ratio of the muscarinic acetylcholine receptor inhibitor to the muscarinic receptor activator is about 1:6 to about 1:33 over the 24-hour period after administration. In some aspects, the area under the curve (AUC) plasma ratio of the muscarinic acetylcholine receptor inhibitor to the muscarinic receptor activator is about 1:7 to about 1:32 over the 24-hour period after administration. In some aspects, the area under the curve (AUC) plasma ratio of the muscarinic acetylcholine receptor inhibitor to the muscarinic receptor activator is about 1:8 to about 1:31 over the 24-hour period after administration. In some aspects, the area under the curve (AUC) plasma ratio of the muscarinic acetylcholine receptor inhibitor to the muscarinic receptor activator is about 1:9 to about 1:30 over the 24-hour period after administration. In some aspects, the area under the curve (AUC) plasma ratio of the muscarinic acetylcholine receptor inhibitor to the muscarinic receptor activator is about 1:10 to about 1:29 over the 24-hour period after administration. In some aspects, the area under the curve (AUC) plasma ratio of the muscarinic acetylcholine receptor inhibitor to the muscarinic receptor activator is about 1:11 to about 1:28 over the 24-hour period after administration. In some aspects, the area under the curve (AUC) plasma ratio of the muscarinic acetylcholine receptor inhibitor to the muscarinic receptor activator is about 1:12 to about 1:27 over the 24-hour period after administration. In some aspects, the area under the curve (AUC) plasma ratio of the muscarinic acetylcholine receptor inhibitor to the muscarinic receptor activator is about 1:13 to about 1:26 over the 24-hour period after administration. In some aspects, the area under the curve (AUC) plasma ratio of the muscarinic acetylcholine receptor inhibitor to the muscarinic receptor activator is about 1:14 to about 1:25 over the 24-hour period after administration. In some aspects, the area under the curve (AUC) plasma ratio of the muscarinic acetylcholine receptor inhibitor to the muscarinic receptor activator is about 1:15 to about 1:24 over the 24-hour period after administration. In some aspects, the area under the curve (AUC) plasma ratio of the muscarinic acetylcholine receptor inhibitor to the muscarinic receptor activator is about 1:16 to about 1:23 over the 24-hour period after administration. In some aspects, the area under the curve (AUC) plasma ratio of the muscarinic acetylcholine receptor inhibitor to the muscarinic receptor activator is about 1:17 to about 1:22 over the 24-hour period after administration. In some aspects, the area under the curve (AUC) plasma ratio of the muscarinic acetylcholine receptor inhibitor to the muscarinic receptor activator is about 1:18 to about 1:21 over the 24-hour period after administration. In some aspects, the area under the curve (AUC) plasma ratio of the muscarinic acetylcholine receptor inhibitor to the muscarinic receptor activator is about 1:14 to about 1:22 over the 24-hour period after administration. In some aspects, the area under the curve (AUC) plasma ratio of the muscarinic acetylcholine receptor inhibitor to the muscarinic receptor activator is about 1:15 to about 1:21 over the 24-hour period after administration. In some aspects, the area under the curve (AUC) plasma ratio of the muscarinic acetylcholine receptor inhibitor to the muscarinic receptor activator is about 1:16 to about 1:20 over the 24-hour period after administration. In some aspects, the area under the curve (AUC) plasma ratio of the muscarinic acetylcholine receptor inhibitor to the muscarinic receptor activator is about 1:17 to about 1:19 over the 24-hour period after administration. In some aspects, the area under the curve (AUC) plasma ratio of the muscarinic acetylcholine receptor inhibitor to the muscarinic receptor activator is about 1:17 to about 1:20 over the 24-hour period after administration.

In some aspects, the AUC plasma ratio of the muscarinic acetylcholine receptor inhibitor to the muscarinic receptor activator is about 1:1 over the 24-hour period after administration. In some aspects, the AUC plasma ratio of the muscarinic acetylcholine receptor inhibitor to the muscarinic receptor activator is about 1:2 over the 24-hour period after administration. In some aspects, the AUC plasma ratio of the muscarinic acetylcholine receptor inhibitor to the muscarinic receptor activator is about 1:3 over the 24-hour period after administration. In some aspects, the AUC plasma ratio of the muscarinic acetylcholine receptor inhibitor to the muscarinic receptor activator is about 1:4 over the 24-hour period after administration. In some aspects, the AUC plasma ratio of the muscarinic acetylcholine receptor inhibitor to the muscarinic receptor activator is about 1:5 over the 24-hour period after administration. In some aspects, the AUC plasma ratio of the muscarinic acetylcholine receptor inhibitor to the muscarinic receptor activator is about 1:6 over the 24-hour period after administration. In some aspects, the AUC plasma ratio of the muscarinic acetylcholine receptor inhibitor to the muscarinic receptor activator is about 1:7 over the 24-hour period after administration. In some aspects, the AUC plasma ratio of the muscarinic acetylcholine receptor inhibitor to the muscarinic receptor activator is about 1:8 over the 24-hour period after administration. In some aspects, the AUC plasma ratio of the muscarinic acetylcholine receptor inhibitor to the muscarinic receptor activator is about 1:9 over the 24-hour period after administration. In some aspects, the AUC plasma ratio of the muscarinic acetylcholine receptor inhibitor to the muscarinic receptor activator is about 1:10 over the 24-hour period after administration. In some aspects, the AUC plasma ratio of the muscarinic acetylcholine receptor inhibitor to the muscarinic receptor activator is about 1:11 over the 24-hour period after administration. In some aspects, the AUC plasma ratio of the muscarinic acetylcholine receptor inhibitor to the muscarinic receptor activator is about 1:12 over the 24-hour period after administration. In some aspects, the AUC plasma ratio of the muscarinic acetylcholine receptor inhibitor to the muscarinic receptor activator is about 1:13 over the 24-hour period after administration. In some aspects, the AUC plasma ratio of the muscarinic acetylcholine receptor inhibitor to the muscarinic receptor activator is about 1:14 over the 24-hour period after administration. In some aspects, the AUC plasma ratio of the muscarinic acetylcholine receptor inhibitor to the muscarinic receptor activator is about 1:15 over the 24-hour period after administration. In some aspects, the AUC plasma ratio of the muscarinic acetylcholine receptor inhibitor to the muscarinic receptor activator is about 1:16 over the 24-hour period after administration. In some aspects, the AUC plasma ratio of the muscarinic acetylcholine receptor inhibitor to the muscarinic receptor activator is about 1:17 over the 24-hour period after administration. In some aspects, the AUC plasma ratio of the muscarinic acetylcholine receptor inhibitor to the muscarinic receptor activator is about 1:18 over the 24-hour period after administration. In some aspects, the AUC plasma ratio of the muscarinic acetylcholine receptor inhibitor to the muscarinic receptor activator is about 1:19 over the 24-hour period after administration. In some aspects, the AUC plasma ratio of the muscarinic acetylcholine receptor inhibitor to the muscarinic receptor activator is about 1:20 over the 24-hour period after administration. In some aspects, the AUC plasma ratio of the muscarinic acetylcholine receptor inhibitor to the muscarinic receptor activator is about 1:21 over the 24-hour period after administration. In some aspects, the AUC plasma ratio of the muscarinic acetylcholine receptor inhibitor to the muscarinic receptor activator is about 1:22 over the 24-hour period after administration. In some aspects, the AUC plasma ratio of the muscarinic acetylcholine receptor inhibitor to the muscarinic receptor activator is about 1:23 over the 24-hour period after administration. In some aspects, the AUC plasma ratio of the muscarinic acetylcholine receptor inhibitor to the muscarinic receptor activator is about 1:24 over the 24-hour period after administration. In some aspects, the AUC plasma ratio of the muscarinic acetylcholine receptor inhibitor to the muscarinic receptor activator is about 1:25 over the 24-hour period after administration. In some aspects, the AUC plasma ratio of the muscarinic acetylcholine receptor inhibitor to the muscarinic receptor activator is about 1:26 over the 24-hour period after administration. In some aspects, the AUC plasma ratio of the muscarinic acetylcholine receptor inhibitor to the muscarinic receptor activator is about 1:27 over the 24-hour period after administration. In some aspects, the AUC plasma ratio of the muscarinic acetylcholine receptor inhibitor to the muscarinic receptor activator is about 1:28 over the 24-hour period after administration. In some aspects, the AUC plasma ratio of the muscarinic acetylcholine receptor inhibitor to the muscarinic receptor activator is about 1:29 over the 24-hour period after administration. In some aspects, the AUC plasma ratio of the muscarinic acetylcholine receptor inhibitor to the muscarinic receptor activator is about 1:30 over the 24-hour period after administration. In some aspects, the AUC plasma ratio of the muscarinic acetylcholine receptor inhibitor to the muscarinic receptor activator is about 1:31 over the 24-hour period after administration. In some aspects, the AUC plasma ratio of the muscarinic acetylcholine receptor inhibitor to the muscarinic receptor activator is about 1:31 over the 24-hour period after administration. In some aspects, the AUC plasma ratio of the muscarinic acetylcholine receptor inhibitor to the muscarinic receptor activator is about 1:32 over the 24-hour period after administration. In some aspects, the AUC plasma ratio of the muscarinic acetylcholine receptor inhibitor to the muscarinic receptor activator is about 1:33 over the 24-hour period after administration. In some aspects, the AUC plasma ratio of the muscarinic acetylcholine receptor inhibitor to the muscarinic receptor activator is about 1:34 over the 24-hour period after administration. In some aspects, the AUC plasma ratio of the muscarinic acetylcholine receptor inhibitor to the muscarinic receptor activator is about 1:35 over the 24-hour period after administration. In some aspects, the AUC plasma ratio of the muscarinic acetylcholine receptor inhibitor to the muscarinic receptor activator is about 1:36 over the 24-hour period after administration. In some aspects, the AUC plasma ratio of the muscarinic acetylcholine receptor inhibitor to the muscarinic receptor activator is about 1:37 over the 24-hour period after administration. In some aspects, the AUC plasma ratio of the muscarinic acetylcholine receptor inhibitor to the muscarinic receptor activator is about 1:38 over the 24-hour period after administration. In some aspects, the AUC plasma ratio of the muscarinic acetylcholine receptor inhibitor to the muscarinic receptor activator is about 1:39 over the 24-hour period after administration. In some aspects, the AUC plasma ratio of the muscarinic acetylcholine receptor inhibitor to the muscarinic receptor activator is about 1:40 over the 24-hour period after administration.

In some aspects, the C(max) plasma ratio of the muscarinic acetylcholine receptor inhibitor to the muscarinic receptor activator is about 1:1 over the 24-hour period after administration. In some aspects, the C(max) plasma ratio of the muscarinic acetylcholine receptor inhibitor to the muscarinic receptor activator is about 1:2 over the 24-hour period after administration. In some aspects, the C(max) plasma ratio of the muscarinic acetylcholine receptor inhibitor to the muscarinic receptor activator is about 1:3 over the 24-hour period after administration. In some aspects, the C(max) plasma ratio of the muscarinic acetylcholine receptor inhibitor to the muscarinic receptor activator is about 1:4 over the 24-hour period after administration. In some aspects, the C(max) plasma ratio of the muscarinic acetylcholine receptor inhibitor to the muscarinic receptor activator is about 1:5 over the 24-hour period after administration. In some aspects, the C(max) plasma ratio of the muscarinic acetylcholine receptor inhibitor to the muscarinic receptor activator is about 1:6 over the 24-hour period after administration. In some aspects, the C(max) plasma ratio of the muscarinic acetylcholine receptor inhibitor to the muscarinic receptor activator is about 1:7 over the 24-hour period after administration. In some aspects, the C(max) plasma ratio of the muscarinic acetylcholine receptor inhibitor to the muscarinic receptor activator is about 1:8 over the 24-hour period after administration. In some aspects, the C(max) plasma ratio of the muscarinic acetylcholine receptor inhibitor to the muscarinic receptor activator is about 1:9 over the 24-hour period after administration. In some aspects, the C(max) plasma ratio of the muscarinic acetylcholine receptor inhibitor to the muscarinic receptor activator is about 1:10 over the 24-hour period after administration. In some aspects, the C(max) plasma ratio of the muscarinic acetylcholine receptor inhibitor to the muscarinic receptor activator is about 1:11 over the 24-hour period after administration. In some aspects, the C(max) plasma ratio of the muscarinic acetylcholine receptor inhibitor to the muscarinic receptor activator is about 1:12 over the 24-hour period after administration. In some aspects, the C(max) plasma ratio of the muscarinic acetylcholine receptor inhibitor to the muscarinic receptor activator is about 1:13 over the 24-hour period after administration. In some aspects, the C(max) plasma ratio of the muscarinic acetylcholine receptor inhibitor to the muscarinic receptor activator is about 1:14 over the 24-hour period after administration. In some aspects, the C(max) plasma ratio of the muscarinic acetylcholine receptor inhibitor to the muscarinic receptor activator is about 1:15 over the 24-hour period after administration. In some aspects, the C(max) plasma ratio of the muscarinic acetylcholine receptor inhibitor to the muscarinic receptor activator is about 1:16 over the 24-hour period after administration. In some aspects, the C(max) plasma ratio of the muscarinic acetylcholine receptor inhibitor to the muscarinic receptor activator is about 1:17 over the 24-hour period after administration. In some aspects, the C(max) plasma ratio of the muscarinic acetylcholine receptor inhibitor to the muscarinic receptor activator is about 1:18 over the 24-hour period after administration. In some aspects, the C(max) plasma ratio of the muscarinic acetylcholine receptor inhibitor to the muscarinic receptor activator is about 1:19 over the 24-hour period after administration. In some aspects, the C(max) plasma ratio of the muscarinic acetylcholine receptor inhibitor to the muscarinic receptor activator is about 1:20 over the 24-hour period after administration.

In some aspects, the muscarinic acetylcholine receptor activator is selected from acetylcholine, A 72055, AF 125, AF 150 (S), AF 185, Alvameline, Amifostine, Arecoline, bethanechol, carbachol, Cevimeline, CI 1017, CMI 1145, CMI 936, CS 932, DM 71, FPL 14995, GSK 1034702, Himbacine, Itameline, KST 2818, KSI 5410, KST 5452, L 670548, L 689660, L 696986, L 705106, LY 316108, MCD 386, methacholine, Milameline, NC 111585, Nebracetam, NGX 267, Norclozapine, ORG 20091, PD 141606, PD 142505, PD 151832, PDC 008004, Pilocarpine, PTAC, RU 35963, Sabcomeline, SDZ 210086, SR 46559A, SR 96777A, Stacofylline, Talsaclidine, Tazomeline, Thiopilocarpine, Ticalopride, U 80816, Vedadidine, WAY 131256, WAY 132983, Xanomeline, YM 796, or YM 954, or a pharmaceutically acceptable salt thereof.

In some aspects, the muscarinic acetylcholine receptor activator is acetylcholine, methacholine, carbachol, pilocarpine, cevimeline, or bethanechol, or a pharmaceutically acceptable salt thereof.

In some aspects, the muscarinic acetylcholine receptor activator is bethanechol or a pharmaceutically acceptable salt thereof. In some aspects, the muscarinic acetylcholine receptor activator is bethanechol. In some aspects, the muscarinic acetylcholine receptor activator is bethanechol salt. In some aspects, the muscarinic acetylcholine receptor activator is bethanechol chloride.

In some aspects, the muscarinic acetylcholine receptor activator is racemic bethanechol or a pharmaceutically acceptable salt thereof. In some aspects, the muscarinic acetylcholine receptor activator is racemic bethanechol. In some aspects, the muscarinic acetylcholine receptor activator is racemic bethanechol chloride.

In some aspects, the muscarinic acetylcholine receptor activator is (S)-bethanechol or a pharmaceutically acceptable salt thereof. In some aspects, the muscarinic acetylcholine receptor activator is (S)-bethanechol. In some aspects, the muscarinic acetylcholine receptor activator is (S)-bethanechol salt. In some aspects, the muscarinic acetylcholine receptor activator is (S)-bethanechol chloride.

In some aspects, the muscarinic acetylcholine receptor activator is (S)-bethanechol having a stereochemical purity of at least 90% enantiomeric excess, or a pharmaceutically acceptable salt thereof. In some aspects, the muscarinic acetylcholine receptor activator is (S)-bethanechol having a stereochemical purity of at least 95% enantiomeric excess, or a pharmaceutically acceptable salt thereof. In some aspects, the muscarinic acetylcholine receptor activator is (S)-bethanechol having a stereochemical purity of at least 98% enantiomeric excess, or a pharmaceutically acceptable salt thereof. In some aspects, the muscarinic acetylcholine receptor activator is (S)-bethanechol having a stereochemical purity of at least 99% enantiomeric excess, or a pharmaceutically acceptable salt thereof.

In some aspects, the muscarinic acetylcholine receptor activator is a (S)-bethanechol salt having a stereochemical purity of at least 90% enantiomeric excess. In some aspects, the muscarinic acetylcholine receptor activator is a (S)-bethanechol salt having a stereochemical purity of at least 95% enantiomeric excess. In some aspects, the muscarinic acetylcholine receptor activator is a (S)-bethanechol salt having a stereochemical purity of at least 98% enantiomeric excess. In some aspects, the muscarinic acetylcholine receptor activator is a (S)-bethanechol salt having a stereochemical purity of at least 99% enantiomeric excess.

In some aspects, the muscarinic acetylcholine receptor activator is a (S)-bethanechol chloride having a stereochemical purity of at least 90% enantiomeric excess. In some aspects, the muscarinic acetylcholine receptor activator is a (S)-bethanechol chloride having a stereochemical purity of at least 95% enantiomeric excess. In some aspects, the muscarinic acetylcholine receptor activator is a (S)-bethanechol chloride having a stereochemical purity of at least 98% enantiomeric excess. In some aspects, the muscarinic acetylcholine receptor activator is a (S)-bethanechol chloride having a stereochemical purity of at least 99% enantiomeric excess.

In some aspects, (a) the muscarinic acetylcholine receptor activator is racemic bethanechol or a pharmaceutically acceptable salt thereof and (b) the muscarinic acetylcholine receptor inhibitor is (R)-trihexyphenidyl having a stereochemical purity of at least 90% enantiomeric excess, or a pharmaceutically acceptable salt thereof. In some aspects, (a) the muscarinic acetylcholine receptor activator is racemic bethanechol or a pharmaceutically acceptable salt thereof and (b) the muscarinic acetylcholine receptor inhibitor is (R)-trihexyphenidyl having a stereochemical purity of at least 95% enantiomeric excess, or a pharmaceutically acceptable salt thereof. In some aspects, (a) the muscarinic acetylcholine receptor activator is racemic bethanechol or a pharmaceutically acceptable salt thereof and (b) the muscarinic acetylcholine receptor inhibitor is (R)-trihexyphenidyl having a stereochemical purity of at least 96% enantiomeric excess, or a pharmaceutically acceptable salt thereof. In some aspects, (a) the muscarinic acetylcholine receptor activator is racemic bethanechol or a pharmaceutically acceptable salt thereof and (b) the muscarinic acetylcholine receptor inhibitor is (R)-trihexyphenidyl having a stereochemical purity of at least 99% enantiomeric excess, or a pharmaceutically acceptable salt thereof.

Administration Features

The method may be characterized by administration features. For example, in some aspects, the muscarinic acetylcholine receptor inhibitor and the muscarinic acetylcholine receptor activator are administered simultaneously to the patient. In some aspects, the muscarinic acetylcholine receptor inhibitor and the muscarinic acetylcholine receptor activator are each present in a single pharmaceutical composition that is administered to the patient.

In some aspects, the trihexyphenidyl or pharmaceutically acceptable salt thereof and the bethanechol or pharmaceutically acceptable salt thereof are each present in a single pharmaceutical composition that is administered to the patient. In some aspects, the racemic trihexyphenidyl or pharmaceutically acceptable salt thereof and the racemic bethanechol or pharmaceutically acceptable salt thereof are each present in a single pharmaceutical composition that is administered to the patient. In some aspects, the (R)-trihexyphenidyl or pharmaceutically acceptable salt thereof and the racemic bethanechol or pharmaceutically acceptable salt thereof are each present in a single pharmaceutical composition that is administered to the patient. In some aspect, the (R)-trihexyphenidyl or pharmaceutically acceptable salt thereof and the (S)-bethanechol or pharmaceutically acceptable salt thereof are each present in a single pharmaceutical composition that is administered to the patient. In some aspects, the muscarinic acetylcholine receptor inhibitor and the muscarinic acetylcholine receptor activator are each present in a single pharmaceutical composition that is administered to the patient. In some aspects, the muscarinic acetylcholine receptor inhibitor and a second therapeutic agent selected from a muscarinic acetylcholine receptor activator, a procholinergic agent, and an acetylcholinesterase inhibitor are each present in a single pharmaceutical composition that is administered to the patient.

In some aspects, the trihexyphenidyl or pharmaceutically acceptable salt thereof and the bethanechol or pharmaceutically acceptable salt thereof are each in different formulations. In some aspects, the racemic trihexyphenidyl or pharmaceutically acceptable salt thereof and the racemic bethanechol or pharmaceutically acceptable salt thereof are each in different formulations. In some aspects, the (R)-trihexyphenidyl or pharmaceutically acceptable salt thereof and the racemic bethanechol or pharmaceutically acceptable salt thereof are each in different formulations. In some aspect, the (R)-trihexyphenidyl or pharmaceutically acceptable salt thereof and the (S)-bethanechol or pharmaceutically acceptable salt thereof are each in different formulations. In some aspects, the muscarinic acetylcholine receptor inhibitor and the muscarinic acetylcholine receptor activator are each in different formulations. In some aspects, the muscarinic acetylcholine receptor inhibitor and a second therapeutic agent selected from a muscarinic acetylcholine receptor activator, a procholinergic agent, and an acetylcholinesterase inhibitor are each in different formulations.

In some aspects, the trihexyphenidyl or pharmaceutically acceptable salt thereof and the bethanechol or pharmaceutically acceptable salt thereof are each in different formulations, and are present in a single pharmaceutical composition that is administered to the patient. In some aspects, the racemic trihexyphenidyl or pharmaceutically acceptable salt thereof and the racemic bethanechol or pharmaceutically acceptable salt thereof are each in different formulations and are present in a single pharmaceutical composition that is administered to the patient. In some aspects, the (R)-trihexyphenidyl or pharmaceutically acceptable salt thereof and the racemic bethanechol or pharmaceutically acceptable salt thereof are each in different formulations and are present in a single pharmaceutical composition that is administered to the patient. In some aspect, the (R)-trihexyphenidyl or pharmaceutically acceptable salt thereof and the (S)-bethanechol or pharmaceutically acceptable salt thereof are each in different formulations and are present in a single pharmaceutical composition that is administered to the patient. In some aspects, the muscarinic acetylcholine receptor inhibitor and the muscarinic acetylcholine receptor activator are each in different formulations and are present in a single pharmaceutical composition that is administered to the patient. In some aspects, the muscarinic acetylcholine receptor inhibitor and a second therapeutic agent selected from a muscarinic acetylcholine receptor activator, a procholinergic agent, and an acetylcholinesterase inhibitor are each in different formulations and are present in a single pharmaceutical composition that is administered to the patient.

In some aspects, the pharmaceutical composition is in the form of a tablet, a bilayer tablet, troche, liquid, drop, capsule, caplet, gel cap, sublingual formulation, or spray. In some aspects, the pharmaceutical composition is in the form of a tablet, troche, capsule, caplet, or gel cap.

As used herein, an "immediate release formulation" refers to a formulation that is absorbed quickly after it enters the bloodstream. In some aspects, the pharmaceutical composition is an immediate release formulation. As used herein, a "controlled release formulation" refers to a formulation that prolongs the effect and plasma and/or serum exposure of the formulation in the body. In some aspects, the pharmaceutical composition is a controlled release formulation. In some aspects, the pharmaceutical composition comprises (i) a controlled release component containing the muscarinic acetylcholine receptor inhibitor and (ii) an immediate release component containing the muscarinic acetylcholine receptor activator. In some aspects, the pharmaceutical composition comprises (i) a controlled release component containing the muscarinic acetylcholine receptor activator and (ii) an immediate release component containing the muscarinic acetylcholine receptor inhibitor. In some aspects, the pharmaceutical composition comprises (i) a controlled release component containing the muscarinic acetylcholine receptor activator and (ii) a controlled release component containing the muscarinic acetylcholine receptor inhibitor.

In some aspects, the pharmaceutical composition comprises (i) a controlled release component containing the trihexyphenidyl or pharmaceutically acceptable salt thereof and (ii) an immediate release component containing the bethanechol or pharmaceutically acceptable salt thereof. In some aspects, the pharmaceutical composition comprises (i) a controlled release component containing the racemic-trihexyphenidyl or pharmaceutically acceptable salt thereof and (ii) an immediate release component containing the racemic-bethanechol or pharmaceutically acceptable salt thereof. In some aspects, pharmaceutical composition comprises (i) a controlled release component containing the (R)-trihexyphenidyl or pharmaceutically acceptable salt thereof and (ii) an immediate release component containing the racemic-bethanechol or pharmaceutically acceptable salt thereof. In some aspects, the pharmaceutical composition comprises (i) a controlled release component containing the (R)-trihexyphenidyl or pharmaceutically acceptable salt thereof and (ii) an immediate release component containing the (S)-bethanechol or pharmaceutically acceptable salt thereof.

In some aspects, the pharmaceutical composition comprises (i) a controlled release component containing the trihexyphenidyl or pharmaceutically acceptable salt thereof and (ii) a controlled release component containing the bethanechol or pharmaceutically acceptable salt thereof. In some aspects, the pharmaceutical composition comprises (i) a controlled release component containing the racemic-trihexyphenidyl or pharmaceutically acceptable salt thereof and (ii) a controlled release component containing the racemic-bethanechol or pharmaceutically acceptable salt thereof. In some aspects, pharmaceutical composition comprises (i) a controlled release component containing the (R)-trihexyphenidyl or pharmaceutically acceptable salt thereof and (ii) a controlled release component containing the racemic-bethanechol or pharmaceutically acceptable salt thereof. In some aspects, the pharmaceutical composition comprises (i) a controlled release component containing the (R)-trihexyphenidyl or pharmaceutically acceptable salt thereof and (ii) a controlled release component containing the (S)-bethanechol or pharmaceutically acceptable salt thereof. In some aspects, the pharmaceutical composition comprises (i) a controlled release component containing the racemic-trihexyphenidyl or pharmaceutically acceptable salt thereof and (ii) a controlled release component containing the (S)-bethanechol or pharmaceutically acceptable salt thereof.

In some aspects, the pharmaceutical composition comprises (i) an immediate release component containing the trihexyphenidyl or pharmaceutically acceptable salt thereof and (ii) a controlled release component containing the bethanechol or pharmaceutically acceptable salt thereof. In some aspects, the pharmaceutical composition comprises (i) an immediate release component containing the racemic-trihexyphenidyl or pharmaceutically acceptable salt thereof and (ii) a controlled release component containing the racemic-bethanechol or pharmaceutically acceptable salt thereof. In some aspects, pharmaceutical composition comprises (i) an immediate release component containing the (R)-trihexyphenidyl or pharmaceutically acceptable salt thereof and (ii) a controlled release component containing the racemic-bethanechol or pharmaceutically acceptable salt thereof. In some aspects, the pharmaceutical composition comprises (i) an immediate release component containing the (R)-trihexyphenidyl or pharmaceutically acceptable salt thereof and (ii) a controlled release component containing the (S)-bethanechol or pharmaceutically acceptable salt thereof. In some aspects, the pharmaceutical composition comprises (i) an immediate release component containing the racemic-trihexyphenidyl or pharmaceutically acceptable salt thereof and (ii) a controlled release component containing the (S)-bethanechol or pharmaceutically acceptable salt thereof.

In some aspects, the pharmaceutical composition comprises (i) an immediate release component containing the trihexyphenidyl or pharmaceutically acceptable salt thereof and (ii) an immediate release component containing the bethanechol or pharmaceutically acceptable salt thereof. In some aspects, the pharmaceutical composition comprises (i) an immediate release component containing the racemic-trihexyphenidyl or pharmaceutically acceptable salt thereof and (ii) an immediate release component containing the racemic-bethanechol or pharmaceutically acceptable salt thereof. In some aspects, pharmaceutical composition comprises (i) an immediate release component containing the (R)-trihexyphenidyl or pharmaceutically acceptable salt thereof and (ii) an immediate release component containing the racemic-bethanechol or pharmaceutically acceptable salt thereof. In some aspects, the pharmaceutical composition comprises (i) an immediate release component containing the (R)-trihexyphenidyl or pharmaceutically acceptable salt thereof and (ii) an immediate release component containing the (S)-bethanechol or pharmaceutically acceptable salt thereof. In some aspects, the pharmaceutical composition comprises (i) an immediate release component containing the racemic-trihexyphenidyl or pharmaceutically acceptable salt thereof and (ii) an immediate release component containing the (S)-bethanechol or pharmaceutically acceptable salt thereof.

In some aspects, the pharmaceutical composition is administered orally to the patient.

In some aspects, the pharmaceutical composition is administered daily. In some aspects, the pharmaceutical composition is administered twice per day. In some aspects, the pharmaceutical composition is administered three times per day. In some aspects, the pharmaceutical composition is administered once every two days. In some aspects, the pharmaceutical composition is administered once every three days. In some aspects, the pharmaceutical composition is administered once every four days. In some aspects, the pharmaceutical composition is administered once every five days. In some aspects, the pharmaceutical composition is administered once every six days. In some aspects, the pharmaceutical composition is administered once every seven days.

In some aspects, the pharmaceutical composition is an oral pharmaceutical composition.

Dosage

The method may be characterized by dosage features. For example, in some aspects, the muscarinic acetylcholine receptor inhibitor is orally administered at a dosage that, in the absence of a muscarinic acetylcholine receptor activator, causes at least one adverse side effect selected from dizziness, lightheadedness, headache, drowsiness, confusion, reduced concentration, reduced thinking, euphoria, elevated mood, hallucinations, agitation, irritability, sensory disturbances, blurry vision, impaired vision, increased intraocular pressure, dry eye, dry mouth, constipation, nausea, cramping, urinary retention, reduced urinary voiding, flushed skin, fever, reduced sweating, tachycardia, and cardiac arrhythmia. In some aspects, the muscarinic acetylcholine receptor inhibitor is orally administered at a dosage that, in the absence of a muscarinic acetylcholine receptor activator, causes at least two adverse side effect selected from dizziness, lightheadedness, headache, drowsiness, confusion, reduced concentration, reduced thinking, euphoria, elevated mood, hallucinations, agitation, irritability, sensory disturbances, blurry vision, impaired vision, increased intraocular pressure, dry eye, dry mouth, constipation, nausea, cramping, urinary retention, reduced urinary voiding, flushed skin, fever, reduced sweating, tachycardia, and cardiac arrhythmia. In some aspects, the muscarinic acetylcholine receptor inhibitor is orally administered at a dosage that, in the absence of a muscarinic acetylcholine receptor activator, causes at least three adverse side effect selected dizziness, lightheadedness, headache, drowsiness, confusion, reduced concentration, reduced thinking, euphoria, elevated mood, hallucinations, agitation, irritability, sensory disturbances, blurry vision, impaired vision, increased intraocular pressure, dry eye, dry mouth, constipation, nausea, cramping, urinary retention, reduced urinary voiding, flushed skin, fever, reduced sweating, tachycardia, and cardiac arrhythmia.

In some aspects, the muscarinic acetylcholine receptor inhibitor is orally administered at a dosage that, in the absence of a muscarinic acetylcholine receptor activator, causes at least one adverse side effect selected from dry mouth, dry eye, blurry vision, tachycardia, constipation, and urine retention. In some aspects, the muscarinic acetylcholine receptor inhibitor is orally administered at a dosage that, in the absence of a muscarinic acetylcholine receptor activator, causes at least one adverse side effect selected from, dry mouth, dry eye, tachycardia, blurred vision, constipation, and urine retention. In some aspects, the muscarinic acetylcholine receptor inhibitor is orally administered at a dosage that, in the absence of a muscarinic acetylcholine receptor activator, causes at least two adverse side effect selected, dry mouth, dry eye, tachycardia, blurred vision, constipation, and urine retention. In some aspects, the muscarinic acetylcholine receptor inhibitor is orally administered at a dosage that, in the absence of a muscarinic acetylcholine receptor activator, causes at least three adverse side effect selected, dry mouth, dry eye, tachycardia, blurred vision, constipation, and urine retention.

In some aspects, the muscarinic acetylcholine receptor inhibitor is orally administered at a dosage in the range of from about 10 mg to about 1000 mg. In some aspects, the muscarinic acetylcholine receptor inhibitor is orally administered at a dosage in the range of from about 1 mg to about 1000 mg. In some aspects, the muscarinic acetylcholine receptor inhibitor is orally administered at a dosage in the range of from about 5 mg to about 1000 mg. In some aspects, the muscarinic acetylcholine receptor inhibitor is orally administered at a dosage greater than 10 mg.

In some aspects, the muscarinic acetylcholine receptor activator is orally administered at a dosage in the range of from about 50 mg to about 1000 mg. In some aspects, the muscarinic acetylcholine receptor activator is orally administered at a dosage in the range of from about 1 mg to about 1000 mg. In some aspects, the muscarinic acetylcholine receptor activator is orally administered at a dosage in the range of from about 10 mg to about 1000 mg. In some aspects, the muscarinic acetylcholine receptor activator is orally administered at a dosage in the range of from about 20 mg to about 1000 mg. In some aspects, the muscarinic acetylcholine receptor activator is orally administered at a dosage greater than 50 mg.

In some aspects, use of the muscarinic acetylcholine receptor inhibitor in combination with the muscarinic acetylcholine receptor activator allows for using a higher initial dosage of muscarinic receptor inhibitor compared to administering the muscarinic receptor inhibitor alone. In some aspects, the muscarinic acetylcholine receptor inhibitor is orally administered at an initial dosage of greater than 1 mg/day. In some aspects, the muscarinic acetylcholine receptor inhibitor is orally administered at an initial dosage of greater than 2 mg/day. In some aspects, the muscarinic acetylcholine receptor inhibitor is orally administered at an initial dosage of greater than 5 mg/day. In some aspects, the muscarinic acetylcholine receptor inhibitor is orally administered at an initial dosage of greater than 10 mg/day.

Identity of the Movement Disorder

The methods may be characterized by identity of the movement disorder. For example, in some aspects, the movement disorder is dystonia. In some aspects, the movement disorder is primary dystonia, secondary dystonia, tardive dystonia, drug-induced dystonia, or cerebral palsy-associated dystonia. In some aspects, the movement disorder is primary dystonia. In some aspects, the movement disorder is secondary dystonia. In some aspects, the movement disorder is drug-induced dystonia. In some aspects, the movement disorder is cerebral palsy-associated dystonia.

In some aspects, the movement disorder is focal dystonia. In some aspects, the focal dystonia is cervical dystonia, blepharospasm, hand dystonia, writer's cramp, musician's dystonia, leg dystonia, or foot dystonia. In some aspects, the focal dystonia is cervical dystonia. In some aspects, the focal dystonia is blepharospasm. In some aspects, the focal dystonia is hand dystonia. In some aspects, the focal dystonia is writer's cramp. In some aspects, the focal dystonia is musician's dystonia. In some aspects, the focal dystonia is leg dystonia. In some aspects, the focal dystonia is foot dystonia.

In some aspects, the movement disorder is segmental dystonia, hemidystonia, multifocal dystonia, or generalized dystonia. In some aspects, the movement disorder is segmental dystonia or generalized dystonia. In some aspects, the movement disorder is segmental dystonia. In some aspects, the movement disorder is generalized dystonia. In some aspects, the movement disorder is hemidystonia. In some aspects, the movement disorder is multifocal dystonia.

In some aspects, the movement disorder is idiopathic in origin. In some aspects, the movement disorder is a genetic dystonia. In some aspects, the genetic dystonia is associated with mutations in one or more genes selected from TOR1A, THAP1, ANO3, GNAL, KMT2B, GCH1, SPR, TAF1, PRKRA, ATP1A3, SGCE, PNKD, PRRT2, SLC2A1, and ECHS1.

In some aspects, the movement disorder is Multiple System Atrophy, Progressive Supranuclear Palsy, or tremor. In some aspects, the movement disorder is Multiple System Atrophy. In some aspects, the movement disorder is Progressive Supranuclear Palsy. In some aspects, the movement disorder is tremor.

In some aspects, the movement disorder is Parkinson's disease, drug-induced Parkinsonism, Huntington's disease, or dementia with Lewy Bodies. In some aspects, the movement disorder is Parkinson's disease. In some aspects, the movement disorder is drug-induced Parkinsonism. In some aspects, the movement disorder is Huntington's disease. In some aspects, the movement disorder is dementia with Lewy Bodies.

Occurrence of Adverse Side Effects

The methods may be characterized by identity, frequency, and/or magnitude of adverse side effects experienced by the patient. For example, in some aspects, the patient experiences less severe dizziness while receiving the muscarinic acetylcholine receptor inhibitor and a muscarinic acetylcholine receptor activator, when compared to receiving the muscarinic acetylcholine receptor inhibitor alone.

In some aspects, the patient experiences fewer than four occurrences of lightheadedness per week while receiving the muscarinic acetylcholine receptor inhibitor and a muscarinic acetylcholine receptor activator. In some aspects, the patient experiences fewer than two occurrences of lightheadedness per week while receiving the muscarinic acetylcholine receptor inhibitor and a muscarinic acetylcholine receptor activator.

In some aspects, the patient experiences fewer than three occurrences of headache per week while receiving the muscarinic acetylcholine receptor inhibitor and a muscarinic acetylcholine receptor activator. In some aspects, the patient experiences fewer than two occurrences of headache per week while receiving the muscarinic acetylcholine receptor inhibitor and a muscarinic acetylcholine receptor activator.

In some aspects, the patient experiences fewer than three occurrences of nausea per week while receiving the muscarinic acetylcholine receptor inhibitor and a muscarinic acetylcholine receptor activator. In some aspects, the patient experiences fewer than two occurrences of nausea per week while receiving the muscarinic acetylcholine receptor inhibitor and a muscarinic acetylcholine receptor activator.

In some aspects, the patient experiences fewer than five occurrences of dry mouth per week while receiving the muscarinic acetylcholine receptor inhibitor and a muscarinic acetylcholine receptor activator. In some aspects, the patient experiences fewer than two occurrences of dry mouth per week while receiving the muscarinic acetylcholine receptor inhibitor and a muscarinic acetylcholine receptor activator. In some aspects, the patient experiences fewer than five occurrences of dry eye per week while receiving the muscarinic acetylcholine receptor inhibitor and a muscarinic acetylcholine receptor activator. In some aspects, the patient experiences fewer than two occurrences of dry eye per week while receiving the muscarinic acetylcholine receptor inhibitor and a muscarinic acetylcholine receptor activator. In some aspects, the patient experiences fewer than five occurrences of constipation or urine retention per week while receiving the muscarinic acetylcholine receptor inhibitor and a muscarinic acetylcholine receptor activator. In some aspects, the patient experiences fewer than two occurrences of constipation or urine retention per week while receiving the muscarinic acetylcholine receptor inhibitor and a muscarinic acetylcholine receptor activator. In some aspects, the patient experiences fewer than five occurrences of hallucination per week while receiving the muscarinic acetylcholine receptor inhibitor and a muscarinic acetylcholine receptor activator. In some aspects, the patient experiences fewer than two occurrences of hallucination per week while receiving the muscarinic acetylcholine receptor inhibitor and a muscarinic acetylcholine receptor activator.

In some aspects, the patient experiences fewer than five occurrences of blurry vision per week while receiving the muscarinic acetylcholine receptor inhibitor and a muscarinic acetylcholine receptor activator. In some aspects, the patient experiences fewer than two occurrences of blurry vision per week while receiving the muscarinic acetylcholine receptor inhibitor and a muscarinic acetylcholine receptor activator.

In some aspects, the patient experiences fewer than five occurrences of drowsiness per week while receiving the muscarinic acetylcholine receptor inhibitor and a muscarinic acetylcholine receptor activator. In some aspects, the patient experiences fewer than two occurrences of drowsiness per week while receiving the muscarinic acetylcholine receptor inhibitor and a muscarinic acetylcholine receptor activator.

In some aspects, the patient experiences fewer than five occurrences of confusion per week while receiving the muscarinic acetylcholine receptor inhibitor and a muscarinic acetylcholine receptor activator. In some aspects, the patient experiences fewer than two occurrences of confusion per week while receiving the muscarinic acetylcholine receptor inhibitor and a muscarinic acetylcholine receptor activator.

In some aspects, the patient experiences fewer than five occurrences of tachycardia per week while receiving the muscarinic acetylcholine receptor inhibitor and a muscarinic acetylcholine receptor activator. In some aspects, the patient experiences fewer than two occurrences of tachycardia per week while receiving the muscarinic acetylcholine receptor inhibitor and a muscarinic acetylcholine receptor activator.

In some aspects, the patient experiences fewer than five occurrences of euphoria per week while receiving the muscarinic acetylcholine receptor inhibitor and a muscarinic acetylcholine receptor activator. In some aspects, the patient experiences fewer than two occurrences of euphoria per week while receiving the muscarinic acetylcholine receptor inhibitor and a muscarinic acetylcholine receptor activator.

In some aspects, the patient experiences fewer than five occurrences of agitation per week while receiving the muscarinic acetylcholine receptor inhibitor and a muscarinic acetylcholine receptor activator. In some aspects, the patient experiences fewer than two occurrences of agitation per week while receiving the muscarinic acetylcholine receptor inhibitor and a muscarinic acetylcholine receptor activator.

In some aspects, the patient experiences fewer than five occurrences of intraocular pressure per week while receiving the muscarinic acetylcholine receptor inhibitor and a muscarinic acetylcholine receptor activator. In some aspects, the patient experiences fewer than two occurrences of intraocular pressure per week while receiving the muscarinic acetylcholine receptor inhibitor and a muscarinic acetylcholine receptor activator.

In some aspects, the patient experiences fewer than five occurrences per week of an adverse side effect selected from vomiting, diarrhea, salivation, and anorexia. In some aspects, the patient experiences fewer than two occurrences per week of an adverse side effect selected from vomiting, diarrhea, salivation, and anorexia. In some aspects, the patient does not experience vomiting, diarrhea, salivation, or anorexia while receiving the muscarinic acetylcholine receptor inhibitor and a muscarinic acetylcholine receptor activator.

In some aspects, the patient experiences (a) fewer than four occurrences of dizziness, lightheadedness, headache, and/or nausea per week; (b) fewer than five occurrences per week of an adverse side effect selected from vomiting, diarrhea, salivation, and anorexia; or both (a) and (b), while receiving the muscarinic acetylcholine receptor inhibitor and a muscarinic acetylcholine receptor activator.

In some aspects, the magnitude of the adverse side effects experienced by the patient is reduced while receiving the muscarinic acetylcholine receptor inhibitor and a muscarinic acetylcholine receptor activator, as compared to an equal amount of the muscarinic receptor inhibitor alone. In some aspects, the patient does not experience any adverse side effects while receiving the muscarinic acetylcholine receptor inhibitor and a muscarinic acetylcholine receptor activator.

In some aspects, the patient experiences fewer than four occurrences of diarrhea per week while receiving the muscarinic acetylcholine receptor inhibitor and a muscarinic acetylcholine receptor activator. In some aspects, the patient experiences fewer than two occurrences of diarrhea per week while receiving the muscarinic acetylcholine receptor inhibitor and a muscarinic acetylcholine receptor activator.

In some aspects, the patient experiences fewer than four occurrences of lacrimation per week while receiving the muscarinic acetylcholine receptor inhibitor and a muscarinic acetylcholine receptor activator. In some aspects, the patient experiences fewer than two occurrences of lacrimation per week while receiving the muscarinic acetylcholine receptor inhibitor and a muscarinic acetylcholine receptor activator.

In some aspects, the patient experiences fewer than four occurrences of salivation per week while receiving the muscarinic acetylcholine receptor inhibitor and a muscarinic acetylcholine receptor activator. In some aspects, the patient experiences fewer than two occurrences of salivation per week while receiving the muscarinic acetylcholine receptor inhibitor and a muscarinic acetylcholine receptor activator.

In some aspects, the patient experiences fewer than four occurrences of urinary urgency per week while receiving the muscarinic acetylcholine receptor inhibitor and a muscarinic acetylcholine receptor activator. In some aspects, the patient experiences fewer than two occurrences of urinary urgency per week while receiving the muscarinic acetylcholine receptor inhibitor and a muscarinic acetylcholine receptor activator.

In some aspects, the methods may be characterized by the timing of onset of adverse side effects experienced by the patient. In some aspects, the patient experiences an adverse side effect more than 30 minutes after receiving a therapeutic dose of the muscarinic acetylcholine receptor inhibitor and a muscarinic acetylcholine receptor activator. In some aspects, the patient experiences an adverse side effect more than 45 minutes after receiving a therapeutic dose of the muscarinic acetylcholine receptor inhibitor and a muscarinic acetylcholine receptor activator. In some aspects, the patient experiences an adverse side effect more than 60 minutes after receiving a therapeutic dose of the muscarinic acetylcholine receptor inhibitor and a muscarinic acetylcholine receptor activator. In some aspects, the patient experiences an adverse side effect more than 90 minutes after receiving a therapeutic dose of the muscarinic acetylcholine receptor inhibitor and a muscarinic acetylcholine receptor activator. In some aspects, the patient experiences an adverse side effect more than 120 minutes after receiving a therapeutic dose of the muscarinic acetylcholine receptor inhibitor and a muscarinic acetylcholine receptor activator. In some aspects, the patient experiences an adverse side effect more than 150 minutes after receiving a therapeutic dose of the muscarinic acetylcholine receptor inhibitor and a muscarinic acetylcholine receptor activator. In some aspects, the patient experiences an adverse side effect more than 180 minutes after receiving a therapeutic dose of the muscarinic acetylcholine receptor inhibitor and a muscarinic acetylcholine receptor activator. In some aspects, the patient dose not experience any adverse side effects after receiving a therapeutic dose of the muscarinic acetylcholine receptor inhibitor and a muscarinic acetylcholine receptor activator.

In some aspects, any adverse side effect experienced by the patient due to the muscarinic acetylcholine receptor inhibitor and/or muscarinic acetylcholine receptor activator occurs more than 30 minutes after receiving the muscarinic acetylcholine receptor inhibitor and muscarinic acetylcholine receptor activator. In some aspects, any adverse side effect experienced by the patient due to the muscarinic acetylcholine receptor inhibitor and/or muscarinic acetylcholine receptor activator occurs more than 45 minutes after receiving the muscarinic acetylcholine receptor inhibitor and muscarinic acetylcholine receptor activator. In some aspects, any adverse side effect experienced by the patient due to the muscarinic acetylcholine receptor inhibitor and/or muscarinic acetylcholine receptor activator occurs more than 60 minutes after receiving the muscarinic acetylcholine receptor inhibitor and muscarinic acetylcholine receptor activator. In some aspects, any adverse side effect experienced by the patient due to the muscarinic acetylcholine receptor inhibitor and/or muscarinic acetylcholine receptor activator occurs more than 90 minutes after receiving the muscarinic acetylcholine receptor inhibitor and muscarinic acetylcholine receptor activator. In some aspects, any adverse side effect experienced by the patient due to the muscarinic acetylcholine receptor inhibitor and/or muscarinic acetylcholine receptor activator occurs more than 120 minutes after receiving the muscarinic acetylcholine receptor inhibitor and muscarinic acetylcholine receptor activator. In some aspects, any adverse side effect experienced by the patient due to the muscarinic acetylcholine receptor inhibitor and/or muscarinic acetylcholine receptor activator occurs more than 150 minutes after receiving the muscarinic acetylcholine receptor inhibitor and muscarinic acetylcholine receptor activator. In some aspects, any adverse side effect experienced by the patient due to the muscarinic acetylcholine receptor inhibitor and/or muscarinic acetylcholine receptor activator occurs more than 180 minutes after receiving the muscarinic acetylcholine receptor inhibitor and muscarinic acetylcholine receptor activator. In some aspects, the patient does not experience any adverse side effects after receiving the muscarinic acetylcholine receptor inhibitor and muscarinic acetylcholine receptor activator.

In some aspects, any dizziness experienced by the patient occurs at a time that is more than 120 minutes after receiving a therapeutic dose of the muscarinic acetylcholine receptor inhibitor and a muscarinic acetylcholine receptor activator. In some aspects, the patient does not experience dizziness after receiving a therapeutic dose of the muscarinic acetylcholine receptor inhibitor and a muscarinic acetylcholine receptor activator. In some aspects, any lightheadedness experienced by the patient occurs at a time that is more than 120 minutes after receiving a therapeutic dose of the muscarinic acetylcholine receptor inhibitor and a muscarinic acetylcholine receptor activator. In some aspects, the patient does not experience lightheadedness after receiving a therapeutic dose of the muscarinic acetylcholine receptor inhibitor and a muscarinic acetylcholine receptor activator. In some aspects, any headache experienced by the patient occurs at a time that is more than 120 minutes after receiving a therapeutic dose of the muscarinic acetylcholine receptor inhibitor and a muscarinic acetylcholine receptor activator. In some aspects, the patient does not experience headache after receiving a therapeutic dose of the muscarinic acetylcholine receptor inhibitor and a muscarinic acetylcholine receptor activator. In some aspects, any drowsiness experienced by the patient occurs at a time that is more than 120 minutes after receiving a therapeutic dose of the muscarinic acetylcholine receptor inhibitor and a muscarinic acetylcholine receptor activator. In some aspects, the patient does not experience drowsiness after receiving a therapeutic dose of the muscarinic acetylcholine receptor inhibitor and a muscarinic acetylcholine receptor activator. In some aspects, any confusion experienced by the patient occurs at a time that is more than 120 minutes after receiving a therapeutic dose of the muscarinic acetylcholine receptor inhibitor and a muscarinic acetylcholine receptor activator. In some aspects, the patient does not experience confusion after receiving a therapeutic dose of the muscarinic acetylcholine receptor inhibitor and a muscarinic acetylcholine receptor activator.

In some aspects, any reduced concentration experienced by the patient occurs at a time that is more than 120 minutes after receiving a therapeutic dose of the muscarinic acetylcholine receptor inhibitor and a muscarinic acetylcholine receptor activator. In some aspects, the patient does not experience reduced concentration after receiving a therapeutic dose of the muscarinic acetylcholine receptor inhibitor and a muscarinic acetylcholine receptor activator. In some aspects, any reduced ability to think experienced by the patient occurs at a time that is more than 120 minutes after receiving a therapeutic dose of the muscarinic acetylcholine receptor inhibitor and a muscarinic acetylcholine receptor activator. In some aspects, the patient does not experience reduced ability to think after receiving a therapeutic dose of the muscarinic acetylcholine receptor inhibitor and a muscarinic acetylcholine receptor activator. In some aspects, any euphoria experienced by the patient occurs at a time that is more than 120 minutes after receiving a therapeutic dose of the muscarinic acetylcholine receptor inhibitor and a muscarinic acetylcholine receptor activator. In some aspects, the patient does not experience euphoria after receiving a therapeutic dose of the muscarinic acetylcholine receptor inhibitor and a muscarinic acetylcholine receptor activator. In some aspects, any elevated mood experienced by the patient occurs at a time that is more than 120 minutes after receiving a therapeutic dose of the muscarinic acetylcholine receptor inhibitor and a muscarinic acetylcholine receptor activator. In some aspects, the patient does not experience elevated mood after receiving a therapeutic dose of the muscarinic acetylcholine receptor inhibitor and a muscarinic acetylcholine receptor activator. In some aspects, any hallucination experienced by the patient occurs at a time that is more than 120 minutes after receiving a therapeutic dose of the muscarinic acetylcholine receptor inhibitor and a muscarinic acetylcholine receptor activator. In some aspects, the patient does not experience hallucination after receiving a therapeutic dose of the muscarinic acetylcholine receptor inhibitor and a muscarinic acetylcholine receptor activator.

In some aspects, any agitation experienced by the patient occurs at a time that is more than 120 minutes after receiving a therapeutic dose of the muscarinic acetylcholine receptor inhibitor and a muscarinic acetylcholine receptor activator. In some aspects, the patient does not experience agitation after receiving a therapeutic dose of the muscarinic acetylcholine receptor inhibitor and a muscarinic acetylcholine receptor activator. In some aspects, any irritability experienced by the patient occurs at a time that is more than 120 minutes after receiving a therapeutic dose of the muscarinic acetylcholine receptor inhibitor and a muscarinic acetylcholine receptor activator. In some aspects, the patient does not experience irritability after receiving a therapeutic dose of the muscarinic acetylcholine receptor inhibitor and a muscarinic acetylcholine receptor activator. In some aspects, any sensory disturbance experienced by the patient occurs at a time that is more than 120 minutes after receiving a therapeutic dose of the muscarinic acetylcholine receptor inhibitor and a muscarinic acetylcholine receptor activator. In some aspects, the patient does not experience sensory disturbance after receiving a therapeutic dose of the muscarinic acetylcholine receptor inhibitor and a muscarinic acetylcholine receptor activator. In some aspects, any blurry vision experienced by the patient occurs at a time that is more than 120 minutes after receiving a therapeutic dose of the muscarinic acetylcholine receptor inhibitor and a muscarinic acetylcholine receptor activator. In some aspects, the patient does not experience blurry vision after receiving a therapeutic dose of the muscarinic acetylcholine receptor inhibitor and a muscarinic acetylcholine receptor activator. In some aspects, any impaired vision experienced by the patient occurs at a time that is more than 120 minutes after receiving a therapeutic dose of the muscarinic acetylcholine receptor inhibitor and a muscarinic acetylcholine receptor activator. In some aspects, the patient does not experience impaired vision after receiving a therapeutic dose of the muscarinic acetylcholine receptor inhibitor and a muscarinic acetylcholine receptor activator. In some aspects, any increase in intraocular pressure experienced by the patient occurs at a time that is more than 120 minutes after receiving a therapeutic dose of the muscarinic acetylcholine receptor inhibitor and a muscarinic acetylcholine receptor activator. In some aspects, the patient does not experience an increase in intraocular pressure after receiving a therapeutic dose of the muscarinic acetylcholine receptor inhibitor and a muscarinic acetylcholine receptor activator.

In some aspects, any dry eye experienced by the patient occurs at a time that is more than 120 minutes after receiving a therapeutic dose of the muscarinic acetylcholine receptor inhibitor and a muscarinic acetylcholine receptor activator. In some aspects, the patient does not experience dry eye after receiving a therapeutic dose of the muscarinic acetylcholine receptor inhibitor and a muscarinic acetylcholine receptor activator. In some aspects, any dry mouth experienced by the patient occurs at a time that is more than 120 minutes after receiving a therapeutic dose of the muscarinic acetylcholine receptor inhibitor and a muscarinic acetylcholine receptor activator. In some aspects, the patient does not experience dry mouth after receiving a therapeutic dose of the muscarinic acetylcholine receptor inhibitor and a muscarinic acetylcholine receptor activator. In some aspects, any constipation experienced by the patient occurs at a time that is more than 120 minutes after receiving a therapeutic dose of the muscarinic acetylcholine receptor inhibitor and a muscarinic acetylcholine receptor activator. In some aspects, the patient does not experience constipation after receiving a therapeutic dose of the muscarinic acetylcholine receptor inhibitor and a muscarinic acetylcholine receptor activator. In some aspects, any nausea experienced by the patient occurs at a time that is more than 120 minutes after receiving a therapeutic dose of the muscarinic acetylcholine receptor inhibitor and a muscarinic acetylcholine receptor activator. In some aspects, the patient does not experience nausea after receiving a therapeutic dose of the muscarinic acetylcholine receptor inhibitor and a muscarinic acetylcholine receptor activator. In some aspects, any cramping experienced by the patient occurs at a time that is more than 120 minutes after receiving a therapeutic dose of the muscarinic acetylcholine receptor inhibitor and a muscarinic acetylcholine receptor activator. In some aspects, the patient does not experience cramping after receiving a therapeutic dose of the muscarinic acetylcholine receptor inhibitor and a muscarinic acetylcholine receptor activator.

In some aspects, any urinary retention experienced by the patient occurs at a time that is more than 120 minutes after receiving a therapeutic dose of the muscarinic acetylcholine receptor inhibitor and a muscarinic acetylcholine receptor activator. In some aspects, the patient does not experience urinary retention after receiving a therapeutic dose of the muscarinic acetylcholine receptor inhibitor and a muscarinic acetylcholine receptor activator. In some aspects, any reduced urinary voiding experienced by the patient occurs at a time that is more than 120 minutes after receiving a therapeutic dose of the muscarinic acetylcholine receptor inhibitor and a muscarinic acetylcholine receptor activator. In some aspects, the patient does not experience reduced urinary voiding after receiving a therapeutic dose of the muscarinic acetylcholine receptor inhibitor and a muscarinic acetylcholine receptor activator. In some aspects, any flushed skin experienced by the patient occurs at a time that is more than 120 minutes after receiving a therapeutic dose of the muscarinic acetylcholine receptor inhibitor and a muscarinic acetylcholine receptor activator. In some aspects, the patient does not experience flushed skin after receiving a therapeutic dose of the muscarinic acetylcholine receptor inhibitor and a muscarinic acetylcholine receptor activator. In some aspects, any fever experienced by the patient occurs at a time that is more than 120 minutes after receiving a therapeutic dose of the muscarinic acetylcholine receptor inhibitor and a muscarinic acetylcholine receptor activator. In some aspects, the patient does not experience fever after receiving a therapeutic dose of the muscarinic acetylcholine receptor inhibitor and a muscarinic acetylcholine receptor activator. In some aspects, any reduced sweating experienced by the patient occurs at a time that is more than 120 minutes after receiving a therapeutic dose of the muscarinic acetylcholine receptor inhibitor and a muscarinic acetylcholine receptor activator. In some aspects, the patient does not experience reduced sweating after receiving a therapeutic dose of the muscarinic acetylcholine receptor inhibitor and a muscarinic acetylcholine receptor activator.

In some aspects, any tachycardia experienced by the patient occurs at a time that is more than 120 minutes after receiving a therapeutic dose of the muscarinic acetylcholine receptor inhibitor and a muscarinic acetylcholine receptor activator. In some aspects, the patient does not experience tachycardia after receiving a therapeutic dose of the muscarinic acetylcholine receptor inhibitor and a muscarinic acetylcholine receptor activator. In some aspects, any cardiac arrhythmia experienced by the patient occurs at a time that is more than 120 minutes after receiving a therapeutic dose of the muscarinic acetylcholine receptor inhibitor and a muscarinic acetylcholine receptor activator. In some aspects, the patient does not experience cardiac arrhythmia after receiving a therapeutic dose of the muscarinic acetylcholine receptor inhibitor and a muscarinic acetylcholine receptor activator.

In some aspects, the patient does not experience any adverse side effect due to the muscarinic acetylcholine receptor activator.

In some aspects, the patient does not experience any adverse side effect due to the muscarinic acetylcholine receptor inhibitor.

Determining a reduced frequency, magnitude, and/or severity of adverse events can be performed using methods known in the art and/or disclosed herein. In some aspects, dizziness in a patient is measured using the Visual Analog Scale (VAS), for example, see Toupet et al., *J. of Vestibular Res.,* 21(4):235-241 (2011). In some aspects, dry eye in a patient is measured using the Schirmer Tear Test, or by self-report, for example, see Kloosterboer et al., *Expert Rev. Ophthalmology,* 14(4-5):237-246 (2019). In some aspects, dry mouth is measured in a patient using salivary flow rate using Passive Drool Collection Test, for example, see Fallon et al., BMC Oral Health, 21(1):191 (2021). In some aspects, excessive salivation is measured in a patient using salivary flow rate using Passive Drool Collection Test, for example, see Fallon et al., BMC Oral Health, 21(1):191 (2021). In some aspects, constipation in a patient is measured using the Bristol Stool Form Scale, for example, see Blake et al., *Aliment Pharmacology Ther.,* 44(7):693-703 (2016). In some aspects, diarrhea in a patient is measured using the Bristol Stool Form Scale, for example, see Blake et al., *Aliment Pharmacology Ther.,* 44(7):693-703 (2016). In some aspects, urinary retention is measured using the Urgency Perception Scale, for example, see Cardozo et al., *BJU Int'l.,* 95(4):591-596 (2005). In some aspects, urinary urgency is measured using the Urgency Perception Scale, for example, see Cardozo et al., *BJU Int'l.,* 95(4):591-596 (2005). In some aspects, memory impacts are measured by the Wechsler Adult Intelligence Scale and includes digit span forward, digit span backward, and digit span sequencing, for example, see Ruchinskas R., Clin. Neuropsychology, 33(8):1436-1444 (2019), and Abdelhamid et al., *Int'l J. of Env't Res. Pub. Health,* 18(13):6835 (2021). In some aspects, alertness is measured using the Karolinska Sleepiness Scale. In some aspects, sleepiness is measured using the Karolinska Sleepiness Scale, for example, see Putilov et al., *Clin. Neurophysiology,* 124(7):1346-1352 (2013), and Kaida et al., *Clin. Neurophysiology,* 117(7):1574-1581 (2006). In some aspects, tachycardia is measured using periodic pulse rate measurements via pulse oximetry, for example, see Padmini et al., *AIP Conf. Proceedings,* 2117(1):020009 (2019). In some aspects, bradycardia is measured using periodic pulse rate measurements via pulse oximetry, for example, see Padmini et al., *AIP Conf. Proceedings,* 2117 (1):020009 (2019). In some aspects, mood is measured using the Profile of Mood State Exam, and includes total mood disturbance and/or assessments of transient, fluctuating feelings, enduring affect states across the five domains of Anger-Hostility, Confusion-Bewilderment, Depression-Dejection, Fatigue-Inertia, Tension-Anxiety, and Vigor-Activity, for example, see Yamanaka et al., *PLos One,* 16(12): e0261762 (2021). In some aspects, pupil size is measured by electronic automated pupillometer, for example, see Smith et al., *Austl Critical Care,* 33(2):162-166 (2020). In some aspects, blood pressure is measured periodically via automated blood pressure cuff, for example, see Nelson et el., *J. Dent. Hygiene,* 82(4):35.

In some aspects, dizziness, confusion, headache, light headedness, nausea, vomiting, hallucinations, euphoria, agitation, blurry vision, drowsiness, and anorexia are measured by patient self-report.

In some aspects, a reduction in frequency of an adverse event is a reduction in the number of occurrences of the adverse event per day. In some aspects, a reduction in frequency of an adverse event is a reduction in the number of occurrences of the adverse event per week. In some aspects, a reduction in frequency of an adverse event is a reduction in the number of occurrences of the adverse event per month. In some aspects, a reduction in frequency of an adverse event is a reduction in the number of occurrences of the adverse event per year.

In some aspects, a reduction in magnitude of an adverse event leads to increased adherence to treatment by a subject. In some aspects, a reduction in magnitude of an adverse event leads to increased compliance by a subject. In some aspects, there is a 50% improvement in adherence and/or compliance over current therapies. In some aspects, there is a 45% improvement in adherence and/or compliance over current therapies. In some aspects, there is a 40% improvement in adherence and/or compliance over current therapies. In some aspects, there is a 35% improvement in adherence and/or compliance over current therapies. In some aspects, there is a 30% improvement in adherence and/or compliance over current therapies. In some aspects, there is a 25% improvement in adherence and/or compliance over current therapies. In some aspects, there is a 20% improvement in adherence and/or compliance over current therapies. In some aspects, there is a 15% improvement in adherence and/or compliance over current therapies. In some aspects, there is a 10% improvement in adherence and/or compliance over current therapies. In some aspects, there is a 5% improvement in adherence and/or compliance over current therapies.

Subjects

As used herein, the terms "subject" and "patient" are interchangeable. In some aspects, the subject is a human. In some aspects, the subject is an adult human. In some aspects, the subject is a pediatric human. In some aspects, the subject is a geriatric human.

In some aspects, the patient is concurrently suffering from glaucoma. In some aspects, the patient is at an increased risk of suffering from glaucoma. In some aspects, the patient is concurrently suffering from obstructive disease of the gastrointestinal or genitourinary tracts. In some aspects, the patient is at an increased risk of suffering from obstructive disease of the gastrointestinal or genitourinary tracts. In some aspects, the patient is concurrently suffering from prostatic hypertrophy. In some aspects, the patient at an increased risk of suffering from prostatic hypertrophy.

In some aspects, the patient is concurrently suffering from asthma. In some aspects, the patient is at an increased risk of suffering from asthma. In some aspects, the patient is concurrently suffering from a bladder infection. In some aspects, the patient is at an increased risk of suffering from a bladder infection. In some aspects, the patient is concurrently suffering from epilepsy. In some aspects, the patient is at an increased risk of suffering from epilepsy. In some aspects, the patient is concurrently suffering from high blood pressure. In some aspects, the patient is at an increased risk of suffering from high blood pressure. In some aspects, the patient is concurrently suffering from heart disease. In some aspects, the patient is at an increased risk of suffering from heart disease. In some aspects, the patient is concurrently suffering from Parkinson's disease. In some aspects, the patient is at an increased risk of suffering from Parkinson's disease. In some aspects, the patient is concurrently suffering from an overactive thyroid gland. In some aspects, the patient is at an increased risk of suffering from an overactive thyroid gland. In some aspects, the patient is concurrently suffering from ulcers. In some aspects, the patient is at an increased risk of suffering from ulcers.

Medical Uses

Another aspect of the invention provides for the use of a compound described herein in the manufacture of a medicament. In some aspects, the medicament is for treating a disorder described herein, such as dystonia. Another aspect of the invention provides for the use of a compound described herein for treating a medical disorder, such as a medical disorder described herein, such as dystonia. Another aspect of the invention provides for a compound described herein for use in medicine. In some aspects, the invention provides for a compound described herein for use in the treatment of a medical disorder described herein, such as a movement disorder described herein, such as dystonia. The details given with respect to the therapeutic methods described herein equally apply to the medical uses described herein.

II. Oral Pharmaceutical Compositions, Unit Dose Formulations, and Combinations

Another aspect of the invention provides an oral pharmaceutical composition, comprising (i) a muscarinic acetylcholine receptor inhibitor, (ii) a muscarinic acetylcholine receptor activator in an amount effective to reduce the frequency and/or magnitude of at least one side effect of the muscarinic acetylcholine receptor inhibitor, and (iii) a pharmaceutically acceptable carrier.

In some aspects, the present disclosure provides an oral pharmaceutical composition, comprising (i) a muscarinic acetylcholine receptor inhibitor, (ii) a muscarinic acetylcholine receptor activator in an amount effective to reduce the frequency or magnitude of at least one side effect of the muscarinic acetylcholine receptor inhibitor, and (iii) a pharmaceutically acceptable carrier.

In some aspects, the present disclosure provides an oral pharmaceutical composition, comprising (i) a muscarinic acetylcholine receptor inhibitor, (ii) a muscarinic acetylcholine receptor activator in an amount effective to reduce the frequency and magnitude of at least one side effect of the muscarinic acetylcholine receptor inhibitor, and (iii) a pharmaceutically acceptable carrier.

In some aspects, the present disclosure provides an oral pharmaceutical composition, comprising (i) a muscarinic acetylcholine receptor inhibitor, (ii) a muscarinic acetylcholine receptor activator in an amount effective to reduce the magnitude of at least one side effect of the muscarinic acetylcholine receptor inhibitor, and (iii) a pharmaceutically acceptable carrier.

In some aspects, the present disclosure provides an oral pharmaceutical composition, comprising (i) a muscarinic acetylcholine receptor inhibitor, (ii) a muscarinic acetylcholine receptor activator in an amount effective to reduce the frequency of at least one side effect of the muscarinic acetylcholine receptor inhibitor, and (iii) a pharmaceutically acceptable carrier.

In some aspects, the present disclosure provides an oral pharmaceutical composition, comprising (i) a muscarinic acetylcholine receptor inhibitor in an amount effective to treat the movement disorder and (ii) a muscarinic acetylcholine receptor activator in an amount effective to reduce the frequency and/or magnitude of at least one side effect of the muscarinic acetylcholine receptor inhibitor, wherein the muscarinic acetylcholine receptor inhibitor is trihexyphenidyl or pharmaceutically acceptable salt thereof, and wherein the muscarinic acetylcholine receptor activator is bethanechol or pharmaceutically acceptable salt thereof, and (iii) a pharmaceutically acceptable carrier.

In some aspects, the present disclosure provides an oral pharmaceutical composition, comprising (i) a muscarinic acetylcholine receptor inhibitor in an amount effective to treat the movement disorder and (ii) a muscarinic acetylcholine receptor activator in an amount effective to reduce the frequency and magnitude of at least one side effect of the muscarinic acetylcholine receptor inhibitor, wherein the muscarinic acetylcholine receptor inhibitor is trihexyphenidyl or pharmaceutically acceptable salt thereof, and wherein the muscarinic acetylcholine receptor activator is bethanechol or pharmaceutically acceptable salt thereof, and (iii) a pharmaceutically acceptable carrier.

In some aspects, the present disclosure provides an oral pharmaceutical composition, comprising (i) a muscarinic acetylcholine receptor inhibitor in an amount effective to treat the movement disorder and (ii) a muscarinic acetylcholine receptor activator in an amount effective to reduce the frequency or magnitude of at least one side effect of the muscarinic acetylcholine receptor inhibitor, wherein the muscarinic acetylcholine receptor inhibitor is trihexyphenidyl or pharmaceutically acceptable salt thereof, and wherein the muscarinic acetylcholine receptor activator is bethanechol or pharmaceutically acceptable salt thereof, and (iii) a pharmaceutically acceptable carrier.

In some aspects, the present disclosure provides an oral pharmaceutical composition, comprising (i) a muscarinic acetylcholine receptor inhibitor in an amount effective to treat the movement disorder and (ii) a muscarinic acetylcholine receptor activator in an amount effective to reduce the frequency of at least one side effect of the muscarinic acetylcholine receptor inhibitor, wherein the muscarinic acetylcholine receptor inhibitor is trihexyphenidyl or pharmaceutically acceptable salt thereof, and wherein the muscarinic acetylcholine receptor activator is bethanechol or pharmaceutically acceptable salt thereof, and (iii) a pharmaceutically acceptable carrier.

In some aspects, the present disclosure provides an oral pharmaceutical composition, comprising (i) a muscarinic acetylcholine receptor inhibitor in an amount effective to treat the movement disorder and (ii) a muscarinic acetylcholine receptor activator in an amount effective to reduce the magnitude of at least one side effect of the muscarinic acetylcholine receptor inhibitor, wherein the muscarinic acetylcholine receptor inhibitor is trihexyphenidyl or pharmaceutically acceptable salt thereof, and wherein the muscarinic acetylcholine receptor activator is bethanechol or pharmaceutically acceptable salt thereof, and (iii) a pharmaceutically acceptable carrier.

Another aspect of the invention provides an oral pharmaceutical composition, comprising (i) a muscarinic acetylcholine receptor inhibitor, (ii) a second therapeutic agent selected from a muscarinic acetylcholine receptor activator, a procholinergic agent, and an acetylcholinesterase inhibitor, and (iii) a pharmaceutically acceptable carrier, wherein the second therapeutic agent is present in an amount effective to reduce the frequency and/or magnitude of at least one side effect of the muscarinic acetylcholine receptor inhibitor.

In some aspects, the present disclosure provides an oral pharmaceutical composition, comprising (i) a muscarinic acetylcholine receptor inhibitor, (ii) a second therapeutic agent selected from a muscarinic acetylcholine receptor activator, a procholinergic agent, and an acetylcholinesterase inhibitor, and (iii) a pharmaceutically acceptable carrier, wherein the second therapeutic agent is present in an amount effective to reduce the frequency and magnitude of at least one side effect of the muscarinic acetylcholine receptor inhibitor.

In some aspects, the present disclosure provides an oral pharmaceutical composition, comprising (i) a muscarinic acetylcholine receptor inhibitor, (ii) a second therapeutic agent selected from a muscarinic acetylcholine receptor activator, a procholinergic agent, and an acetylcholinesterase inhibitor, and (iii) a pharmaceutically acceptable carrier, wherein the second therapeutic agent is present in an amount effective to reduce the frequency or magnitude of at least one side effect of the muscarinic acetylcholine receptor inhibitor.

In some aspects, the present disclosure provides an oral pharmaceutical composition, comprising (i) a muscarinic acetylcholine receptor inhibitor, (ii) a second therapeutic agent selected from a muscarinic acetylcholine receptor activator, a procholinergic agent, and an acetylcholinesterase inhibitor, and (iii) a pharmaceutically acceptable carrier, wherein the second therapeutic agent is present in an amount effective to reduce the frequency of at least one side effect of the muscarinic acetylcholine receptor inhibitor.

In some aspects, the present disclosure provides an oral pharmaceutical composition, comprising (i) a muscarinic acetylcholine receptor inhibitor, (ii) a second therapeutic agent selected from a muscarinic acetylcholine receptor activator, a procholinergic agent, and an acetylcholinesterase inhibitor, and (iii) a pharmaceutically acceptable carrier, wherein the second therapeutic agent is present in an amount effective to reduce the magnitude of at least one side effect of the muscarinic acetylcholine receptor inhibitor.

Another aspect of the invention provides an oral pharmaceutical composition, comprising (i) a muscarinic acetylcholine receptor inhibitor, (ii) a muscarinic acetylcholine receptor activator, and (iii) a pharmaceutically acceptable carrier. Another aspect of the invention provides oral pharmaceutical composition, comprising (i) a muscarinic acetylcholine receptor inhibitor, (ii) a second therapeutic agent selected from a muscarinic acetylcholine receptor activator, a procholinergic agent, and an acetylcholinesterase inhibitor, and (iii) a pharmaceutically acceptable carrier.

In some aspects, the muscarinic acetylcholine receptor inhibitor distributes to the central nervous system and the peripheral nervous system in the patient. In some aspects, the muscarinic acetylcholine receptor inhibitor distributes to the central nervous system in the patient. In some aspects, the muscarinic acetylcholine receptor inhibitor distributes to the peripheral nervous system in the patient. In some aspects, the muscarinic acetylcholine receptor activator distributes predominately to the peripheral nervous system in the patient.

In some aspects, upon oral administration of the pharmaceutical composition to a human patient, the mole ratio of (i) muscarinic acetylcholine receptor activator present in the peripheral nervous system of the patient to (ii) muscarinic acetylcholine receptor activator present in the central nervous system of the patient is at least 1 to 1. In some aspects, upon oral administration of the pharmaceutical composition to a human patient, the mole ratio of (i) muscarinic acetylcholine receptor activator present in the peripheral nervous system of the patient to (ii) muscarinic acetylcholine receptor activator present in the central nervous system of the patient is at least 2 to 1. In some aspects, upon oral administration of the pharmaceutical composition to a human patient, the mole ratio of (i) muscarinic acetylcholine receptor activator present in the peripheral nervous system of the patient to (ii) muscarinic acetylcholine receptor activator present in the central nervous system of the patient is at least 3 to 1. In some aspects, upon oral administration of the pharmaceutical composition to a human patient, the mole ratio of (i) muscarinic acetylcholine receptor activator present in the peripheral nervous system of the patient to (ii) muscarinic acetylcholine receptor activator present in the central nervous system of the patient is at least 4 to 1. In some aspects, upon oral administration of the pharmaceutical composition to a human patient, the mole ratio of (i) muscarinic acetylcholine receptor activator present in the peripheral nervous system of the patient to (ii) muscarinic acetylcholine receptor activator present in the central nervous system of the patient is at least 5 to 1. In some aspects, upon oral administration of the pharmaceutical composition to a human patient, the mole ratio of (i) muscarinic acetylcholine receptor activator present in the peripheral nervous system of the patient to (ii) muscarinic acetylcholine receptor activator present in the central nervous system of the patient is at least 10 to 1. In some aspects, upon oral administration of the pharmaceutical composition to a human patient, the mole ratio of (i) muscarinic acetylcholine receptor activator present in the peripheral nervous system of the patient to (ii) muscarinic acetylcholine receptor activator present in the central nervous system of the patient is at least 15 to 1. In some aspects, upon oral administration of the pharmaceutical composition to a human patient, the mole ratio of (i) muscarinic acetylcholine receptor activator present in the peripheral nervous system of the patient to (ii) muscarinic acetylcholine receptor activator present in the central nervous system of the patient is at least 20 to 1.

In some aspects the (i) a muscarinic acetylcholine receptor inhibitor in an amount effective to treat the movement disorder and (ii) a second therapeutic agent selected from a muscarinic acetylcholine receptor activator, a procholinergic agent, and an acetylcholine esterase inhibitor are present in a single pharmaceutical composition that is administered to the patient. In some aspect, the single pharmaceutical composition is administered orally.

In some aspects, the muscarinic acetylcholine receptor inhibitor distributes to the central nervous system and the peripheral nervous system in the patient. In some aspects, the muscarinic acetylcholine receptor activator distributes predominately to the peripheral nervous system in the patient. In some aspects, the second therapeutic agent is a procholinergic agent. In some aspects, the second therapeutic agent is an acetylcholinesterase inhibitor. In some aspects, the second therapeutic agent is pyridostigmine, neostigmine, physostigmine, edrophonium, or a pharmaceutically acceptable salt thereof. In some aspects, the second therapeutic agent is pyridostigmine or a pharmaceutically acceptable salt thereof. In some aspects, the second therapeutic agent is neostigmine or a pharmaceutically acceptable salt thereof. In some aspects, the second therapeutic agent is physostigmine or a pharmaceutically acceptable salt thereof. In some aspects, the second therapeutic agent is edrophonium or a pharmaceutically acceptable salt thereof. In some aspects, the second therapeutic agent is distigmine bromide.

In some aspects, the muscarinic acetylcholine receptor inhibitor is trihexyphenidyl or a pharmaceutically acceptable salt thereof. In some aspects, the muscarinic acetylcholine receptor inhibitor is trihexyphenidyl. In some aspects, the muscarinic acetylcholine receptor inhibitor is trihexyphenidyl hydrochloride.

In some aspects, muscarinic acetylcholine receptor inhibitor is racemic-trihexyphenidyl or a pharmaceutically acceptable salt thereof. In some aspects, the muscarinic acetylcholine receptor inhibitor is racemic-trihexyphenidyl. In some aspects, the muscarinic acetylcholine receptor inhibitor is racemic-trihexyphenidyl hydrochloride.

In some aspects, the muscarinic acetylcholine receptor inhibitor is (R)-trihexyphenidyl or a pharmaceutically acceptable salt thereof. In some aspects, the muscarinic acetylcholine receptor inhibitor is (R)-trihexyphenidyl. In some aspects, the muscarinic acetylcholine receptor inhibitor is (R)-trihexyphenidyl hydrochloride.

In some aspects, the muscarinic acetylcholine receptor inhibitor is (R)-trihexyphenidyl having a stereochemical purity of at least 90% enantiomeric excess, or a pharmaceutically acceptable salt thereof. In some aspects, the muscarinic acetylcholine receptor inhibitor is (R)-trihexyphenidyl having a stereochemical purity of at least 95% enantiomeric excess, or a pharmaceutically acceptable salt thereof. In some aspects, the muscarinic acetylcholine receptor inhibitor is (R)-trihexyphenidyl having a stereochemical purity of at least 98% enantiomeric excess, or a pharmaceutically acceptable salt thereof. In some aspects, the muscarinic acetylcholine receptor inhibitor is (R)-trihexyphenidyl having a stereochemical purity of at least 99% enantiomeric excess, or a pharmaceutically acceptable salt thereof.

Another aspect of the invention provides a pharmaceutical composition, comprising (i) a muscarinic acetylcholine receptor inhibitor selected from (R)-trihexyphenidyl having a stereochemical purity of at least 95% enantiomeric excess or a pharmaceutically acceptable salt thereof, (ii) a muscarinic acetylcholine receptor activator, and (iii) a pharmaceutically acceptable carrier.

In some aspects, (a) the muscarinic acetylcholine receptor activator is racemic bethanechol or a pharmaceutically acceptable salt thereof and (b) the muscarinic acetylcholine receptor inhibitor is (R)-trihexyphenidyl or a pharmaceutically acceptable salt thereof.

In some aspects, the muscarinic acetylcholine receptor activator is racemic bethanechol or a pharmaceutically acceptable salt thereof and the muscarinic acetylcholine receptor inhibitor is racemic trihexyphenidyl or a pharmaceutically acceptable salt thereof.

In some aspects, the muscarinic acetylcholine receptor activator is (S)-bethanechol or a pharmaceutically acceptable salt thereof and the muscarinic acetylcholine receptor inhibitor is (R)-trihexyphenidyl or a pharmaceutically acceptable salt thereof.

In some aspects, muscarinic acetylcholine receptor activator is present in an amount effective to reduce side effects of the muscarinic acetylcholine receptor inhibitor.

In some aspects, the pharmaceutical composition is formulated for oral administration.

In some aspects, the muscarinic acetylcholine receptor activator is bethanechol or a pharmaceutically acceptable salt thereof. In some aspects, the muscarinic acetylcholine receptor activator is bethanechol. In some aspects, the muscarinic acetylcholine receptor activator is a bethanechol salt. In some aspects, the muscarinic acetylcholine receptor activator is bethanechol chloride.

In some aspects, the muscarinic acetylcholine receptor activator is racemic bethanechol or a pharmaceutically acceptable salt thereof. In some aspects, the muscarinic acetylcholine receptor activator is racemic bethanechol. In some aspects, the muscarinic acetylcholine receptor activator is racemic bethanechol salt. In some aspects, the muscarinic acetylcholine receptor activator is racemic bethanechol chloride.

In some aspects, the muscarinic acetylcholine receptor activator is (S)-bethanechol or a pharmaceutically acceptable salt thereof. In some aspects, the muscarinic acetylcholine receptor activator is (S)-bethanechol. In some aspects, the muscarinic acetylcholine receptor activator is (S)-bethanechol salt. In some aspects, the muscarinic acetylcholine receptor activator is (S)-bethanechol chloride.

In some aspects, the muscarinic acetylcholine receptor activator is (S)-bethanechol having a stereochemical purity of at least 90% enantiomeric excess, or a pharmaceutically acceptable salt thereof. In some aspects, the muscarinic acetylcholine receptor activator is (S)-bethanechol having a stereochemical purity of at least 95% enantiomeric excess, or a pharmaceutically acceptable salt thereof. In some aspects, the muscarinic acetylcholine receptor activator is (S)-bethanechol having a stereochemical purity of at least 98% enantiomeric excess, or a pharmaceutically acceptable salt thereof. In some aspects, the muscarinic acetylcholine receptor activator is (S)-bethanechol having a stereochemical purity of at least 99% enantiomeric excess, or a pharmaceutically acceptable salt thereof.

In some aspects, the muscarinic acetylcholine receptor activator is a (S)-bethanechol salt having a stereochemical purity of at least 90% enantiomeric excess. In some aspects, the muscarinic acetylcholine receptor activator is (S)-bethanechol salt having a stereochemical purity of at least 95% enantiomeric excess. In some aspects, the muscarinic acetylcholine receptor activator is (S)-bethanechol salt having a stereochemical purity of at least 98% enantiomeric excess. In some aspects, the muscarinic acetylcholine receptor activator is (S)-bethanechol salt having a stereochemical purity of at least 99% enantiomeric excess.

In some aspects, (a) the muscarinic acetylcholine receptor activator is racemic bethanechol or a pharmaceutically acceptable salt thereof and (b) the muscarinic acetylcholine receptor inhibitor is (R)-trihexyphenidyl having a stereochemical purity of at least 96% enantiomeric excess, or a pharmaceutically acceptable salt thereof.

In some aspects, the pharmaceutical composition is in the form of a tablet, troche, liquid, drop, capsule, caplet, gel cap, sublingual formulation, or spray. In some aspects, the pharmaceutical composition is in the form of a tablet, troche, capsule, caplet, or gel cap. In some aspects, the pharmaceutical compositions is in the form of a tablet. In some aspects, the pharmaceutical compositions is in the form of a troche. In some aspects, the pharmaceutical compositions is in the form of a capsule. In some aspects, the pharmaceutical compositions is in the form of a caplet. In some aspects, the pharmaceutical compositions is in the form of a gel cap.

In some aspects, the pharmaceutical composition is a controlled release formulation. In some aspects, the pharmaceutical composition comprises (i) a controlled release component containing the muscarinic acetylcholine receptor inhibitor and (ii) an immediate release component containing the muscarinic acetylcholine receptor activator. In some aspects, the pharmaceutical composition comprises (i) a controlled release component containing the muscarinic acetylcholine receptor activator and (ii) an immediate release component containing the muscarinic acetylcholine receptor inhibitor. In some aspects, the pharmaceutical composition comprises (i) a controlled release component containing the muscarinic acetylcholine receptor activator and (ii) a controlled release component containing the muscarinic acetylcholine receptor inhibitor.

In some aspects, the pharmaceutical composition comprises (i) a muscarinic acetylcholine receptor inhibitor and (ii) a muscarinic receptor activator, wherein the amount of muscarinic acetylcholine receptor inhibitor is at a dose level insufficient to reach an efficacious dose if it were to be dosed in the absence of the muscarinic receptor activator.

In some aspects, the present disclosure provides a pharmaceutical composition comprising (i) (R)-trihexyphenidyl or pharmaceutically acceptable salt thereof and (ii) a muscarinic receptor activator, wherein the amount of the (R)-trihexyphenidyl or pharmaceutically acceptable salt thereof is at a dose level insufficient to reach an efficacious dose if it were to be dosed in the absence of the muscarinic receptor activator.

In some aspects, the present disclosure provides a pharmaceutical composition comprising (i) racemic-trihexyphenidyl or pharmaceutically acceptable salt thereof and (ii) a muscarinic receptor activator, wherein the amount of the racemic-trihexyphenidyl or pharmaceutically acceptable salt thereof is at a dose level insufficient to reach an efficacious dose if it were to be dosed in the absence of the muscarinic receptor activator.

In some aspects, the present disclosure provides a pharmaceutical composition comprising (i) a muscarinic acetylcholine receptor inhibitor and (ii) a second therapeutic agent selected from a muscarinic acetylcholine receptor activator, a procholinergic agent, and an acetylcholinesterase inhibitor, wherein the amount of a muscarinic acetylcholine receptor inhibitor is at a dose level insufficient to reach an efficacious dose if it were to be dosed in the absence of a second therapeutic agent selected from a muscarinic acetylcholine receptor activator, a procholinergic agent, and an acetylcholinesterase inhibitor.

In some aspects, the present disclosure provides pharmaceutical composition comprising (i) a muscarinic acetylcholine receptor inhibitor and (ii) a muscarinic receptor activator, wherein if the subject is administered a standard, monotherapy dose of a muscarinic acetylcholine receptor inhibitor, which would be known in the art, in combination with a muscarinic receptor activator, the subject would experience increased frequency, increased magnitude, or more severe adverse effects compared to a subject who was administered a standard, monotherapy dose of a muscarinic acetylcholine receptor inhibitor.

In some aspects, the present disclosure provides a pharmaceutical composition comprising (i) (R)-trihexyphenidyl or pharmaceutically acceptable salt thereof and (ii) a muscarinic receptor activator, wherein if the subject is administered a standard, monotherapy dose of (R)-trihexyphenidyl or a pharmaceutically acceptable salt thereof, which would be known in the art, in combination with a muscarinic receptor activator, the subject would experience increased frequency, increased magnitude, or more severe adverse effects compared to a subject who was administered a standard, monotherapy dose of (R)-trihexyphenidyl alone.

In some aspects, the present disclosure provides a pharmaceutical composition comprising (i) racemic-trihexyphenidyl or pharmaceutically acceptable salt thereof and (ii) a muscarinic receptor activator, wherein if the subject is administered a standard, monotherapy dose of racemic-trihexyphenidyl or a pharmaceutically acceptable salt thereof, which would be known in the art, in combination with a muscarinic receptor activator, the subject would experience increased frequency, increased magnitude, or more severe adverse effects compared to a subject who was administered a standard, monotherapy dose of racemic-trihexyphenidyl alone.

In some aspects, the present disclosure provides a pharmaceutical composition comprising (i) a muscarinic acetylcholine receptor inhibitor and (ii) a second therapeutic agent selected from a muscarinic acetylcholine receptor activator, a procholinergic agent, and an acetylcholinesterase inhibitor, to thereby treat the movement disorder, wherein if the subject is administered a standard, monotherapy dose of a muscarinic acetylcholine receptor inhibitor, which would be known in the art, in combination with a second therapeutic agent selected from a muscarinic acetylcholine receptor activator, a procholinergic agent, and an acetylcholinesterase inhibitor, the subject would experience increased frequency, increased magnitude, or more severe adverse effects compared to a subject who was administered a standard dose of a muscarinic acetylcholine receptor inhibitor.

In some aspects, the magnitude or severity of at least one side effect of the muscarinic acetylcholine receptor inhibitor is reduced in the subject compared to a subject administered an immediate release formulation of the muscarinic acetylcholine receptor inhibitor alone. In some aspects, the magnitude of at least one side effect of the muscarinic acetylcholine receptor inhibitor is reduced in the subject compared to a subject administered an immediate release formulation of the muscarinic acetylcholine receptor inhibitor alone. In some aspects, the severity of at least one side effect of the muscarinic acetylcholine receptor inhibitor is reduced in the subject compared to a subject administered an immediate release formulation of the muscarinic acetylcholine receptor inhibitor alone. In some aspects, the magnitude and severity of at least one side effect of the muscarinic acetylcholine receptor inhibitor is reduced in the subject compared to a subject administered an immediate release formulation of the muscarinic acetylcholine receptor inhibitor alone.

In some aspects, the weight ratio of (1) racemic trihexyphenidyl to (2) racemic bethanechol in the pharmaceutical composition is about 1:2 to about 1:20. In some aspects, the weight ratio of (1) racemic trihexyphenidyl to (2) racemic bethanechol in the pharmaceutical composition is about 1:3 to about 1:19. In some aspects, the weight ratio of (1) racemic trihexyphenidyl to (2) racemic bethanechol in the pharmaceutical composition is about 1:4 to about 1:18. In some aspects, the weight ratio of (1) racemic trihexyphenidyl to (2) racemic bethanechol in the pharmaceutical composition is about 1:5 to about 1:17. In some aspects, the weight ratio of (1) racemic trihexyphenidyl to (2) racemic bethanechol in the pharmaceutical composition is about 1:6 to about 1:16. In some aspects, the weight ratio of (1) racemic trihexyphenidyl to (2) racemic bethanechol in the pharmaceutical composition is about 1:7 to about 1:15. In some aspects, the weight ratio of (1) racemic trihexyphenidyl to (2) racemic bethanechol in the pharmaceutical composition is about 1:8 to about 1:14. In some aspects, the weight ratio of (1) racemic trihexyphenidyl to (2) racemic bethanechol in the pharmaceutical composition is about 1:9 to about 1:13. In some aspects, the weight ratio of (1) racemic trihexyphenidyl to (2) racemic bethanechol in the pharmaceutical composition is about 1:10 to about 1:12.

In some aspects, the weight ratio of (1) racemic trihexyphenidyl to (2) racemic bethanechol in the pharmaceutical composition is about 1:2. In some aspects, the weight ratio of (1) racemic trihexyphenidyl to (2) racemic bethanechol in the pharmaceutical composition is about 1:3. In some aspects, the weight ratio of (1) racemic trihexyphenidyl to (2) racemic bethanechol in the pharmaceutical composition is about 1:4. In some aspects, the weight ratio of (1) racemic trihexyphenidyl to (2) racemic bethanechol in the pharmaceutical composition is about 1:5. In some aspects, the weight ratio of (1) racemic trihexyphenidyl to (2) racemic bethanechol in the pharmaceutical composition is about 1:6. In some aspects, the weight ratio of (1) racemic trihexyphenidyl to (2) racemic bethanechol in the pharmaceutical composition is about 1:7. In some aspects, the weight ratio of (1) racemic trihexyphenidyl to (2) racemic bethanechol in the pharmaceutical composition is about 1:8. In some aspects, the weight ratio of (1) racemic trihexyphenidyl to (2) racemic bethanechol in the pharmaceutical composition is about 1:9. In some aspects, the weight ratio of (1) racemic trihexyphenidyl to (2) racemic bethanechol in the pharmaceutical composition is about 1:10. In some aspects, the weight ratio of (1) racemic trihexyphenidyl to (2) racemic bethanechol is about 1:11. In some aspects, the weight ratio of (1) racemic trihexyphenidyl to (2) racemic bethanechol in the pharmaceutical composition is about 1:12. In some aspects, the weight ratio of (1) racemic trihexyphenidyl to (2) racemic bethanechol in the pharmaceutical composition is about 1:13. In some aspects, the weight ratio of (1) racemic trihexyphenidyl to (2) racemic bethanechol in the pharmaceutical composition is about 1:14. In some aspects, the weight ratio of (1) racemic trihexyphenidyl to (2) racemic bethanechol in the pharmaceutical composition is about 1:15. In some aspects, the weight ratio of (1) racemic trihexyphenidyl to (2) racemic bethanechol in the pharmaceutical composition is about 1:16. In some aspects, the weight ratio of (1) racemic trihexyphenidyl to (2) racemic bethanechol in the pharmaceutical composition is about 1:17. In some aspects, the weight ratio of (1) racemic trihexyphenidyl to (2) racemic bethanechol in the pharmaceutical composition is about 1:18. In some aspects, the weight ratio of (1) racemic trihexyphenidyl to (2) racemic bethanechol in the pharmaceutical composition is about 1:19. In some aspects, the weight ratio of (1) racemic trihexyphenidyl to (2) racemic bethanechol in the pharmaceutical composition is about 1:20.

In some aspects, the weight ratio of (1) (R)-trihexyphenidyl to (2) racemic bethanechol in the pharmaceutical composition is about 1:4 to about 1:40. In some aspects, the weight ratio of (1) (R)-trihexyphenidyl to (2) racemic bethanechol in the pharmaceutical composition is about 1:5 to about 1:39. In some aspects, the weight ratio of (1) (R)-trihexyphenidyl to (2) racemic bethanechol in the pharmaceutical composition is about 1:6 to about 1:38. In some aspects, the weight ratio of (1) (R)-trihexyphenidyl to (2) racemic bethanechol in the pharmaceutical composition is about 1:7 to about 1:37. In some aspects, the weight ratio of (1) (R)-trihexyphenidyl to (2) racemic bethanechol in the pharmaceutical composition is about 1:8 to about 1:36. In some aspects, the weight ratio of (1) (R)-trihexyphenidyl to (2) racemic bethanechol in the pharmaceutical composition is about 1:9 to about 1:35. In some aspects, the weight ratio of (1) (R)-trihexyphenidyl to (2) racemic bethanechol in the pharmaceutical composition is about 1:10 to about 1:34. In some aspects, the weight ratio of (1) (R)-trihexyphenidyl to (2) racemic bethanechol in the pharmaceutical composition is about 1:11 to about 1:33. In some aspects, the weight ratio of (1) (R)-trihexyphenidyl to (2) racemic bethanechol in the pharmaceutical composition is about 1:12 to about 1:32. In some aspects, the weight ratio of (1) (R)-trihexyphenidyl to (2) racemic bethanechol in the pharmaceutical composition is about 1:13 to about 1:31. In some aspects, the weight ratio of (1) (R)-trihexyphenidyl to (2) racemic bethanechol in the pharmaceutical composition is about 1:14 to about 1:30. In some aspects, the weight ratio of (1) (R)-trihexyphenidyl to (2) racemic bethanechol in the pharmaceutical composition is about 1:15 to about 1:29. In some aspects, the weight ratio of (1) (R)-trihexyphenidyl to (2) racemic bethanechol in the pharmaceutical composition is about 1:16 to about 1:28. In some aspects, the weight ratio of (1) (R)-trihexyphenidyl to (2) racemic bethanechol in the pharmaceutical composition is about 1:17 to about 1:27. In some aspects, the weight ratio of (1) (R)-trihexyphenidyl to (2) racemic bethanechol in the pharmaceutical composition is about 1:18 to about 1:26. In some aspects, the weight ratio of (1) (R)-trihexyphenidyl to (2) racemic bethanechol in the pharmaceutical composition is about 1:19 to about 1:25. In some aspects, the weight ratio of (1) (R)-trihexyphenidyl to (2) racemic bethanechol in the pharmaceutical composition is about 1:20 to about 1:24. In some aspects, the weight ratio of (1) (R)-trihexyphenidyl to (2) racemic bethanechol in the pharmaceutical composition is about 1:21 to about 1:23.

In some aspects, the weight ratio of (1) (R)-trihexyphenidyl to (2) racemic bethanechol in the pharmaceutical composition is about 1:4. In some aspects, the weight ratio of (1) (R)-trihexyphenidyl to (2) racemic bethanechol in the pharmaceutical composition is about 1:5. In some aspects, the weight ratio of (1) (R)-trihexyphenidyl to (2) racemic bethanechol in the pharmaceutical composition is about 1:6. In some aspects, the weight ratio of (1) (R)-trihexyphenidyl to (2) racemic bethanechol in the pharmaceutical composition is about 1:7. In some aspects, the weight ratio of (1) (R)-trihexyphenidyl to (2) racemic bethanechol in the pharmaceutical composition is about 1:8. In some aspects, the weight ratio of (1) (R)-trihexyphenidyl to (2) racemic bethanechol in the pharmaceutical composition is about 1:9. In some aspects, the weight ratio of (1) (R)-trihexyphenidyl to (2) racemic bethanechol in the pharmaceutical composition is about 1:10. In some aspects, the weight ratio of (1) (R)-trihexyphenidyl to (2) racemic bethanechol in the pharmaceutical composition is about 1:11. In some aspects, the weight ratio of (1) (R)-trihexyphenidyl to (2) racemic bethanechol in the pharmaceutical composition is about 1:12. In some aspects, the weight ratio of (1) (R)-trihexyphenidyl to (2) racemic bethanechol in the pharmaceutical composition is about 1:13. In some aspects, the weight ratio of (1) (R)-trihexyphenidyl to (2) racemic bethanechol in the pharmaceutical composition is about 1:14. In some aspects, the weight ratio of (1) (R)-trihexyphenidyl to (2) racemic bethanechol in the pharmaceutical composition is about 1:15. In some aspects, the weight ratio of (1) (R)-trihexyphenidyl to (2) racemic bethanechol in the pharmaceutical composition is about 1:16. In some aspects, the weight ratio of (1) (R)-trihexyphenidyl to (2) racemic bethanechol in the pharmaceutical composition is about 1:17. In some aspects, the weight ratio of (1) (R)-trihexyphenidyl to (2) racemic bethanechol in the pharmaceutical composition is about 1:18. In some aspects, the weight ratio of (1) (R)-trihexyphenidyl to (2) racemic bethanechol in the pharmaceutical composition is about 1:19. In some aspects, the weight ratio of (1) (R)-trihexyphenidyl to (2) racemic bethanechol in the pharmaceutical composition is about 1:20. In some aspects, the weight ratio of (1) (R)-trihexyphenidyl to (2) racemic bethanechol in the pharmaceutical composition is about 1:21. In some aspects, the weight ratio of (1) (R)-trihexyphenidyl to (2) racemic bethanechol in the pharmaceutical composition is about 1:22. In some aspects, the weight ratio of (1) (R)-trihexyphenidyl to (2) racemic bethanechol in the pharmaceutical composition is about 1:23. In some aspects, the weight ratio of (1) (R)-trihexyphenidyl to (2) racemic bethanechol in the pharmaceutical composition is about 1:24. In some aspects, the weight ratio of (1) (R)-trihexyphenidyl to (2) racemic bethanechol in the pharmaceutical composition is about 1:25. In some aspects, the weight ratio of (1) (R)-trihexyphenidyl to (2) racemic bethanechol in the pharmaceutical composition is about 1:26. In some aspects, the weight ratio of (1) (R)-trihexyphenidyl to (2) racemic bethanechol in the pharmaceutical composition is about 1:27. In some aspects, the weight ratio of (1) (R)-trihexyphenidyl to (2) racemic bethanechol in the pharmaceutical composition is about 1:28. In some aspects, the weight ratio of (1) (R)-trihexyphenidyl to (2) racemic bethanechol in the pharmaceutical composition is about 1:29. In some aspects, the weight ratio of (1) (R)-trihexyphenidyl to (2) racemic bethanechol in the pharmaceutical composition is about 1:30. In some aspects, the weight ratio of (1) (R)-trihexyphenidyl to (2) racemic bethanechol in the pharmaceutical composition is about 1:31. In some aspects, the weight ratio of (1) (R)-trihexyphenidyl to (2) racemic bethanechol in the pharmaceutical composition is about 1:32. In some aspects, the weight ratio of (1) (R)-trihexyphenidyl to (2) racemic bethanechol in the pharmaceutical composition is about 1:33. In some aspects, the weight ratio of (1) (R)-trihexyphenidyl to (2) racemic bethanechol in the pharmaceutical composition is about 1:34. In some aspects, the weight ratio of (1) (R)-trihexyphenidyl to (2) racemic bethanechol in the pharmaceutical composition is about 1:35. In some aspects, the weight ratio of (1) (R)-trihexyphenidyl to (2) racemic bethanechol in the pharmaceutical composition is about 1:36. In some aspects, the weight ratio of (1) (R)-trihexyphenidyl to (2) racemic bethanechol in the pharmaceutical composition is about 1:37. In some aspects, the weight ratio of (1) (R)-trihexyphenidyl to (2) racemic bethanechol in the pharmaceutical composition is about 1:38. In some aspects, the weight ratio of (1) (R)-trihexyphenidyl to (2) racemic bethanechol in the pharmaceutical composition is about 1:39. In some aspects, the weight ratio of (1) (R)-trihexyphenidyl to (2) racemic bethanechol in the pharmaceutical composition is about 1:40.

In some aspects, the oral pharmaceutical composition comprises (R)-trihexyphenidyl or pharmaceutically acceptable salt thereof and racemic bethanechol or pharmaceutically acceptable salt thereof, wherein the trihexyphenidyl and bethanechol in the pharmaceutical composition are present at a weight ratio of about 1:4 to about 1:20.

In some aspects, the oral pharmaceutical composition comprises trihexyphenidyl or pharmaceutically acceptable salt thereof and bethanechol or pharmaceutically acceptable salt thereof, wherein the trihexyphenidyl and bethanechol are administered at a weight ratio of trihexyphenidyl to bethanechol of 1 to greater than 1.

In some aspects, the weight ratio of trihexyphenidyl to bethanechol is about 1:1.1 to about 1:10. In some aspects, the weight ratio of trihexyphenidyl to bethanechol is about 1:2 to about 1:9. In some aspects, the weight ratio of trihexyphenidyl to bethanechol is about 1:3 to about 1:8. In some aspects, the weight ratio of trihexyphenidyl to bethanechol is about 1:4 to about 1:7. In some aspects, the weight ratio of trihexyphenidyl to bethanechol is about 1:5 to about 1:6. In some aspects, the weight ratio of trihexyphenidyl to bethanechol is about 1:1.1. In some aspects, the weight ratio of trihexyphenidyl to bethanechol is about 1:2. In some aspects, the weight ratio of trihexyphenidyl to bethanechol is about 1:3. In some aspects, the weight ratio of trihexyphenidyl to bethanechol is about 1:4. In some aspects, the weight ratio of trihexyphenidyl to bethanechol is about 1:5. In some aspects, the weight ratio of trihexyphenidyl to bethanechol is about 1:6. In some aspects, the weight ratio of trihexyphenidyl to bethanechol is about 1:7. In some aspects, the weight ratio of trihexyphenidyl to bethanechol is about 1:8. In some aspects, the weight ratio of trihexyphenidyl to bethanechol is about 1:9. In some aspects, the weight ratio of trihexyphenidyl to bethanechol is about 1:10.

In some aspects, the oral pharmaceutical composition comprises racemic-trihexyphenidyl or pharmaceutically acceptable salt thereof and racemic-bethanechol or pharmaceutically acceptable salt thereof, wherein the racemic-trihexyphenidyl and racemic-bethanechol are administered at a weight ratio of racemic-bethanechol to racemic-trihexyphenidyl of 1 to greater than 1. In some aspects, the weight ratio of racemic-trihexyphenidyl to racemic-bethanechol is about 1:1.1 to about 1:10. In some aspects, the weight ratio of racemic-trihexyphenidyl to racemic-bethanechol is about 1:2 to about 1:9. In some aspects, the weight ratio of racemic-trihexyphenidyl to racemic-bethanechol is about 1:3 to about 1:8. In some aspects, the weight ratio of racemic-trihexyphenidyl to racemic-bethanechol is about 1:4 to about 1:7. In some aspects, the weight ratio of racemic-trihexyphenidyl to racemic-bethanechol is about 1:5 to about 1:6. In some aspects, the weight ratio of racemic-trihexyphenidyl to racemic-bethanechol is about 1:1.1. In some aspects, the weight ratio of racemic-trihexyphenidyl to racemic-bethanechol is about 1:2. In some aspects, the weight ratio of racemic-trihexyphenidyl to racemic-bethanechol is about 1:3. In some aspects, the weight ratio of racemic-trihexyphenidyl to racemic-bethanechol is about 1:4. In some aspects, the weight ratio of racemic-trihexyphenidyl to racemic-bethanechol is about 1:5. In some aspects, the weight ratio of racemic-trihexyphenidyl to racemic-bethanechol is about 1:6. In some aspects, the weight ratio of racemic-trihexyphenidyl to racemic-bethanechol is about 1:7. In some aspects, the weight ratio of racemic-trihexyphenidyl to racemic-bethanechol is about 1:8. In some aspects, the weight ratio of racemic-trihexyphenidyl to racemic-bethanechol is about 1:9. In some aspects, the weight ratio of racemic-trihexyphenidyl to racemic-bethanechol is about 1:10.

In some aspects, the oral pharmaceutical composition comprises (R)-trihexyphenidyl or pharmaceutically acceptable salt thereof and racemic-bethanechol or pharmaceutically acceptable salt thereof, wherein the (R)-trihexyphenidyl and racemic-bethanechol are administered at a weight ratio of (R)-trihexyphenidyl to racemic-bethanechol of 1 to greater than 1. In some aspects, the weight ratio of (R)-trihexyphenidyl to racemic-bethanechol is about 1:1.1 to about 1:10. In some aspects, the weight ratio of (R)-trihexyphenidyl to racemic-bethanechol is about 1:2 to about 1:9. In some aspects, the weight ratio of (R)-trihexyphenidyl to racemic-bethanechol is about 1:3 to about 1:8. In some aspects, the weight ratio of (R)-trihexyphenidyl to racemic-bethanechol is about 1:4 to about 1:7. In some aspects, the weight ratio of (R)-trihexyphenidyl to racemic-bethanechol is about 1:5 to about 1:6. In some aspects, the weight ratio of (R)-trihexyphenidyl to racemic-bethanechol is about 1:1.1. In some aspects, the weight ratio of (R)-trihexyphenidyl to racemic-bethanechol is about 1:2. In some aspects, the weight ratio of (R)-trihexyphenidyl to racemic-bethanechol is about 1:3. In some aspects, the weight ratio of (R)-trihexyphenidyl to racemic-bethanechol is about 1:4. In some aspects, the weight ratio of (R)-trihexyphenidyl to racemic-bethanechol is about 1:5. In some aspects, the weight ratio of (R)-trihexyphenidyl to racemic-bethanechol is about 1:6. In some aspects, the weight ratio of (R)-trihexyphenidyl to racemic-bethanechol is about 1:7. In some aspects, the weight ratio of (R)-trihexyphenidyl to racemic-bethanechol is about 1:8. In some aspects, the weight ratio of (R)-trihexyphenidyl to racemic-bethanechol is about 1:9. In some aspects, the weight ratio of (R)-trihexyphenidyl to racemic-bethanechol is about 1:10

In some aspects, the oral pharmaceutical composition comprises (R)-trihexyphenidyl or pharmaceutically acceptable salt thereof and (S)-bethanechol or pharmaceutically acceptable salt thereof, wherein the (R)-trihexyphenidyl and (S)-bethanechol are administered at a weight ratio of (R)-trihexyphenidyl to (S)-bethanechol of 1 to greater than 1. In some aspects, the weight ratio of (R)-trihexyphenidyl to (S)-bethanechol is about 1:1.1 to about 1:10. In some aspects, the weight ratio of (R)-trihexyphenidyl to (S)-bethanechol is about 1:2 to about 1:9. In some aspects, the weight ratio of (R)-trihexyphenidyl to (S)-bethanechol is about 1:3 to about 1:8. In some aspects, the weight ratio of (R)-trihexyphenidyl to (S)-bethanechol is about 1:4 to about 1:7. In some aspects, the weight ratio of (R)-trihexyphenidyl to (S)-bethanechol is about 1:5 to about 1:6. In some aspects, the weight ratio of (R)-trihexyphenidyl to (S)-bethanechol is about 1:1.1. In some aspects, the weight ratio of (R)-trihexyphenidyl to (S)-bethanechol is about 1:2. In some aspects, the weight ratio of (R)-trihexyphenidyl to (S)-bethanechol is about 1:3. In some aspects, the weight ratio of (R)-trihexyphenidyl to (S)-bethanechol is about 1:4. In some aspects, the weight ratio of (R)-trihexyphenidyl to (S)-bethanechol is about 1:5. In some aspects, the weight ratio of (R)-trihexyphenidyl to (S)-bethanechol is about 1:6. In some aspects, the weight ratio of (R)-trihexyphenidyl to (S)-bethanechol is about 1:7. In some aspects, the weight ratio of (R)-trihexyphenidyl to (S)-bethanechol is about 1:8. In some aspects, the weight ratio of (R)-trihexyphenidyl to (S)-bethanechol is about 1:9. In some aspects, the weight ratio of (R)-trihexyphenidyl to (S)-bethanechol is about 1:10.

In some aspects, the oral pharmaceutical composition comprises a muscarinic acetylcholine receptor inhibitor and a muscarinic acetylcholine receptor activator, wherein the muscarinic acetylcholine receptor inhibitor and the muscarinic acetylcholine receptor activator are administered at a weight ratio of muscarinic acetylcholine receptor activator to muscarinic acetylcholine receptor inhibitor of 1 to greater than 1. In some aspects, the weight ratio of muscarinic acetylcholine receptor activator to muscarinic acetylcholine receptor inhibitor is about 1:1.1 to about 1:10. In some aspects, the weight ratio of muscarinic acetylcholine receptor activator to muscarinic acetylcholine receptor inhibitor is about 1:2 to about 1:9. In some aspects, the weight ratio of muscarinic acetylcholine receptor activator to muscarinic acetylcholine receptor inhibitor is about 1:3 to about 1:8. In some aspects, the weight ratio of muscarinic acetylcholine receptor activator to muscarinic acetylcholine receptor inhibitor is about 1:4 to about 1:7. In some aspects, the weight ratio of muscarinic acetylcholine receptor activator to muscarinic acetylcholine receptor inhibitor is about 1:5 to about 1:6. In some aspects, the weight ratio of muscarinic acetylcholine receptor activator to muscarinic acetylcholine receptor inhibitor is about 1:1.1. In some aspects, the weight ratio of muscarinic acetylcholine receptor activator to muscarinic acetylcholine receptor inhibitor is about 1:2. In some aspects, the weight ratio of muscarinic acetylcholine receptor activator to muscarinic acetylcholine receptor inhibitor is about 1:3. In some aspects, the weight ratio of muscarinic acetylcholine receptor activator to muscarinic acetylcholine receptor inhibitor is about 1:4. In some aspects, the weight ratio of muscarinic acetylcholine receptor activator to muscarinic acetylcholine receptor inhibitor is about 1:5. In some aspects, the weight ratio of muscarinic acetylcholine receptor activator to muscarinic acetylcholine receptor inhibitor is about 1:6. In some aspects, the weight ratio of muscarinic acetylcholine receptor activator to muscarinic acetylcholine receptor inhibitor is about 1:7. In some aspects, the weight ratio of muscarinic acetylcholine receptor activator to muscarinic acetylcholine receptor inhibitor is about 1:8. In some aspects, the weight ratio of muscarinic acetylcholine receptor activator to muscarinic acetylcholine receptor inhibitor is about 1:9. In some aspects, the weight ratio of muscarinic acetylcholine receptor activator to muscarinic acetylcholine receptor inhibitor is about 1:10.

Another aspect of the invention provides a unit dose formulation, comprising a pharmaceutical composition described herein. In some aspects, the invention provides a unit dose formulation, comprising an oral pharmaceutical composition comprising (i) a muscarinic acetylcholine receptor inhibitor, (ii) a muscarinic acetylcholine receptor activator in an amount effective to reduce the frequency and/or magnitude of at least one side effect of the muscarinic acetylcholine receptor inhibitor, and (iii) a pharmaceutically acceptable carrier.

In some aspects, the unit dose formulation comprises from about 10 mg to about 1000 mg of the muscarinic acetylcholine receptor inhibitor.

In some aspects, the unit dose formulation comprises from about 50 mg to about 1000 mg of the muscarinic acetylcholine receptor activator.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 20 ng/mL/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 19 ng/mL/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 18 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 17 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 16 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 15 ng/mL/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 14 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 13 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 12 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 11 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 10 ng/mL/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 9 ng/mL/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 8 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 7 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 6 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 5 ng/mL/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 4 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 3 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 2 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the rate of rise of the serum concentration of the muscarinic acetylcholine receptor inhibitor is less than about 1 ng/mL/hr.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:5 to about 1:50 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:6 to about 1:49 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:7 to about 1:48 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:8 to about 1:47 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:9 to about 1:46 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:10 to about 1:45 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:11 to about 1:44 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:12 to about 1:43 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:13 to about 1:42 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:14 to about 1:41 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:15 to about 1:40 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:16 to about 1:39 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:17 to about 1:38 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:18 to about 1:37 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:19 to about 1:36 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:20 to about 1:35 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:21 to about 1:34 over the 24-hour period after administration. In some aspects, the oral pharmaceutical composition comprises (i) a muscarinic acetylcholine receptor inhibitor in an amount effective to treat a movement disorder and (ii) a muscarinic acetylcholine a patient in need thereof, the composition is sufficient to provide an in vivo serum profile, wherein the C(average) serum concentration ratio of the muscarinic acetylcholine receptor inhibitor to the muscarinic receptor activator is about 1:22 to about 1:33 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:23 to about 1:32 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:24 to about 1:31 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:25 to about 1:30 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:26 to about 1:29 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(average) serum concentration ratio of the muscarinic acetylcholine receptor inhibitor to the muscarinic receptor activator is about 1:27 to about 1:28 over the 24-hour period after administration.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the area under the curve (AUC) serum ratio of the muscarinic acetylcholine receptor inhibitor to the muscarinic receptor activator is about 1:1 to about 1:42 and (ii) the C(max) serum concentration ratio of the muscarinic acetylcholine receptor inhibitor to the muscarinic receptor activator is about 1:5 to about 1:50 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:2 to about 1:41 and (ii) the C(max) serum concentration ratio of the muscarinic acetylcholine receptor inhibitor to the muscarinic receptor activator is about 1:6 to about 1:4 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:3 to about 1:40 and (ii) the C(max) serum concentration ratio of the muscarinic acetylcholine receptor inhibitor to the muscarinic receptor activator is about 1:7 to about 1:48 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:4 to about 1:39 and (ii) the C(max) serum concentration ratio of the muscarinic acetylcholine receptor inhibitor to the muscarinic receptor activator is about 1:8 to about 1:47 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:5 to about 1:38 and (ii) the C(max) serum concentration ratio of the muscarinic acetylcholine receptor inhibitor to the muscarinic receptor activator is about 1:9 to about 1:46 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:6 to about 1:37 and (ii) the C(max) serum concentration ratio of the muscarinic acetylcholine receptor inhibitor to the muscarinic receptor activator is about 1:10 to about 1:45 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:7 to about 1:36 and (ii) the C(max) serum concentration ratio of the muscarinic acetylcholine receptor inhibitor to the muscarinic receptor activator is about 1:11 to about 1:44 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:8 to about 1:35 and (ii) the C(max) serum concentration ratio of the muscarinic acetylcholine receptor inhibitor to the muscarinic receptor activator is about 1:12 to about 1:43 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:9 to about 1:33 and (ii) the C(max) serum concentration ratio of the muscarinic acetylcholine receptor inhibitor to the muscarinic receptor activator is about 1:13 to about 1:42 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:10 to about 1:32 and (ii) the C(max) serum concentration ratio of the muscarinic acetylcholine receptor inhibitor to the muscarinic receptor activator is about 1:14 to about 1:41 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:11 to about 1:31 and (ii) the C(max) serum concentration ratio of the muscarinic acetylcholine receptor inhibitor to the muscarinic receptor activator is about 1:15 to about 1:40 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:12 to about 1:29 and (ii) the C(max) serum concentration ratio of the muscarinic acetylcholine receptor inhibitor to the muscarinic receptor activator is about 1:16 to about 1:39 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:13 to about 1:28 and (ii) the C(max) serum concentration ratio of the muscarinic acetylcholine receptor inhibitor to the muscarinic receptor activator is about 1:17 to about 1:38 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:14 to about 1:27 and (ii) the C(max) serum concentration ratio of the muscarinic acetylcholine receptor inhibitor to the muscarinic receptor activator is about 1:18 to about 1:37 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:15 to about 1:26 and (ii) the C(max) serum concentration ratio of the muscarinic acetylcholine receptor inhibitor to the muscarinic receptor activator is about 1:19 to about 1:36 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:16 to about 1:25 and (ii) the C(max) serum concentration ratio of the muscarinic acetylcholine receptor inhibitor to the muscarinic receptor activator is about 1:20 to about 1:35 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:17 to about 1:24 and (ii) the C(max) serum concentration ratio of the muscarinic acetylcholine receptor inhibitor to the muscarinic receptor activator is about 1:21 to about 1:34 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:18 to about 1:23 and (ii) the C(max) serum concentration ratio of the muscarinic acetylcholine receptor inhibitor to the muscarinic receptor activator is about 1:22 to about 1:33 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:19 to about 1:22 and (ii) the C(max) serum concentration ratio of the muscarinic acetylcholine receptor inhibitor to the muscarinic receptor activator is about 1:23 to about 1:32 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:20 to about 1:21 and (ii) the C(max) serum concentration ratio of the muscarinic acetylcholine receptor inhibitor to the muscarinic receptor activator is about 1:24 to about 1:31 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:15 to about 1:21 and (ii) the C(max) serum concentration ratio of the muscarinic acetylcholine receptor inhibitor to the muscarinic receptor activator is about 1:25 to about 1:30 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:16 to about 1:20 and (ii) the C(max) serum concentration ratio of the muscarinic acetylcholine receptor inhibitor to the muscarinic receptor activator is about 1:26 to about 1:29 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:17 to about 1:18 and (ii) the C(max) serum concentration ratio of the muscarinic acetylcholine receptor inhibitor to the muscarinic receptor activator is about 1:27 to about 1:28 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:16 to about 1:20 and (ii) the C(max) serum concentration ratio of the muscarinic acetylcholine receptor inhibitor to the muscarinic receptor activator is about 1:8 to about 1:11 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein (i) the AUC serum ratio of the muscarinic acetylcholine receptor inhibitor to the muscarinic receptor activator is about 1:17 to about 1:18 and (ii) the C(max) serum concentration ratio of the muscarinic acetylcholine receptor inhibitor to the muscarinic receptor activator is about 1:9 to about 1:10 over the 24-hour period after administration.

In some aspects, the C(max) serum ratio of the muscarinic acetylcholine receptor inhibitor to the muscarinic receptor activator is about 1:1 to about 1:20 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:2 to about 1:19 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:3 to about 1:18 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:4 to about 1:17 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:5 to about 1:16 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:6 to about 1:15 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:7 to about 1:14 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:8 to about 1:13 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:9 to about 1:12 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:10 to about 1:11 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:9 to about 1:11 over the 24-hour period after administration.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:1 to about 1:38 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:2 to about 1:37 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:3 to about 1:36 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:4 to about 1:35 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:5 to about 1:34 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:6 to about 1:33 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:7 to about 1:32 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:8 to about 1:31 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:9 to about 1:30 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:10 to about 1:29 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:11 to about 1:28 over the 24-hour period after administration. In some aspects, the oral pharmaceutical composition comprises (i) a muscarinic acetylcholine receptor inhibitor in an amount effective to treat a movement disorder and (ii) a muscarinic acetylcholine a patient in need thereof, the composition is sufficient to provide an in vivo serum profile, wherein the area under the curve (AUC) serum ratio of the muscarinic acetylcholine receptor inhibitor to the muscarinic receptor activator is about 1:12 to about 1:27 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:13 to about 1:26 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:14 to about 1:25 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:15 to about 1:24 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:16 to about 1:23 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:17 to about 1:22 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:18 to about 1:21 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:14 to about 1:22 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:15 to about 1:21 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:16 to about 1:20 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:17 to about 1:19 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the area under the curve (AUC) serum ratio of the muscarinic acetylcholine receptor inhibitor to the muscarinic receptor activator is about 1:17 to about 1:20 over the 24-hour period after administration.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:1 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:2 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:3 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:4 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:5 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:6 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:7 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:8 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:9 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:10 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:11 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:12 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:13 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:14 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:15 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:16 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:17 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:18 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:19 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:20 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:21 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:22 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:23 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:24 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:25 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:26 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:27 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:28 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:29 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:30 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:31 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:31 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:32 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:33 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:34 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:35 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:36 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:37 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:38 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:39 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the AUC serum ratio of the muscarinic acetylcholine receptor inhibitor to the muscarinic receptor activator is about 1:40 over the 24-hour period after administration.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:1 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:2 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:3 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:4 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:5 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:6 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:7 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:8 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:9 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:10 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:11 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:12 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:13 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:14 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:15 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:16 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:17 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:18 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:19 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo serum profile, wherein the C(max) serum ratio of the muscarinic acetylcholine receptor inhibitor to the muscarinic receptor activator is about 1:20 over the 24-hour period after administration.

In some aspects, the pharmaceutical composition that provides the in vivo serum profile is a controlled release formulation. In some aspects, the pharmaceutical composition that provides the in vivo serum profile comprises (i) a controlled release component containing the muscarinic acetylcholine receptor inhibitor and (ii) an immediate release component containing the muscarinic acetylcholine receptor activator. In some aspects, the pharmaceutical composition that provides the in vivo serum profile comprises (i) a controlled release component containing the muscarinic acetylcholine receptor activator and (ii) an immediate release component containing the muscarinic acetylcholine receptor inhibitor. In some aspects, the pharmaceutical composition that provides the in vivo serum profile comprises (i) a controlled release component containing the muscarinic acetylcholine receptor activator and (ii) a controlled release component containing the muscarinic acetylcholine receptor inhibitor.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 20 ng/mL/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 19 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 18 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 17 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 16 ng/mL/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 15 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 14 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 13 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 12 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 11 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 10 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 9 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 8 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 7 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 6 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 5 ng/mL/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 4 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 3 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 2 ng/ml/hr. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the rate of rise of the plasma concentration of the muscarinic acetylcholine receptor inhibitor is less than about 1 ng/ml/hr.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:5 to about 1:50 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:6 to about 1:49 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:7 to about 1:48 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:8 to about 1:47 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:9 to about 1:46 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:10 to about 1:45 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:11 to about 1:44 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:12 to about 1:43 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:13 to about 1:42 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:14 to about 1:41 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:15 to about 1:40 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:16 to about 1:39 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:17 to about 1:38 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:18 to about 1:37 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:19 to about 1:36 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:20 to about 1:35 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:21 to about 1:34 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:22 to about 1:33 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:23 to about 1:32 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:24 to about 1:31 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:25 to about 1:30 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:26 to about 1:29 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(average) plasma concentration ratio of the muscarinic acetylcholine receptor inhibitor to the muscarinic receptor activator is about 1:27 to about 1:28 over the 24-hour period after administration.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the area under the curve (AUC) plasma ratio of the muscarinic acetylcholine receptor inhibitor to the muscarinic receptor activator is about 1:1 to about 1:42 and (ii) the C(max) plasma concentration ratio of the muscarinic acetylcholine receptor inhibitor to the muscarinic receptor activator is about 1:5 to about 1:50 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:2 to about 1:41 and (ii) the C(max) plasma concentration ratio of the muscarinic acetylcholine receptor inhibitor to the muscarinic receptor activator is about 1:6 to about 1:4 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:3 to about 1:40 and (ii) the C(max) plasma concentration ratio of the muscarinic acetylcholine receptor inhibitor to the muscarinic receptor activator is about 1:7 to about 1:48 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:4 to about 1:39 and (ii) the C(max) plasma concentration ratio of the muscarinic acetylcholine receptor inhibitor to the muscarinic receptor activator is about 1:8 to about 1:47 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:5 to about 1:38 and (ii) the C(max) plasma concentration ratio of the muscarinic acetylcholine receptor inhibitor to the muscarinic receptor activator is about 1:9 to about 1:46 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:6 to about 1:37 and (ii) the C(max) plasma concentration ratio of the muscarinic acetylcholine receptor inhibitor to the muscarinic receptor activator is about 1:10 to about 1:45 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:7 to about 1:36 and (ii) the C(max) plasma concentration ratio of the muscarinic acetylcholine receptor inhibitor to the muscarinic receptor activator is about 1:11 to about 1:44 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:8 to about 1:35 and (ii) the C(max) plasma concentration ratio of the muscarinic acetylcholine receptor inhibitor to the muscarinic receptor activator is about 1:12 to about 1:43 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:9 to about 1:33 and (ii) the C(max) plasma concentration ratio of the muscarinic acetylcholine receptor inhibitor to the muscarinic receptor activator is about 1:13 to about 1:42 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:10 to about 1:32 and (ii) the C(max) plasma concentration ratio of the muscarinic acetylcholine receptor inhibitor to the muscarinic receptor activator is about 1:14 to about 1:41 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:11 to about 1:31 and (ii) the C(max) plasma concentration ratio of the muscarinic acetylcholine receptor inhibitor to the muscarinic receptor activator is about 1:15 to about 1:40 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:12 to about 1:29 and (ii) the C(max) plasma concentration ratio of the muscarinic acetylcholine receptor inhibitor to the muscarinic receptor activator is about 1:16 to about 1:39 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:13 to about 1:28 and (ii) the C(max) plasma concentration ratio of the muscarinic acetylcholine receptor inhibitor to the muscarinic receptor activator is about 1:17 to about 1:38 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:14 to about 1:27 and (ii) the C(max) plasma concentration ratio of the muscarinic acetylcholine receptor inhibitor to the muscarinic receptor activator is about 1:18 to about 1:37 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:15 to about 1:26 and (ii) the C(max) plasma concentration ratio of the muscarinic acetylcholine receptor inhibitor to the muscarinic receptor activator is about 1:19 to about 1:36 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:16 to about 1:25 and (ii) the C(max) plasma concentration ratio of the muscarinic acetylcholine receptor inhibitor to the muscarinic receptor activator is about 1:20 to about 1:35 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:17 to about 1:24 and (ii) the C(max) plasma concentration ratio of the muscarinic acetylcholine receptor inhibitor to the muscarinic receptor activator is about 1:21 to about 1:34 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:18 to about 1:23 and (ii) the C(max) plasma concentration ratio of the muscarinic acetylcholine receptor inhibitor to the muscarinic receptor activator is about 1:22 to about 1:33 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:19 to about 1:22 and (ii) the C(max) plasma concentration ratio of the muscarinic acetylcholine receptor inhibitor to the muscarinic receptor activator is about 1:23 to about 1:32 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:20 to about 1:21 and (ii) the C(max) plasma concentration ratio of the muscarinic acetylcholine receptor inhibitor to the muscarinic receptor activator is about 1:24 to about 1:31 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:15 to about 1:21 and (ii) the C(max) plasma concentration ratio of the muscarinic acetylcholine receptor inhibitor to the muscarinic receptor activator is about 1:25 to about 1:30 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:16 to about 1:20 and (ii) the C(max) plasma concentration ratio of the muscarinic acetylcholine receptor inhibitor to the muscarinic receptor activator is about 1:26 to about 1:29 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:17 to about 1:18 and (ii) the C(max) plasma concentration ratio of the muscarinic acetylcholine receptor inhibitor to the muscarinic receptor activator is about 1:27 to about 1:28 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:16 to about 1:20 and (ii) the C(max) plasma concentration ratio of the muscarinic acetylcholine receptor inhibitor to the muscarinic receptor activator is about 1:8 to about 1:11 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein (i) the AUC plasma ratio of the muscarinic acetylcholine receptor inhibitor to the muscarinic receptor activator is about 1:17 to about 1:18 and (ii) the C(max) plasma concentration ratio of the muscarinic acetylcholine receptor inhibitor to the muscarinic receptor activator is about 1:9 to about 1:10 over the 24-hour period after administration.

In some aspects, the C(max) plasma ratio of the muscarinic acetylcholine receptor inhibitor to the muscarinic receptor activator is about 1:1 to about 1:20 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:2 to about 1:19 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:3 to about 1:18 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:4 to about 1:17 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:5 to about 1:16 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:6 to about 1:15 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:7 to about 1:14 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:8 to about 1:13 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:9 to about 1:12 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:10 to about 1:11 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:9 to about 1:11 over the 24-hour period after administration.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:1 to about 1:38 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:2 to about 1:37 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:3 to about 1:36 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:4 to about 1:35 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:5 to about 1:34 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:6 to about 1:33 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:7 to about 1:32 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:8 to about 1:31 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:9 to about 1:30 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:10 to about 1:29 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:11 to about 1:28 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:12 to about 1:27 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:13 to about 1:26 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:14 to about 1:25 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:15 to about 1:24 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:16 to about 1:23 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:17 to about 1:22 over the 24-hour period after administration. In some aspects, the oral pharmaceutical composition comprises (i) a muscarinic acetylcholine receptor inhibitor in an amount effective to treat a movement disorder and (ii) a muscarinic acetylcholine a patient in need thereof, the composition is sufficient to provide an in vivo plasma profile, wherein the area under the curve (AUC) plasma ratio of the muscarinic acetylcholine receptor inhibitor to the muscarinic receptor activator is about 1:18 to about 1:21 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:14 to about 1:22 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:15 to about 1:21 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:16 to about 1:20 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:17 to about 1:19 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the area under the curve (AUC) plasma ratio of the muscarinic acetylcholine receptor inhibitor to the muscarinic receptor activator is about 1:17 to about 1:20 over the 24-hour period after administration.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:1 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:2 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:3 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:4 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:5 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:6 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:7 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:8 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:9 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:10 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:11 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:12 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:13 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:14 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:15 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:16 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:17 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:18 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:19 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:20 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:21 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:22 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:23 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:24 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:25 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:26 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:27 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:28 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:29 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:30 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:31 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:31 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:32 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:33 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:34 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:35 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:36 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:37 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:38 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:39 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the AUC plasma ratio of the muscarinic acetylcholine receptor inhibitor to the muscarinic receptor activator is about 1:40 over the 24-hour period after administration.

In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:1 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:2 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:3 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:4 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:5 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:6 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:7 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:8 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:9 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:10 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:11 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:12 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:13 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:14 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:15 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:16 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:17 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:18 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:19 over the 24-hour period after administration. In some aspects, the oral pharmaceutical composition comprises (i) a muscarinic acetylcholine receptor inhibitor in an amount effective to treat a movement disorder and (ii) a muscarinic acetylcholine receptor activator, and (iii) a pharmaceutically acceptable carrier, wherein when administered to a patient in need thereof, the composition is sufficient to provide an in vivo plasma profile, wherein the C(max) plasma ratio of the muscarinic acetylcholine receptor inhibitor to the muscarinic receptor activator is about 1:20 over the 24-hour period after administration.

In some aspects, the invention provides a combination comprising a muscarinic acetylcholine receptor inhibitor and a muscarinic acetylcholine receptor activator for use in medicine. In some aspects, the invention provides a combination comprising a muscarinic acetylcholine receptor inhibitor and a muscarinic acetylcholine receptor activator for use in the treatment of a medical disorder described herein, such as a movement disorder described herein. In some aspects, the invention provides a combination comprising (i) a muscarinic acetylcholine receptor inhibitor and (ii) a second therapeutic agent selected from a muscarinic acetylcholine receptor activator, a procholinergic agent, and an acetylcholinesterase inhibitor for use in medicine. In some aspects, the invention provides a combination comprising (i) a muscarinic acetylcholine receptor inhibitor and (ii) a second therapeutic agent selected from a muscarinic acetylcholine receptor activator, a procholinergic agent, and an acetylcholinesterase inhibitor for use in the treatment of a medical disorder described herein, such as a movement disorder described herein. In some aspects, the combination further comprises a pharmaceutically acceptable carrier. The details given with respect to the therapeutic methods described herein equally apply to the medical uses described herein.

In some aspects, the pharmaceutical composition that provides the in vivo plasma profile is a controlled release formulation. In some aspects, the pharmaceutical composition that provides the in vivo plasma profile comprises (i) a controlled release component containing the muscarinic acetylcholine receptor inhibitor and (ii) an immediate release component containing the muscarinic acetylcholine receptor activator. In some aspects, the pharmaceutical composition that provides the in vivo plasma profile comprises (i) a controlled release component containing the muscarinic acetylcholine receptor activator and (ii) an immediate release component containing the muscarinic acetylcholine receptor inhibitor. In some aspects, the pharmaceutical composition that provides the in vivo plasma profile comprises (i) a controlled release component containing the muscarinic acetylcholine receptor activator and (ii) a controlled release component containing the muscarinic acetylcholine receptor inhibitor.

In some aspects the combination comprises (i) trihexyphenidyl or a pharmaceutically acceptable salt thereof and (ii) bethanechol or a pharmaceutically acceptable salt thereof. In some aspects, the trihexyphenidyl or a pharmaceutically acceptable salt thereof is racemic trihexyphenidyl. In some aspects, the trihexyphenidyl or a pharmaceutically acceptable salt thereof is (R)-trihexyphenidyl. In some aspects, the (R)-trihexyphenidyl or a pharmaceutically acceptable salt thereof has a stereochemical purity of at least 95% enantiomeric excess. In some aspect, the bethanechol or a pharmaceutically acceptable salt thereof is racemic bethanechol. In some aspects, the bethanechol or a pharmaceutically acceptable salt thereof is (S)-bethanechol. In some aspects, the (S)-bethanechol or a pharmaceutically acceptable salt thereof has a stereochemical purity of at least 95% enantiomeric excess.

In some aspects, the weight ratio of (1) racemic trihexyphenidyl to (2) racemic bethanechol in the combination is about 1:2 to about 1:20. In some aspects, the weight ratio of (1) racemic trihexyphenidyl to (2) racemic bethanechol in the combination is about 1:3 to about 1:19. In some aspects, the weight ratio of (1) racemic trihexyphenidyl to (2) racemic bethanechol in the combination is about 1:4 to about 1:18. In some aspects, the weight ratio of (1) racemic trihexyphenidyl to (2) racemic bethanechol in the combination is about 1:5 to about 1:17. In some aspects, the weight ratio of (1) racemic trihexyphenidyl to (2) racemic bethanechol in the combination is about 1:6 to about 1:16. In some aspects, the weight ratio of (1) racemic trihexyphenidyl to (2) racemic bethanechol in the combination is about 1:7 to about 1:15. In some aspects, the weight ratio of (1) racemic trihexyphenidyl to (2) racemic bethanechol in the combination is about 1:8 to about 1:14. In some aspects, the weight ratio of (1) racemic trihexyphenidyl to (2) racemic bethanechol in the combination is about 1:9 to about 1:13. In some aspects, the weight ratio of (1) racemic trihexyphenidyl to (2) racemic bethanechol in the combination is about 1:10 to about 1:12.

In some aspects, the weight ratio of (1) racemic trihexyphenidyl to (2) racemic bethanechol in the combination is about 1:2. In some aspects, the weight ratio of (1) racemic trihexyphenidyl to (2) racemic bethanechol in the combination is about 1:3. In some aspects, the weight ratio of (1) racemic trihexyphenidyl to (2) racemic bethanechol in the combination is about 1:4. In some aspects, the weight ratio of (1) racemic trihexyphenidyl to (2) racemic bethanechol in the combination is about 1:5. In some aspects, the weight ratio of (1) racemic trihexyphenidyl to (2) racemic bethanechol in the combination is about 1:6. In some aspects, the weight ratio of (1) racemic trihexyphenidyl to (2) racemic bethanechol in the combination is about 1:7. In some aspects, the weight ratio of (1) racemic trihexyphenidyl to (2) racemic bethanechol in the combination is about 1:8. In some aspects, the weight ratio of (1) racemic trihexyphenidyl to (2) racemic bethanechol in the combination is about 1:9. In some aspects, the weight ratio of (1) racemic trihexyphenidyl to (2) racemic bethanechol in the combination is about 1:10. In some aspects, the weight ratio of (1) racemic trihexyphenidyl to (2) racemic bethanechol is about 1:11. In some aspects, the weight ratio of (1) racemic trihexyphenidyl to (2) racemic bethanechol in the combination is about 1:12. In some aspects, the weight ratio of (1) racemic trihexyphenidyl to (2) racemic bethanechol in the combination is about 1:13. In some aspects, the weight ratio of (1) racemic trihexyphenidyl to (2) racemic bethanechol in the combination is about 1:14. In some aspects, the weight ratio of (1) racemic trihexyphenidyl to (2) racemic bethanechol in the combination is about 1:15. In some aspects, the weight ratio of (1) racemic trihexyphenidyl to (2) racemic bethanechol in the combination is about 1:16. In some aspects, the weight ratio of (1) racemic trihexyphenidyl to (2) racemic bethanechol in the combination is about 1:17. In some aspects, the weight ratio of (1) racemic trihexyphenidyl to (2) racemic bethanechol in the combination is about 1:18. In some aspects, the weight ratio of (1) racemic trihexyphenidyl to (2) racemic bethanechol in the combination is about 1:19. In some aspects, the weight ratio of (1) racemic trihexyphenidyl to (2) racemic bethanechol in the combination is about 1:20.

In some aspects, the combination comprises racemic trihexyphenidyl or pharmaceutically acceptable salt thereof, and racemic bethanechol or pharmaceutically acceptable salt thereof, wherein the trihexyphenidyl and bethanechol in the combination are administered at a weight ratio of about 1:1.1 to about 1:10. In some aspects, the weight ratio of (1) (R)-trihexyphenidyl to (2) racemic bethanechol in the combination is about 1:4 to about 1:40. In some aspects, the weight ratio of (1) (R)-trihexyphenidyl to (2) racemic bethanechol in the combination is about 1:5 to about 1:39. In some aspects, the weight ratio of (1) (R)-trihexyphenidyl to (2) racemic bethanechol in the combination is about 1:6 to about 1:38. In some aspects, the weight ratio of (1) (R)-trihexyphenidyl to (2) racemic bethanechol in the combination is about 1:7 to about 1:37. In some aspects, the weight ratio of (1) (R)-trihexyphenidyl to (2) racemic bethanechol in the combination is about 1:8 to about 1:36. In some aspects, the weight ratio of (1) (R)-trihexyphenidyl to (2) racemic bethanechol in the combination is about 1:9 to about 1:35. In some aspects, the weight ratio of (1) (R)-trihexyphenidyl to (2) racemic bethanechol in the combination is about 1:10 to about 1:34. In some aspects, the weight ratio of (1) (R)-trihexyphenidyl to (2) racemic bethanechol in the combination is about 1:11 to about 1:33. In some aspects, the weight ratio of (1) (R)-trihexyphenidyl to (2) racemic bethanechol in the combination is about 1:12 to about 1:32. In some aspects, the weight ratio of (1) (R)-trihexyphenidyl to (2) racemic bethanechol in the combination is about 1:13 to about 1:31. In some aspects, the weight ratio of (1) (R)-trihexyphenidyl to (2) racemic bethanechol in the combination is about 1:14 to about 1:30. In some aspects, the weight ratio of (1) (R)-trihexyphenidyl to (2) racemic bethanechol in the combination is about 1:15 to about 1:29. In some aspects, the weight ratio of (1) (R)-trihexyphenidyl to (2) racemic bethanechol in the combination is about 1:16 to about 1:28. In some aspects, the weight ratio of (1) (R)-trihexyphenidyl to (2) racemic bethanechol in the combination is about 1:17 to about 1:27. In some aspects, the weight ratio of (1) (R)-trihexyphenidyl to (2) racemic bethanechol in the combination is about 1:18 to about 1:26. In some aspects, the weight ratio of (1) (R)-trihexyphenidyl to (2) racemic bethanechol in the combination is about 1:19 to about 1:25. In some aspects, the weight ratio of (1) (R)-trihexyphenidyl to (2) racemic bethanechol in the combination is about 1:20 to about 1:24. In some aspects, the weight ratio of (1) (R)-trihexyphenidyl to (2) racemic bethanechol in the combination is about 1:21 to about 1:23.

In some aspects, the weight ratio of (1) (R)-trihexyphenidyl to (2) racemic bethanechol in the combination is about 1:4. In some aspects, the weight ratio of (1) (R)-trihexyphenidyl to (2) racemic bethanechol in the combination is about 1:5. In some aspects, the weight ratio of (1) (R)-trihexyphenidyl to (2) racemic bethanechol in the combination is about 1:6. In some aspects, the weight ratio of (1) (R)-trihexyphenidyl to (2) racemic bethanechol in the combination is about 1:7. In some aspects, the weight ratio of (1) (R)-trihexyphenidyl to (2) racemic bethanechol in the combination is about 1:8. In some aspects, the weight ratio of (1) (R)-trihexyphenidyl to (2) racemic bethanechol in the combination is about 1:9. In some aspects, the weight ratio of (1) (R)-trihexyphenidyl to (2) racemic bethanechol in the combination is about 1:10. In some aspects, the weight ratio of (1) (R)-trihexyphenidyl to (2) racemic bethanechol in the combination is about 1:11. In some aspects, the weight ratio of (1) (R)-trihexyphenidyl to (2) racemic bethanechol in the combination is about 1:12. In some aspects, the weight ratio of (1) (R)-trihexyphenidyl to (2) racemic bethanechol in the combination is about 1:13. In some aspects, the weight ratio of (1) (R)-trihexyphenidyl to (2) racemic bethanechol in the combination is about 1:14. In some aspects, the weight ratio of (1) (R)-trihexyphenidyl to (2) racemic bethanechol in the combination is about 1:15. In some aspects, the weight ratio of (1) (R)-trihexyphenidyl to (2) racemic bethanechol in the combination is about 1:16. In some aspects, the weight ratio of (1) (R)-trihexyphenidyl to (2) racemic bethanechol in the combination is about 1:17. In some aspects, the weight ratio of (1) (R)-trihexyphenidyl to (2) racemic bethanechol in the combination is about 1:18. In some aspects, the weight ratio of (1) (R)-trihexyphenidyl to (2) racemic bethanechol in the combination is about 1:19. In some aspects, the weight ratio of (1) (R)-trihexyphenidyl to (2) racemic bethanechol in the combination is about 1:20. In some aspects, the weight ratio of (1) (R)-trihexyphenidyl to (2) racemic bethanechol in the combination is about 1:21. In some aspects, the weight ratio of (1) (R)-trihexyphenidyl to (2) racemic bethanechol in the combination is about 1:22. In some aspects, the weight ratio of (1) (R)-trihexyphenidyl to (2) racemic bethanechol in the combination is about 1:23. In some aspects, the weight ratio of (1) (R)-trihexyphenidyl to (2) racemic bethanechol in the combination is about 1:24. In some aspects, the weight ratio of (1) (R)-trihexyphenidyl to (2) racemic bethanechol in the combination is about 1:25. In some aspects, the weight ratio of (1) (R)-trihexyphenidyl to (2) racemic bethanechol in the combination is about 1:26. In some aspects, the weight ratio of (1) (R)-trihexyphenidyl to (2) racemic bethanechol in the combination is about 1:27. In some aspects, the weight ratio of (1) (R)-trihexyphenidyl to (2) racemic bethanechol in the combination is about 1:28. In some aspects, the weight ratio of (1) (R)-trihexyphenidyl to (2) racemic bethanechol in the combination is about 1:29. In some aspects, the weight ratio of (1) (R)-trihexyphenidyl to (2) racemic bethanechol in the combination is about 1:30. In some aspects, the weight ratio of (1) (R)-trihexyphenidyl to (2) racemic bethanechol in the combination is about 1:31. In some aspects, the weight ratio of (1) (R)-trihexyphenidyl to (2) racemic bethanechol in the combination is about 1:32. In some aspects, the weight ratio of (1) (R)-trihexyphenidyl to (2) racemic bethanechol in the combination is about 1:33. In some aspects, the weight ratio of (1) (R)-trihexyphenidyl to (2) racemic bethanechol in the combination is about 1:34. In some aspects, the weight ratio of (1) (R)-trihexyphenidyl to (2) racemic bethanechol in the combination is about 1:35. In some aspects, the weight ratio of (1) (R)-trihexyphenidyl to (2) racemic bethanechol in the combination is about 1:36. In some aspects, the weight ratio of (1) (R)-trihexyphenidyl to (2) racemic bethanechol in the combination is about 1:37. In some aspects, the weight ratio of (1) (R)-trihexyphenidyl to (2) racemic bethanechol in the combination is about 1:38. In some aspects, the weight ratio of (1) (R)-trihexyphenidyl to (2) racemic bethanechol in the combination is about 1:39. In some aspects, the weight ratio of (1) (R)-trihexyphenidyl to (2) racemic bethanechol in the combination is about 1:40.

In some aspects, the combination comprises (R)-trihexyphenidyl or pharmaceutically acceptable salt thereof and racemic bethanechol or pharmaceutically acceptable salt thereof, wherein the trihexyphenidyl and bethanechol in the combination are present at a weight ratio of about 1:4 to about 1:20.

In some aspects, the combination comprises trihexyphenidyl or pharmaceutically acceptable salt thereof and bethanechol or pharmaceutically acceptable salt thereof, wherein the trihexyphenidyl and bethanechol are present at a weight ratio of trihexyphenidyl to bethanechol of 1 to greater than 1. In some aspects, the weight ratio of trihexyphenidyl to bethanechol is about 1:1.1 to about 1:10. In some aspects, the weight ratio of trihexyphenidyl to bethanechol is about 1:2 to about 1:9. In some aspects, the weight ratio of trihexyphenidyl to bethanechol is about 1:3 to about 1:8. In some aspects, the weight ratio of trihexyphenidyl to bethanechol is about 1:4 to about 1:7. In some aspects, the weight ratio of trihexyphenidyl to bethanechol is about 1:5 to about 1:6.

In some aspects, the combination comprises racemic-trihexyphenidyl or pharmaceutically acceptable salt thereof and racemic-bethanechol or pharmaceutically acceptable salt thereof, wherein the racemic-trihexyphenidyl and racemic-bethanechol are present at a weight ratio of racemic-bethanechol to racemic-trihexyphenidyl of 1 to greater than 1. In some aspects, the weight ratio of racemic-trihexyphenidyl to racemic-bethanechol is about 1:1.1 to about 1:10. In some aspects, the weight ratio of racemic-trihexyphenidyl to racemic-bethanechol is about 1:2 to about 1:9. In some aspects, the weight ratio of racemic-trihexyphenidyl to racemic-bethanechol is about 1:3 to about 1:8. In some aspects, the weight ratio of racemic-trihexyphenidyl to racemic-bethanechol is about 1:4 to about 1:7. In some aspects, the weight ratio of racemic-trihexyphenidyl to racemic-bethanechol is about 1:5 to about 1:6.

In some aspects, the combination comprises (R)-trihexyphenidyl or pharmaceutically acceptable salt thereof and racemic-bethanechol or pharmaceutically acceptable salt thereof, wherein the (R)-trihexyphenidyl and racemic-bethanechol are present at a weight ratio of greater racemic-bethanechol to (R)-trihexyphenidyl of 1 to greater than 1. In some aspects, the weight ratio of (R)-trihexyphenidyl to racemic-bethanechol is about 1:1.1 to about 1:10. In some aspects, the weight ratio of (R)-trihexyphenidyl to racemic-bethanechol is about 1:2 to about 1:9. In some aspects, the weight ratio of (R)-trihexyphenidyl to racemic-bethanechol is about 1:3 to about 1:8. In some aspects, the weight ratio of (R)-trihexyphenidyl to racemic-bethanechol is about 1:4 to about 1:7. In some aspects, the weight ratio of (R)-trihexyphenidyl to racemic-bethanechol is about 1:5 to about 1:6.

In some aspects, the combination comprises a muscarinic acetylcholine receptor inhibitor and a muscarinic acetylcholine receptor activator, wherein the muscarinic acetylcholine receptor inhibitor and the muscarinic acetylcholine receptor activator are present at a weight ratio of muscarinic acetylcholine receptor activator to muscarinic acetylcholine receptor inhibitor of 1 to greater than 1. In some aspects, the weight ratio of muscarinic acetylcholine receptor activator to muscarinic acetylcholine receptor inhibitor is about 1:1.1 to about 1:10. In some aspects, the weight ratio of muscarinic acetylcholine receptor activator to muscarinic acetylcholine receptor inhibitor is about 1:2 to about 1:9. In some aspects, the weight ratio of muscarinic acetylcholine receptor activator to muscarinic acetylcholine receptor inhibitor is about 1:3 to about 1:8. In some aspects, the weight ratio of muscarinic acetylcholine receptor activator to muscarinic acetylcholine receptor inhibitor is about 1:4 to about 1:7. In some aspects, the weight ratio of muscarinic acetylcholine receptor activator to muscarinic acetylcholine receptor inhibitor is about 1:5 to about 1:6.

General Aspects of Pharmaceutical Compositions and Dosing Considerations

As indicated above, the invention provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. In some aspects, the invention provides a pharmaceutical composition comprising a compound described herein and a pharmaceutically acceptable carrier.

The phrase "therapeutically effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In some aspects, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In some aspects, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, beads, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, beads, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Granules or beads may comprise multiple layers. Each layer may comprise an active ingredient mixed with one or more pharmaceutically-acceptable carriers. In some embodiments, the core comprises a polymer. In some aspects, the core polymer is a cellulose polymer. In some of these embodiments, the cellulose polymer is microcrystalline cellulose. In other embodiments, the core comprises a sugar. In some aspects, the sugar is selected from the group consisting of glucose, sucrose, lactose, mannitol, maltodextrin, xylitol, and sorbitol. In further embodiments, the core comprises silicon dioxide.

Granules or beads may be comprised in a single dosage form, such as a capsule. In some aspects, different types of granules or beads may be comprised in a single dosage form.

In some aspects, the pharmaceutical composition comprises (i) a controlled release bead or granule and (ii) an immediate release bead or granule.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc.; administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound of the invention will be that amount of the compound which is the lowest dose effective to produce a therapeutic effect. Such an effective dose will generally depend upon the factors described above. If desired, the effective daily dose of the active compound may be administered as two, three, four, five, six or more sub-doses administered separately at appropriate intervals throughout the day, optionally, in unit dosage forms. Preferred dosing is one administration per day.

The invention further provides a unit dosage form (such as a tablet or capsule) comprising a compound described herein in a therapeutically effective amount for the treatment of a medical disorder described herein.

In some aspects, the invention provides a pharmaceutical composition described herein for use in medicine. In some aspects, the invention provides a pharmaceutical composition described herein for use in the treatment of a medical disorder described herein, such as a movement disorder described herein. In some aspects the pharmaceutical composition comprises (i) trihexyphenidyl or a pharmaceutically acceptable salt thereof and (ii) bethanechol or a pharmaceutically acceptable salt thereof. In some aspects, the trihexyphenidyl or a pharmaceutically acceptable salt thereof is racemic trihexyphenidyl. In some aspects, the trihexyphenidyl or a pharmaceutically acceptable salt thereof is (R)-trihexyphenidyl. In some aspects, the (R)-trihexyphenidyl or a pharmaceutically acceptable salt thereof has a stereochemical purity of at least 95% enantiomeric excess. In some aspect, the bethanechol or a pharmaceutically acceptable salt thereof is racemic bethanechol. In some aspects, the bethanechol or a pharmaceutically acceptable salt thereof is (S)-bethanechol. In some aspects, the (S)-bethanechol or a pharmaceutically acceptable salt thereof has a stereochemical purity of at least 95% enantiomeric excess. In some aspects, the combination further comprises a pharmaceutically acceptable carrier. The details given with respect to the therapeutic methods described herein equally apply to the medical uses described herein.

Muscarinic Acetylcholine Receptor Inhibitor Abuse

Abuse of anticholinergic drugs is known in the art. In particular, there are reports detailing abuse, harmful use, and/or misuse of a muscarinic acetylcholine receptor inhibitor to procure psychotic, euphoriant, and hallucinogenic effects, for example. See, Jon. S. Rubinstein, *New. Eng. J. Med.*, (1978) 834; Mohan et al., *Brit. J. of Addiction,* 76 (1981) 195-197; and Torrents, et al., *J. Clinical Psychopharmacology,* 38:3 (2018) 250-235.

EXAMPLES

The invention now being generally described, will be more readily understood by reference to the following examples, which are included merely for purposes of illustration of certain aspects and embodiments of the present invention, and is not intended to limit the invention.

Example 1—Preparation of (S)-trihexyphenidyl hydrochloride ((S)-THP) and (R)-trihexyphenidyl hydrochloride ((R)-THP)

The title compounds were prepared using the following procedures.

Step 1: Preparation of rac-trihexyphenidyl

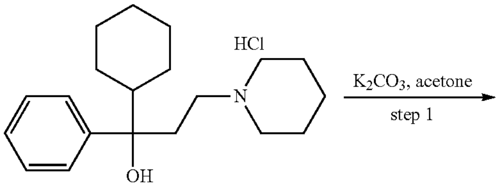

1

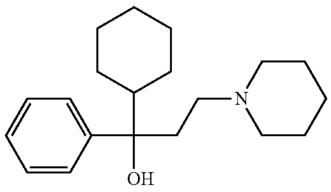

2

A solution of rac-trihexyphenidyl hydrochloride (2 g, 5.92 mmol, 1 equiv) and $K_2CO_3$ (8.18 g, 59.18 mmol, 10 equiv) in acetone (20 mL) was stirred for overnight at 50° C. The resulting mixture was filtered, the filter cake was washed with acetone (2×10 mL). The filtrate was concentrated under reduced pressure. This resulted in rac-trihexyphenidyl (800 mg, 44.84%) as a white solid. $^1H$ NMR analysis indicated it was the desired product.

Step 2: Preparation of (S)-trihexyphenidyl and (R)-trihexyphenidyl

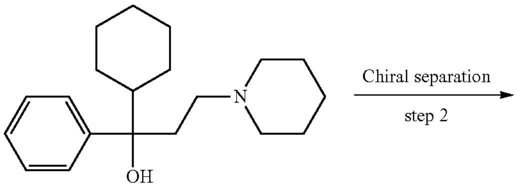

2

-continued

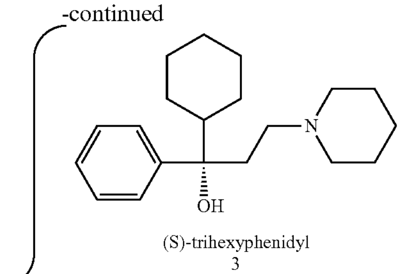

(S)-trihexyphenidyl
3

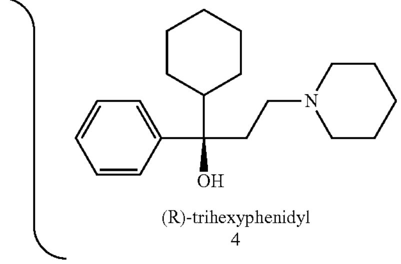

(R)-trihexyphenidyl
4

Rac-Trihexyphenidyl (800 mg) was separated by supercritical fluid chromatograph (SFC) using the following conditions: Column: CHIRALPAK IG-3, 4.6*50 mm, 3 um; Gradient: 15% MeOH (with 20 mM $NH_3$) to afford(S)-trihexyphenidyl (300 mg) and (R)-trihexyphenidyl (300 mg) as a white solid. The first peak to elute was compound having the (S)-stereochemical configuration. The second peak to eluate was compound having the (R) stereochemical configuration. LC-MS: MH ($C_{20}H_{31}NO$)=301.24; should be: 302.25; observed ($M+H^+$): 302.30.

Step 3: Preparation of (S)-trihexyphenidyl hydrochloride ((S)-THP)

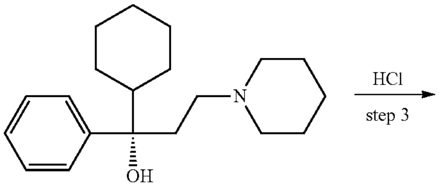

(S)-trihexyphenidyl

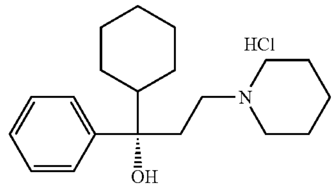

(S)-trihexyphenidyl hydrochloride

A solution of (S)-trihexyphenidyl (300 mg, 0.995 mmol, 1 equiv) in 3M HCl(aq) was stirred for overnight at room temperature. The resulting mixture was concentrated under vacuum. 1H-NMR analysis indicated it was the desired product. The residue was purified by reversed-phase flash chromatography with the following conditions: column, C18 silica gel; mobile phase, MeCN in Water (0.1% HCl), 10% to 50% gradient in 20 min; detector, UV 220 nm. This resulted in (S)-trihexyphenidyl hydrochloride (270 mg, 80.29%) as a white solid. LC-MS: MH ($C_9H_4ClFN_2O_2$)

=301.24; should be: 302.25; observed (M+$H^+$): 302.30. $^1H$ NMR (400 MHZ, DMSO-d6) δ 10.00 (s, 1H), 7.38 (d, J=7.6 Hz, 2H), 7.32 (t, J=7.6 Hz, 2H), 7.21 (t, J=7.2 Hz, 1H), 4.90 (s, 1H), 3.33 (s, 1H), 3.31 (s, 1H), 2.97-2.93 (m, 1H), 2.84-2.65 (m, 2H), 2.49-2.32 (m, 2H), 2.30-2.25 (m, 1H), 1.88-1.82 (m, 1H), 1.80-1.70 (m, 5H), 1.69-1.46 (m, 4H), 1.41-1.25 (m, 2H), 1.21-0.77 (m, 5H).

Step 3: Preparation of Preparation of (R)-trihexyphenidyl hydrochloride ((R)-THP)

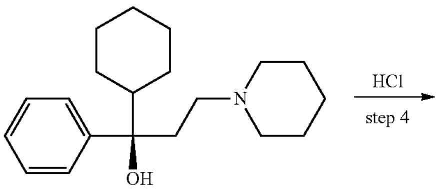

(R)-trihexyphenidyl

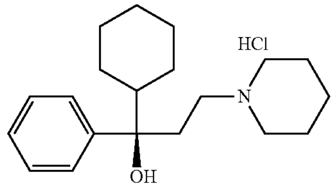

(R)-trihexyphenidyl hydrochloride

A solution of (R)-trihexyphenidyl (300 mg, 0.995 mmol, 1 equiv) in 3M HCl (aq) was stirred for overnight at room temperature. The resulting mixture was concentrated under vacuum. 1H-NMR analysis indicated it was the desired product. The residue was purified by reversed-phase flash chromatography with the following conditions: column, C18 silica gel; mobile phase, MeCN in water (0.1% HCl), 10% to 50% gradient in 20 min; detector, UV 220 nm. This resulted in (R)-trihexyphenidyl hydrochloride (250 mg, 74.34%) as a white solid. LC-MS: MH ($C_9H_4ClFN_2O_2$) =301.24; should be: 302.25; observed (M+$H^+$): 302.30. $^1H$ NMR (400 MHZ, DMSO-d6) δ 9.72 (s, 1H), 7.42-7.29 (m, 4H), 7.26-7.18 (m, 1H), 4.91 (s, 1H), 3.38-3.36 (s, 1H), 3.35-3.28 (s, 1H), 3.04-2.89 (m, 1H), 2.82-2.68 (m, 2H), 2.49-2.31 (m, 1H), 2.28-2.15 (m, 1H), 1.85 (d, J=12.7 Hz, 1H), 1.80-1.45 (m, 9H), 1.39-1.30 (m, 2H), 1.21-0.78 (m, 5H).

Example 2—Preparation of (R)-bethanechol chloride

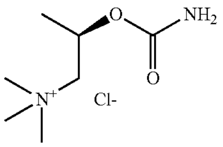

The title compound was prepared using the following procedures.

Step 1: Preparation of (2R)-1-(dimethylamino)propan-2-ol

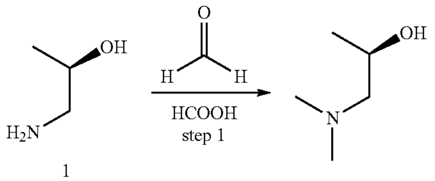

1

2

To a stirred solution of (R)-1-amino-2-propanol (10 g, 133.136 mmol, 1 equiv) in HCOOH (28.80 g, 625.7 mmol, 4.7 equiv) was added formaldehyde (7.20 g, 239.7 mmol, 1.80 equiv) dropwise at room temperature under nitrogen atmosphere. The resulting mixture was stirred for overnight at 90° C. under nitrogen atmosphere. Desired product could be detected by LCMS. The mixture was acidified to pH 1 with 6N HCl (aq)(40 mL). The resulting mixture was washed with 3×30 mL of dichloromethane. The water layer was basified to pH 13 with 50% NaOH(aq) (60 mL) and extracted with $CH_2Cl_2$ (3×50 mL). The combined organic layers were washed with brine (1×80 mL), dried over anhydrous $Na_2SO_4$. After filtration, the filtrate was concentrated under reduced pressure. The crude (2R)-1-(dimethylamino)propan-2-ol (5 g) was used in the next step directly without further purification. LC-MS: MH ($C_5H_{13}NO$) =103.10; should be: 104.11; observed (M+$H^+$): 104.10.

Step 2: Preparation of (2R)-1-(dimethylamino)propan-2-yl carbamate

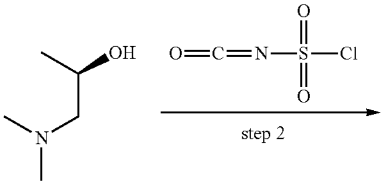

2

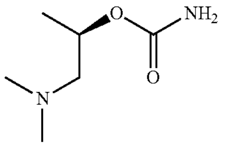

3

To a stirred solution of (2R)-1-(dimethylamino)propan-2-ol (5 g, 48.46 mmol, 1 equiv) in hexane (50 mL) was added chlorosulfonyl isocyanate (27.44 g, 193.8 mmol, 4 equiv) dropwise at 0° C. under nitrogen atmosphere. The resulting mixture was stirred overnight at room temperature under nitrogen atmosphere. Desired product could be detected by LCMS. The resulting mixture was diluted with water (150 mL) and washed with 3×30 mL of DCM. The aqueous layer was basified to pH 13 with 50% NaOH(aq) (50 mL) and extracted with 3×80 mL of DCM. The combined organic layers were washed with brine (1×70 mL), dried over anhydrous $Na_2SO_4$. After filtration, the filtrate was concentrated under reduced pressure. The crude (2R)-

1-(dimethylamino)propan-2-yl carbamate (4 g) was used in the next step directly without further purification. LC-MS: MH ($C_6H_{14}N_2O_2$)=146.11; should be: 147.11; observed ($M+H^+$): 147.00.

Step 3: Preparation of (R)-bethanechol chloride

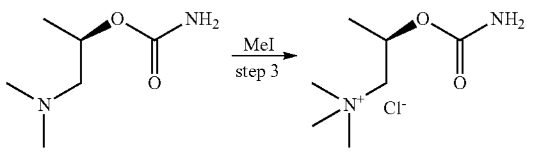

3

A solution of (2R)-1-(dimethylamino)propan-2-yl carbamate (1 g, 6.840 mmol, 1 equiv) and methyl iodide (4.85 g, 34.2 mmol, 5 equiv) in dichloromethane (DCM) (15 mL) was stirred for overnight at room temperature under nitrogen atmosphere. The resulting mixture was concentrated under vacuum. The resulting residue was dissolved in water (20 mL) and washed with DCM (3x10 mL). The aqueous layer was concentrated to a minimum volume of water, charged on chloride-exchange resin column, and eluted with distilled water. The elution was completed when a drop of the eluent did not precipitate with silver ions. The combined eluent was evaporated and lyophilization to afford (R)-bethanechol chloride (300 mg, 22.30%) as a white solid. LC-MS: MH ($C_7H_{17}ClN_2O_2$)=196.10; should be: 161.13; observed ($M+H^+$): 161.15. $^1H$ NMR (400 MHZ, DMSO-d6) δ 5.21-5.17 (m, 1H), 3.65 (dd, J=14.4, 9.6 Hz, 1H), 3.42 (dd, J=14.4, 1.6 Hz, 1H), 3.10 (s, 9H), 1.23 (d, J=6.4 Hz, 3H).

Example 3—Preparation of (S)-bethanechol chloride

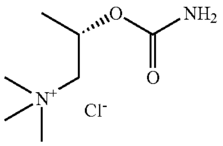

The title compound was prepared using the following procedures.

Step 1: Preparation of (2S)-1-(dimethylamino)propan-2-ol

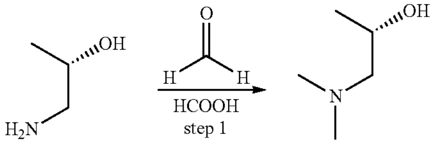

1 2

To a stirred solution of (S)-1-amino-2-propanol (10 g, 133.136 mmol, 1 equiv) in HCOOH (28.80 g, 625.7 mmol, 4.7 equiv) was added formaldehyde (7.20 g, 239.7 mmol, 1.80 equiv) dropwise at room temperature under nitrogen atmosphere. The resulting mixture was stirred for overnight at 90° C. under nitrogen atmosphere. Desired product could be detected by LCMS. The mixture was acidified to pH 1 with 6N HCl (aq)(40 mL). The resulting mixture was washed with 3x30 mL of dichloromethane. The water layer was basified to pH 13 with 50% NaOH (aq) (60 mL) and extracted with $CH_2Cl_2$ (3x50 mL). The combined organic layers were washed with brine (1x80 mL), dried over anhydrous $Na_2SO_4$. After filtration, the filtrate was concentrated under reduced pressure. The crude (2S)-1-(dimethylamino)propan-2-ol (5 g) was used in the next step directly without further purification. LC-MS: MH ($C_5H_{13}NO$) =103.10; should be: 104.11; observed ($M+H^+$): 104.10.

Step 2: Preparation of (2S)-1-(dimethylamino)propan-2-yl carbamate

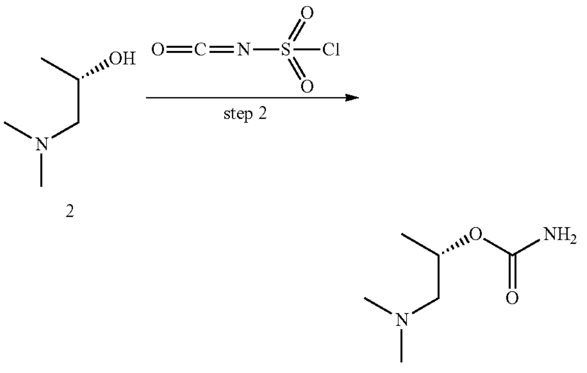

2

3

To a stirred solution of (2S)-1-(dimethylamino)propan-2-ol (5 g, 48.46 mmol, 1 equiv) in hexane (50 mL) was added chlorosulfonyl isocyanate (27.44 g, 193.8 mmol, 4 equiv) dropwise at 0° C. under nitrogen atmosphere. The resulting mixture was stirred for overnight at room temperature under nitrogen atmosphere. Desired product could be detected by LCMS. The resulting mixture was diluted with water (150 mL) and washed with 3x30 mL of DCM. The aqueous layer was basified to pH 13 with 50% NaOH (aq) (50 mL) and extracted with 3x80 mL of DCM. The combined organic layers were washed with brine (1x70 mL), dried over anhydrous $Na_2SO_4$. After filtration, the filtrate was concentrated under reduced pressure. The crude (2S)-1-(dimethylamino)propan-2-yl carbamate (4 g) was used in the next step directly without further purification. LC-MS: MH ($C_6H_{14}N_2O_2$)=146.11; should be: 147.11; observed ($M+H^+$): 147.00.

Step 3: Preparation of (S)-bethanechol chloride

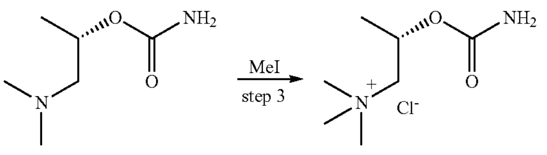

3

A solution of (2S)-1-(dimethylamino)propan-2-yl carbamate (1 g, 6.840 mmol, 1 equiv) and methyl iodide (4.85 g, 34.2 mmol, 5 equiv) in DCM (15 mL) was stirred for overnight at room temperature under nitrogen atmosphere. The resulting mixture was concentrated under vacuum. The resulting residue was dissolved in water (20 mL), washed with DCM (3×10 mL). The aqueous layer was concentrated to a minimum volume of water, charged on chloride-exchange resin column, and eluted with distilled water. The elution was completed when a drop of the eluent did not precipitate with silver ions. The combined eluent was evaporated and lyophilization to afford(S)-bethanechol chloride (300 mg, 22.30%) as a white solid. LC-MS: MH ($C_7H_{17}ClN_2O_2$)=196.10; should be: 161.13; observed ($M+H^+$): 161.15. $^1H$ NMR (400 MHz, DMSO-d6) δ 5.25-5.14 (m, 1H), 3.64 (dd, J=14.4, 9.6 Hz, 1H), 3.42 (dd, J=14.4, 1.6 Hz, 1H), 3.10 (s, 9H), 1.23 (d, J=6.4 Hz, 3H).

Example 4—Activity Towards Muscarinic Receptors

Compounds (R)-trihexyphenidyl-HCl ((R)-THP) and (S)-trihexyphenidyl-HCl ((S)-THP) were evaluated for inhibitory activity towards muscarinic receptors. Compounds (S)-bethanechol chloride ((S)-BTC) and (R)-bethanechol chloride ((R)-BTC) were evaluated for activation activity towards muscarinic receptors. Experimental procedures and results are provided below.

Part I—Experimental Procedures

All cells used in the following experiments were clonal populations of Chinese Hamster Ovary (CHO) cells stably expressing the corresponding human muscarinic receptor, except for the M4 cell line, which was a population of CHO cells transiently transfected with the human M4 receptor. Muscarinic agonism and antagonism of each receptor was measured by a quantitative calcium flux assay that is used for multiple classes of G-protein-coupled receptors, or GPCRs, as described elsewhere (e.g., Arkin et al., 2021, PMID: 22553878). Acetylcholine and atropine were used as positive controls for receptor agonism and antagonism, respectively. The procedure was as follows:

1. Cells were thawed and cultured in cell culture medium (DMEM/F12 containing 10% FBS, 1× penicillin-streptomycin and 600 μg/ml hygromycin B) at 37° C. in 5% (v/v) CO2.
2. One day before the assays, cells were detached using TrypLE™ and counted using a cell-counter. Only cells with >85% viability are used for the assay.
3. 12,000 cells/well were seeded in 30 μl/well culture medium in a 384-well cell plate and incubated overnight at 37 C, 5% (v/v) CO2.
4. On the assay day, 2× dye solution was prepared following the manual of the FLIPR® Calcium 6 Assay Kit:
   i. The dye was diluted with assay buffer (20 mM HEPES in 1×HBSS, PH 7.4);
   ii. Probenecid was added to a final concentration of 5 mM;
   iii. Cells were vortexed vigorously for 1-2 minutes.
5. Medium was removed from the cell plate by flicking the cell plate on paper towels.
6. 10 μl of assay buffer and 10 μl of 2× dye solution was added to each well of the cell plate.
7. The cell plate was shaken on a plate shaker at 600 rpm for 2 minutes and incubated at 37° C. for 2 hours followed by an additional 15-minute incubation at 25° C.
8. The test compounds were next prepared in assay buffer:
   a. All compounds were diluted to the required concentration with DMSO and added to a 384-well compound plate;
   b. All compounds were serially diluted;
      1. Starting with 10 mM concentration of each test compound, all samples were serially diluted in 3-fold dilutions.
      2. 90 nl/well of each compound was transferred from the source plate to a 384-well compound plate using an Echo liquid handler.
      3. 30 μl/well assay buffer was added to the compound plate;
   c. The plates were mixed on a plate shaker for 2 mins;
9. The cell plate, compound plate and pipette tips were placed in the FLIPR screening system and 10 μl of each compound was added to a well of the cell plate.
10. Plates were read for 160 sec with 1 sec intervals to obtain the data in agonist mode, then kept at 25° C. in the dark for 30 min.
11. As a positive control, the $EC_{80}$ of the agonist reference compound, Acetylcholine (Ach), was calculated.
12. To measure receptor antagonism, samples of Ach were prepared at its $EC_{80}$ concentration in assay buffer, and 30 μl was added to each well of a new 384-well compound plate.
13. After a 30-minute incubation at 25° C. in the dark, the cell plate and compound plate containing $EC_{80}$ Ach were added to the FLIPR screening system and 10 μL of $EC_{80}$ Ach was added to each well of the cell plate.
14. Plates were read for 160 sec with 1 sec intervals, thereby measuring the ability for test compounds to antagonize the activation of muscarinic receptors by Ach.

Part II—Results

Inhibitory activity of compounds (R)-THP and (S)-THP towards muscarinic receptors is provided in Table 1. Data in Table 1 show that (R)-THP is a much more potent inhibitor of muscarinic receptors M1, M2, M3, M4, and M5 than (S)-THP.

TABLE 1

| | $IC_{50}$ (nM) | | | | |
|---|---|---|---|---|---|
| Compound | M1 | M2 | M3 | M4 | M5 |
| (S)-THP | 494 | 1668 | 942 | 209 | 4329 |
| (R)-THP | 1.63 | 22.2 | 3.17 | 0.31 | 11.54 |

Agonist activity of compounds(S)-BTC and (R)-BTC towards muscarinic receptors is provided in Table 2. Data in Table 2 show that (S)-BTC is a much more potent activator of muscarinic receptors M1, M2, M3, and M5 than (R)-BTC. Neither BTC enantiomer activated the M4 receptor, despite the positive control activating M4 with an $EC_{50}$ of 200 nM.

TABLE 2

| | $EC_{50}$ (nM) | | | | |
|---|---|---|---|---|---|
| Compound | M1 | M2 | M3 | M4 | M5 |
| (S)-BTC | 195 | 405 | 20.78 | >10000 | 124 |
| (R)-BTC | >10000 | >10000 | 7566 | >10000 | >10000 |

Example 5—Activity of Combined Trihexyphenidyl Hydrochloride and Bethanechol Chloride Towards Muscarinic Receptor M1

The effect of (S)-BTC on the M1 Muscarinic Receptor in the presence of increasing concentrations of (R)-THP was evaluated. Experimental procedures and results are provided below.

Part I—Experimental Procedures

The cell-based muscarinic receptor assay with both compounds was performed as in Example 4, except that only the M1 receptor was tested, and four separate titration curves were performed for(S)-BTC: [i] (S)-BTC alone and (S)-BTC in the presence of (R)-THP at three fixed concentrations. The (R)-THP concentrations used were [ii] 58.5 nM, or 0.3× the $EC_{50}$ of (S)-BTC [iii] 195 nM, or 1× the $EC_{50}$ of (S)-BTC, and [iv] 585 nM, or 3× the $EC_{50}$ of (S)-BTC. M1 receptor agonist activity was measured to determine the impact of (R)-THP on the potency (S)-BTC.

Part II—Results

Figure 2:
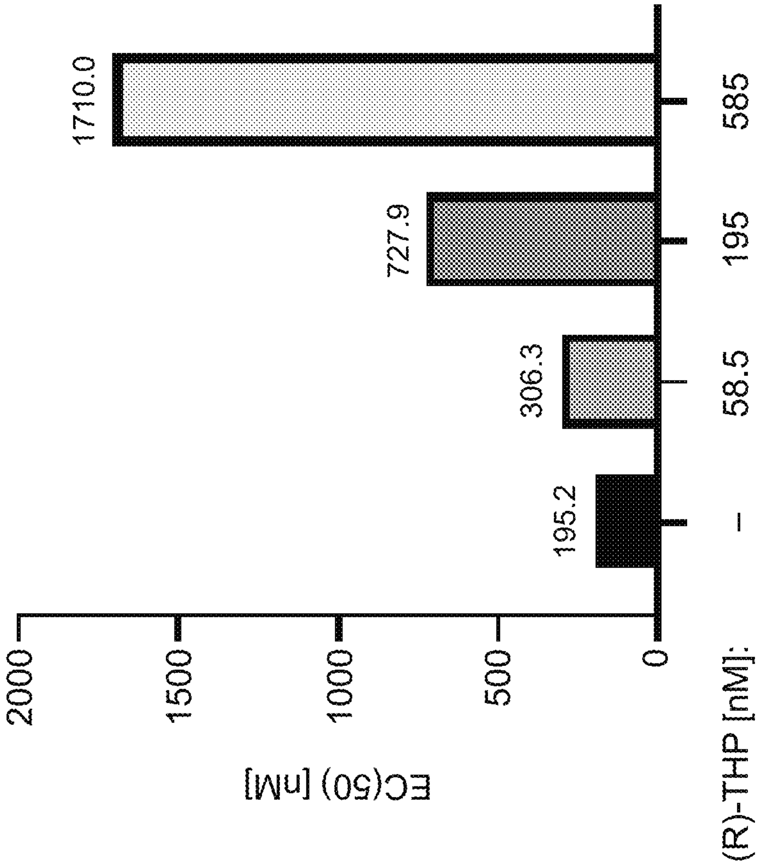
FIG. 2 is a graph depicting changes in the $EC_{50}$ of (S)-BTC toward the human M1 muscarinic receptor by the addition of (R)-THP, as described in more detail in Example 5.

Agonist activity of (S)-BTC toward the M1 muscarinic receptor in the presence of (R)-THP is shown in FIG. 1. The graph in FIG. 1 shows that the agonist effect of (S)-BTC toward the M1 muscarinic receptor decreases substantially with increasing concentration of (R)-THP. The $EC_{50}$ values of (S)-BTC in the presence of the three concentrations of (R)-THP are shown in FIG. 2.

Example 6—In Vitro Metabolic Stability of (R)-THP and (S)-BTC in Different Species The metabolic stability of (R)-THP and (S)-BTC were measured in (i) whole blood, (ii) liver microsomes, and (iii) hepatocytes, with cells and extracts prepared from rat, dog, and human.

Part I—Experimental Procedures

For the whole blood stability assay:

Preparation of Stock Solutions

200 μM test compound working solutions were prepared in DMSO, while 1 mM propantheline working solution was prepared in acetonitrile. 1 mM mevinolin working solution was prepared in DMSO.

Procedures for Blood Stability.

A. 398 μL of blood from each species was added to an incubation plate, which was pre-warmed at 37 C for 15 minutes.

B. After the pre-incubation, 2 μL of working solution (test compounds or control compounds) was spiked to 398 μL of blood to reach a final concentration of 1 μM for test compounds and 5 μM for control compounds. The final concentration of organic solvents is 0.5%. The assays were performed in duplicate.

C. The reaction samples were incubated at 37 C.

D. Aliquots of 50 μL were taken from the reaction samples at 0, 15, 30, 60 and 120 minutes. The reaction was stopped by the addition of 50 μL ultrapure water and 400 μL cold acetonitrile.

E. All samples were vortexed for 10 minutes, followed by centrifugation at 3,220 g for 40 minutes to precipitate proteins. 100 μL of the supernatant was then transferred to a new plate. The supernatant was diluted with ultrapure water as needed for detection by LC-MS/MS.

Sample Analysis

Samples were analyzed by LC-MS/MS to measure the concentration of the test compounds.

Data Analysis

All calculations were carried out using Microsoft Excel and according to standard analysis methods that are known in the art.

For the liver microsome assay:

1. The master solution was prepared according to Table 3. All liver microsome samples were purchased from BD Gentest.

TABLE 3

| Reagent | Stock Concentration | Volume | Final Concentration |
|---|---|---|---|
| Phosphate buffer | 100 mM | 216.25 μL | 100 mM |
| Microsomes | 20 mg/mL | 6.25 μL | 0.5 mg/mL |

2. Two separate experiments were performed as follows: (i) With Cofactors (NADPH): 25 μL of 10 mM NADPH was added to the incubations. The final concentrations of microsomes and NADPH were 0.5 mg/mL and 1 mM, respectively; and (ii) a negative control without Cofactors (NADPH): 25 μL of 100 mM Phosphate buffer was added to the incubations. The final concentration of microsomes was 0.5 mg/mL. The mixture was pre-warmed at 37 C for 10 minutes. The data table in the corresponding section below shows results in the presence of co-factors.
3. The reaction was started with the addition of 2.5 μL of 100 μM control compound or test compound solutions. The final concentration of test compound or control compound was 1 μM. The incubation solution was incubated in a water bath at 37 C.
4. Aliquots of 30 μL were taken from the reaction solution at 0.5, 5, 15, 30 and 60 minutes. The reaction was stopped by the addition of 5 volumes of cold acetonitrile with IS (100 nM alprazolam, 200 nM caffeine and 100 nM tolbutamide). Samples were centrifuged at 3,220 g for 40 minutes. Aliquots of 100 μL of the supernatant was mixed with 100 μL of ultra-pure H2O and then used for LC-MS/MS analysis to detect the levels of the test compound.
5. All calculations were carried out using Microsoft Excel and according to standard analysis methods that are known in the art.

For the hepatocyte assay:

Preparation of Working Solutions 1. 10 mM stock solutions of test compounds and positive control compound were prepared in appropriate solvent (DMSO).
2. In separate conical tubes, 10 mM test compound and positive controls were diluted to 100 μM by combining 198 μL of 50% acetonitrile/50% water and 2 μL of 10 mM stock.

Preparation of Hepatocytes

1. Incubation medium (William's E Medium supplemented with GlutaMAX) and hepatocyte thawing medium were placed in a 37 C water bath and warmed for at least 15 minutes prior to use.
2. A vial of cryopreserved hepatocytes was thawed by placing the vial in a 37 C water bath and gently shaken for 2 minutes. After thawing was completed, the vial was cleaned with 70% ethanol and transferred to a biosafety cabinet.
3. Using wide-bore pipette tips, hepatocytes were transferred into a 50 ml conical tube containing thawing medium. The 50 mL conical tube was placed into a centrifuge and spun at 100 g for 10 minutes. Upon completion of the spin, thawing medium was aspirated and hepatocytes were resuspended in enough incubation medium to yield ~$1.5\times10^6$ cells/mL.

4. Using AO/PI Staining, cells were counted to determine the viable cell density. Cells were diluted with incubation medium to a working cell density of $0.5\times10^6$ viable cells/mL.

Procedure for Stability Determination 1. 198 μL of hepatocytes were pipetted into each well of a 96-well non-coated plate. The plate was placed in the incubator to allow the hepatocytes to warm for 10 minutes.
2. 2 μL of the 100 μM test compound or positive control was pipetted into respective wells of the 96-well non-coated plate to start the reaction. The plate was returned to the incubator for the designed time points.
3. The contents of the wells were removed in 25 μL aliquots at time points of 0.5, 15, 30, 60, 90 and 120 minutes. The aliquots were then mixed with 6 volumes (150 μL) of acetonitrile containing an internal standard, IS (100 nM alprazolam, 200 nM caffeine and 100 nM tolbutamide), to terminate the reaction. Samples were vortexed for 5 minutes and centrifuged for 45 minutes at 3,220 g. Aliquots of 100 μL of supernatant were diluted with 100 μL ultra-pure water, and the mixture was used for LC/MS/MS analysis. All incubations were performed in duplicate.

Data Analysis

All calculations were carried out using Microsoft Excel and according to standard analysis methods that are known in the art.

Part II—Results

Whole blood stability data are shown in Table 4. Neither (R)-THP nor (S)-BTC were metabolized in whole blood from any of the tested species (>95% test molecule remaining after 120 minutes in all conditions). Propantheline and Mevinolin were used as species-specific positive controls.

TABLE 4

| | | Remaining Percentages (%) | | | | | $t_{1/2}$ |
|---|---|---|---|---|---|---|---|
| Compound | Species | 0 min | 15 min | 30 min | 60 min | 120 min | (min) |
| Propantheline | Human | 100.00 | 71.54 | 57.19 | 25.74 | 6.31 | 30.99 |
| | Dog | 100.00 | 91.17 | 90.30 | 85.38 | 62.08 | 184.41 |
| Mevinolin | Rat | 100.00 | 9.32 | 1.68 | 2.21 | 2.47 | 4.38 |
| (R)-THP | Human | 100.00 | 100.88 | 109.79 | 103.53 | 103.55 | ∞ |
| | Dog | 100.00 | 97.05 | 102.64 | 107.75 | 98.55 | ∞ |
| | Rat | 100.00 | 101.46 | 97.10 | 109.34 | 98.05 | ∞ |
| (S)-BTC | Human | 100.00 | 98.98 | 97.28 | 106.52 | 95.48 | ∞ |
| | Dog | 100.00 | 96.39 | 97.57 | 93.83 | 96.58 | ∞ |
| | Rat | 100.00 | 101.13 | 96.95 | 95.54 | 97.12 | ∞ |

Liver microsome stability data are shown in Table 5. (R)-THP was metabolized in the presence of liver microsomes from all three species, with the greatest reduction in signal observed in rat (Hepatic Extraction Ratio of 0.99 vs. 0.51 in human and 0.89 in dog). (S)-BTC was not metabolized to any extent by liver microsomes from any of the three species. Verapamil was used as a positive control.

TABLE 5

| Compound | Species | in vitro $t_{1/2}$ (min) | in vitro $CL_{int}$ (μL/min/mg) | Scale-up $CL_{int}$ (mL/min/Kg) | Predicted Hepatic $CL_H$ (mL/min/kg) | Hepatic Extraction Ratio |
|---|---|---|---|---|---|---|
| Verapamil | Human | 4.65 | 298.46 | 306.82 | 19.65 | 0.94 |
| | Dog | 5.27 | 263.13 | 463.12 | 29.05 | 0.94 |
| | Rat | 2.58 | 537.44 | 1311.35 | 64.65 | 0.95 |
| (R)-THP | Human | 65.76 | 21.22 | 21.82 | 10.68 | 0.51 |
| | Dog | 9.51 | 146.18 | 257.27 | 27.66 | 0.89 |
| | Rat | 0.58 | 2380.77 | 5809.08 | 67.21 | 0.99 |
| (S)-BTC | Human | ∞ | 0.00 | 0.00 | 0.00 | 0.00 |
| | Dog | ∞ | 0.00 | 0.00 | 0.00 | 0.00 |
| | Rat | ∞ | 0.00 | 0.00 | 0.00 | 0.00 |

Hepatocyte stability data are shown in Table 6. Similar to the liver microsome data shown above, (R)-THP was metabolized in the presence of hepatocytes from all three species, with the greatest metabolism observed in rat (Hepatic Extraction Ratio of 0.98 vs. 0.73 in human and 0.86 in dog). (S)-BTC was not metabolized to any extent by hepatocytes from any of the three species. Verapamil was used as a positive control.

TABLE 6

| Compound | Species | in vitro $t_{1/2}$ (min) | in vitro $CL_{int}$ (μL/min/$10^6$ cells) | Scale-up $CL_{int}$ (mL/min/Kg) | Predicted Hepatic $CL_H$ (mL/min/kg) | Hepatic Extraction Ratio |
|---|---|---|---|---|---|---|
| Verapamil | Human | 21.20 | 65.67 | 167.08 | 18.65 | 0.89 |
| | Dog | 29.61 | 46.81 | 253.17 | 27.62 | 0.89 |
| | Rat | 6.06 | 229.10 | 1072.17 | 63.94 | 0.94 |
| (R)-THP | Human | 63.32 | 21.89 | 55.70 | 15.25 | 0.73 |
| | Dog | 40.19 | 34.51 | 186.63 | 26.58 | 0.86 |
| | Rat | 1.47 | 945.33 | 4424.16 | 66.97 | 0.98 |
| (S)-BTC | Human | ∞ | 0 | 0 | 0 | 0 |
| | Dog | ∞ | 0 | 0 | 0 | 0 |
| | Rat | ∞ | 0 | 0 | 0 | 0 |

Together, the in vitro stability data demonstrate that the active enantiomers of THP and BTC have differential metabolic properties, and that THP is likely metabolized by liver enzymes, while BTC is not a metabolic substrate in any of the tested settings.

Example 7—In Vivo Pharmacokinetic Profile of (S)-BTC in Rats

The in vivo PK properties of (S)-BTC were measured in rats after a single oral dose to determine the relative distribution of the compound to brain and plasma. Experimental procedures and results are provided below. Relative distribution of (S)-BTC is important because substantial restriction of (S)-BTC to the periphery supports using(S)-BTC to offset peripheral side effects that would otherwise be caused by administration of THP.

Part I—Experimental Procedures (S)-BTC was dissolved in 0.9% saline to a final concentration of 1 mg/mL. 6-8-week-old male Sprague Dawley rats were fasted overnight prior to treatment. The study consisted of 3 rats per group at five time points; 30 minutes, 1 hour, 2 hours, 4 hours, and 8 hours. Rats were treated with 10 mg/kg (S)-BTC solution by oral gavage and sacrificed at the specified time points.

20-30 μL CSF samples were collected from each rat and stored at −80° C. prior to analysis. 0.3 mL blood samples were collected from each rat and processed to obtain plasma, which was stored at −80° C. prior to analysis. Treated animals were exsanguinated prior to brain collection, and brain samples were frozen at −80° C. Brain samples were weighed and homogenized at a water by brain weight (g) to water volume (mL) ratio of 1:3 before analysis.

Concentrations of compounds in the plasma, brain, CSF samples were analyzed using a standard LC-MS/MS method to detect parent test compound from each of the processed tissues. The following pharmacokinetic parameters were calculated and analyzed using WinNonlin (Phoenix™, version 8.3): $T_{1/2}$, $C_{max}$, $T_{max}$, MRT, $AUC_{inf}$, $AUC_{last}$, F %, ratio of brain/plasma, ratio of CSF/plasma, and ratio of CSF/brain.

Part II—Results

Figure 3:
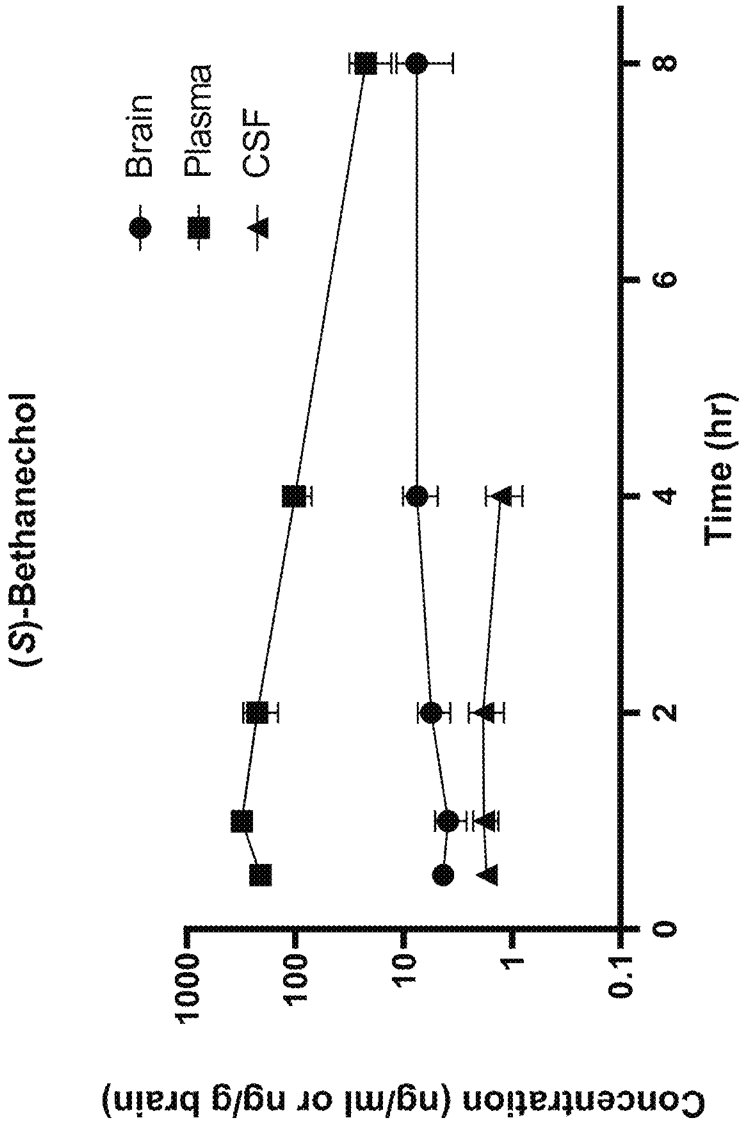
FIG. 3 is a graph depicting the concentration of (S)-bethanechol in rat plasma, brain tissue, and cerebrospinal fluid after a single oral dose, as described in more detail in Example 7.
Figure 4:
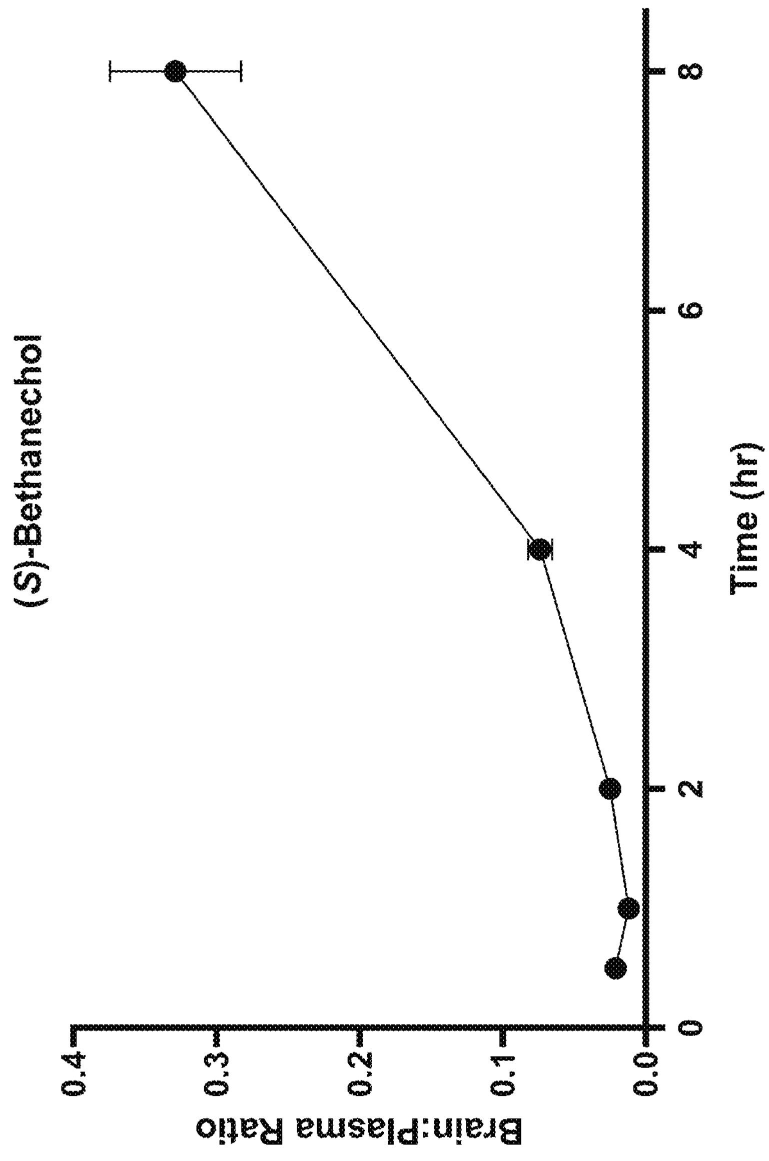
FIG. 4 is a graph depicting the ratio of (S)-bethanechol in brain tissue compared to plasma of a rat after a single oral dose, as described in more detail in Example 7.

Plasma, total brain, and CSF samples were isolated from 3 rats at each time point of 30 minutes, 1 hour, 2 hours, 4 hours, and 8 hours (15 animals total). The concentration of (S)-BTC was determined in all samples according to the Experimental Procedures. Results are shown in the Tables below and in FIGS. 3 and 4. Maximal concentration of (S)-BTC was substantially higher in plasma than in brain or CSF (41-fold higher $C_{max}$ in plasma than in brain and 181-fold higher $C_{max}$ in plasma than in CSF). The brain: plasma ratio of (S)-BTC was at least 1:3 over the 8-hour time course, demonstrating the peripheral restriction of (S)-BTC in rats after oral administration (FIG. 4).

TABLE 7

Plasma concentration of (S)-BTC, 10 mg/kg, single oral dose

| PK parameters | Unit | Mean |
|---|---|---|
| $T_{1/2}$ | h | 1.81 |
| $T_{max}$ | h | 1.00 |
| $C_{max}$ | ng/mL | 314 |
| $AUC_{last}$ | h*ng/mL | 1026 |
| $AUC_{Inf}$ | h*ng/mL | 1085 |
| $AUC_{_\%Extrap_}$obs | % | 5.42 |
| $MRT_{Inf}$_obs | h | 2.91 |
| $AUC_{last}$/D | h*mg/mL | 103 |
| F | % | 12.4 |

TABLE 8

Brain concentration of (S)-BTC, 10 mg/kg, single oral dose

| PK parameters | Unit | Mean |
|---|---|---|
| $T_{1/2}$ | H | NA |
| $T_{max}$ | H | 8.00 |
| $C_{max}$ | ng/g | 7.60 |
| $AUC_{last}$ | h*ng/g | 51.2 |
| $AUC_{Inf}$ | h*ng/g | NA |
| $AUC_{_\%Extrap_}$obs | % | NA |
| $MRT_{Inf}$_obs | H | NA |
| $AUC_{last}$/D | h*mg/g | 5.12 |
| $AUC_{last}$ Ratio (Brain/Plasma) | NA | 0.0499 |
| $C_{max}$ Ratio (Brain/Plasma) | NA | 0.0242 |

TABLE 9

CSF concentration of (S)-BTC, 10 mg/kg, single oral dose

| PK parameters | Unit | Mean |
|---|---|---|
| $T_{1/2}$ | H | NA |
| $T_{max}$ | H | 0.500 |
| $C_{max}$ | ng/mL | 1.74 |
| $AUC_{last}$ | h*ng/mL | 6.31 |
| $AUC_{Inf}$ | h*ng/mL | NA |
| $AUC_{_\%Extrap_}$obs | % | NA |
| $MRT_{Inf}$_obs | H | NA |
| $AUC_{last}$/D | h*mg/mL | 0.631 |
| $AUC_{last}$ Ratio (CSF/Plasma) | NA | 0.00615 |
| $C_{max}$ Ratio (CSF/Plasma) | NA | 0.00553 |
| $AUC_{last}$ Ratio (CSF/Brain) | NA | 0.123 |
| $C_{max}$ Ratio (CSF/Brain) | NA | 0.229 |

Example 8—In Vitro Safety Panel Screen Demonstrates Differences Between Enantiomers of Trihexyphenidyl Hydrochloride The (R) and (S) enantiomers of BTC and THP were screened in a Cerep87 Safety Panel (Eurofins) to determine whether the molecules displayed activity against targets other than muscarinic receptors. Four compounds were included in the safety panel study with receptor-specific controls according to the manufacturer's protocol. Activity against a receptor was measured as either a positive or a negative signal from baseline. Negative values were assigned a value of zero according to manufacturer's guidance and assay limitations. Positive values between 25 and 50% represent mild signaling through the receptor, and values above 50% represent significant signaling through the receptor.

For (R)-BTC, no receptor demonstrated 50% or greater signal. For (S)-BTC, only muscarinic receptors demonstrated greater than 50% antagonism. For THP, there were several differences between the (R) and (S) enantiomers (Table 10). Both enantiomers showed signal against all four muscarinic receptors included in the receptor panel at the tested concentration. For (R)-THP, only one other receptor (kappa opioid receptor) demonstrated greater than 25% signal. Conversely, (S)-THP signaled through nine non-muscarinic receptors. PCP (NMDA receptor), H1 (histamine), several ion channels, and several dopamine pathway receptors were detected as targets for (S)-THP in this study. This enantiospecific signaling of (S)-THP may explain reports of anti-NMDA and antihistamine activity for racemic THP. Since (R)-THP lacks this activity, administration of this substantially pure (R)-THP supports both an efficacy and safety benefit compared to racemic THP.

TABLE 10

| Target | R-THP | S-THP |
|---|---|---|
| M4 (h) (antagonist radioligand) | 98.88 | 97.82 |
| M1 (h) (antagonist radioligand) | 99.70 | 96.53 |
| M3 (h) (antagonist radioligand) | 99.77 | 85.43 |
| M2 (h) (antagonist radioligand) | 98.95 | 77.76 |
| H1 (h) (antagonist radioligand) | 15.16 | 56.31 |
| 5-HT2A (h) (agonist radioligand) | 15.98 | 42.80 |
| PCP (antagonist radioligand) | 0.00 | 42.75 |
| $Na^+$ channel (site 2) (antagonist radioligand) | 24.13 | 42.54 |
| Potassium Channel hERG (human)-[3H] Dofetilide | 18.14 | 41.35 |
| D2S (h) (agonist radioligand) | 0.23 | 35.79 |
| kappa (h) (KOP) (agonist radioligand) | 26.19 | 34.64 |
| $Ca^{2+}$ channel (L, verapamil site) (antagonist radioligand) | 4.67 | 34.01 |
| D2L (h) (antagonist radioligand) | 0.32 | 28.50 |

Example 9—Analysis of Impact of Trihexyphenidyl on Haloperidol-Induced Catalepsy The efficacy of trihexyphenidyl on treating haloperidol-induced catalepsy was evaluated, which has been used as a model to study extrapyramidal symptoms of human disease. Experimental procedures and results are provided below.

Part I—Methods and Materials

Animals: Adult male Sprague Dawley rats (230-235 g) from Envigo were used in this study. Upon receipt, rats were group housed in ventilated cages and acclimated for one week prior to testing. Animals were maintained in a 12/12 h light/dark cycle (with room temperature maintained at 22±1 C with the relative humidity maintained at approximately 50%. Food and water were provided ad libitum. All animals were examined, handled, and weighed prior to initiation of the study to assure adequate health and to minimize the non-specific stress associated with testing. Each animal was randomly assigned across the treatment groups. The experiments were conducted during the animal's light cycle.

Compound Formulations: The test compounds were prepared as follows:

Haloperidol (1 mg/kg) was dissolved in 10% DMSO in saline and administered by subcutaneous injection at a dose volume of 1 ml/kg, 30 minutes before test.

Racemic Trihexyphenidyl (Rac-THP; 10, 20 and 30 mg/kg) was formulated in 20% HPβCD and administered by intraperitoneal injection at a dose volume of 5 ml/kg 30 minutes before test.

R-Trihexyphenidyl (R-THP; 5, 10 and 15 mg/kg) was formulated in 20% HPβCD and administered by intraperitoneal injection at a dose volume of 5 ml/kg 30 minutes before test.

S-Trihexyphenidyl (S-THP; 5, 10 and 15 mg/kg) was formulated in 20% HPβCD and injected administered by intraperitoneal injection at a dose volume of 5 ml/kg 30 minutes before test.

Data Collection: The following data points were collected and analyzed for results:

Body Weight—Body weights were measured prior to treatment.

Haloperidol-induced Catalepsy—Rats were allowed to acclimate to the experimental room for at least 1 hr prior to testing. Rats were administered haloperidol, THP, R-THP or S-THP 30 minutes prior to test and placed in holding cages for 30 minutes prior to test. The front paws of a rat were placed then on a horizontal metal bar raised 6" above a Plexiglas platform. Each rat underwent 3 trials of 60 seconds each. The test ended when the animal's front paws return to the platform or after 60 seconds. Rats were tested at 30 and 60 minutes after treatment.

Plasma Collections—At the completion of the study, plasma was collected from rats treated with R-THP. Rats were decapitated and trunk blood was collected in $K_2$EDTA tubes. Within 15 minutes the tubes were centrifuged immediately for 10 minutes at 10,000-12,000 RPM in a refrigerated centrifuge. Plasma was extracted and samples were stored at −80° C.

Data were analyzed by one-way analysis of variance (ANOVA) followed by Tukey's post-hoc comparisons, where appropriate. Data are represented as mean and standard error to the mean (SEM).

Part II—Results

Results from the study are provided below.

Body Weight: Analysis of body weight measurements using one-way ANOVA found no significant differences in the body weight of the rats prior to treatment ($F(10,99)=0.169$, $P=0.998$).

Time Spent Holding Bar: The effects of THP on haloperidol-induced catalepsy at two time points after injection were measured and analyzed using one-way analysis of variance (ANOVA) followed by Tukey's post-hoc comparisons.

Figure 5:
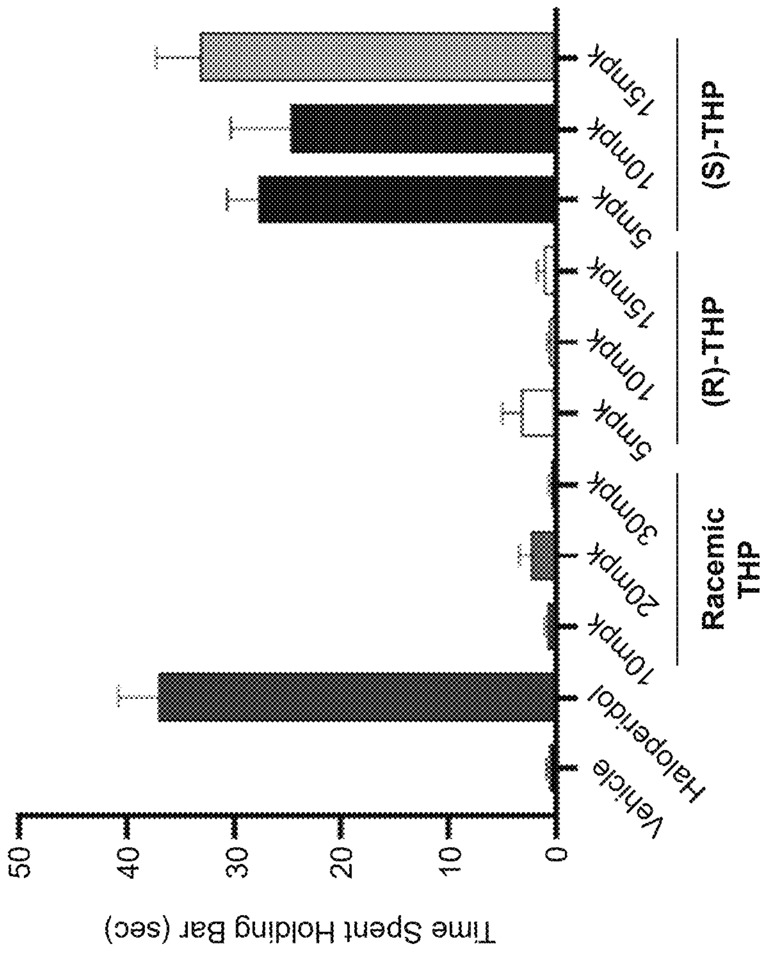
FIG. 5 is a graph depicting the effects of different forms of trihexyphenidyl on haloperidol-induced catalepsy in rats at 30 minutes after injection, as described in more detail in Example 9.

At the 30 minute time point, the effects of THP on haloperidol-induced catalepsy 30 minutes after injection is shown in FIG. 5. One-way ANOVA found a significant treatment effect ($F(10,99)=23.880$, $P<0.001$). Tukey's post hoc analysis found that haloperidol (1 mg/kg) significantly increased the time the rats spend holding the bar compared to vehicle-injected rats. Treatment with Rac-THP (10, 20 and 30 mg/kg) as well as R-THP (5, 10 and 15 mg/kg) significantly attenuated haloperidol-induced catalepsy as measured by the decreased time the rats spend holding the bar. Rats injected with S-THP (5, 10 and 15 mg/kg) spent significantly more time holding the bar compared to vehicle-vehicle-, R-THP- or Rac-THP-treated rats but their times did not significantly differ from those of haloperidol-treated rats.

At the 60 minute time point, analysis of results from the 60-minute time point by one-way ANOVA found a significant treatment effect ($F(10,99)=29.601$, $P<0.001$). Tukey's post hoc analysis found that haloperidol (1 mg/kg) alone significantly increased the time the rats spend holding the bar compared to vehicle-injected rats. Rac-THP (10, 20 and 30 mg/kg) as well as R-THP (5, 10 and 15 mg/kg) significantly attenuated haloperidol-induced catalepsy. No significant differences in the magnitude of effect was found among the different doses of Rac-THP or R-THP. Similarly no differences were seen between R-THP and Rac-THP. Rats injected with S-THP (5, 10 and 15 mg/kg) spent significantly more time holding the bar compared to vehicle-vehicle-, R-THP- or Rac-THP-treated rats. The combination of S-THP (5, 10 and 15 mg/kg) with haloperidol showed no significant differences on the time the rats spent holding the bar when compared to haloperidol alone.

Figure 6:
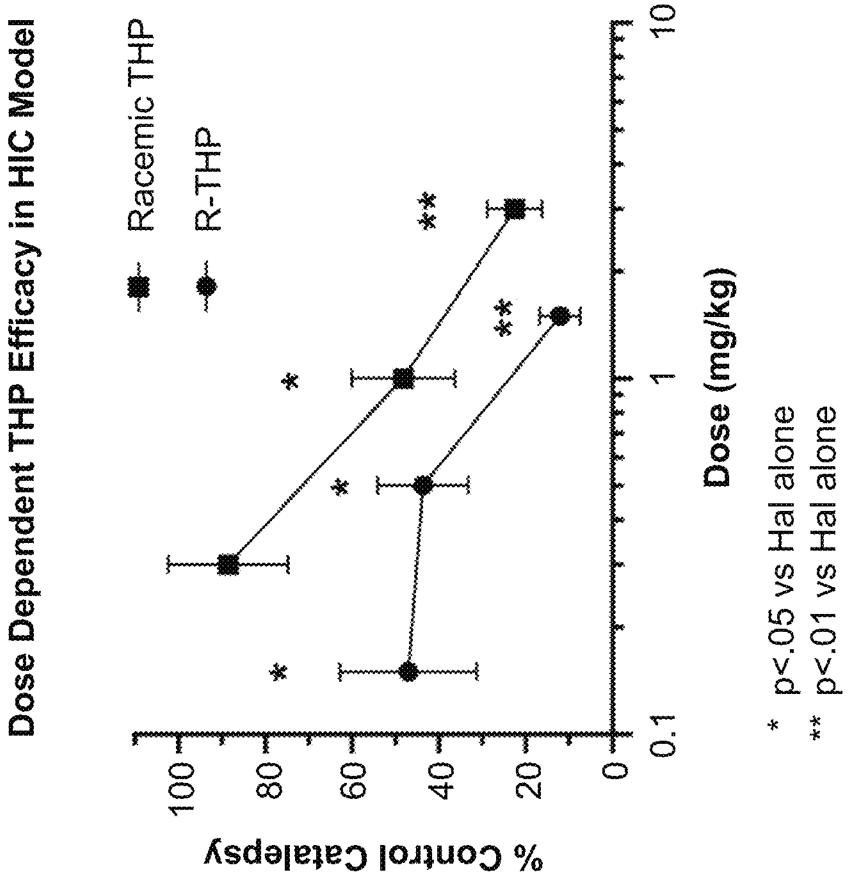
FIG. 6 is a graph depicting the efficacy of (R)-THP and racemic THP in the haloperidol-induced catalepsy assay at different doses, as described in more detail in Example 9.

Efficacy of R-THP versus Rac-THP: The efficacy of R-THP and Rac-THP over a dosage range was measured. FIG. 6 shows that half a dose of R-THP controls catalepsy at least as effectively as a full dose of Rac-THP. These data indicate that all the efficacious THP dose is in one enantiomer (R-THP). These data also indicate that both R-THP and Rac-THP are effective in controlling catalepsy, and that a lower dose of R-THP may be administered to achieve the same level of catalepsy control as a higher dose of Rac-THP.

Part III—Conclusion

The current study evaluated the effects of racemic THP (Rac-THP) and its R and S enantiomers on haloperidol-induced catalepsy in rats as measured by the time the rats spent holding the bar. Acute, IP injection of Rac-THP (10, 20 and 30 mg/kg) as well as R-THP (5, 10 and 15 mg/kg) significantly attenuated haloperidol-induced catalepsy 30 and 60-minutes post injection. None of the doses of S-THP (5, 10 and 15 mg/kg) showed efficacy in this test at either time point.

Example 10—THP Relaxation of the Guinea Pig Ileum is Reversed by BTC

The potency and efficacy of THP and BTC on contractions induced by electrical field stimulation (EFS) in guinea pig ileum myenteric plexus-longitudinal muscle (MPLM) strips was evaluated and compared. The procedure and results are provided below.

Part I—Materials and Methods

Exclusion Criteria: Only macroscopically normal tissue obtained from male adult Dunken Hartley guinea pigs sacrificed by $CO_2$ asphyxiation was used. Tissue strips that did not respond to EFS were excluded. There were no other exclusion criteria.

Experimental Design: Tissue was collected in warm Poly (sodium 4-styrenesulfonate) solution (PSS) (approximately 37° C., composition: 119.0 mM NaCl, 4.70 mM KCl, 1.20 mM $MgSO_4$, 24.9 mM $NaHCO_3$, 1.20 mM $KH_2PO_4$, 2.50 mM $CaCl_2$), 11.1 mM glucose), warmed and previously aerated with 95% $O_2$/5% $CO_2$ gas mix. Dissection was carried out in warm PSS. A 15 cm ileum segment was excised from the small intestine and MPLM strips were dissected from the ileal segment by the method of Paton and Zar (1968), after discarding the first 5 cm length closest to the ileo-caecal junction. Briefly, a 8-10 cm length of the ileum was flushed of its contents with PSS solution and slipped over a glass rod. After trimming the mesentery, the longitudinal muscle with the adherent myenteric plexus was separated from the underlying circular muscle layer by gentle stroking with a cotton bud soaked with PSS, starting at the mesenteric border and working along and around the circumference of whole ileum.

The muscle strips were cut to the appropriate length, tied with cotton thread and mounted on mounting hooks with attached platinum electrodes. The hooks were attached to the organ baths (Panlabs), which were filled with PSS, gassed with 95% $O_2$/5% $CO_2$ gas mix and set to a temperature of approximately 30° C. The muscle strips were left to equilibrate for 30 minutes to reach a temperature of approximately 37° C. before being set to a resting tension. They were then washed over an equilibration period, with re-tensioning if required. Changes in force production were detected by force transducers and data was captured using Lab Chart 7 software (ADInstruments).

The muscle strips were stimulated with an electrical field in order to generate electrically evoked, neuronally mediated contractions of the muscle. The optimum voltage was determined by performing a voltage response curve in all tissues, whilst the tissue was paced with EFS at a frequency of 0.1 Hz, 0.5 msec pulse width. The stimulation period was followed by a wash and equilibration period wherein stable responses to EFS at optimal voltage were obtained. These stable responses represented the baseline measurement of EFS in the absence of the test article. The EFS at optimal voltage was then continued throughout the protocol.

Upon stabilization of EFS baseline, each muscle strip was randomly allocated to a treatment group—the test conditions performed in each experiment are described in tables 11-14 below. At the end of each test article cumulative concentration response curve (CCRC), 1 μM atropine was added to all baths as a final functional check. In experiment 1, 1 μM tetrodotoxin (TTX) was also added to all baths to further abolish nerve-stimulated contractile responses.

TABLE 11

| Test Conditions-Experiment 1 | |
|---|---|
| CCRC | Replicates |
| THP: 1 nM, 3 nM, 10 nM, 30 nM, 100 nM, 300 nM, 1 μM | 4 |
| BTC: 10 nM, 30 nM, 100 nM, 300 nM, 1 μM, 10 μM | 4 |
| Vehicle (dH2O): matched volume additions | 5 |

TABLE 12

| Test Conditions-Experiment 2 | | |
|---|---|---|
| Pre-treatment | CCRC | Replicates |
| N/A | THP: 1 nM, 3 nM, 10 nM, 30 nM, 100 nM, 300 nM, 1 μM | 2 |
| N/A | BTC: 30 nM, 100 nM, 300 nM, 1 μM, 10 μM | 3 |
| N/A | Vehicle (dH2O): matched volume additions | 2 |
| THP 30 nM | BTC: 30 nM, 100 nM, 300 nM, 1 μM, 10 μM | 3 |
| THP 100 nM | BTC: 30 nM, 100 nM, 300 nM, 1 μM, 10 μM | 4 |

TABLE 13

| Test Conditions-Experiment 3 | | |
|---|---|---|
| Pre-treatment | CCRC | Replicates |
| N/A | THP: 10 nM, 30 nM, 100 nM, 300 nM, 1 μM | 1 |
| N/A | BTC: 100 nM, 300 nM, 1 μM, 10 μM, 30 μM | 1 |
| N/A | Vehicle (dH2O): matched volume additions | 2 |
| THP 30 nM | BTC: 100 nM, 300 nM, 1 μM, 10 μM, 30 μM | 4 |
| BTC 10 nM | THP: 10 nM, 30 nM, 100 nM, 300 nM, 1 μM | 5 |

TABLE 14

| Test Conditions-Experiment 4 | | |
|---|---|---|
| Pre-treatment | CCRC | Replicates |
| N/A | R-THP: 10 nM, 30 nM, 100 nM, 300 nM, 1 μM | 2 |
| N/A | BTC: 100 nM, 300 nM, 1 μM, 10 μM, 30 μM | 2 |
| N/A | Vehicle (dH2O): matched volume additions | 2 |
| R-THP 15 nM | BTC: 100 nM, 300 nM, 1 μM, 10 μM, 30 μM | 4 |
| BTC 10 nM | R-THP: 10 nM, 30 nM, 100 nM, 300 nM, 1 μM | 5 |

The magnitude of the response was measured by calculating the mean peak height or integral of 3 stable successive peaks of the EFS contractile response. The data was expressed as the percentage change in activity of baseline EFS. Analyzed data is displayed graphically using GraphPad Prism.

Part II—Results

Figure 7A:
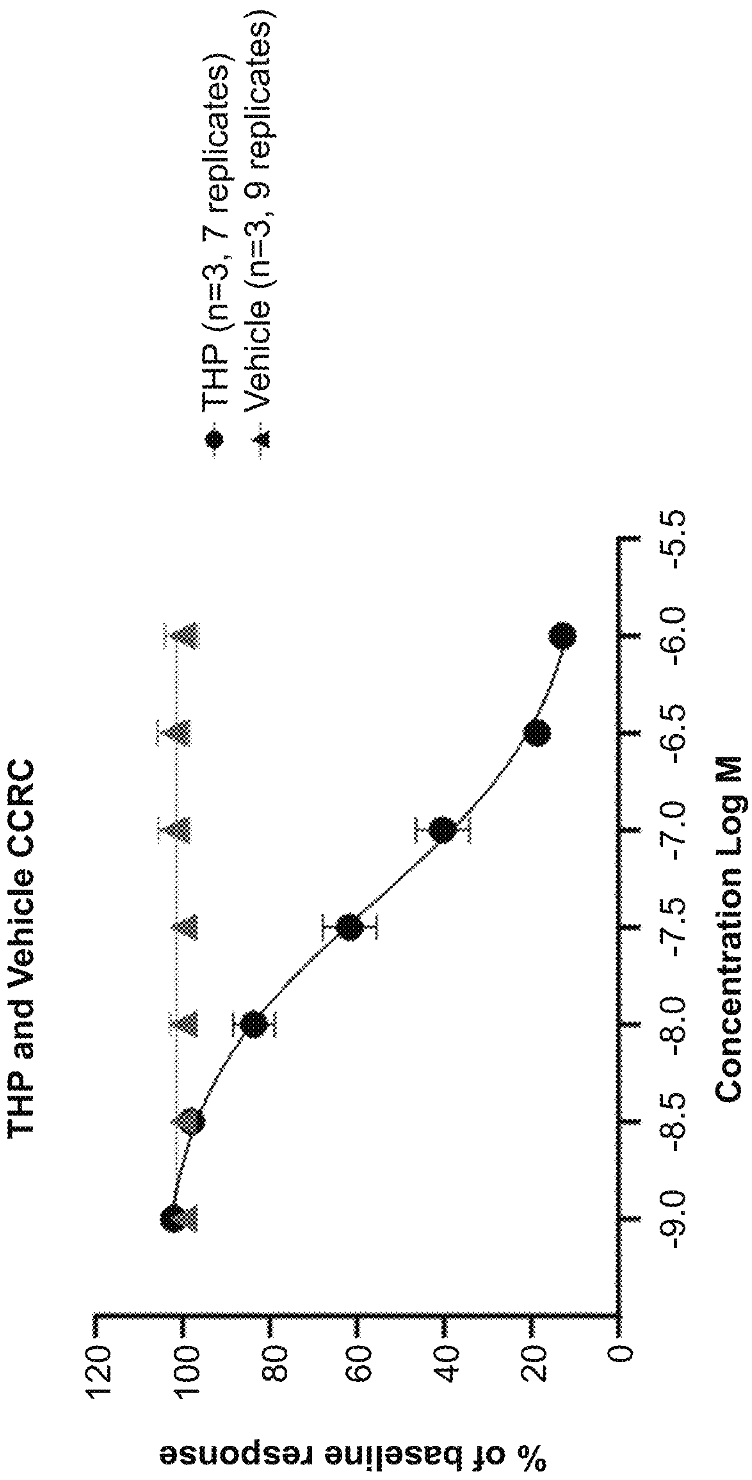
FIGS. 7A-7C are graphs depicting the potency and efficacy of THP alone (FIG. 7A), BTC alone (FIG. 7B), and THP in combination with BTC (FIG. 7C) on contractions induced by electrical field stimulation (EFS) in guinea pig ileum myenteric plexus-longitudinal muscle (MPLM) strips, as described in more detail in Example 10.

In guinea pig isolated MPLM strips stimulated with electrical field, Rac-THP was found to produce a concentration-dependent relaxation response which was found to be significantly different to the vehicle group at a concentration of 10 nM to 1 μM (FIG. 7A).

Figure 7B:
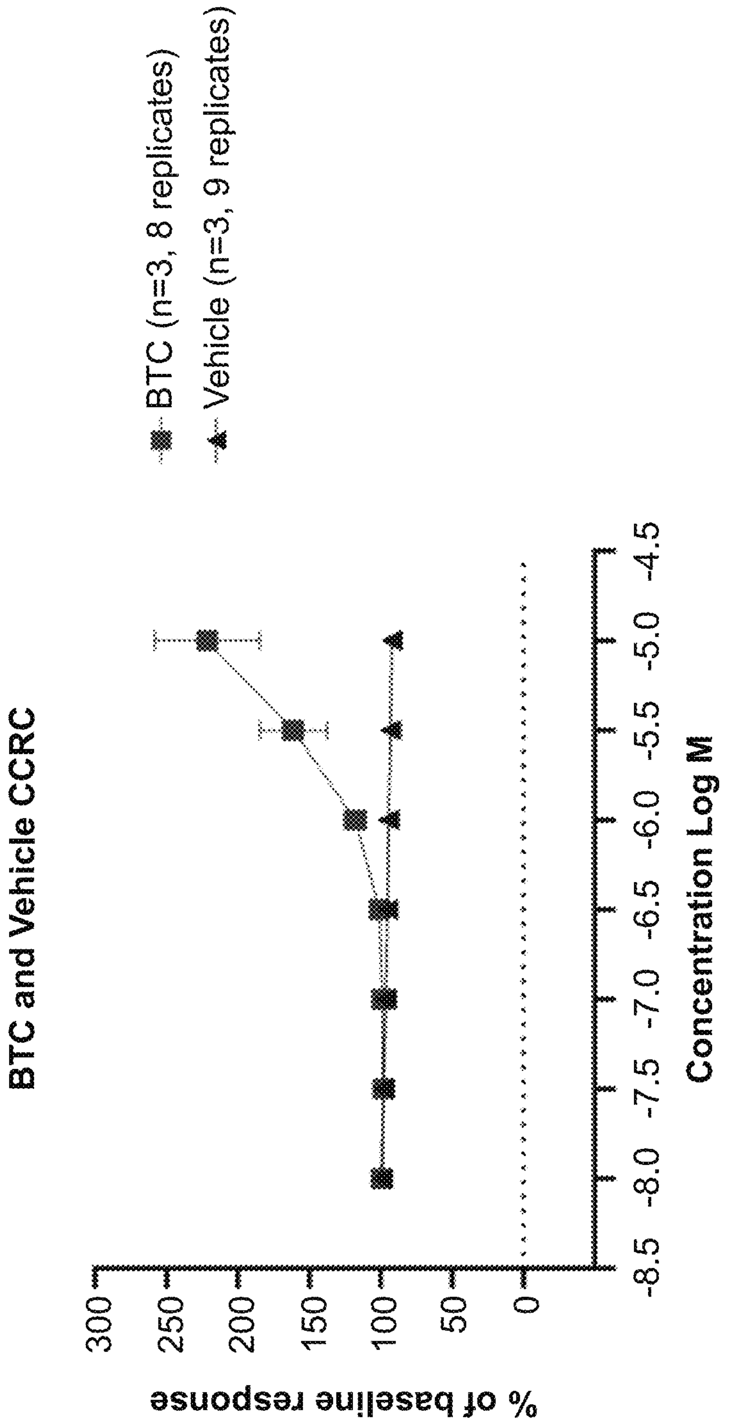

BTC was found to produce a concentration-dependent contraction of guinea pig isolated MPLM strips which was significantly different to the vehicle group at a concentration of 3 μM and 10 μM (FIG. 7B).

Figure 7C:
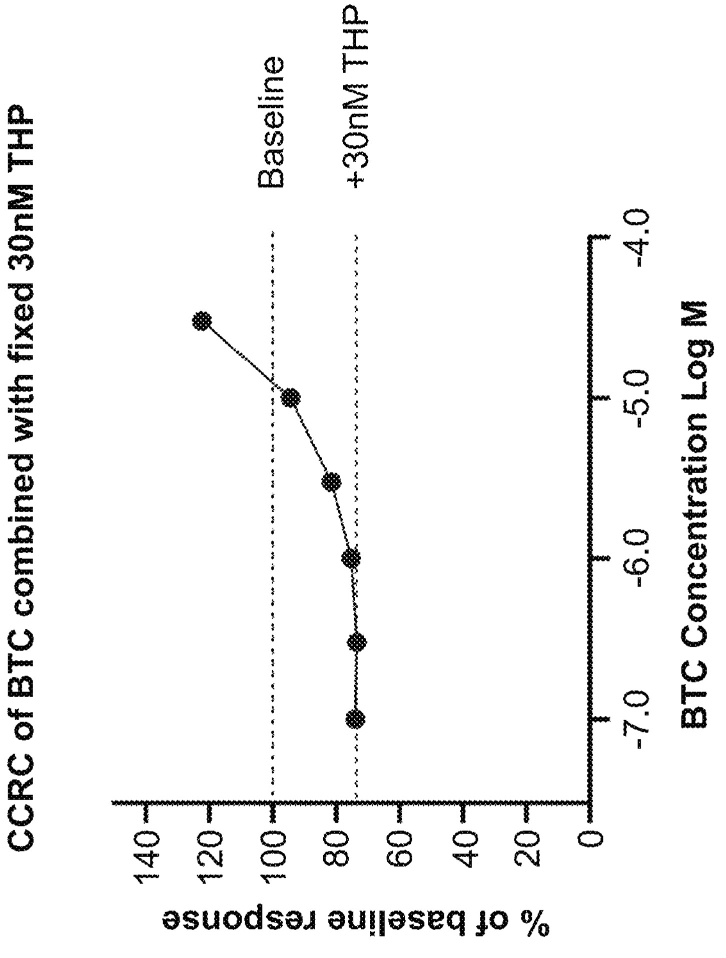

Following pre-treatment with an intermediate dose of Rac-THP at 30 nM, BTC was found to produce a concentration-dependent relaxation of the isolated MPLM strips back to baseline and up to 50% over baseline at 30 μM (FIG. 7C).

Part III—Conclusions

FIG. 7A shows a dose-dependent relaxation of guinea pig ileum with THP, and FIG. 7B shows a dose dependent contraction of guinea pig ileum with BTC. FIG. 7C shows that THP-mediated relaxation can be offset with BTC to restore tissue tension to normal levels. These data demonstrate that administering THP in combination with BTC can reduce adverse effects associated with THP.

Example 11—BTC Prevents THP-Induced Dry Eye in Dogs in a Dose-Dependent Manner Beagles (N=6 per group) were orally administered either Rac-THP alone, Rac-BTC alone, or Rac-THP in combination with Rac-BTC at two relative ratios of Rac-BTC. One group was pre-dosed with Rac-BTC 30 minutes prior to Rac-THP dosing. The results are shown in FIG. 8.

THP alone caused a near complete reduction of tears at 1 hour post administration. The 1:3 ratio of Rac-THP:Rac-BTC group showed amelioration of tear production compared to the THP alone group at 1 hour and at 4 hours post administration. The 1:5 ratio of Rac-THP:Rac-BTC group showed the tear production percentage to be above 100% of the baseline level 1 hour after administration, and at 4 hours after administration.

A side effect of THP is dry eye. BTC alone causes no major change in eye dryness, but THP administered in combination with BTC (either simultaneously or pre-dosed with BTC) restored THP-induced dry eye to baseline levels. A 1:5 (THP:BTC) ratio was able to increase lacrimation above baseline, demonstrating that BTC can offset THP peripheral adverse effects in vivo (FIG. 8).

Figure 8:
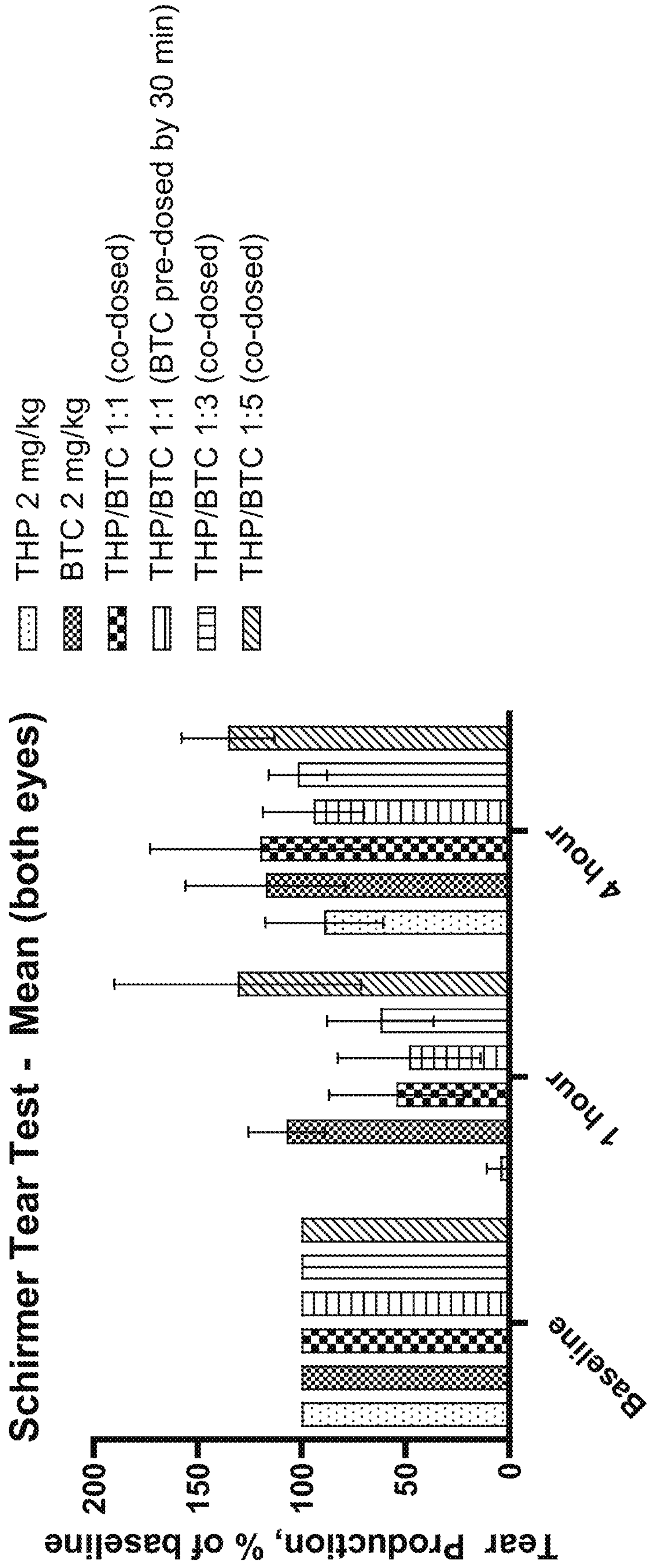
FIG. 8 is a graph depicting the effects of racemic THP alone, racemic BTC alone, and racemic THP administered in combination with racemic BTC on tear production, as described in more detail in Example 11.
Figures 9A, 9B, 9C, 9D, 9E, 9F:
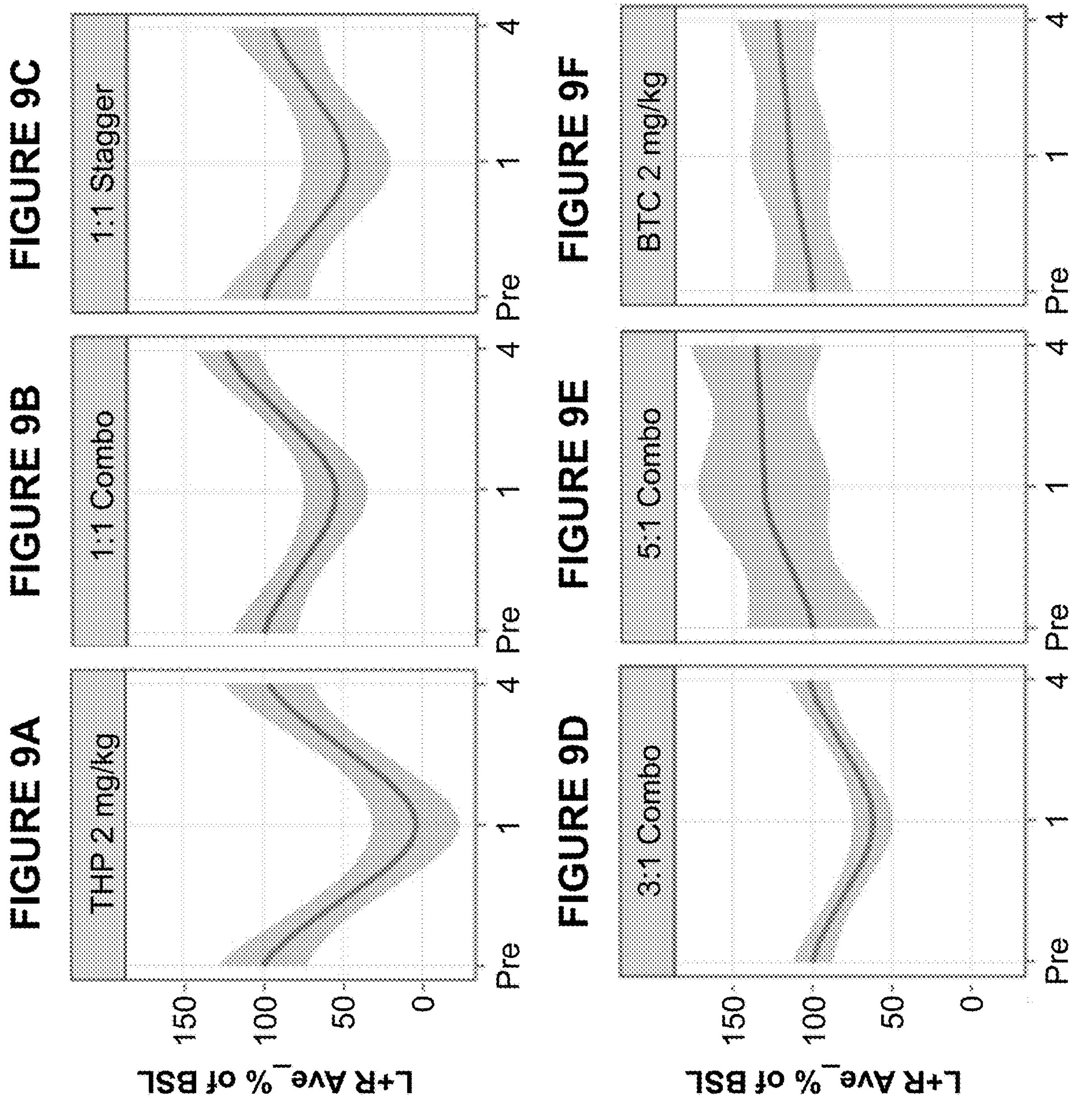
FIGS. 9A-9F are a series of graphs depicting the 95% confidence interval of each treatment group from FIG. 8, as described in more detail in Example 11.

FIGS. 9A-9F show the 95% confidence interval (CI) of each treatment group from FIG. 8, and demonstrates that resolution of dry eye to baseline levels is BTC dose-dependent and time-dependent. Table 15 shows the percentage of baseline tear production and serum concentrations of THP and BTC after treatment with THP monotherapy, BTC monotherapy, 1:3 (THP:BTC) combination therapy, and 1:5 (THP:BTC) combination therapy at 1 hour post administration, and 4 hours post administration.

TABLE 15

| | THP (2 mpk) | BTC (2 mpk) | THP (2 mpk) + BTC (6 mpk) | THP (2 mpk) + BTC (10 mpk) |
|---|---|---|---|---|
| 1 hour post administration | | | | |
| THP concentration in plasma (ng/mL) | 14 | 0 | 23.1 | 23.4 |
| BTC concentration in plasma (ng/mL) | 0 | 215 | 472 | 761 |
| % Baseline tear | 4.4% | 107% | 62% | 131% |

TABLE 15-continued

| | THP (2 mpk) | BTC (2 mpk) | THP (2 mpk) + BTC (6 mpk) | THP (2 mpk) + BTC (10 mpk) |
|---|---|---|---|---|
| production | | | | |
| 4 hours post administration | | | | |
| THP concentration in plasma (ng/mL) | 3.4 | 0 | 5.9 | 4.4 |
| BTC concentration in plasma (ng/mL) | 0 | 268 | 340 | 254 |
| % Baseline tear production | 89.1% | 117% | 102% | 135% |

Concordance between bladder and ocular adverse events, ex vivo, driven by anticholinergics with different potency and selectivity has been previously demonstrated. This data showing that THP and BTC combination therapy was able to retain lacrimation at or above baseline should translate to alleviating other adverse effects in other target peripheral organs, such as bladder for example. See Choppin et al., *Brit. J. of Pharmacology,* 124(5):883-888 (1998).

Example 12—THP:BTC Interaction in Dogs

Figure 10A:
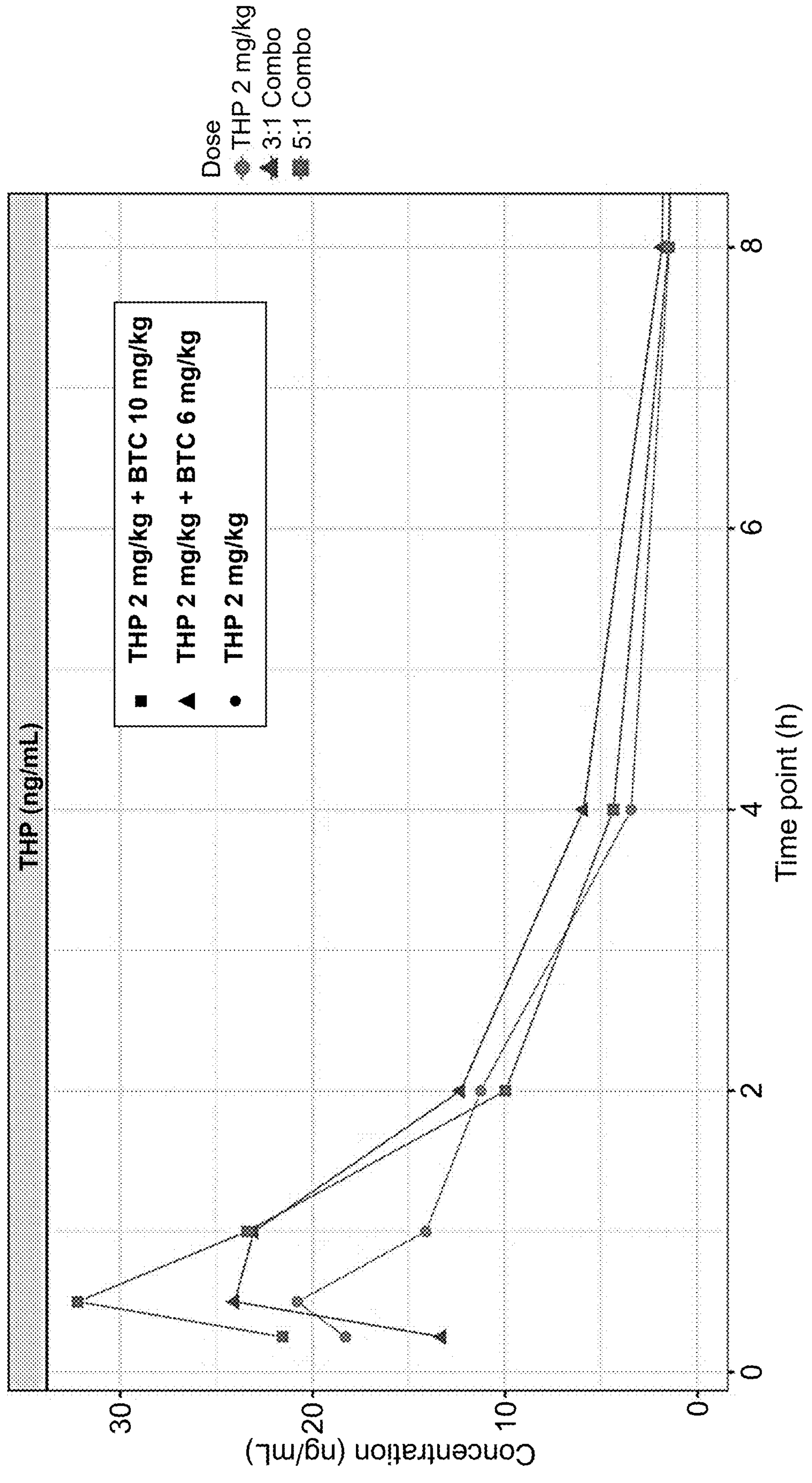
FIGS. 10A and 10B are graphs depicting the plasma THP concentration (ng/ml) (FIG. 10A) and plasma BTC concentration (ng/mL) (FIG. 10B) in dogs when administered THP alone, BTC alone, and different ratios of THP:BTC, as explained in more detail in Example 12.

Beagles were orally administered either Rac-THP alone (N=2 per group), Rac-BTC alone (N=2 per group), Rac-THP in combination with Rac-BTC (N=4 per group). FIG. 10A shows the plasma concentration of THP (ng/mL) after administration of THP alone (2 mg/kg), a 1:3 ratio of THP:BTC (2 mg/kg THP and 6 mg/kg BTC), and a 1:5 ratio of THP:BTC (2 mg/kg THP and 10 mg/kg BTC). FIG. 10A shows that administering THP in combination with BTC increases the serum concentration of THP compared to the plasma concentration of THP administered alone. The 1:5 ratio of THP:BTC showed the greatest increase in plasma concentration of THP.

Figure 10B:
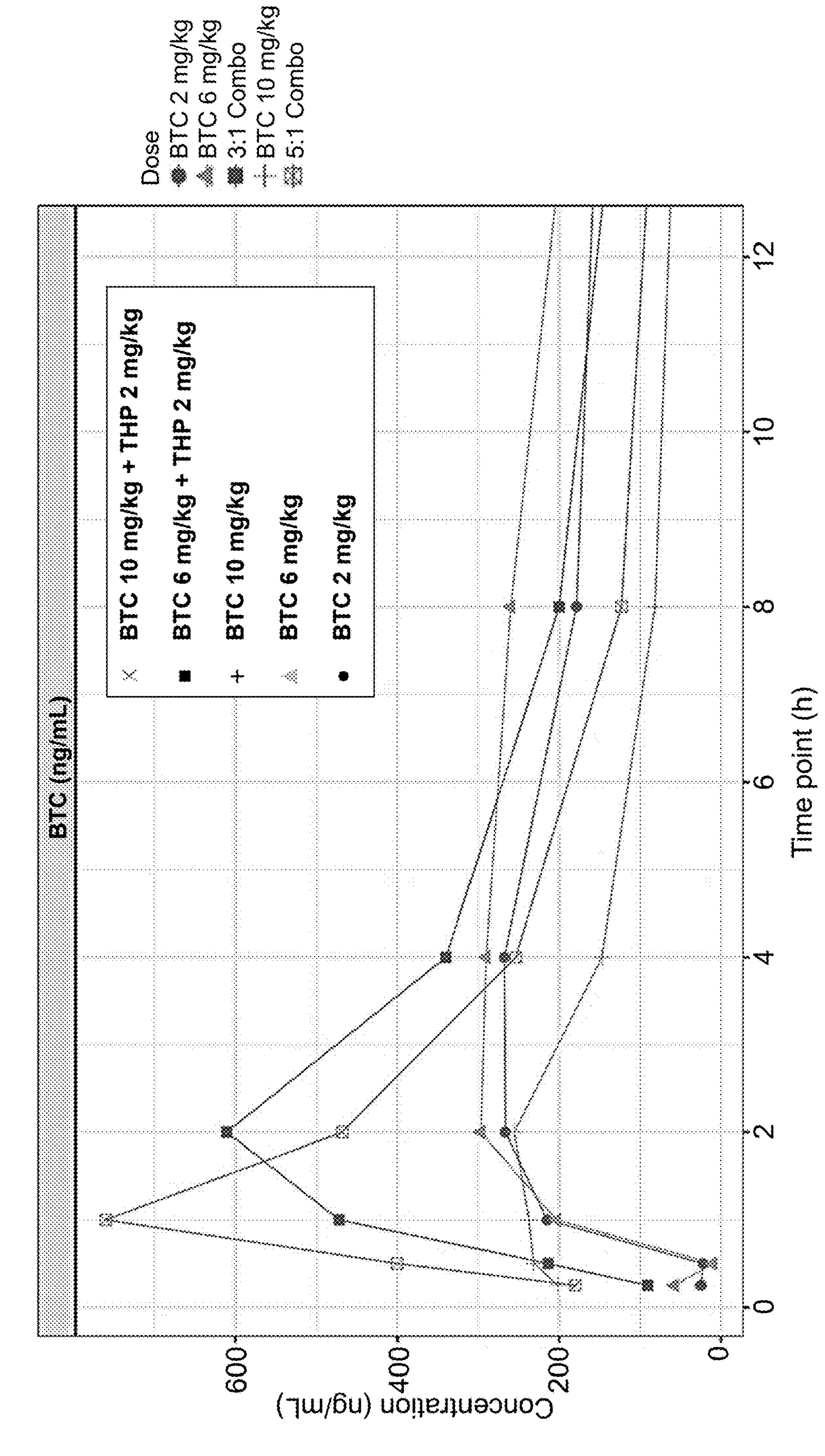

FIG. 10B shows the plasma concentration of BTC (ng/ml) after administration of BTC alone (2 mg/kg, 6 mg/kg, and 10 mg/kg), a 1:3 ratio of BTC:THP (2 mg/kg BTC and 6 mg/kg THP), and a 1:5 ratio of BTC:THP (2 mg/kg BTC and 10 mg/kg THP). FIG. 10B shows administering BTC in combination with THP increases the plasma concentration of BTC compared to the plasma concentration of BTC administered alone. The 1:5 ratio of BTC:THP showed the greatest increase in plasma concentration of BTC.

Without ascribing this result to any mechanism, these results indicate that a lower dose of THP may unexpectedly be used in combination with BTC to achieve the same or higher THP plasma concentration as a higher dose of THP monotherapy. These results also indicate that a lower dose of BTC may unexpectedly be used in combination with THP to achieve the same or higher BTC plasma concentration as a higher dose of BTC monotherapy.

In addition, these results suggest that simple co-administration of THP and BTC may result in an unexpected risk of over-exposure of THP, and also increase the likelihood of adverse effects at a dose of THP that may otherwise drive efficacy when administered alone.

Example 13—THP:BTC Interaction in Humans

Figure 11:
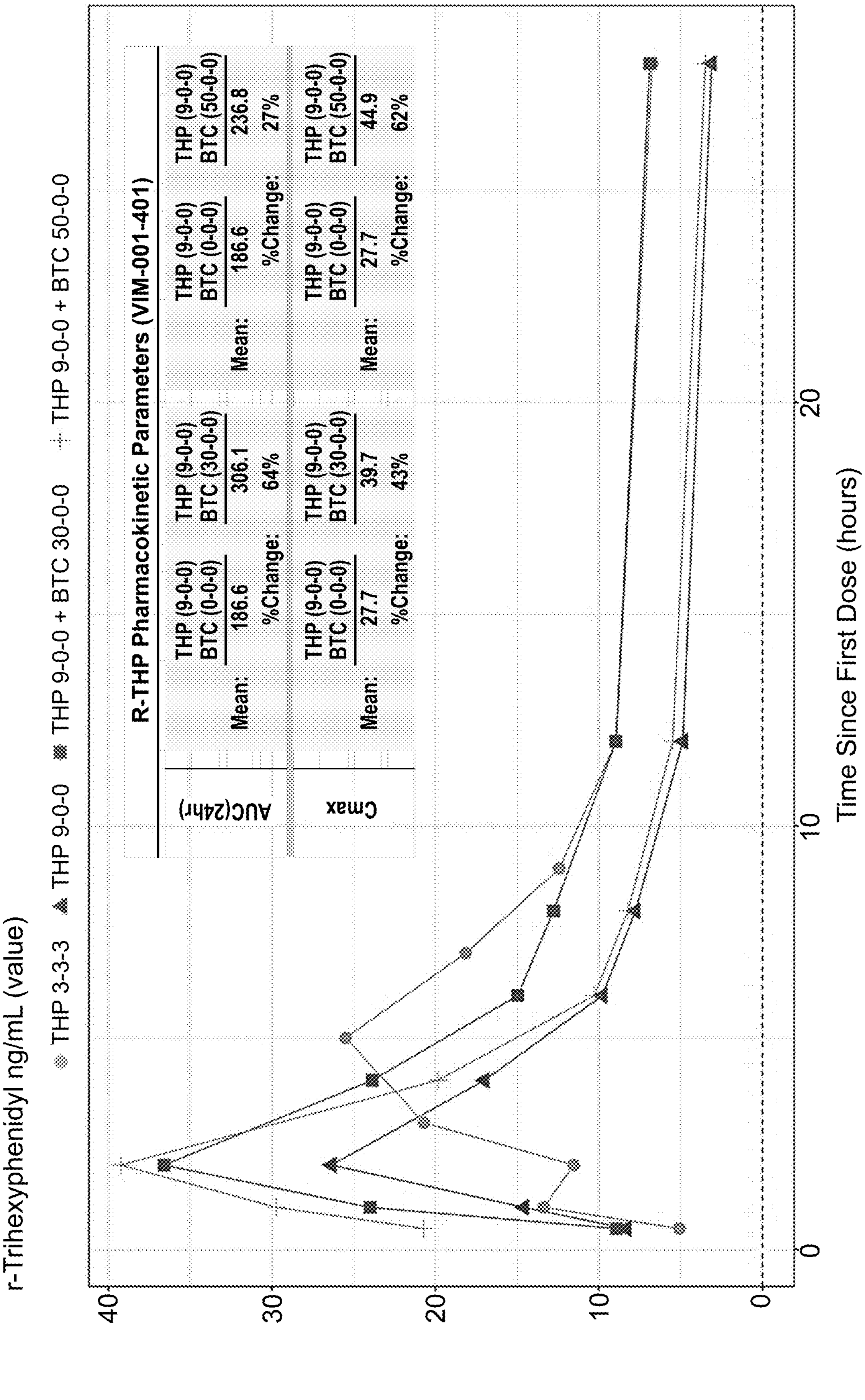
FIG. 11 is a graph depicting the plasma exposure levels of racemic-THP monotherapy compared to racemic-THP:racemic-BTC combination therapy, as explained in more detail in Example 13.

FIG. 11 shows the serum exposure levels of Rac-THP monotherapy compared to Rac-THP:Rac-BTC combination therapy in humans. Subjects were dosed with 9 mg Rac-THP alone, or 9 mg Rac-THP plus either 30 mg Rac-BTC or 50 mg Rac-BTC. These data show that administering THP in combination with either dose of BTC unexpectedly results in a higher THP plasma exposure when compared to the plasma exposure of the same dosage of THP monotherapy. Without ascribing this result to any mechanism, this result indicates that a lower dose of THP may unexpectedly be used in combination with BTC to achieve the same THP plasma exposure level as a higher dose of THP monotherapy.

Furthermore, prior to observing this drug-drug interaction, an efficacious dose of THP, if combined with Bethanechol to offset peripheral adverse events, would result in unexpectedly high levels of THP that could result in central adverse events, or increase the risk of abuse of THP. These data and those in the Examples herein indicate an unexpected drug-drug interaction between THP and BTC and that co-dosing of THP and BTC must take that drug-drug interaction into account to reduce the frequency and/or magnitude of at least one side effect of THP.

Additional PK parameters of THP were measured in the groups described in this example. Summary data describing the area under the curve (AUC) of plasma R-THP, and the maximal concentration (Cmax) of plasma R-THP are shown below in Tables 16 and 17. As referred to below in Example 14, R-THP was measured because it is the predominate enantiomer found in plasma following administration of racemic THP. These data demonstrate that AUC ratios of about 1:5-1:20 (R-THP:BTC) are detected, when correcting for relative protein binding of the two molecules. Cmax ratios of about 1:5-1:10 (R-THP:BTC) are detected, when correcting for relative protein binding of the two molecules.

TABLE 16

BTC and R-THP AUC(0-28 hr) Values in VIM-001-401

| 9-0-0 30-0-0 | | | 9-0-0 50-0-0 | | |
|---|---|---|---|---|---|
| BTC | R-THP | Ratio | BTC | R-THP | Ratio |
| 68.7 | 91.2 | 0.75 | 145 | 115 | 1.26 |
| 107 | 23.6 | N/C | 176 | 282 | 0.62 |
| 77 | 533 | 0.14 | 146 | 355 | 0.41 |
| 82.6 | 399 | 0.21 | 149 | 282 | 0.53 |
| 141 | 394 | 0.36 | 240 | 178 | 1.35 |
| 56.1 | 351 | 0.16 | 170 | 300 | 0.57 |
| | Geometric Mean: | 0.26 | | Geometric Mean: | 0.71 |
| | Corrected for Protein Binding: | 6.6 | | Corrected for Protein Binding: | 17.8 |

TABLE 17

| BTC and R-THP Cmax Values Values in VIM-001-401 | | | | | |
|---|---|---|---|---|---|
| 9-0-0 30-0-0 | | | 9-0-0 50-0-0 | | |
| BTC | R-THP | Ratio | BTC | R-THP | Ratio |
| 6.7 | 31.1 | 0.22 | 19.1 | 21.3 | 0.90 |
| 9.4 | 29.8 | N/C | 14.6 | 41.1 | 0.36 |
| 9.1 | 71.6 | 0.13 | 14.6 | 53.2 | 0.27 |
| 8.7 | 45 | 0.19 | 14.7 | 70.2 | 0.21 |
| 14.2 | 33 | 0.43 | 20.4 | 32.2 | 0.63 |
| 6 | 27.8 | 0.22 | 16.6 | 51.4 | 0.32 |
| | Geometric Mean: | 0.22 | | Geometric Mean: | 0.39 |
| | Corrected for Protein Binding: | 5.4 | | Corrected for Protein Binding: | 9.9 |

Example 14—Timing of the THP Dose Affects the Adverse Effect Profile

Dizziness may be an adverse effect of THP in humans. The effects of the timing of administering the THP dose on dizziness was evaluated in humans.

Experimental Design: All of the data collected in this example were run in a double-blind, randomized, placebo controlled setting of normal healthy adults. The THP and BTC used in this example were commercial, racemic, branded THP and BTC. Dizziness was measured by the visual analog scale (VAS), a common clinical measure of dizziness.

Figure 12A:
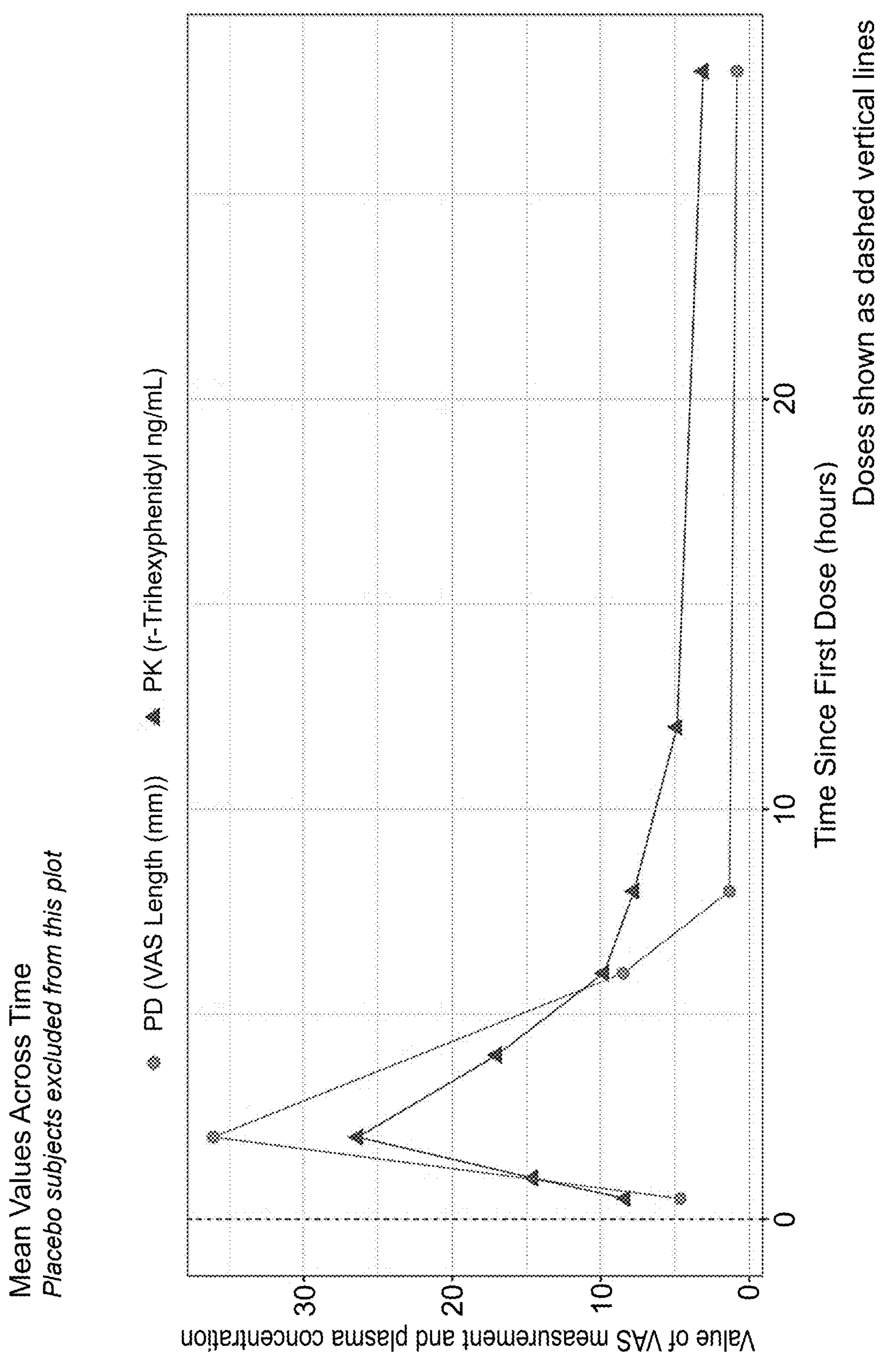
FIGS. 12A and 12B are graphs depicting the plasma THP concentration (ng/ml) and visual analog scale (VAS), a common clinical measure of dizziness, in human subjects, when 9 mg THP immediate release is administered once (FIG. 12A), and when 3 mg THP administered 3 times sequentially at 0 hours, 2 hours, and 4 hours (FIG. 12B), as explained in more detail in Example 14.
Figure 12B:
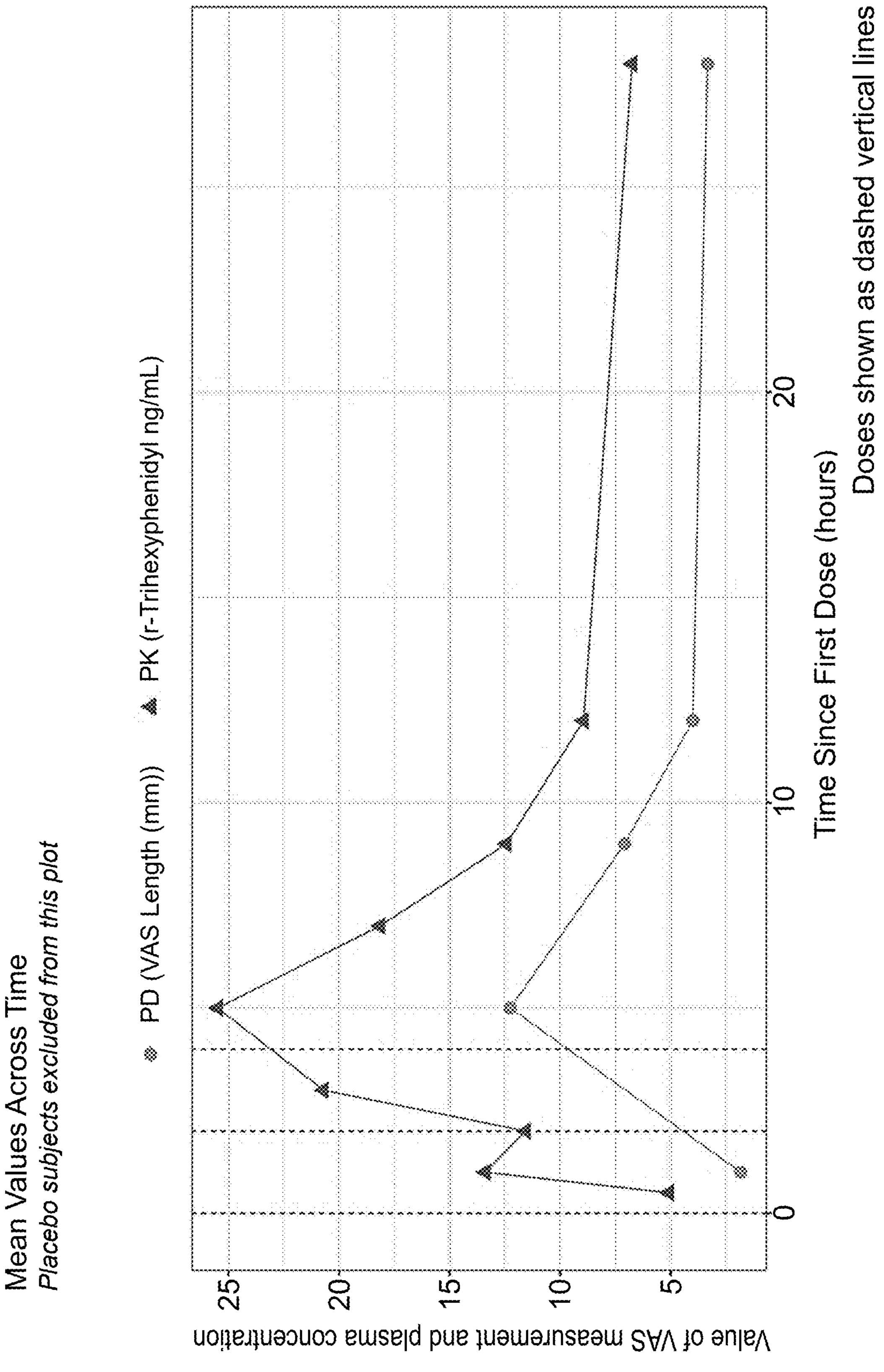

Results: FIGS. 12A and 12B show that the timing of the THP dose effects dizziness. In FIG. 12A, 9 mg of THP immediate release was administered. In FIG. 12B, 3 mg of THP immediate release was administered at 3 separate times (at 0 hours, 2 hours, and 4 hours). Both FIGS. 12A and 12B have an equivalent Cmax value, however, FIG. 12B shows a decreased rate of rise in serum levels of THP when the THP dosage was spread out over three administrations. The decreased rate of rise in serum levels of THP is associated with significantly reduced dizziness. These data indicate that spreading out the dosage of THP decreases the rate of rise in serum levels of THP and unexpectedly decreases adverse effects without changing the THP Cmax. The Cmax parameters measured in this study are shown below in Table 18, demonstrating that a rate of rise (RoR) was reduced by interval dosing versus a single oral dose of the same total amount (6.7 ng/ml/h vs. 14.9 ng/mL/h, respectively). A trihexyphenidyl dosing paradigm that reduces rate of rise may therefore be preferred to reduce central adverse events.

TABLE 18

| R-THP Rate of Rise (ng/mL/hr) | | | | | | |
|---|---|---|---|---|---|---|
| | 9-0-0 mg Rac THP dosing | | | 3-3-3 mg Rac THP dosing | | |
| | Cmax | Tmax | RoR | Cmax | Tmax | RoR |
| Subject 1 | 23.0 | 1 | 23.0 | 34.3 | 3 | 11.4 |
| Subject 2 | 26.2 | 2 | 13.1 | 11.6 | 3 | 3.9 |
| Subject 3 | 20.6 | 4 | 5.2 | 34.3 | 5 | 6.9 |
| Subject 4 | 25.8 | 2 | 12.9 | 25.3 | 5 | 5.1 |
| Subject 5 | 30.0 | 2 | 15.0 | 44.2 | 5 | 8.8 |
| Subject 6 | 40.6 | 2 | 20.3 | 21.0 | 5 | 4.2 |
| | | Mean: | 14.9 | | Mean: | 6.7 |

Figure 13A:
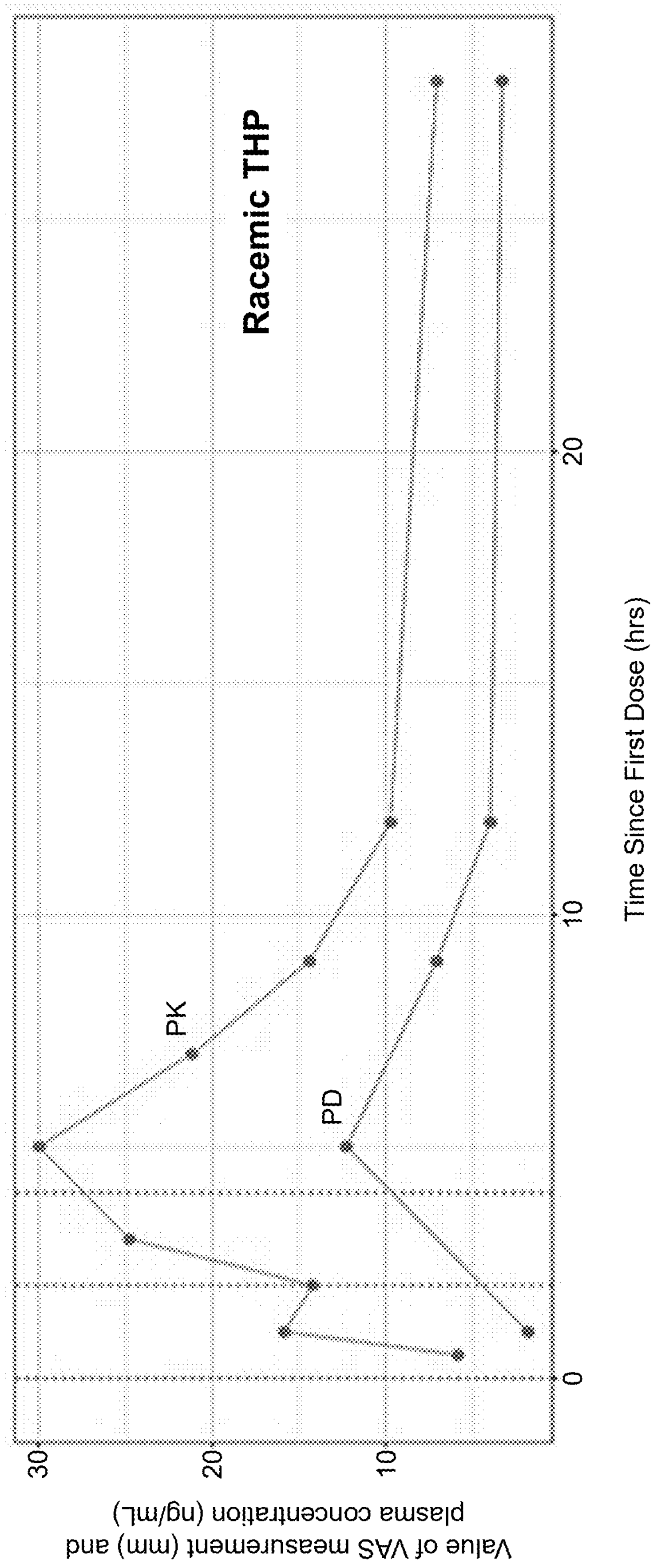
FIGS. 13A and 13B are graphs depicting the plasma concentration of racemic THP (FIG. 13A, labeled as PK) and the plasma concentration of (R)-THP (FIG. 13B, labeled as PK) (ng/mL) after administration of racemic THP in human subjects, and also shows a quantitative measure of dizziness using the visual analog scale (VAS, labeled as PD), as explained in more detail in Example 14.
Figure 13B:
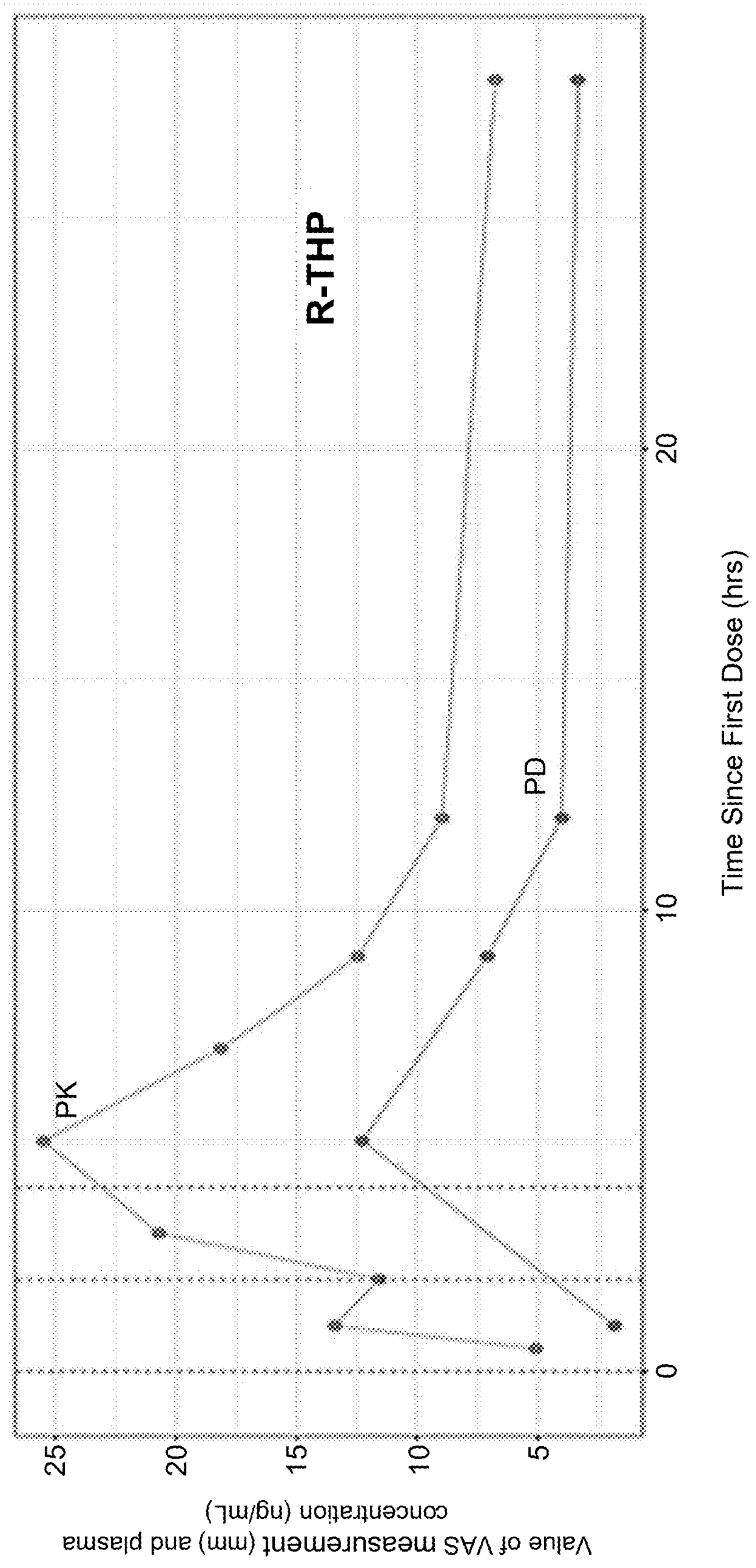
Figure 14A:
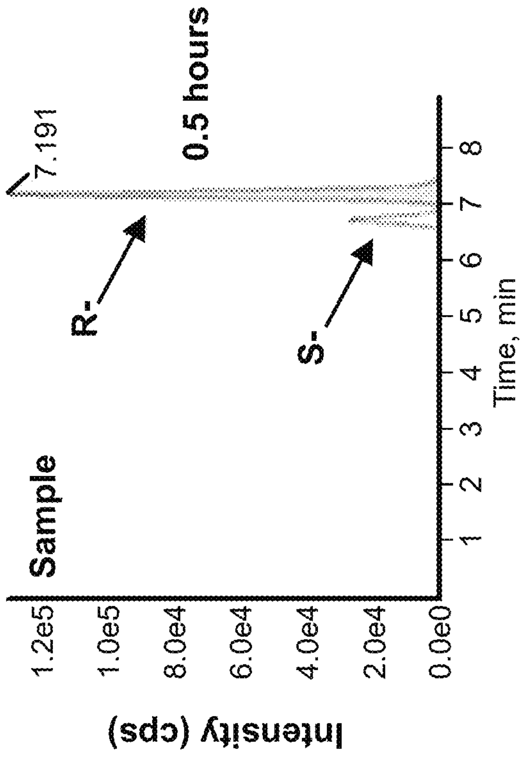
FIGS. 14A and 14B are graphs depicting the enantiomer plasma exposure of R-THP and S-THP in humans at 0.5 hours (FIG. 14A), and at 9 hours (FIG. 14B).
Figure 14B:
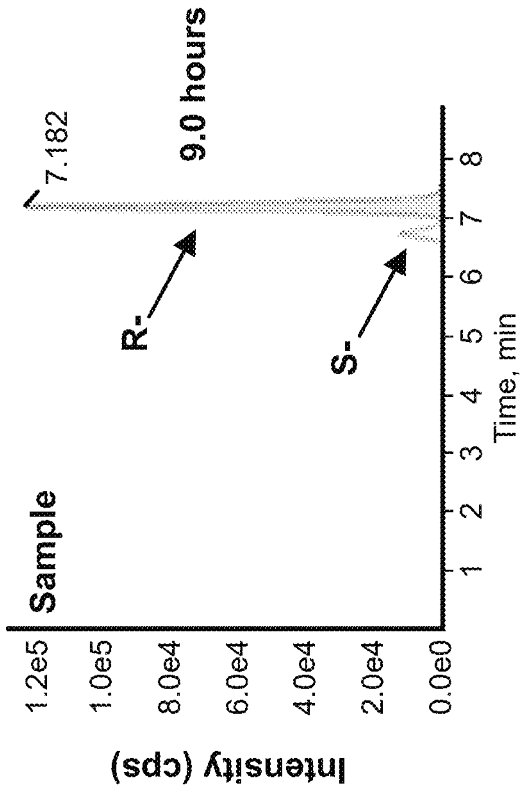

FIGS. 13A and 13B show the plasma concentration and dizziness (VAS) in humans after treatment with racemic-THP, from the same experiment shown in FIG. 11B. Serum samples were analyzed for the presence of total THP (i.e., not considering the enantiomeric composition of the THP) or (R)-THP using a chiral detection column (CHIRALPAK IG-3 3 μm Chiral, 100×2.1 mm) using methods known in the art. The amount of (R)-THP was greater than the anticipated 50% fraction from dosing racemic THP (FIG. 13A shows total THP, FIG. 13B shows (R)-THP). This suggests that (R)-THP and (S)-THP have differential metabolic or absorption pathways in humans. FIGS. 14A and 14B show the enantiomer exposure of R-THP and S-THP at 0.5 hours (FIG. 14A), and at 9 hours (FIG. 14B) after dosing humans with Rac-THP. These data indicate that human PK profile of racemic THP elucidates unequal enantiomer exposure; R-THP represents 85% exposure.

Figure 15:
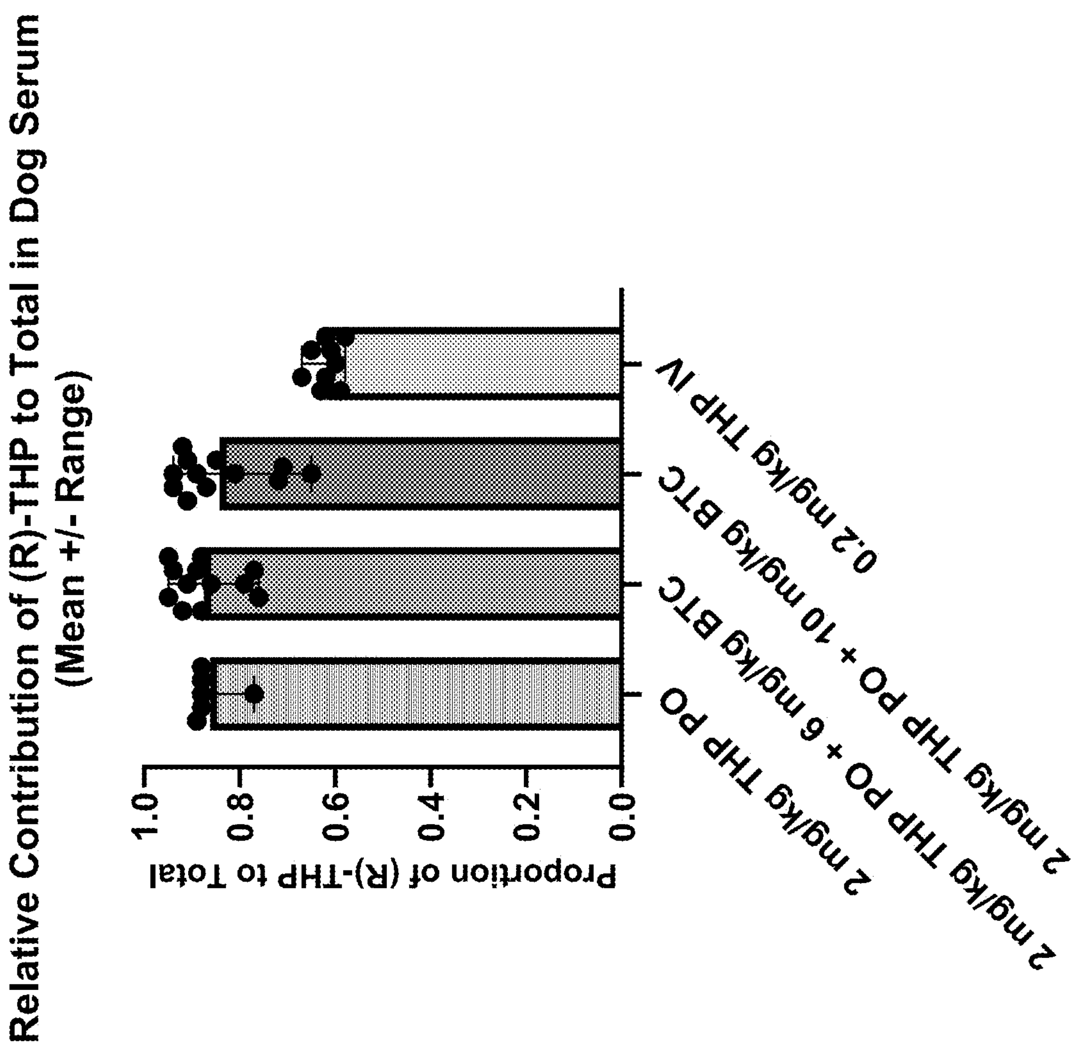
FIG. 15 is a graph depicting the enantiomer plasma exposure of R-THP as a fraction of total THP in dogs after dosing oral and IV.

To determine whether (R)-THP was selectively retained in a second species, Beagle dogs were dosed orally with 2 mg/kg Racemic THP (N=6), 2 mg/kg Racemic THP+6 mg/kg Racemic Bethanechol (N=12), 2 mg/kg Racemic THP+10 mg/kg Racemic Bethanechol (N=12), or dosed IV with 0.2 mg/kg Racemic THP (N=9). Total serum THP and total serum (S)-THP were measured after administration. FIG. 15 shows that over 80% of serum THP detected was (R)-THP after oral dosing, whether dosed as monotherapy or co-dosed with Bethanechol, similar to the enantiomeric composition identified in humans. Surprisingly, when administered IV, (R)-THP made up only ~60% of total THP. Summary statistics of this study are shown below in Table 19.

TABLE 19

| Dog R-THP Proportion in Plasma | | | |
|---|---|---|---|
| Oral | | IV | |
| Mean | 0.86 | Mean | 0.62 |
| Max | 0.95 | Max | 0.67 |
| Min | 0.65 | Min | 0.58 |

These data indicate that serum exposure of THP will largely be from only the R-THP enantiomer, indicating that the dosing of Rac-THP must take into account that only half the dose will be efficacious and that (S)-THP has an unexpected pharmacokinetic and metabolic profile. Selective metabolism of (S)-THP was observed to a substantially lower extent when dosed IV, suggesting that first pass metabolism after oral dosing could result in unpredictable metabolites of (S)-THP, while the active parent (R)-THP molecule is retained for longer periods. Furthermore, the dog data demonstrate that Bethanechol does not impact the selective metabolism of (S)-THP when co-dosed.

Example 15—R-THP Versus S-THP in Vitro

The in vitro half-life of R-THP and S-THP was measured by incubating with liver microsomes from humans, dogs, rats, and mice (Table 20). The in vitro $CL_{int}$, scale-up $CL_{int}$, predicted hepatic $CL_H$, and hepatic extraction ratio (ER) is also shown in Table 20. These data show that in humans and dogs, S-THP is metabolized significantly faster than R-THP. This may motivate one to select R-THP over S-THP because the PK of S-THP is unpredictable and may be metabolized differently in different species.

TABLE 20

| Compound ID | Species | in vitro $t_{1/2}$ (min) | in vitro $CL_{int}$ (μL/min/mg) | Scale-up $CL_{int}$ (mL/min/Kg) | Predicted Hepatic $CL_H$ (mL/min/Kg) | Hepatic Extraction Ratio (ER) |
|---|---|---|---|---|---|---|
| (R)-THP | Human | 69.69 | 19.89 | 20.44 | 10.36 | 0.49 |
| | Dog | 7.69 | 180.43 | 317.55 | 28.24 | 0.91 |
| | Rat | 0.63 | 2186.46 | 5334.96 | 67.14 | 0.99 |
| | Mouse | 2.82 | 491.54 | 2033.01 | 86.18 | 0.96 |
| (S)-THP | Human | 24.21 | 57.26 | 58.86 | 15.48 | 0.74 |
| | Dog | 5.72 | 243.57 | 428.69 | 28.90 | 0.93 |
| | Rat | 1.80 | 768.34 | 1874.75 | 65.62 | 0.96 |
| | Mouse | 5.56 | 249.48 | 1031.85 | 82.78 | 0.92 |

R-THP and S-THP were also incubated with individual recombinant CYP enzymes. Tables 21 and 22 demonstrate that R-THP is not metabolized by CYP1A2, while S-THP is metabolized by CYP1A2. Additionally, S-THP has an extremely short half-life upon incubation with CYP2D6 (~35 seconds), substantially shorter than R-THP half-life with any CYP. This result suggests that S-THP would be rapidly metabolized in vivo, with a large contribution from CYP2D6. Several other CYPs metabolize each enantiomer of THP and racemic THP non-selectively.

TABLE 21

| Compound ID | CYP isoform | $t_{1/2}$ | $CL_{int}$ (μL/min/pmol) |
|---|---|---|---|
| (R)-THP | CYP1A2 | ∞ | 0.00 |
| | CYP2A6 | ∞ | 0.00 |
| | CYP2B6 | ∞ | 0.00 |
| | CYP2C8 | ∞ | 0.00 |
| | CYP2C9 | ∞ | 0.00 |
| | CYP2C19 | 2.96 | 2.34 |
| | CYP2D6 | 3.39 | 2.04 |
| | CYP2E1 | ∞ | 0.00 |
| | CYP3A4 | 30.72 | 0.23 |
| | CYP3A5 | 55.21 | 0.13 |
| (S)-THP | CYP1A2 | 34.64 | 0.20 |
| | CYP2A6 | ∞ | 0.00 |
| | CYP2B6 | ∞ | 0.00 |
| | CYP2C8 | ∞ | 0.00 |
| | CYP2C9 | ∞ | 0.00 |
| | CYP2C19 | 9.14 | 0.76 |
| | CYP2D6 | 0.59 | 11.78 |
| | CYP2E1 | ∞ | 0.00 |
| | CYP3A4 | 16.74 | 0.41 |
| | CYP3A5 | 48.70 | 0.14 |
| Racemic THP | CYP1A2 | 55.63 | 0.13 |
| | CYP2A6 | ∞ | 0.00 |
| | CYP2B6 | ∞ | 0.00 |
| | CYP2C8 | ∞ | 0.00 |
| | CYP2C9 | ∞ | 0.00 |
| | CYP2C19 | 6.39 | 1.09 |
| | CYP2D6 | 2.31 | 3.02 |
| | CYP2E1 | ∞ | 0.00 |
| | CYP3A4 | 17.64 | 0.39 |
| | CYP3A5 | 53.33 | 0.13 |

TABLE 22

| CYP isoform | Substrates |
|---|---|
| CYP1A2 | S and Rac, no R |
| CYP2A6 | N/A |
| CYP2B6 | N/A |
| CYP2C8 | N/A |
| CYP2C9 | N/A |
| CYP2C19 | Rac, R and S |
| CYP2D6 | Rac, R and S |

TABLE 22-continued

| CYP isoform | Substrates |
|---|---|
| CYP2E1 | N/A |
| CYP3A4 | Rac, R and S |
| CYP3A5 | Rac, R and S |

Taken together, these data indicate that R-THP may be advantageous over S-THP. For example, administering racemic THP to patients with slow metabolizing CYP2D6 phenotypes may result in higher levels of total THP in blood due to limited metabolism of S-THP, while administering R-THP alone would be less impacted by variants in human CYP2D6 metabolism.

Example 16—Metabolic Differences Between (R) and (S) THP In Vitro

Figure 16:
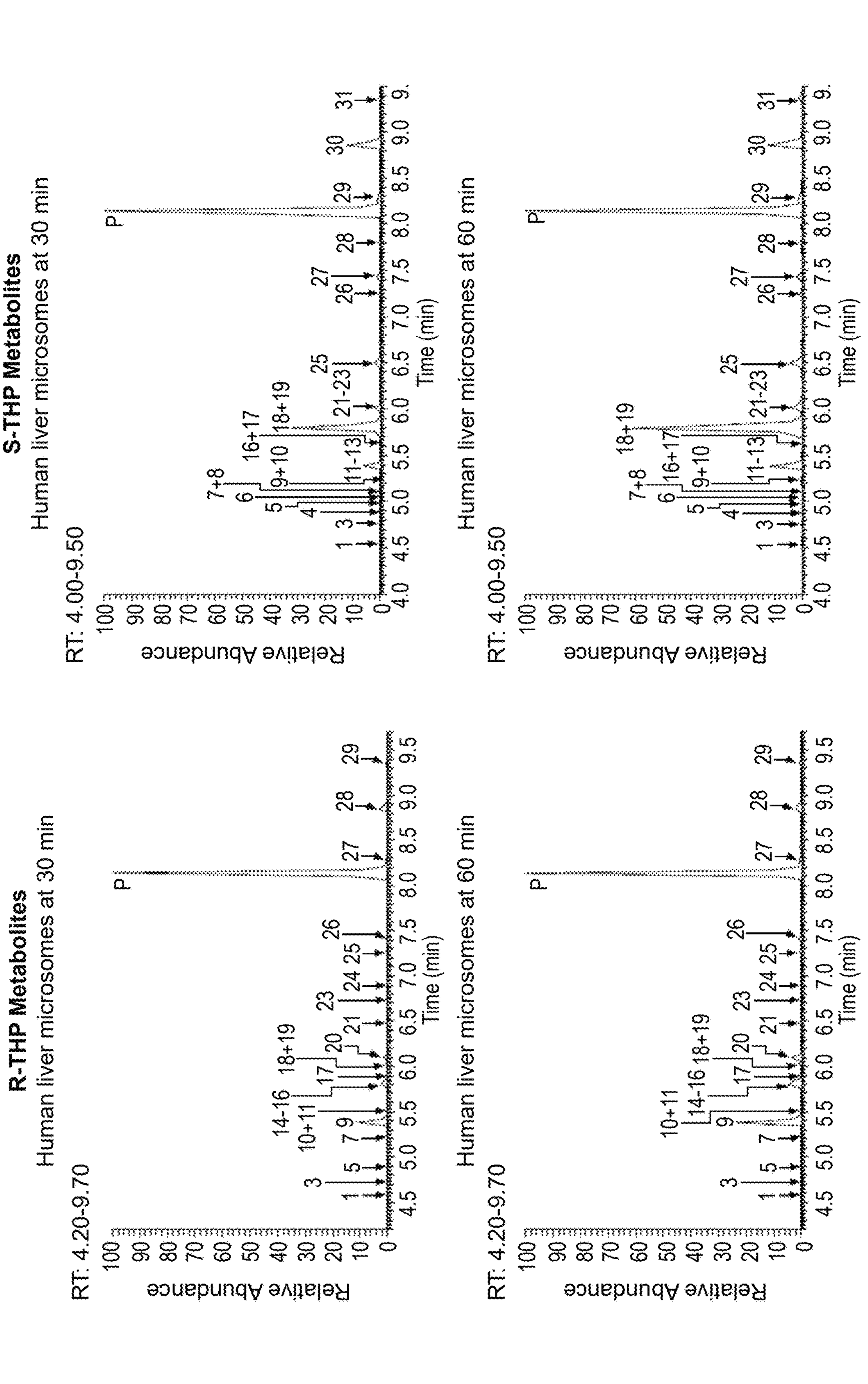
FIG. 16 is a series of graphs showing the metabolite profile of R-THP, S-THP, and Racemic THP after incubation in human liver microsomes at 30 minutes and 60 minutes.
Figure 16:
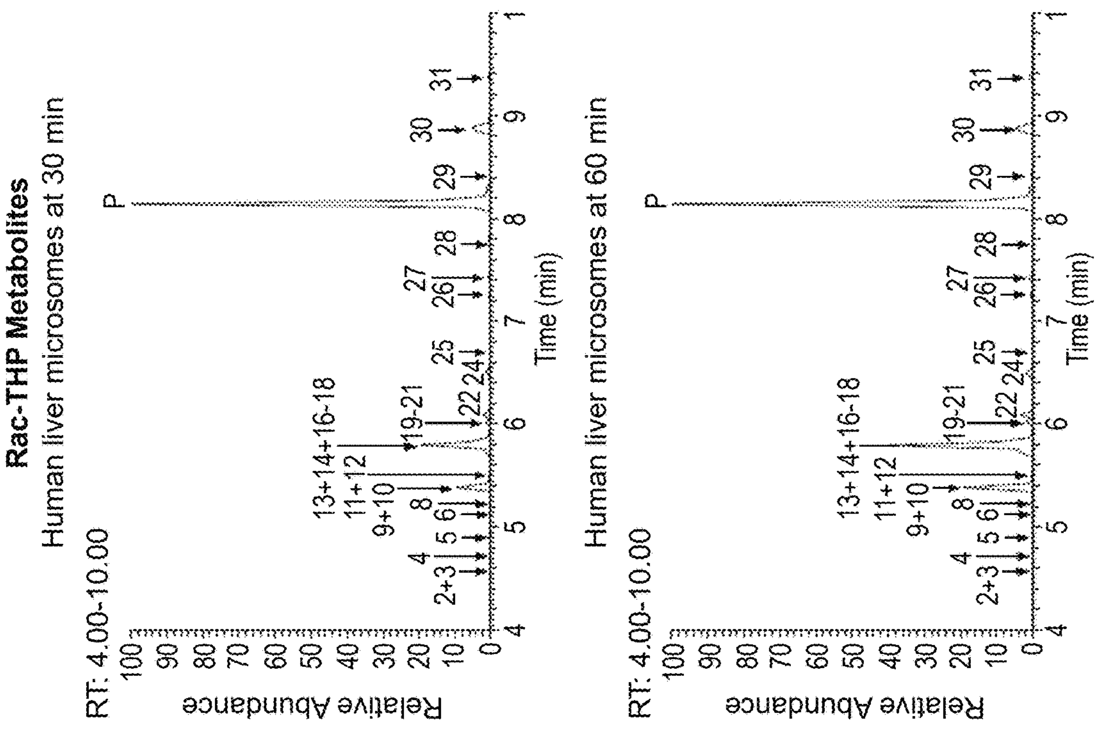

Racemic THP, (R)-THP and (S)-THP were incubated with human liver microsomes for 30 or 60 minutes. The resulting metabolites were analyzed by liquid chromatography-mass spectrometry, and metabolite peaks were detected and measured. As shown in FIG. 16, no (R)-THP metabolites were present at a significant level above parent molecule (indicated as P). Conversely, two metabolites 18 and 19 were detected at substantial levels when(S)-THP was incubated with microsomes at both time points. Racemic THP, a 50:50 mixture of (R)- and (S)-THP, also resulted in metabolite 18 when incubated with microsomes, but additional metabolites 13, 14, and 16 were also observed. These data demonstrate that each of the three THP species result in different metabolite profiles, and that (R)-THP yields the fewest metabolites. These data demonstrate that dosing (R)-THP instead of racemic THP would be preferable due to a more predictable metabolic profile.

INCORPORATION BY REFERENCE

The entire disclosure of each of the patent documents, publications, and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. An oral pharmaceutical composition, comprising:

(i) a muscarinic acetylcholine receptor inhibitor in an amount effective to treat a movement disorder, (ii) a muscarinic acetylcholine receptor activator in an amount effective to reduce the frequency of at least one side effect of the muscarinic acetylcholine receptor inhibitor, and (iii) a pharmaceutically acceptable carrier, wherein the muscarinic acetylcholine receptor inhibitor is (R)-trihexyphenidyl or a pharmaceutically acceptable salt thereof, wherein the muscarinic acetylcholine receptor activator is bethanechol or a pharmaceutically acceptable salt thereof, and wherein the pharmaceutical composition comprises the (R)-trihexyphenidyl and the bethanechol in a weight ratio of (R)-trihexyphenidyl to bethanechol of about 1:1.1 to about 1:20.

2. The oral pharmaceutical composition of claim 1, wherein the (R)-trihexyphenidyl or pharmaceutically acceptable salt thereof has a stereochemical purity of at least 95% enantiomeric excess.

3. The oral pharmaceutical composition of claim 1, wherein the oral pharmaceutical composition is a controlled release formulation.

4. The oral pharmaceutical composition of claim 1, wherein the oral pharmaceutical composition is dosed once per day.

5. The oral pharmaceutical composition of claim 1, wherein the oral pharmaceutical composition is dosed twice per day.

6. The oral pharmaceutical composition of claim 1, wherein the movement disorder is selected from the group consisting of dystonia, primary dystonia, secondary dystonia, multifocal dystonia, tardive dystonia, drug-induced dystonia, cerebral palsy-associated dystonia, focal dystonia, cervical dystonia, blepharospasm, hand dystonia, writer's cramp, musician's dystonia, leg dystonia, foot dystonia, segmental dystonia, generalized dystonia, genetic dystonia, Multiple System Atrophy, Progressive Supranuclear Palsy, tremor, Parkinson's disease, drug-induced Parkinsonism, Huntington's disease, and dementia with Lewy Bodies.

7. The oral pharmaceutical composition of claim 1, wherein the side effect is selected from the group consisting of dry mouth, dry eye, blurry vision, tachycardia, constipation, urine retention, impaired vision, nausea, cramping, reduced urinary voiding, flushed skin, fever, reduced sweating, cardiac arrhythmia, and combinations thereof.

8. The oral pharmaceutical composition of claim 1, wherein the movement disorder is dystonia.

9. The oral pharmaceutical composition of claim 1, wherein the side effect is constipation.

10. The oral pharmaceutical composition of claim 1, wherein the side effect is dizziness.

11. An oral pharmaceutical composition, comprising:

(i) a muscarinic acetylcholine receptor inhibitor in an amount effective to treat a movement disorder (ii) a muscarinic acetylcholine receptor activator in an amount effective to reduce the frequency of at least one side effect of the muscarinic acetylcholine receptor inhibitor, and (iii) a pharmaceutically acceptable carrier, wherein the composition is sufficient to provide an in vivo plasma profile of the muscarinic acetylcholine receptor inhibitor when administered to a subject in need thereof, wherein the rate of rise of the plasma concentration of the muscarinic acetylcholine receptor inhibitor is less than about 15 ng/mL/hr, wherein the muscarinic acetylcholine receptor inhibitor is (R)-trihexyphenidyl or a pharmaceutically acceptable salt thereof, wherein the muscarinic acetylcholine receptor activator is bethanechol or a pharmaceutically acceptable salt thereof, and wherein the oral pharmaceutical composition is a controlled release formulation.

12. The oral pharmaceutical composition of claim 11, wherein the magnitude or severity of at least one side effect of the (R)-trihexyphenidyl or a pharmaceutically acceptable salt thereof is reduced in a subject administered the oral pharmaceutical composition compared to a subject administered an immediate release formulation of trihexyphenidyl or a pharmaceutically acceptable salt thereof alone.

13. The oral pharmaceutical composition of claim 12, wherein the side effect is selected from the group consisting of dizziness, lightheadedness, headache, drowsiness, confusion, reduced concentration, euphoria, elevated mood, hallucinations, agitation, irritability, sensory disturbances, blurry vision, and impaired vision.

14. The oral pharmaceutical composition of claim 11, wherein the movement disorder is selected from the group consisting of dystonia, primary dystonia, secondary dystonia, multifocal dystonia, tardive dystonia, drug-induced dystonia, cerebral palsy-associated dystonia, focal dystonia, cervical dystonia, blepharospasm, hand dystonia, writer's cramp, musician's dystonia, leg dystonia, foot dystonia, segmental dystonia, generalized dystonia, genetic dystonia, Multiple System Atrophy, Progressive Supranuclear Palsy, tremor, Parkinson's disease, drug-induced Parkinsonism, Huntington's disease, and dementia with Lewy Bodies.

15. The oral pharmaceutical composition of claim 11, wherein the side effect is selected from the group consisting of dry mouth, dry eye, blurry vision, tachycardia, constipation, urine retention, impaired vision, nausea, cramping, reduced urinary voiding, flushed skin, fever, reduced sweating, cardiac arrhythmia, and combinations thereof.

16. The oral pharmaceutical composition of claim 11, wherein the movement disorder is dystonia.

17. The oral pharmaceutical composition of claim 11, wherein the side effect is constipation.

18. The oral pharmaceutical composition of claim 11, wherein the side effect is dizziness.

* * * * *